(12) United States Patent
Tyson et al.

(10) Patent No.: US 11,484,360 B2
(45) Date of Patent: Nov. 1, 2022

(54) USER INTERFACE AND LOCK FEATURES FOR POSITIONING MULTIPLE COMPONENTS WITHIN A BODY

(71) Applicant: GYRUS ACMI, INC., Westborough, MA (US)

(72) Inventors: Taylor N. Tyson, Seattle, WA (US); Madeline C. Graham, Woodinville, WA (US); Christine N. Jurevicius, Issaquah, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 1199 days.

(21) Appl. No.: 15/933,337

(22) Filed: Mar. 22, 2018

(65) Prior Publication Data

US 2018/0271594 A1 Sep. 27, 2018

Related U.S. Application Data

(63) Continuation-in-part of application No. 15/462,880, filed on Mar. 19, 2017, now abandoned, and a
(Continued)

(51) Int. Cl.
*A61B 18/14* (2006.01)
*A61B 18/12* (2006.01)
(Continued)

(52) U.S. Cl.
CPC ...... *A61B 18/1492* (2013.01); *A61B 18/1206* (2013.01); *A61B 18/14* (2013.01);
(Continued)

(58) Field of Classification Search
CPC . A61B 18/1492; A61B 18/1206; A61B 18/14; A61B 2017/00973;
(Continued)

(56) References Cited

U.S. PATENT DOCUMENTS

| 4,869,259 A | 9/1989 | Elkins |
| 5,035,695 A * | 7/1991 | Weber, Jr. .......... A61B 18/1402 606/49 |

(Continued)

OTHER PUBLICATIONS

International Search Report and Written Opinion rcvd in related application PCT/US2017/023242.
(Continued)

*Primary Examiner* — Eun Hwa Kim
*Assistant Examiner* — Adam Z Minchella
(74) *Attorney, Agent, or Firm* — Schwegman Lundberg & Woessner, P.A.

(57) ABSTRACT

Disclosed embodiments include apparatuses, systems, and methods for positioning electrodes within a body. In an illustrative embodiment, an apparatus for slidably moving multiple features relative to a sheath insertable into a body and positionable relative to a reference point includes a primary actuator configured to move a primary electrode to a first position. A secondary actuator is configured to move a secondary electrode to a second position. A shrouding device is configured to selectively prevent access to the secondary actuator until the primary actuator has been manipulated to extend the primary electrode to the first position.

52 Claims, 63 Drawing Sheets

Related U.S. Application Data continuation-in-part of application No. 15/462,872, filed on Mar. 19, 2017, now Pat. No. 10,987,161.

(51) Int. Cl.
  *A61B 18/00* (2006.01)
  *A61B 17/00* (2006.01)

(52) U.S. Cl.
  CPC ............... *A61B 2017/00973* (2013.01); *A61B 2018/00577* (2013.01); *A61B 2018/00589* (2013.01); *A61B 2018/00607* (2013.01); *A61B 2018/126* (2013.01); *A61B 2018/1246* (2013.01); *A61B 2018/1253* (2013.01); *A61B 2018/1435* (2013.01); *A61B 2018/1467* (2013.01); *A61B 2018/1475* (2013.01); *A61B 2218/002* (2013.01)

(58) Field of Classification Search
  CPC ........... A61B 2018/00577; A61B 2018/00589; A61B 2018/00607; A61B 2018/1246; A61B 2018/1253; A61B 2018/126; A61B 2018/1435; A61B 2018/1467; A61B 2018/1475; A61B 2218/002
  See application file for complete search history.

(56) References Cited

U.S. PATENT DOCUMENTS

| | | | |
|---|---|---|---|
| 5,665,100 A * | 9/1997 | Yoon | A61B 17/1285 606/205 |
| 5,919,202 A | 7/1999 | Yoon | |
| 6,416,510 B1 | 7/2002 | Altman et al. | |
| 6,749,604 B1 | 6/2004 | Eggers et al. | |
| 7,357,798 B2 | 4/2008 | Sharps et al. | |
| 7,419,488 B2 | 9/2008 | Ciarrocca et al. | |
| 8,043,286 B2 | 10/2011 | Palanker et al. | |
| 8,114,071 B2 | 2/2012 | Woloszko et al. | |
| 8,361,066 B2 | 1/2013 | Long et al. | |
| 9,539,012 B2 | 1/2017 | Landry et al. | |
| 9,888,926 B2 | 2/2018 | Phan et al. | |
| 10,542,872 B2 | 1/2020 | Shuman et al. | |
| 2002/0091382 A1 | 7/2002 | Hooven | |
| 2003/0028231 A1 | 2/2003 | Partridge et al. | |
| 2003/0083682 A1 | 5/2003 | Heise | |
| 2004/0059328 A1 | 3/2004 | Daniel et al. | |
| 2005/0113827 A1 | 5/2005 | Dumbauld et al. | |
| 2009/0076412 A1 * | 3/2009 | Rioux | A61B 18/1482 600/564 |
| 2009/0299362 A1 | 12/2009 | Long et al. | |
| 2010/0004723 A1 | 1/2010 | Foster et al. | |
| 2010/0256627 A1 | 10/2010 | Ma et al. | |
| 2010/0324637 A1 | 12/2010 | Trip et al. | |
| 2012/0035474 A1 | 2/2012 | Deckman et al. | |
| 2012/0053485 A1 | 3/2012 | Bloom | |
| 2013/0190609 A1 | 7/2013 | Fischer, Jr. | |
| 2013/0204068 A1 | 8/2013 | Gnanashanmugam et al. | |
| 2013/0226026 A1 | 8/2013 | Dillard et al. | |
| 2013/0310823 A1 | 11/2013 | Gelfand et al. | |
| 2014/0276764 A1 | 9/2014 | Shuman et al. | |
| 2015/0005769 A1 | 1/2015 | Klink et al. | |
| 2016/0015451 A1 * | 1/2016 | Shikhman | A61B 18/1492 606/41 |
| 2016/0235431 A1 * | 8/2016 | Brown | A61B 17/3472 |
| 2018/0206903 A1 | 7/2018 | Podany | |
| 2018/0263473 A1 | 9/2018 | Shuman et al. | |
| 2021/0259766 A1 | 8/2021 | Mills | |

OTHER PUBLICATIONS

"U.S. Appl. No. 15/462,876, Notice of Allowance dated Sep. 30, 2019", 10 pgs.
"U.S. Appl. No. 15/462,876, Preliminary Amendment filed May 2, 2017", 6 pgs.
"International Application Serial No. PCT/US2017/023242, International Search Report dated Jul. 3, 2017", 3 pgs.
"International Application Serial No. PCT/US2017/023242, Written Opinion dated Jul. 3, 2017", 6 pgs.

* cited by examiner

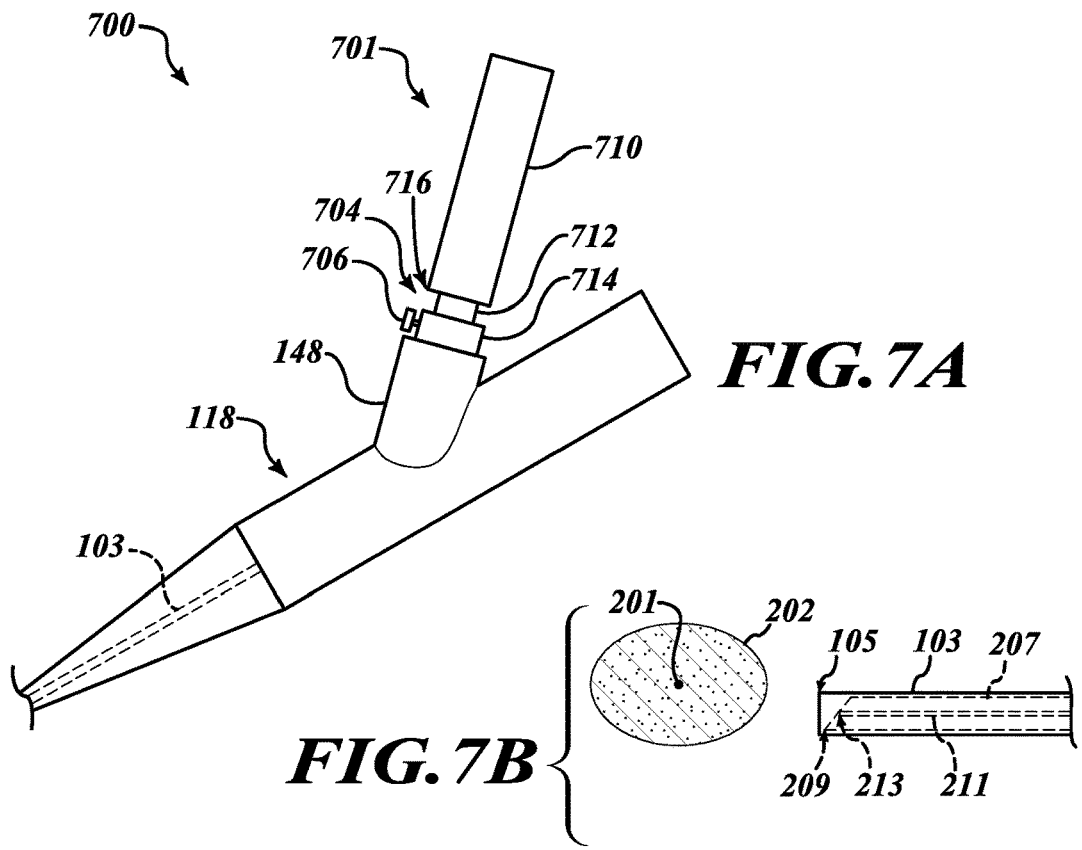
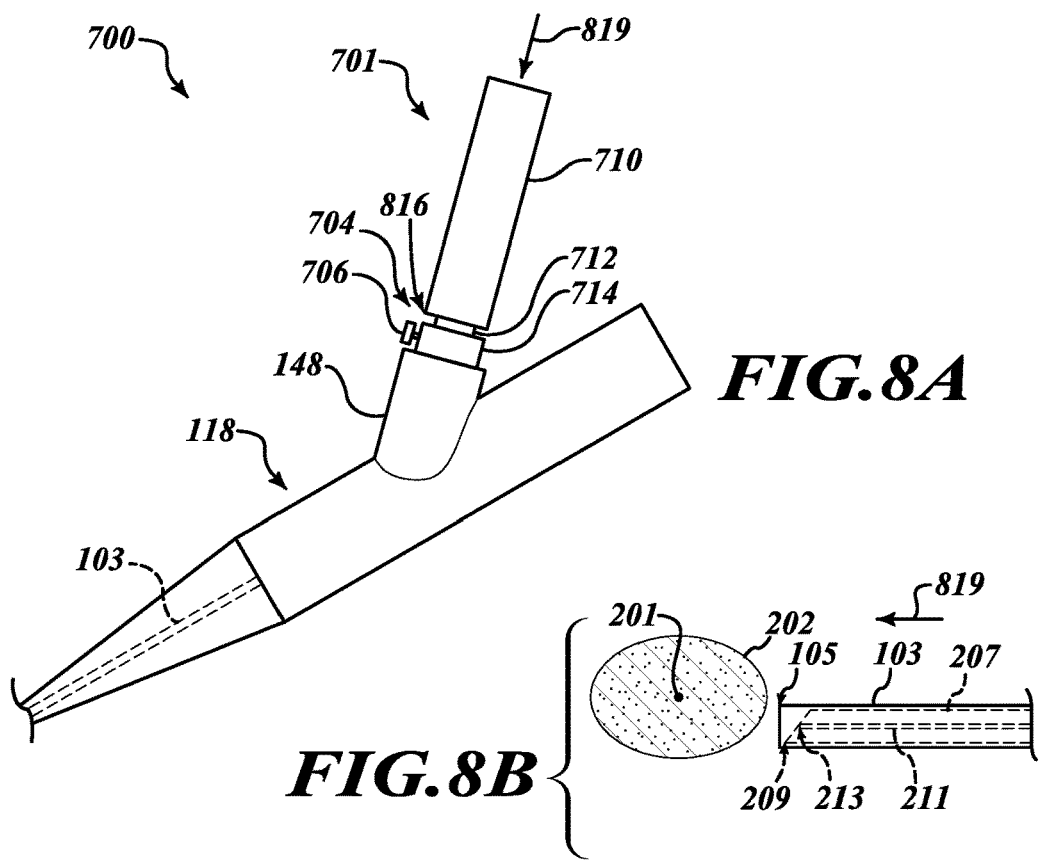

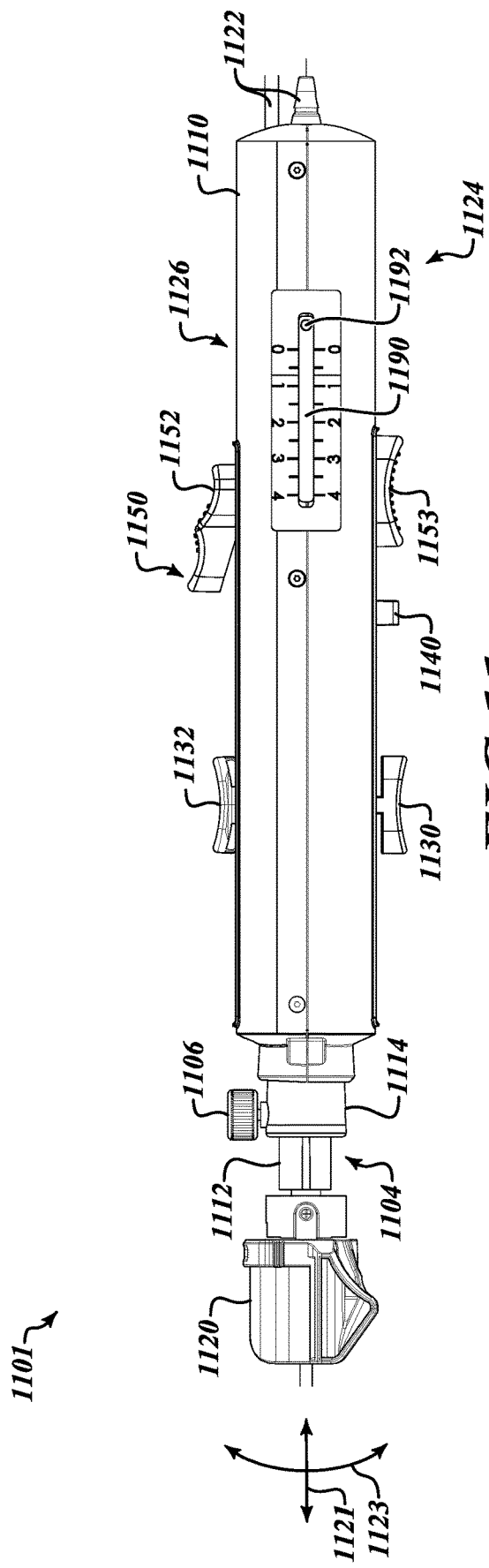

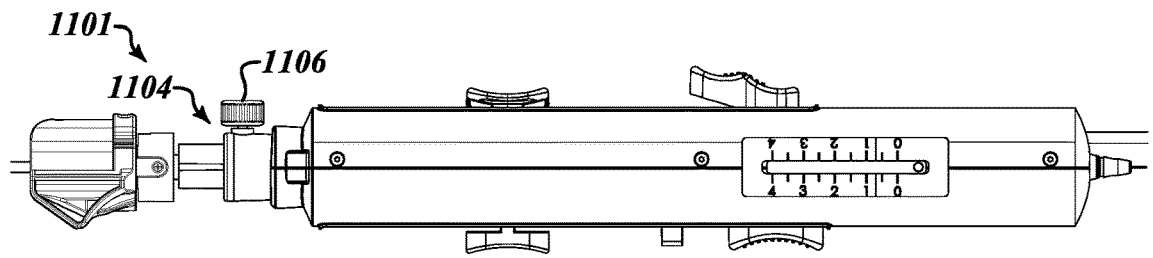
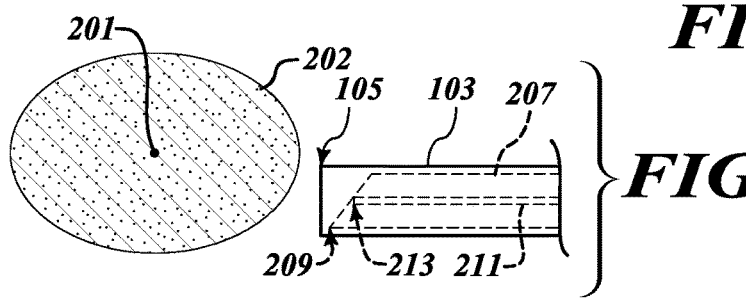
*FIG.12A*
*FIG.12B*
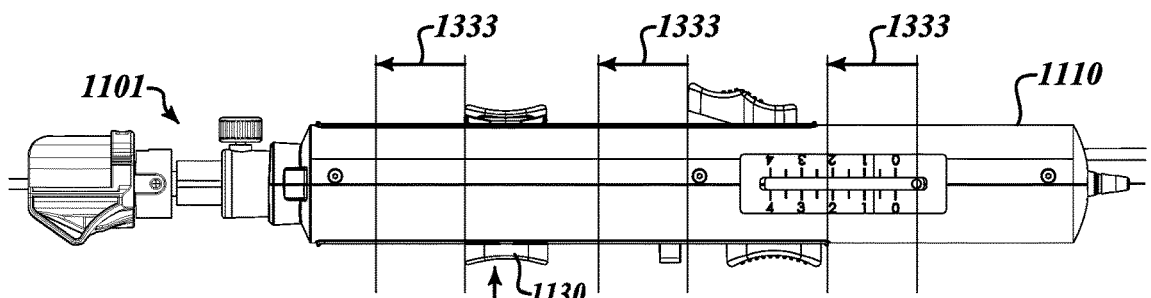
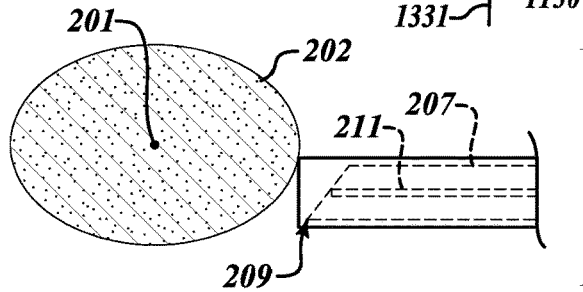
*FIG.13A*
*FIG.13B*
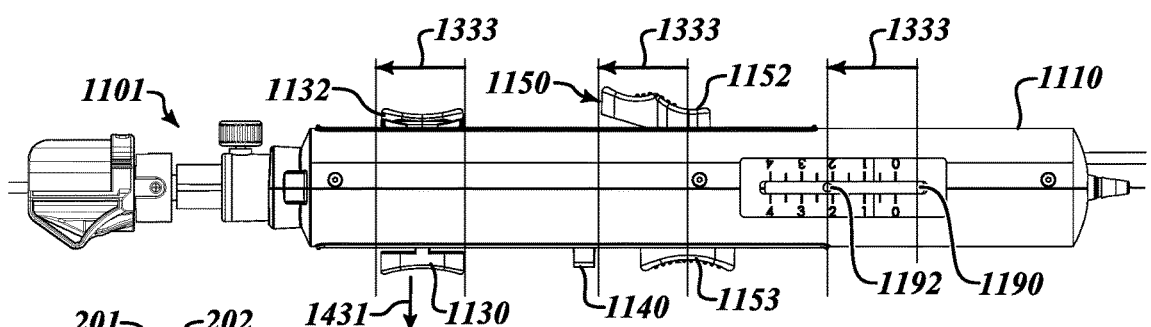
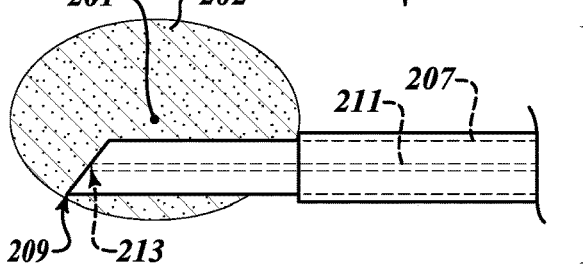
*FIG.14A*
*FIG.14B*

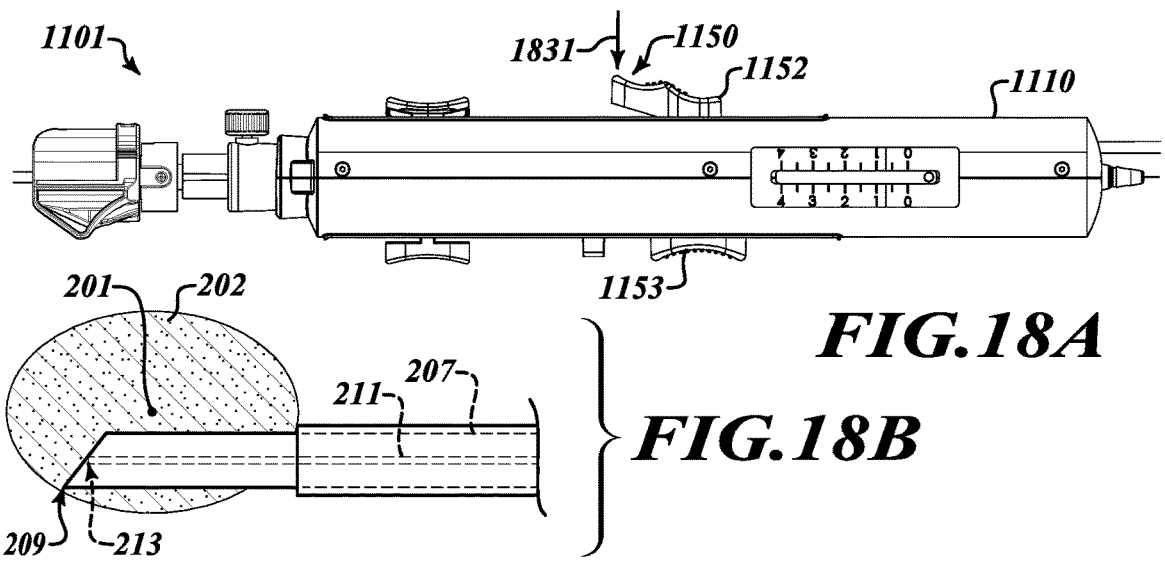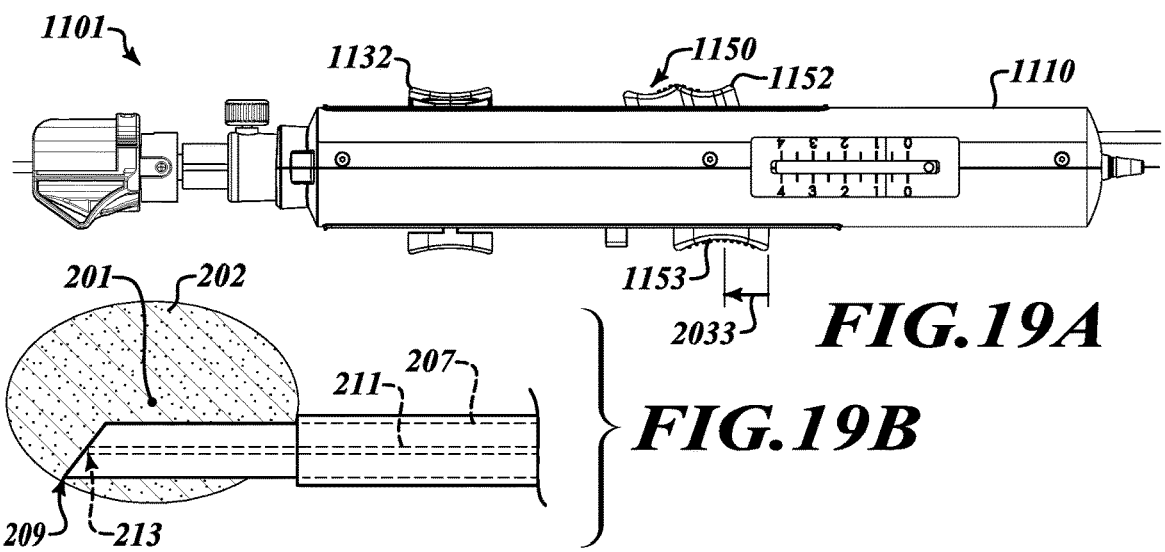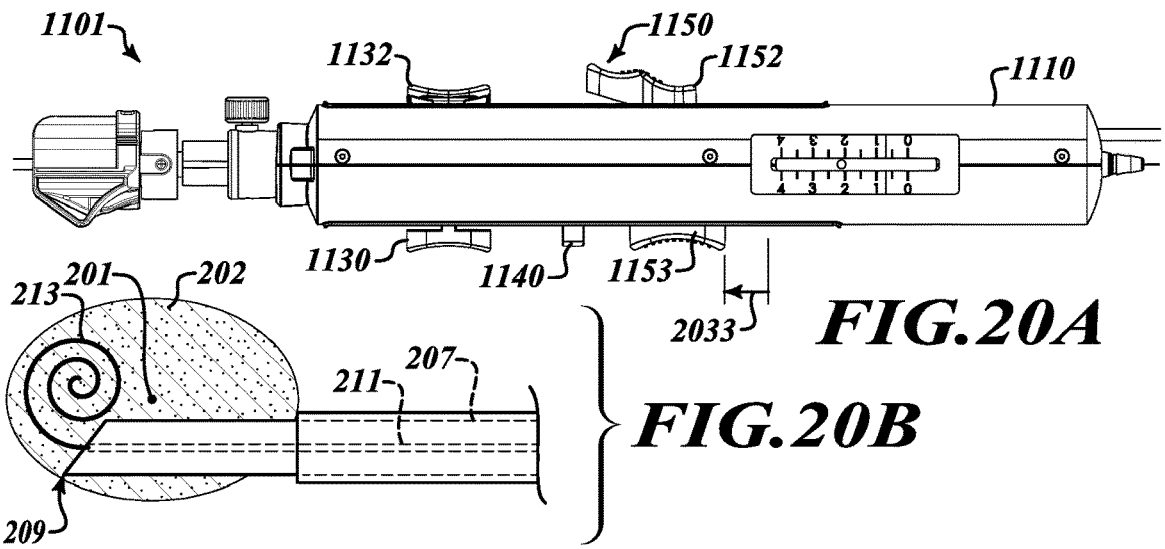

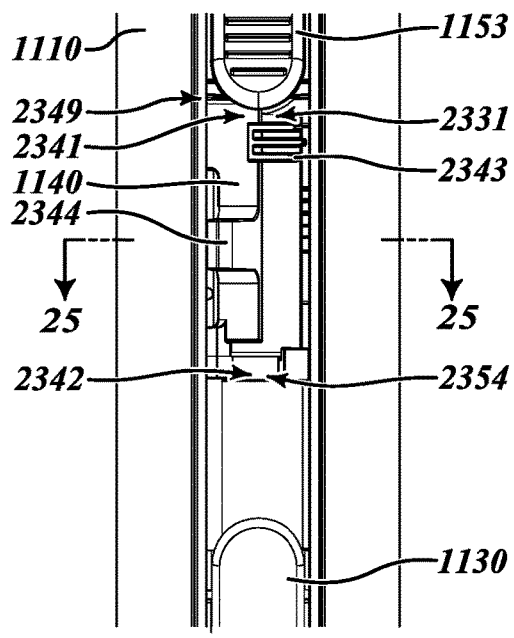
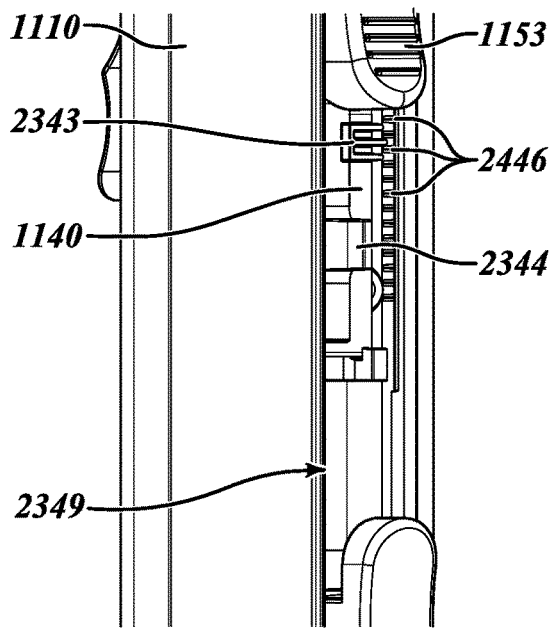
FIG.23   FIG.24
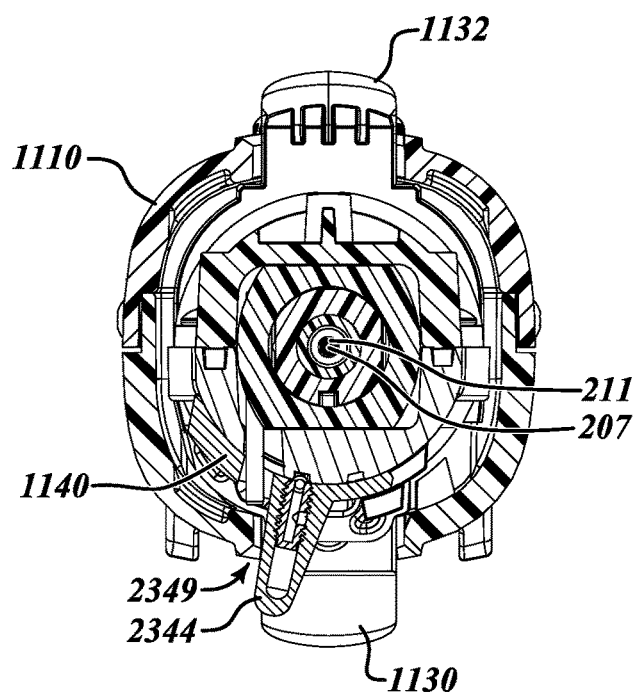
FIG.25

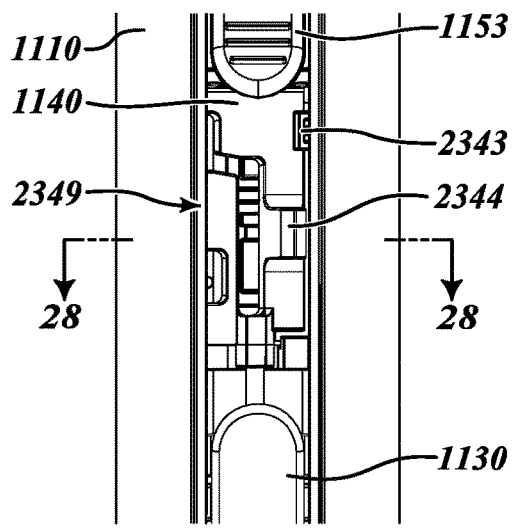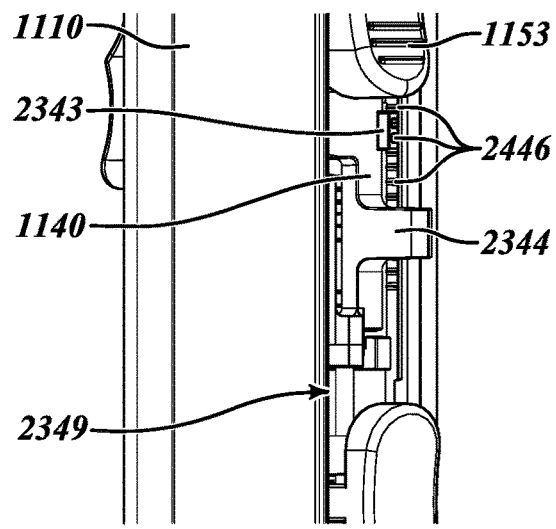
FIG.26     FIG.27
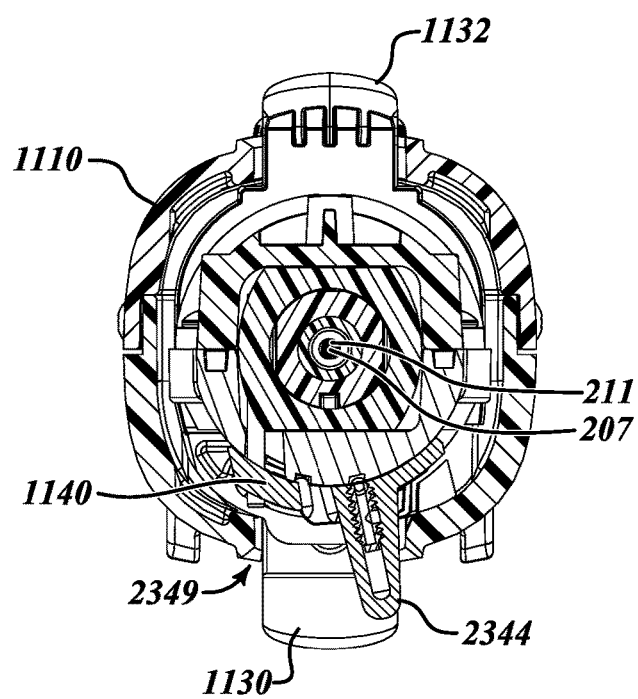
FIG.28

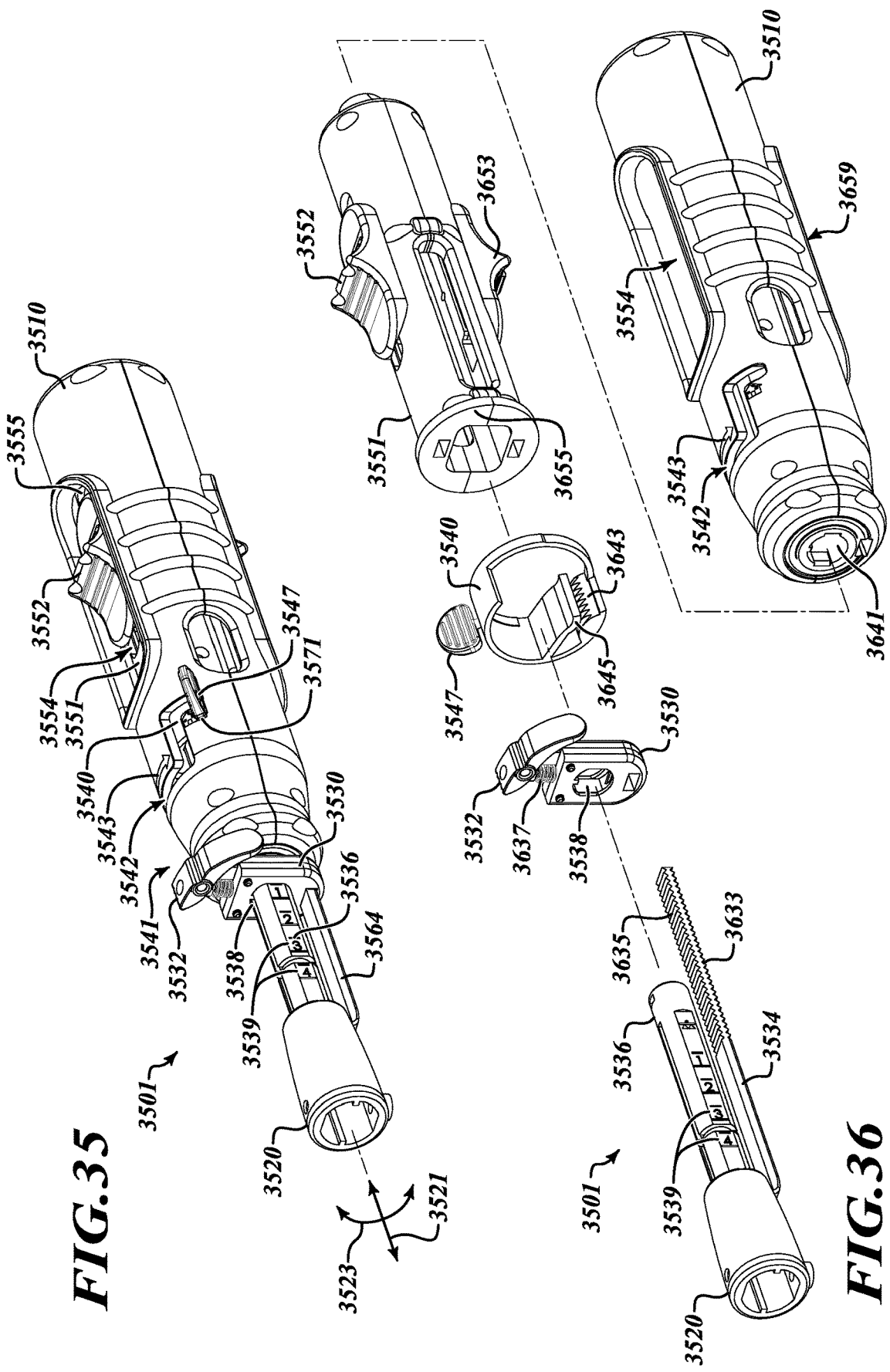

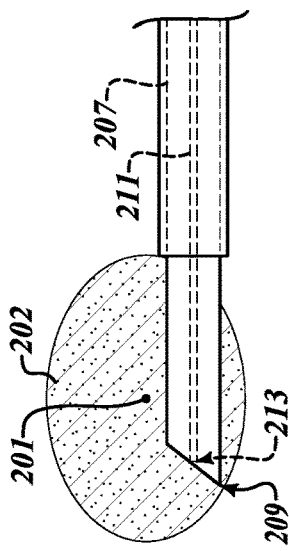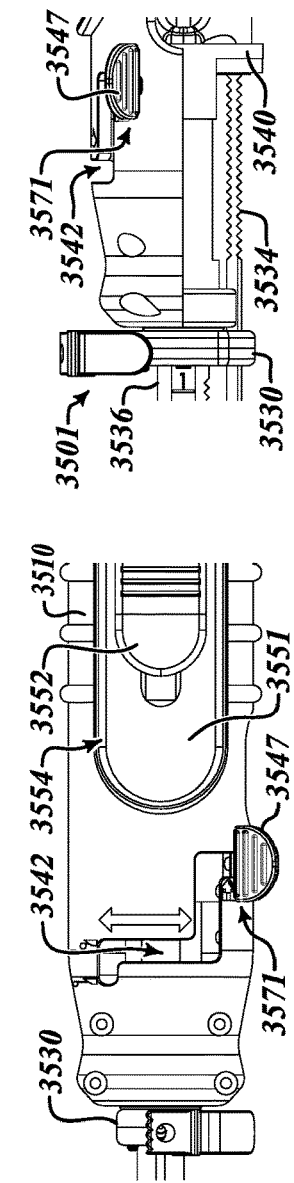
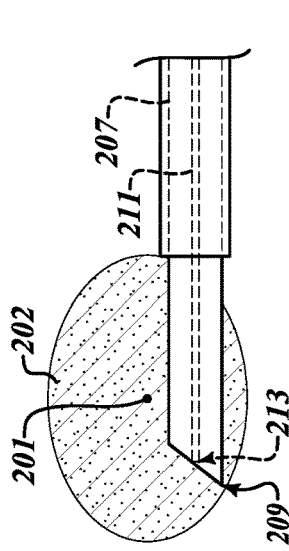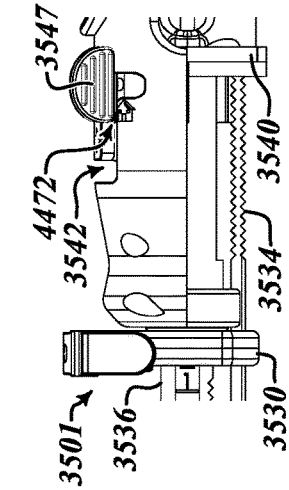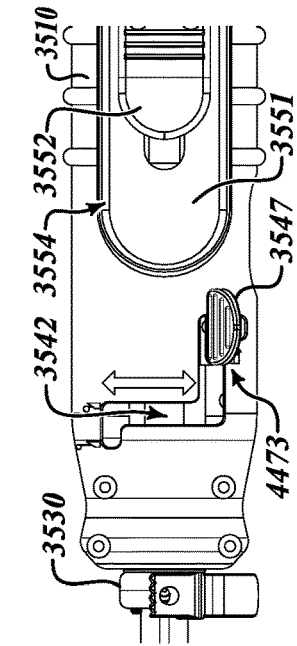
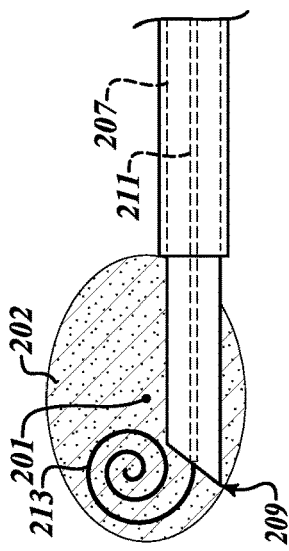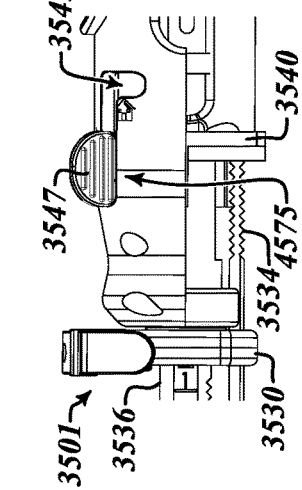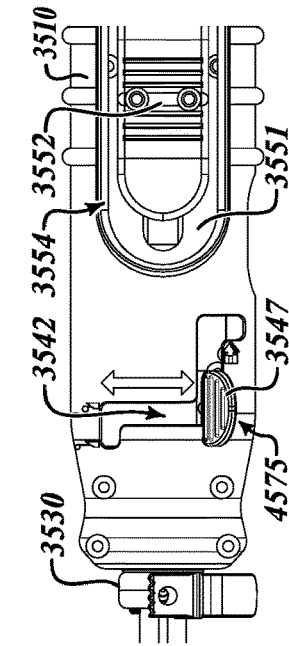

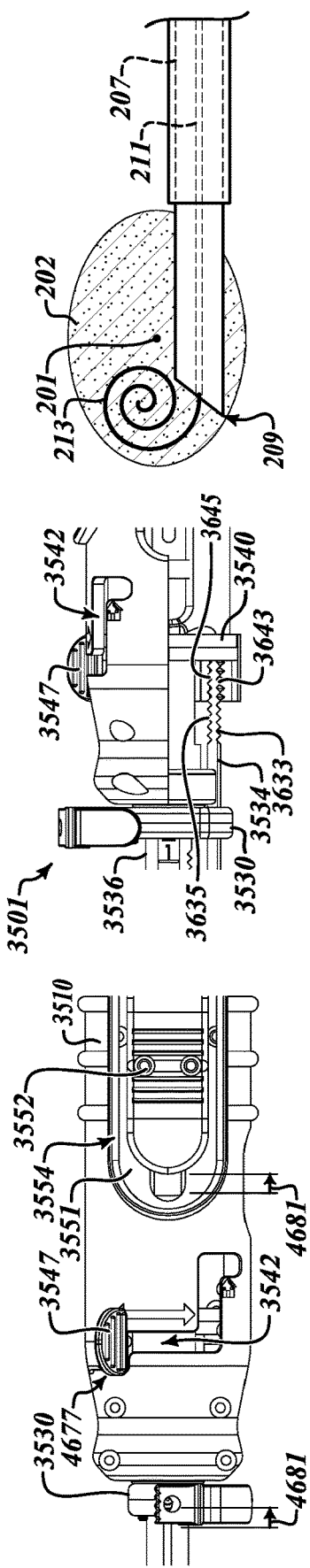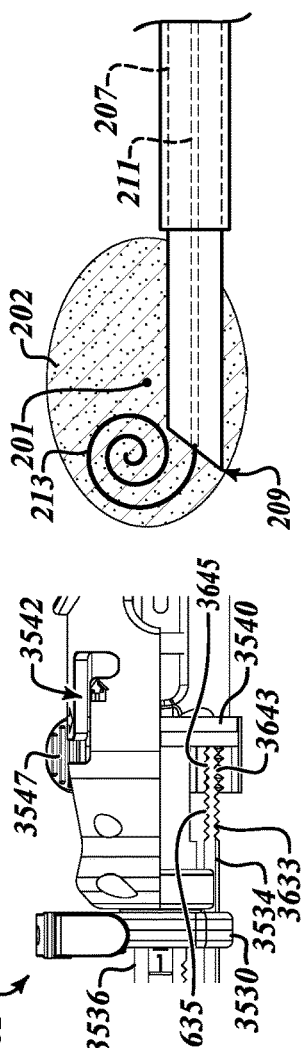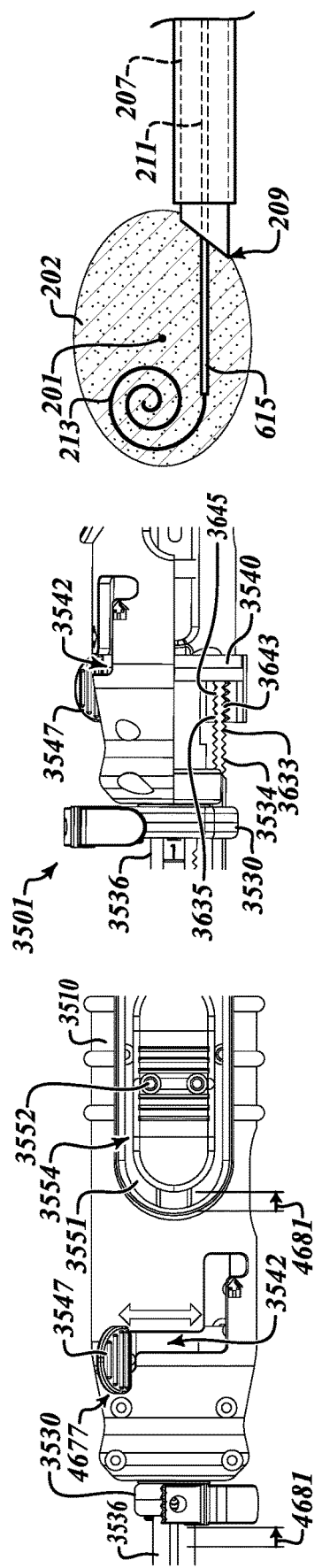

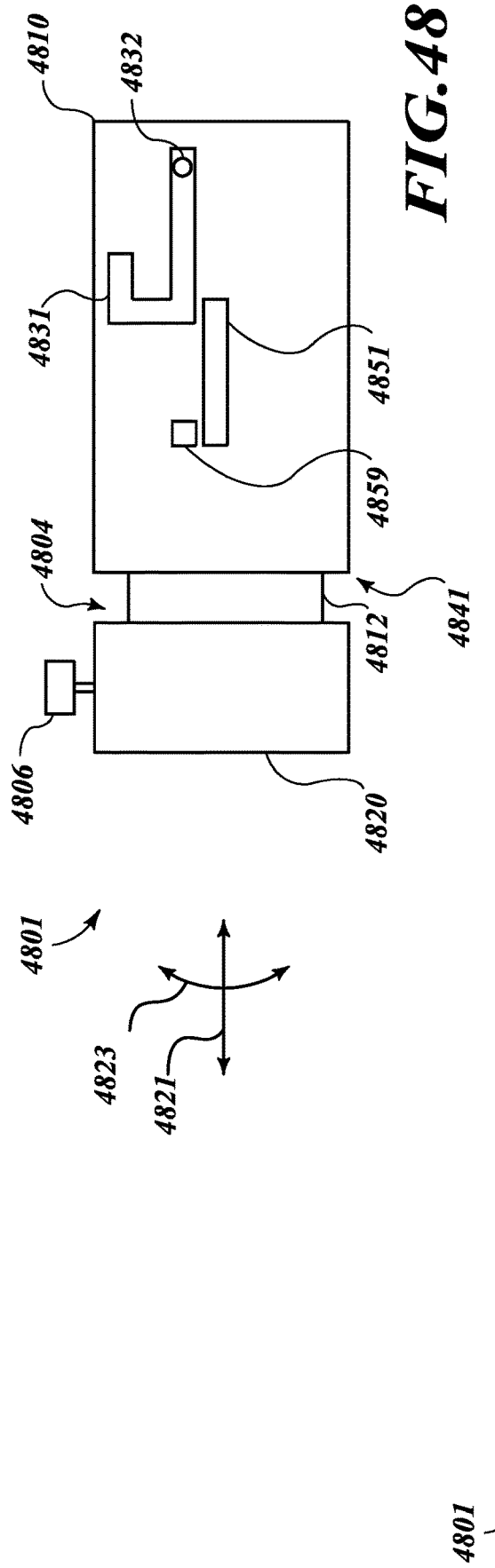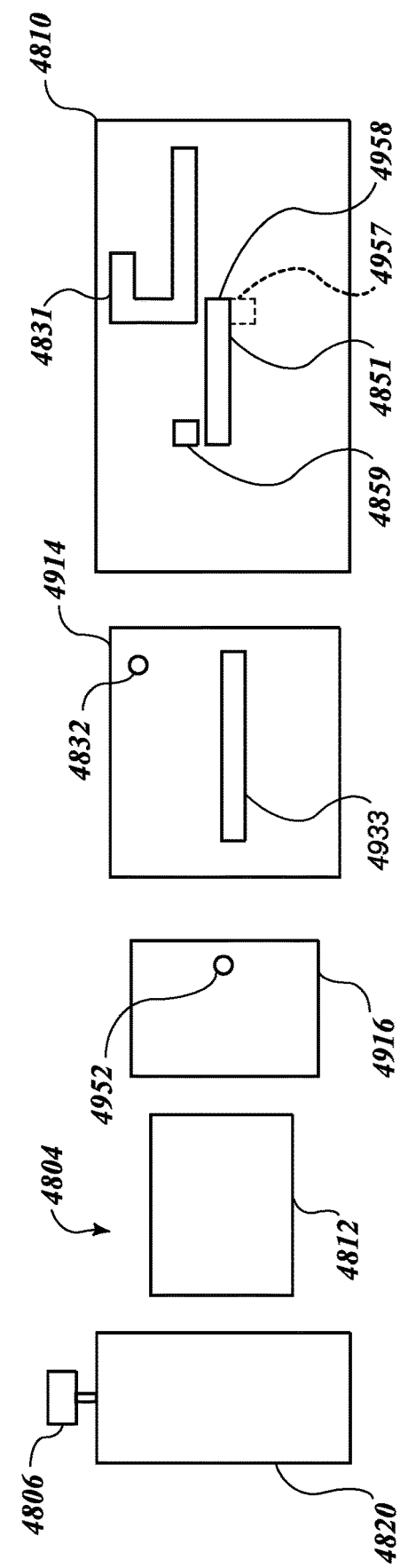

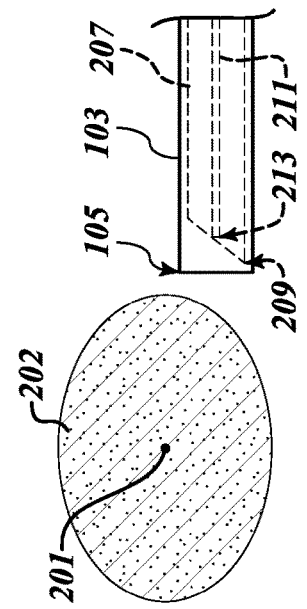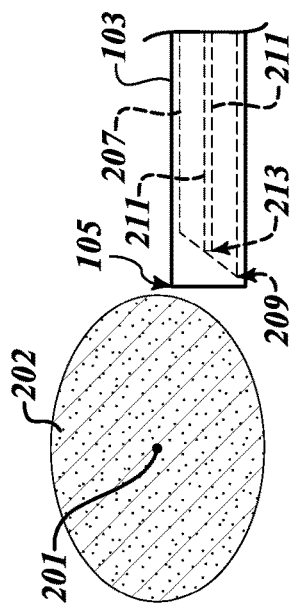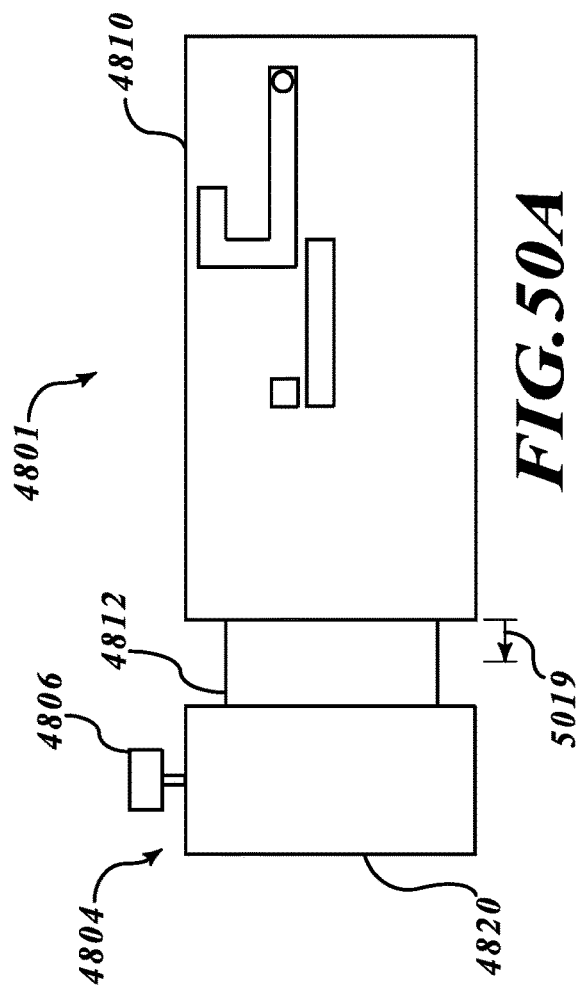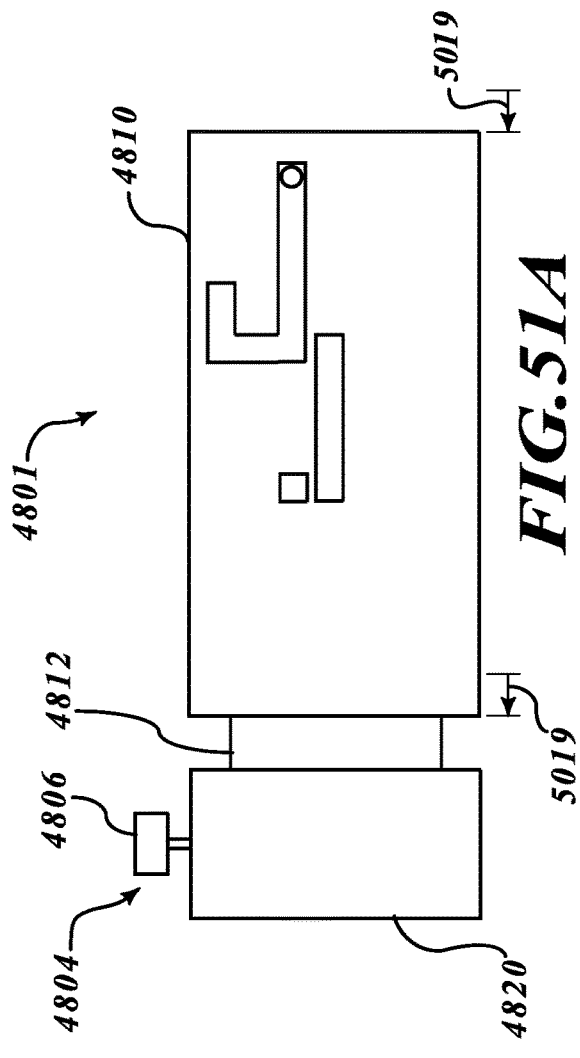

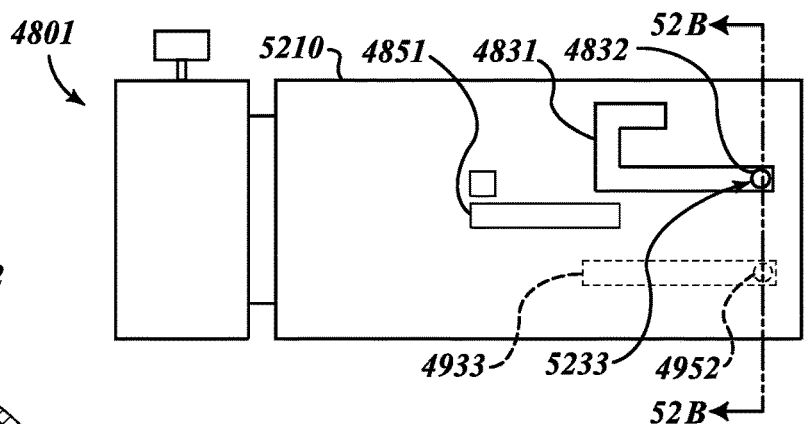
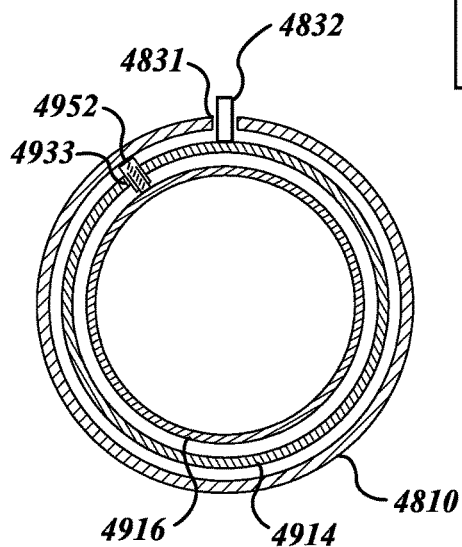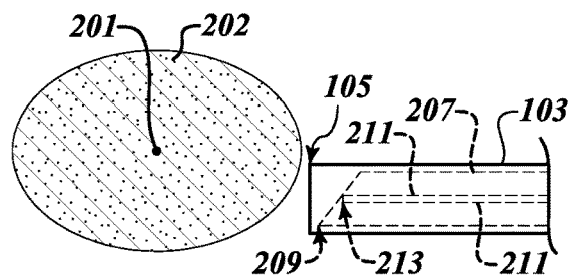
FIG.52A
FIG.52B
FIG.52C
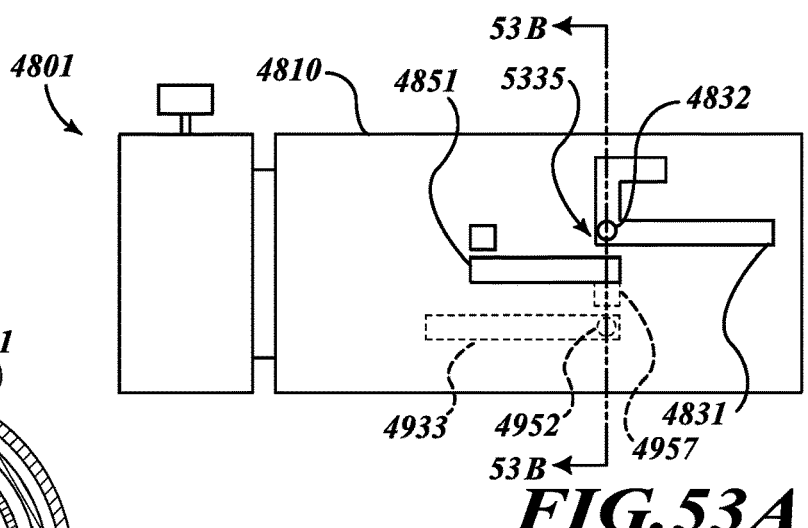
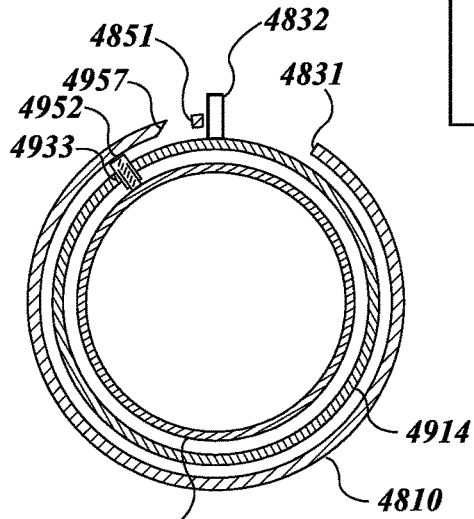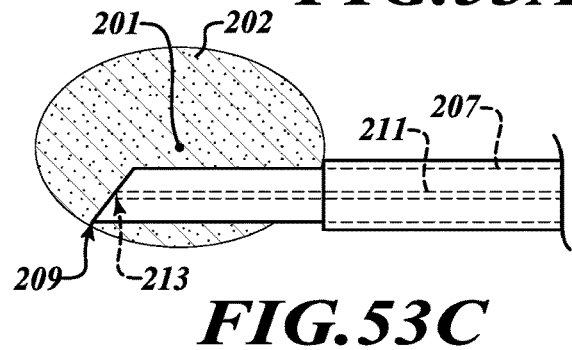
FIG.53A
FIG.53B
FIG.53C

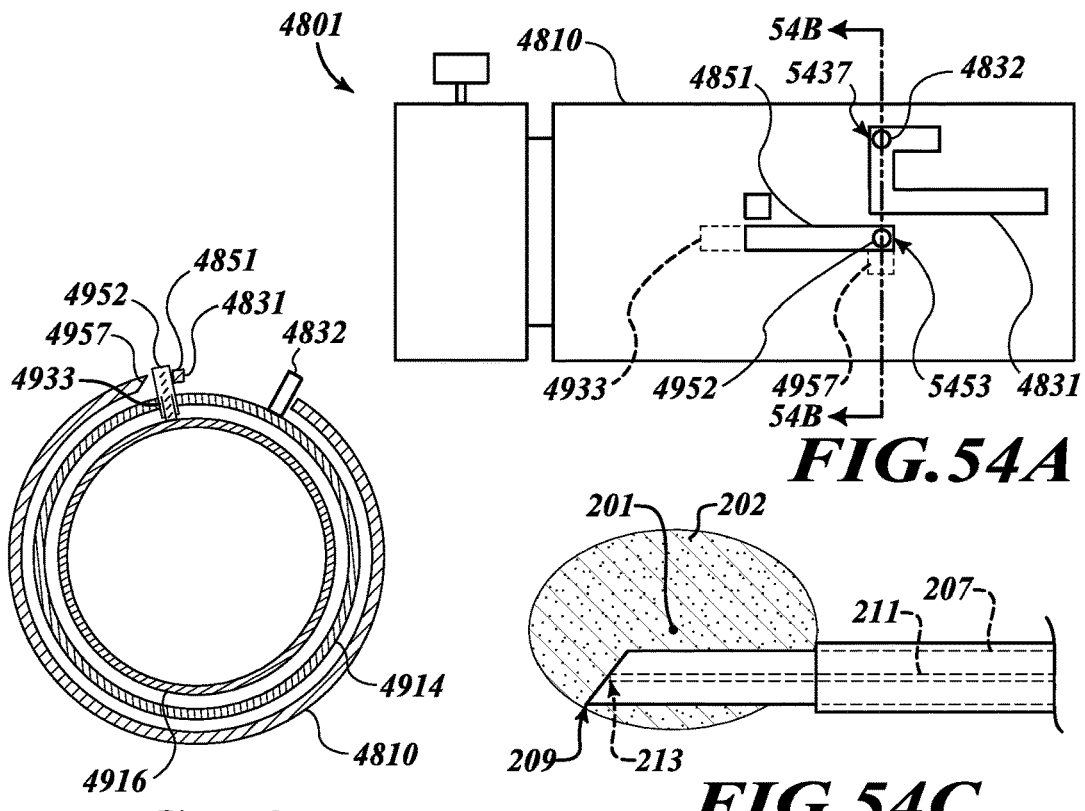
FIG.54A
FIG.54B
FIG.54C
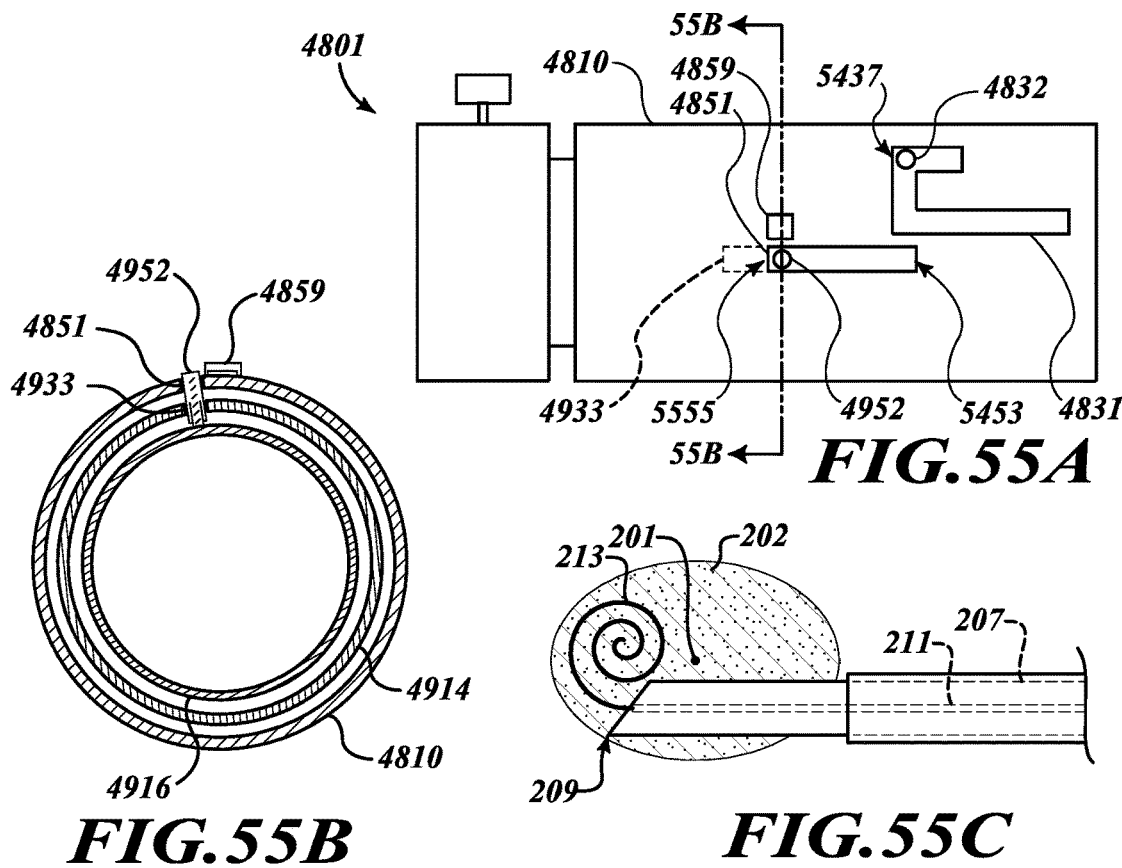
FIG.55A
FIG.55B
FIG.55C

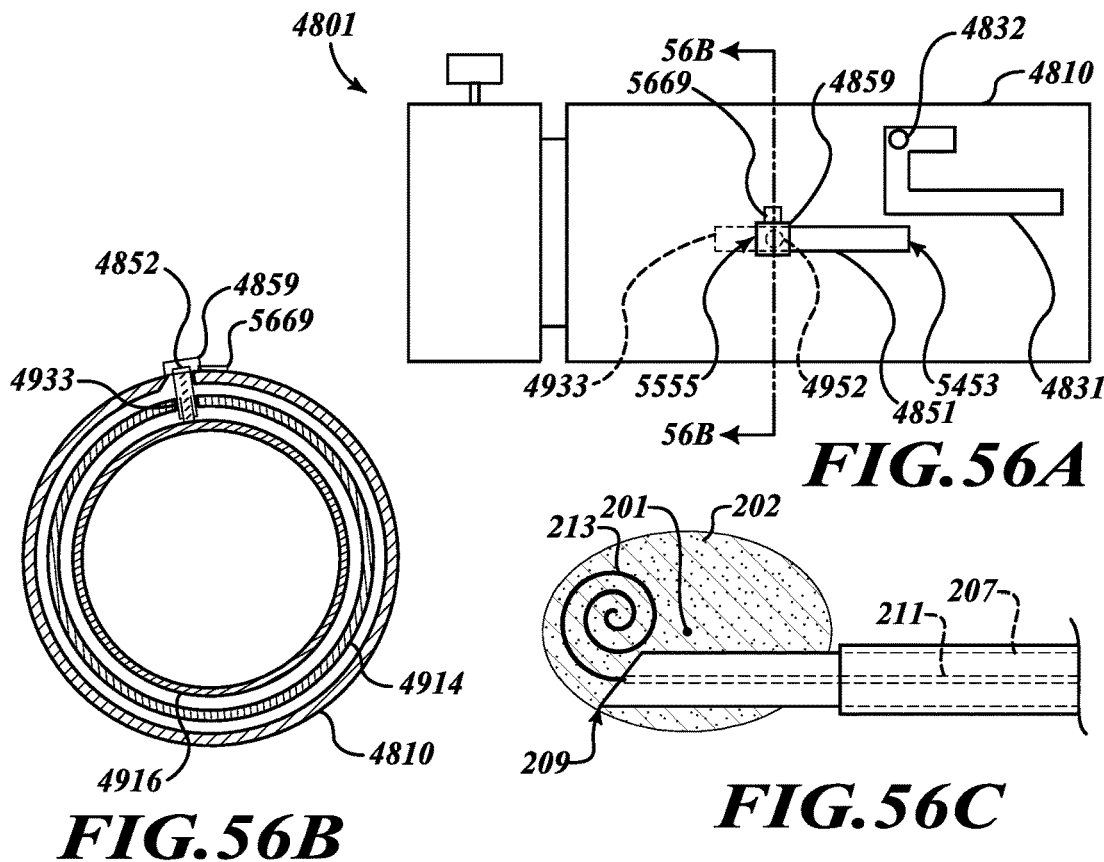
FIG.56A
FIG.56B
FIG.56C
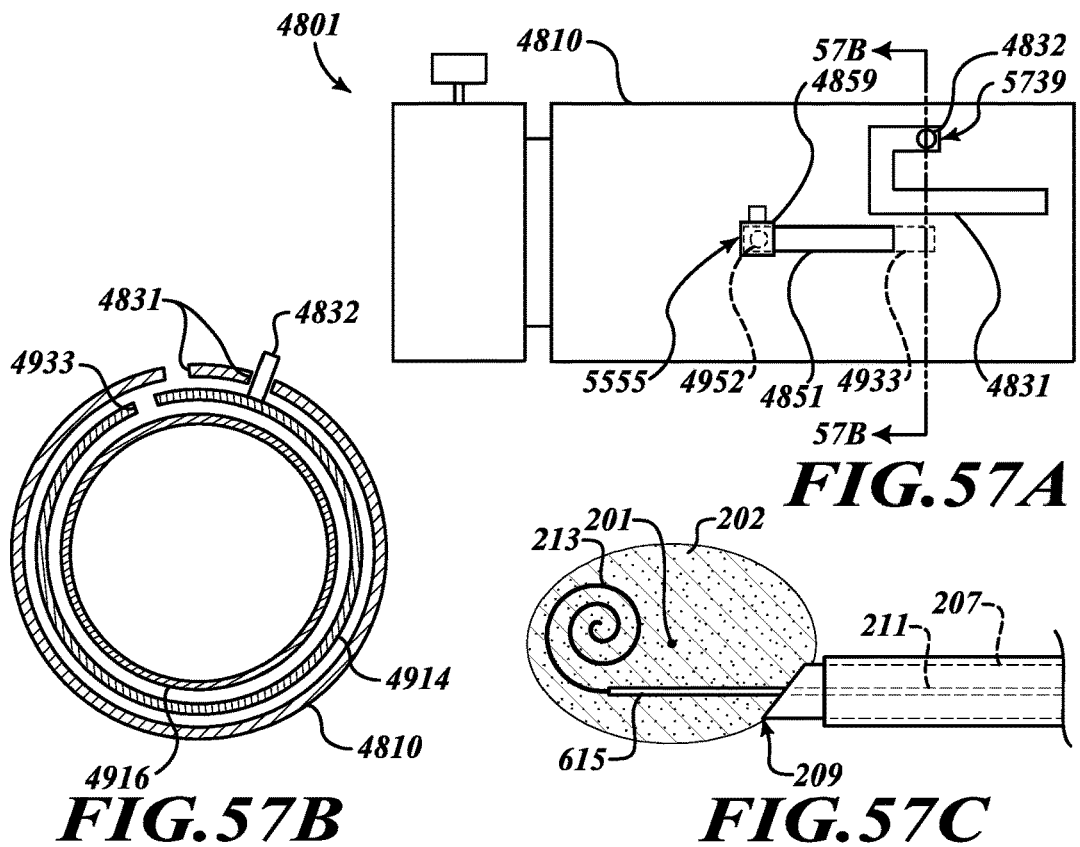
FIG.57A
FIG.57B
FIG.57C

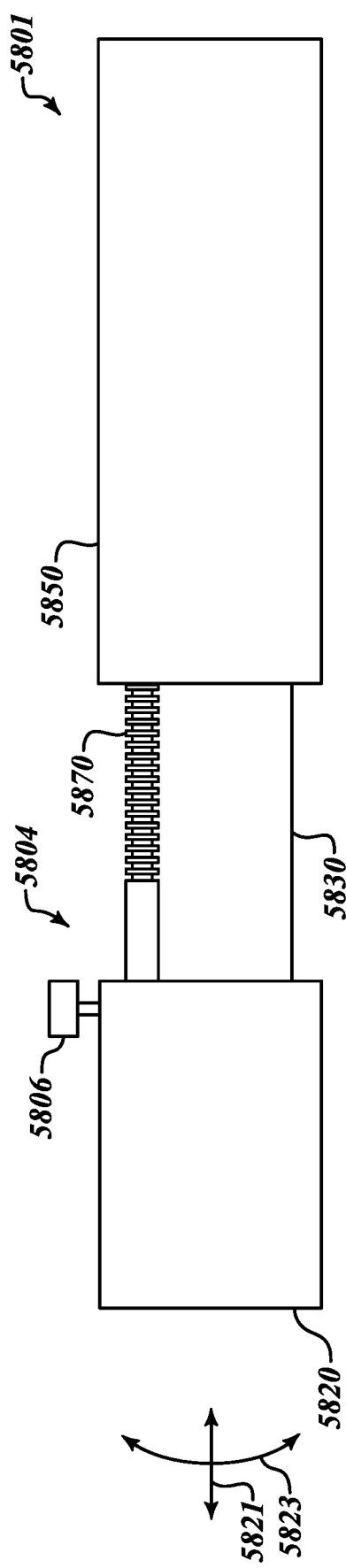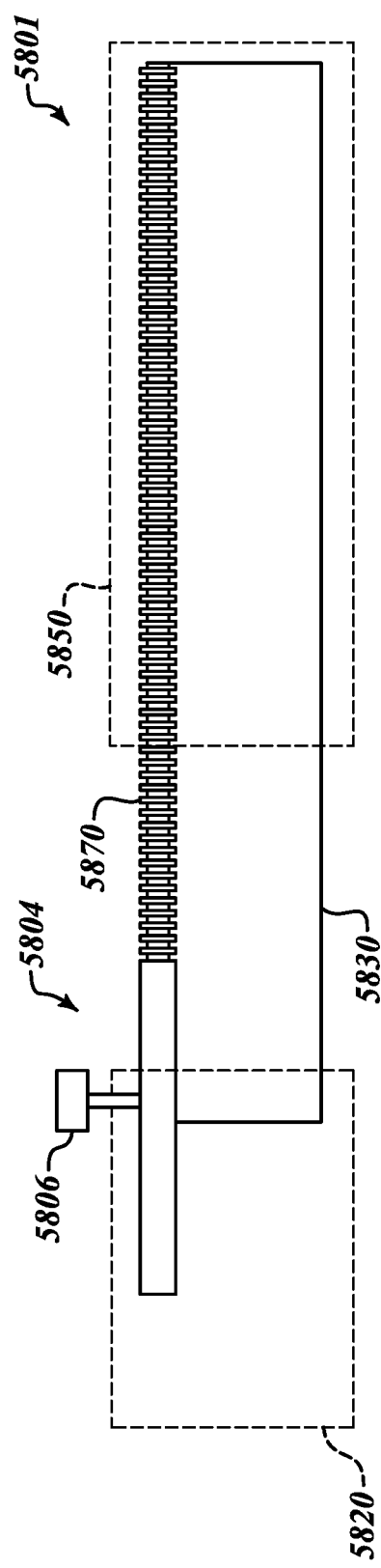

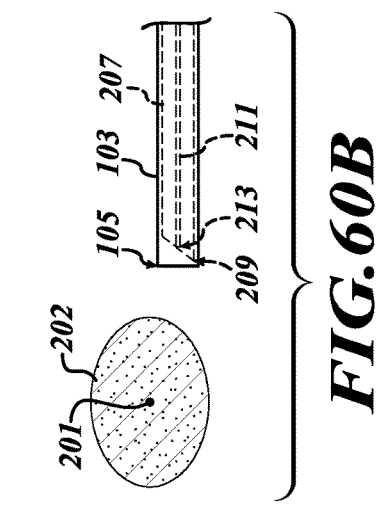
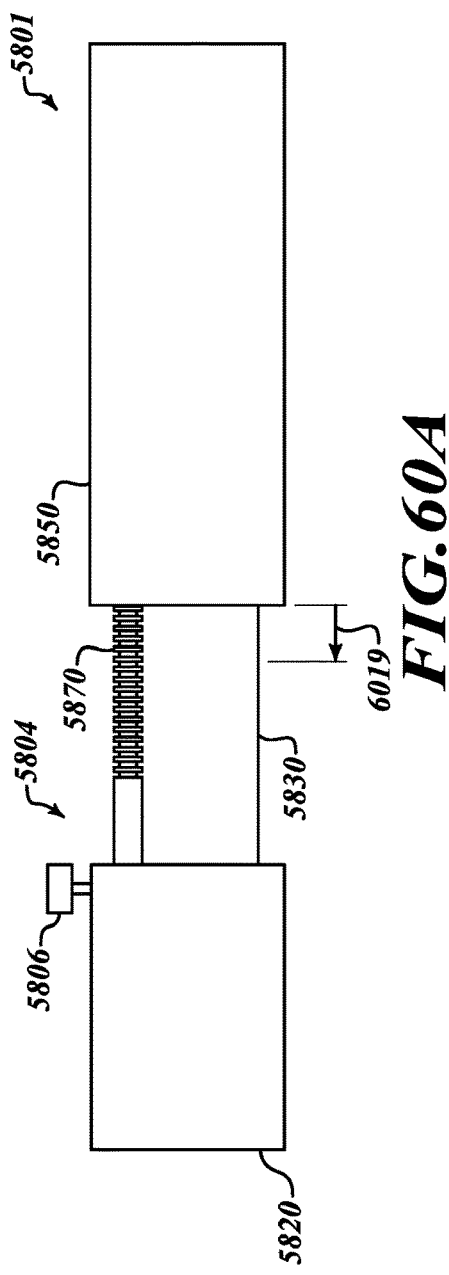
FIG.60B
FIG.60A
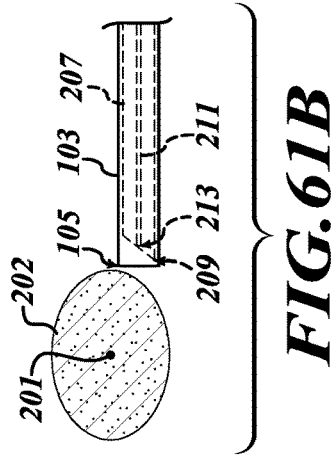
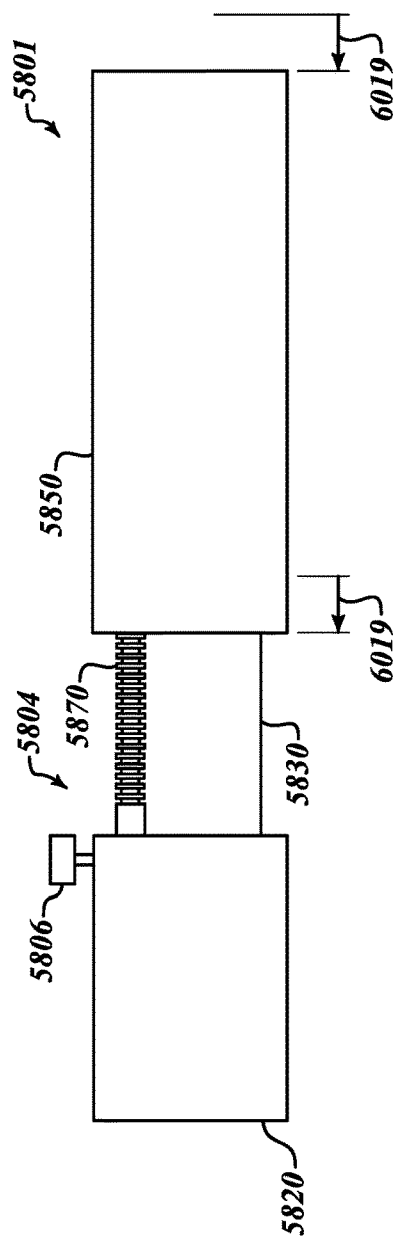
FIG.61B
FIG.61A

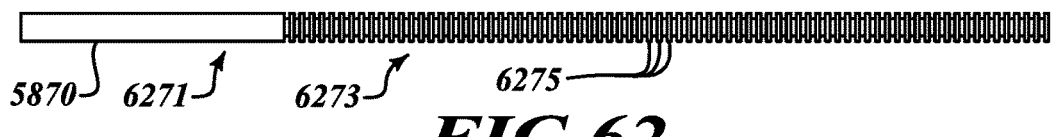
*FIG.62*
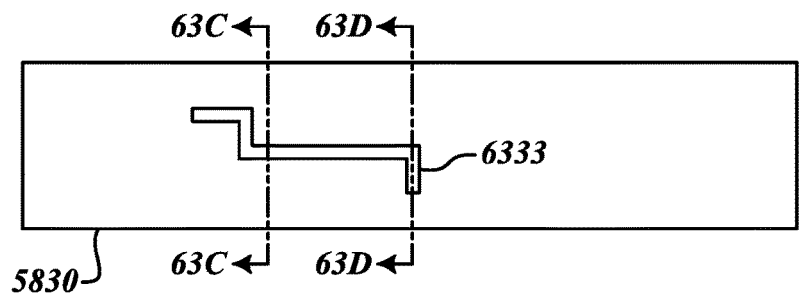
*FIG.63A*
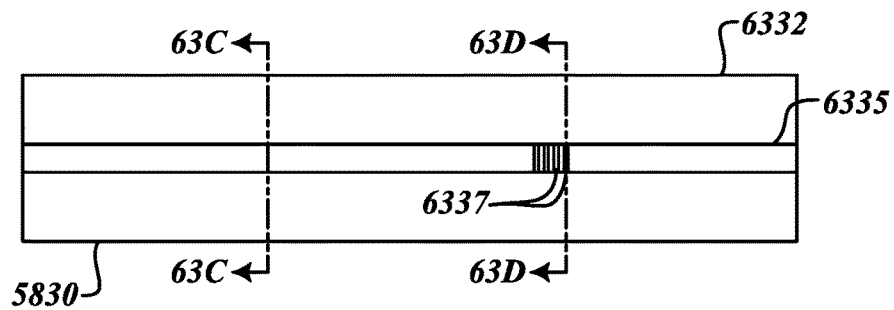
*FIG.63B*
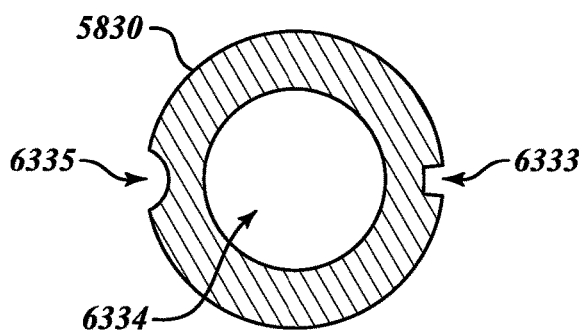 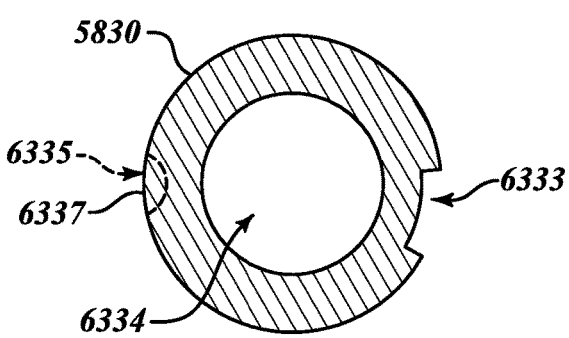
*FIG.63C*  *FIG.63D*

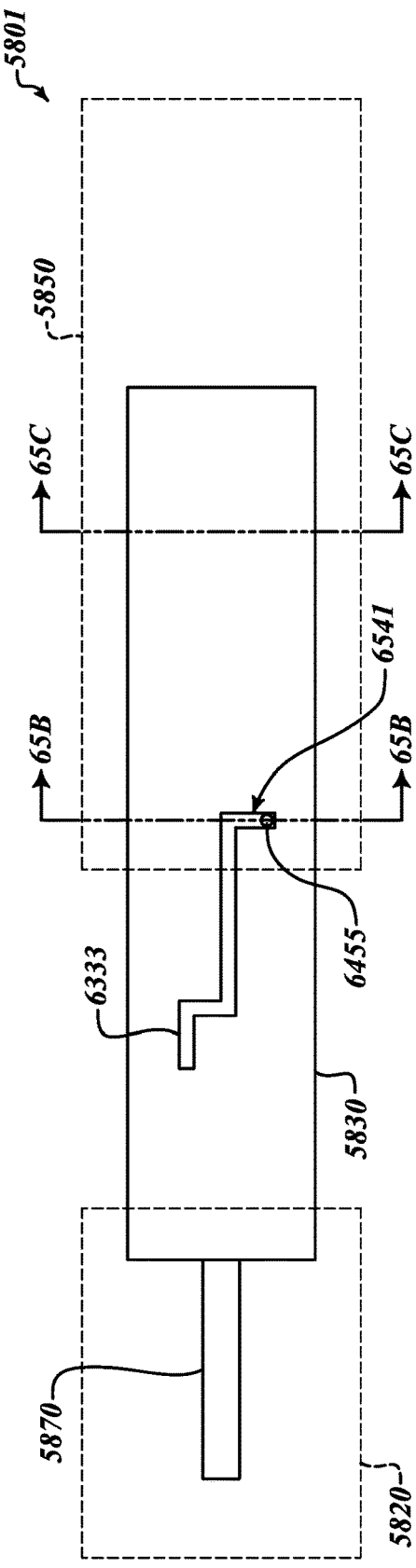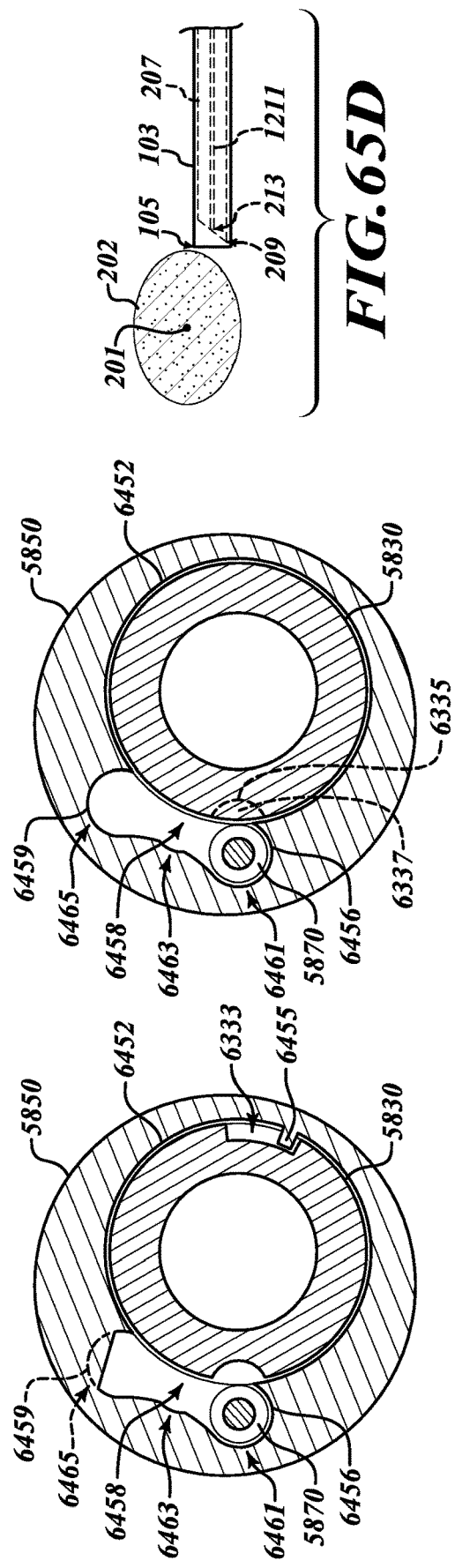

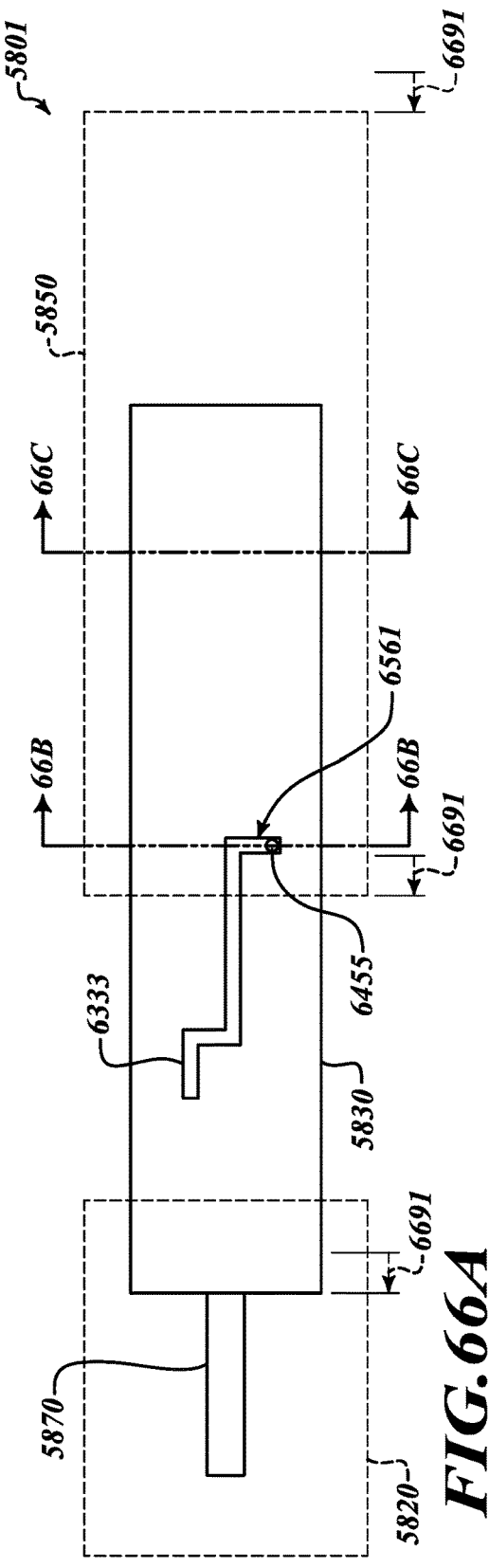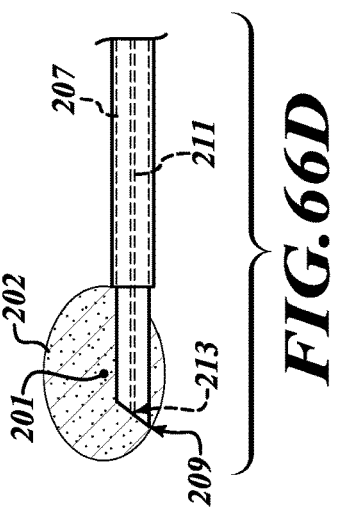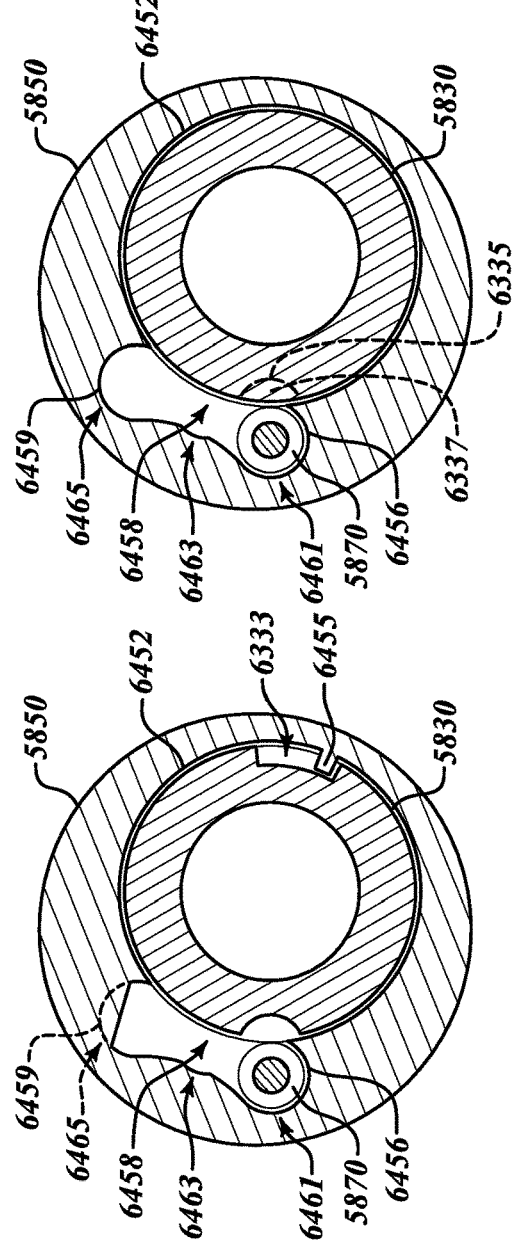

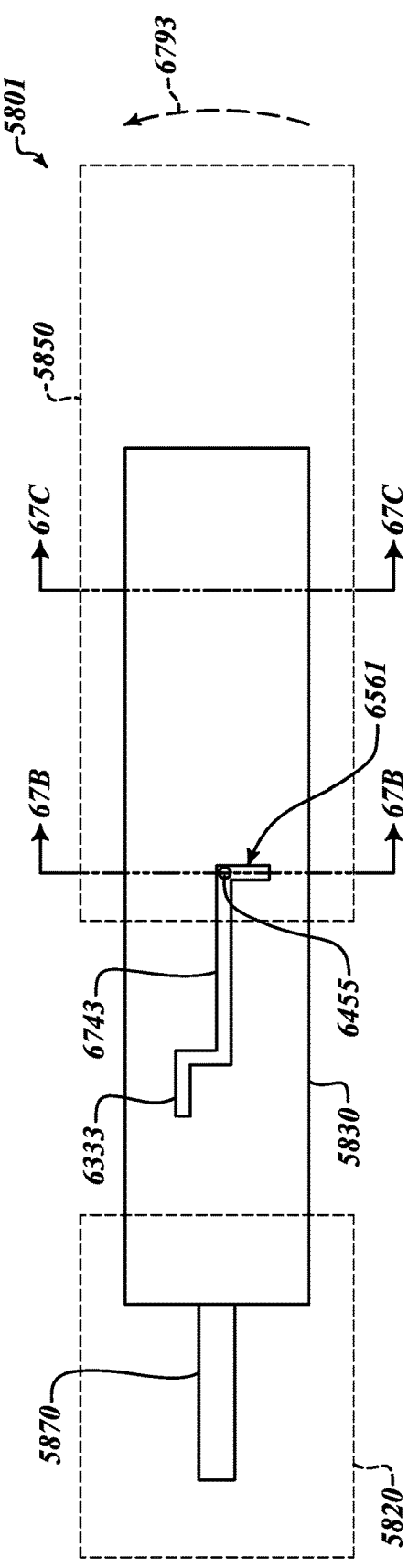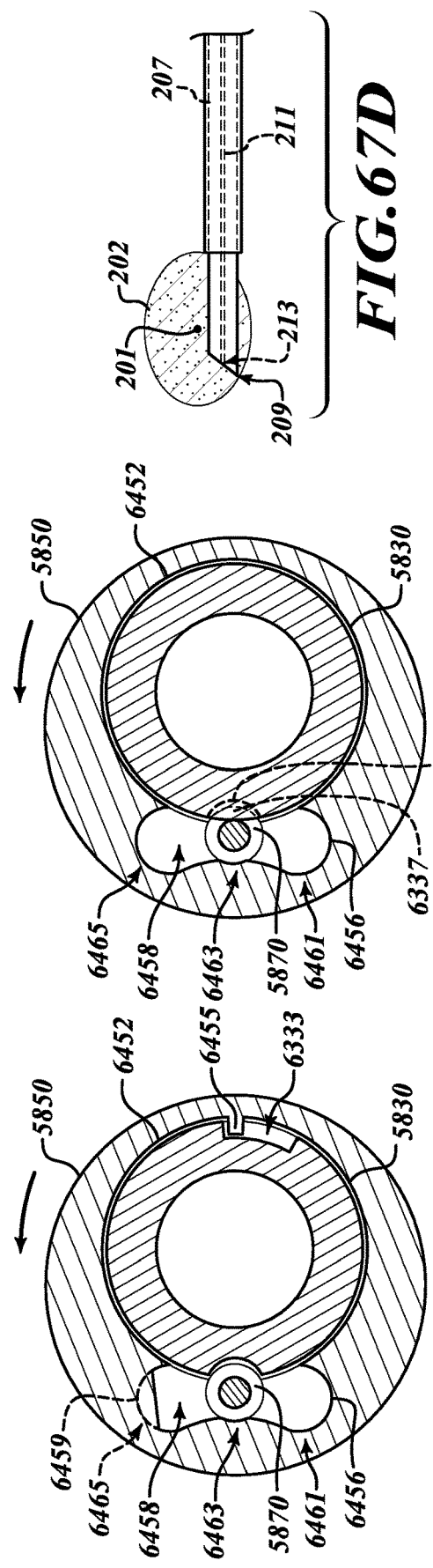

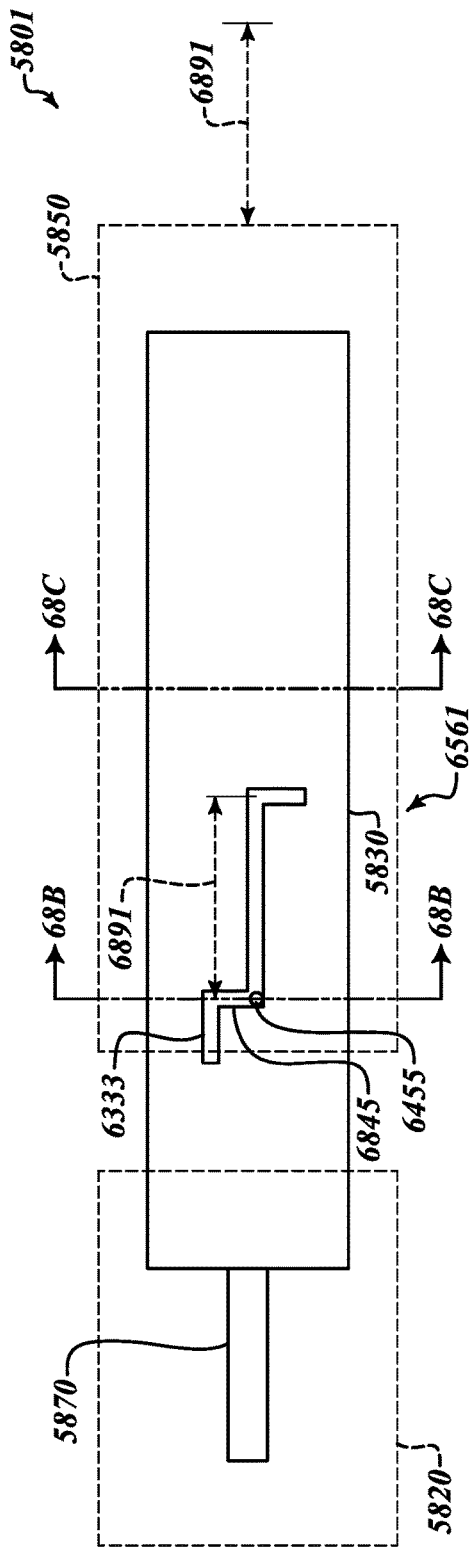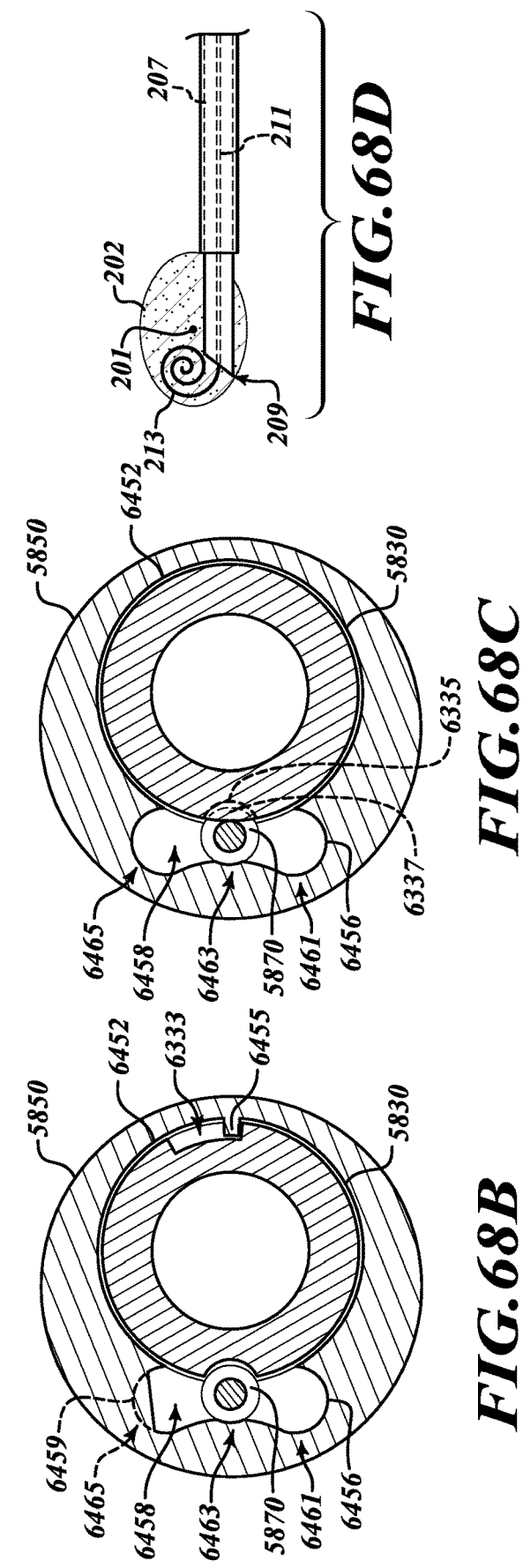

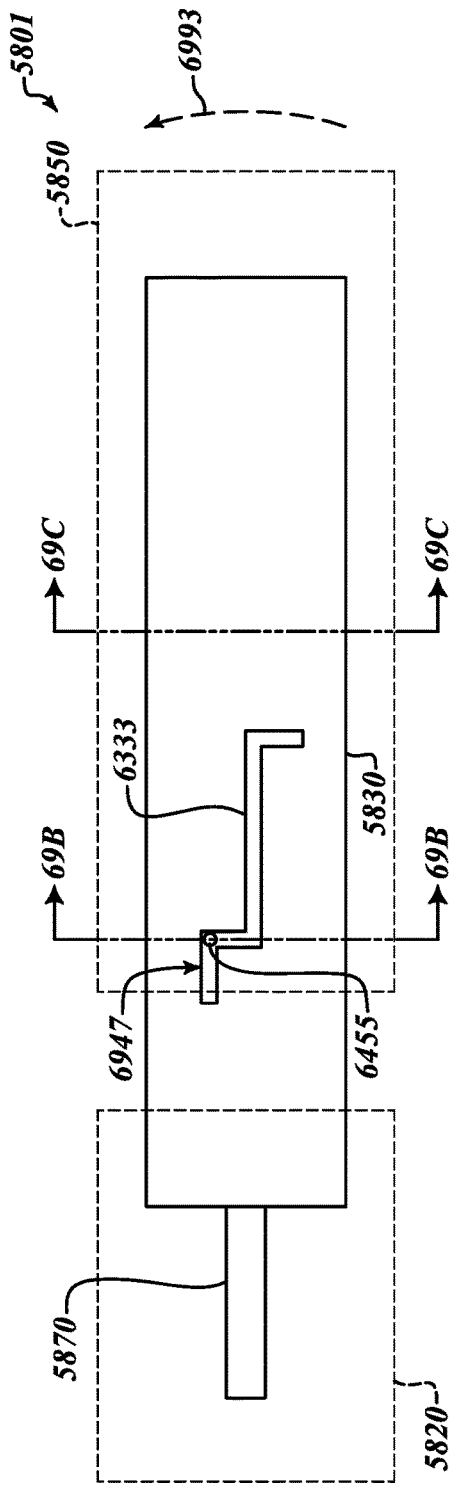
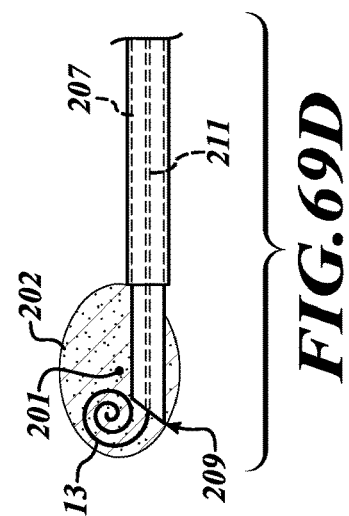
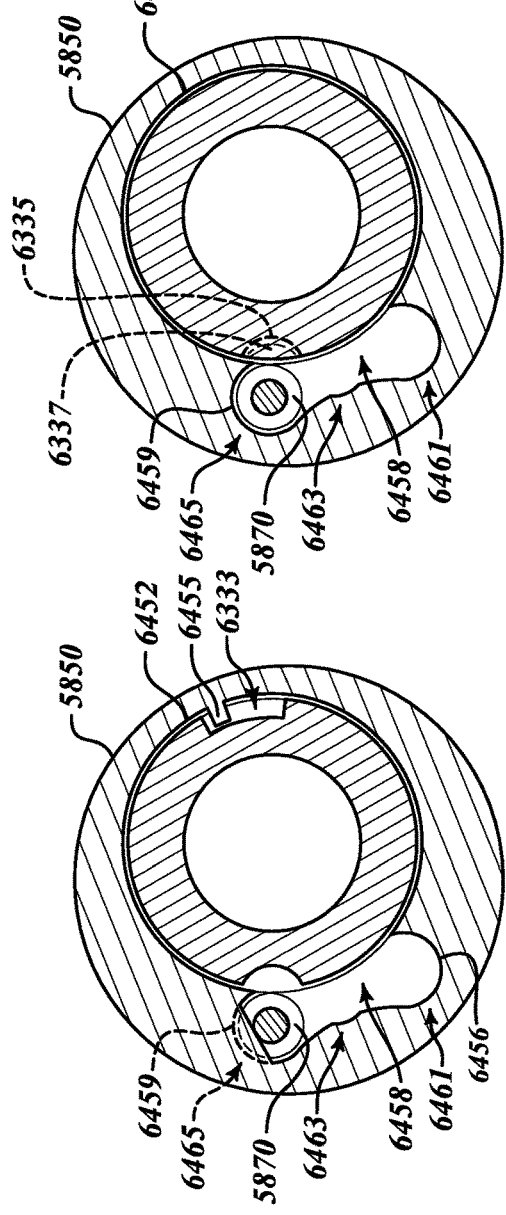
FIG.69A
FIG.69B
FIG.69C
FIG.69D

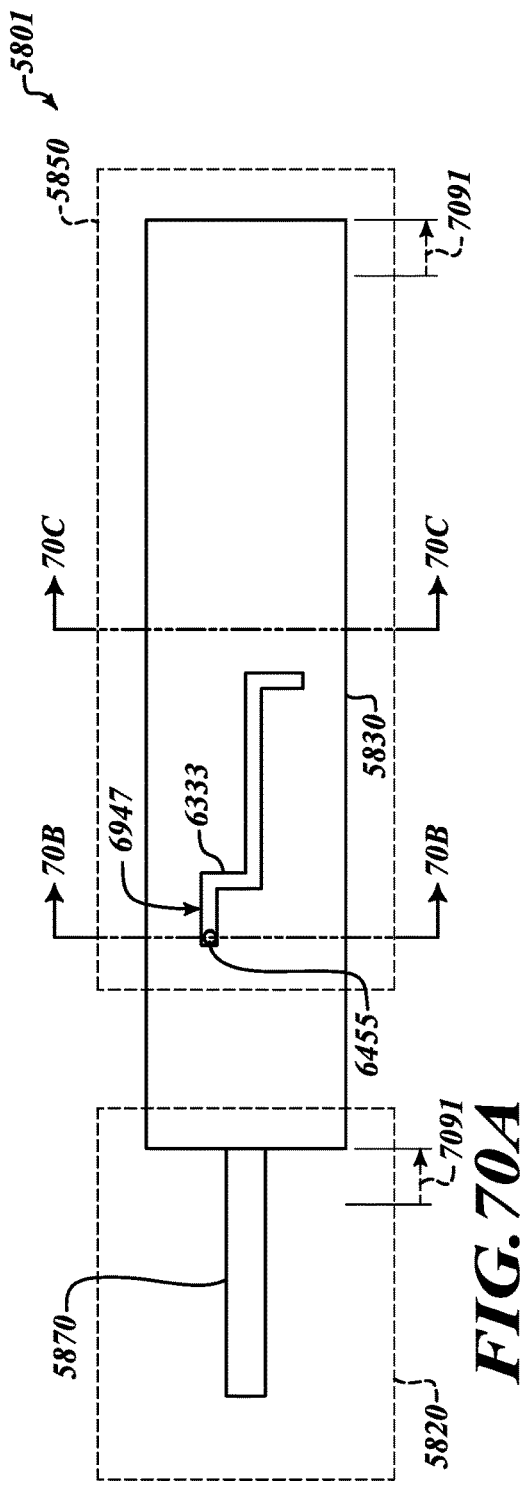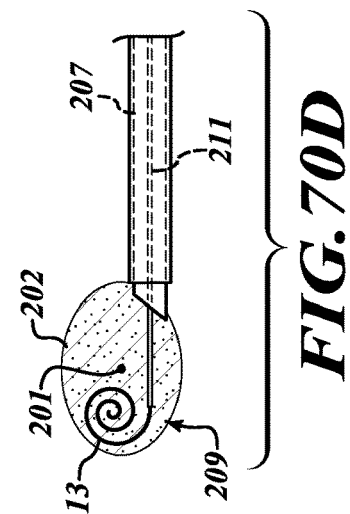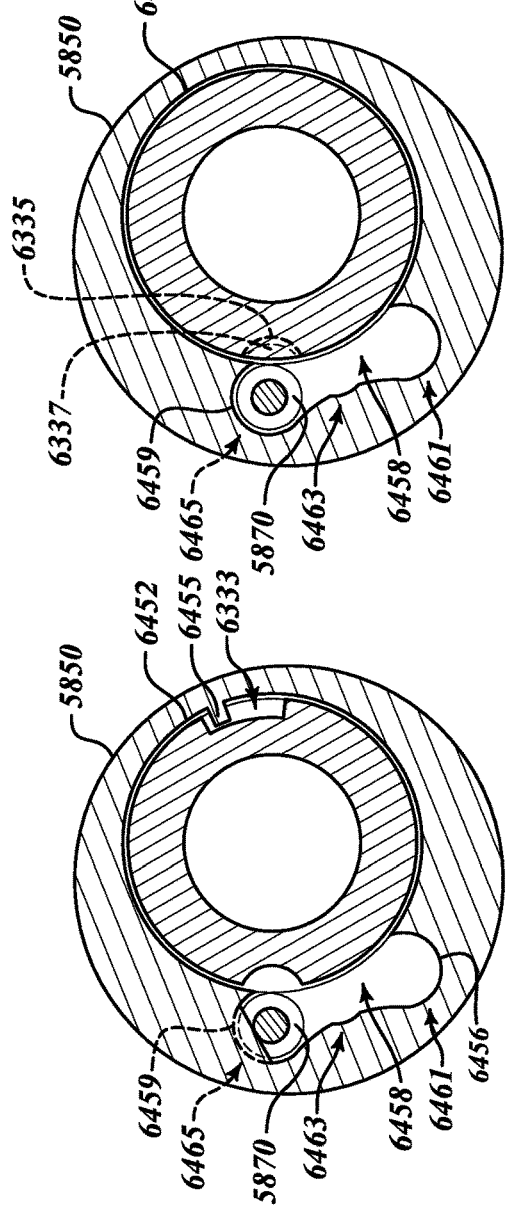

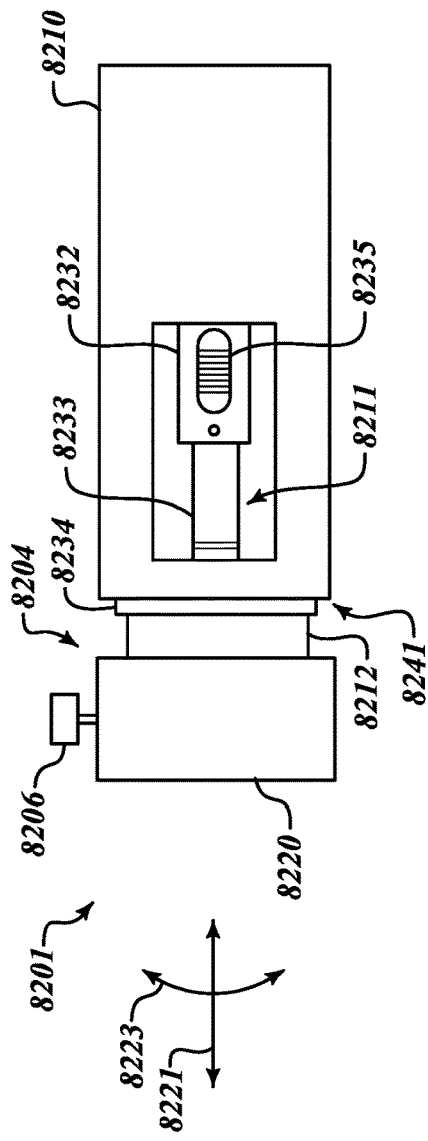
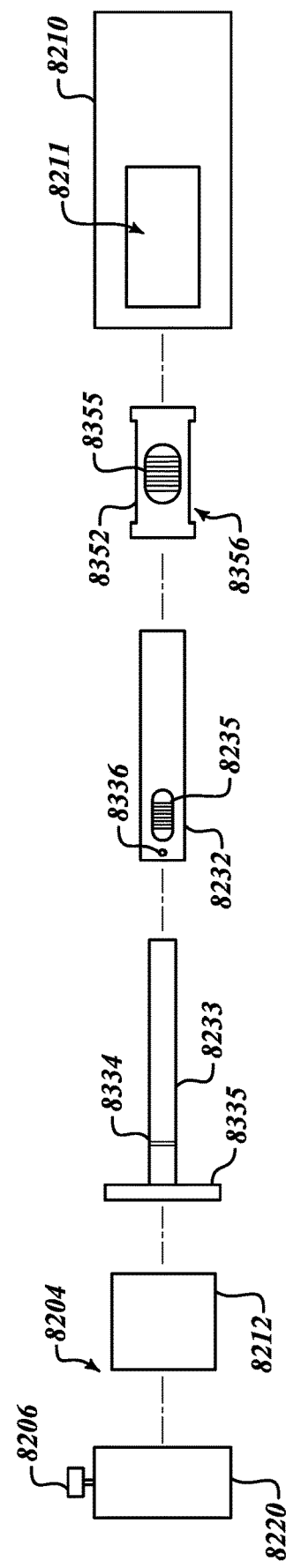
FIG. 82
FIG. 83

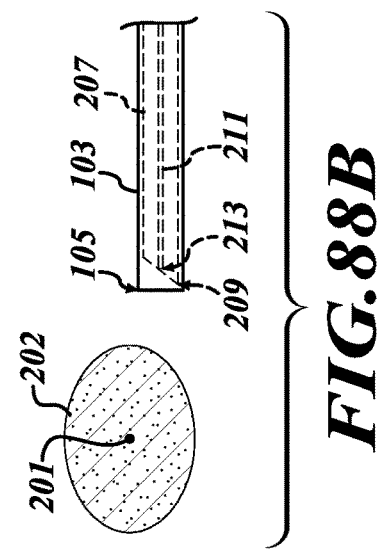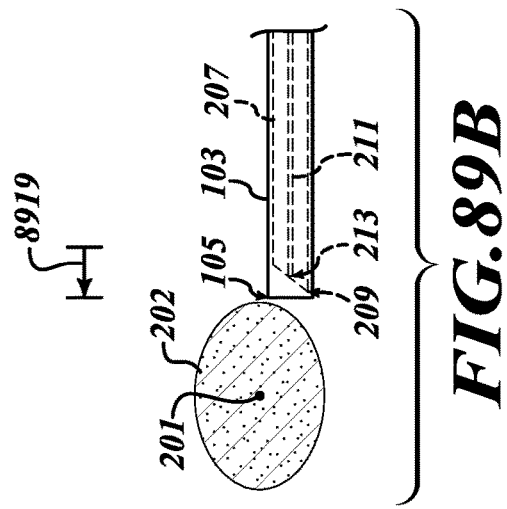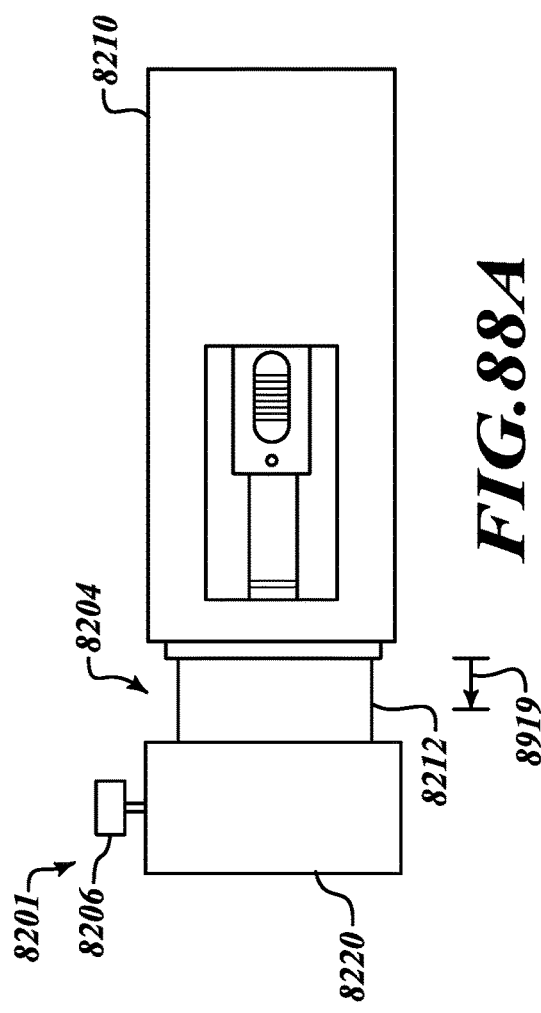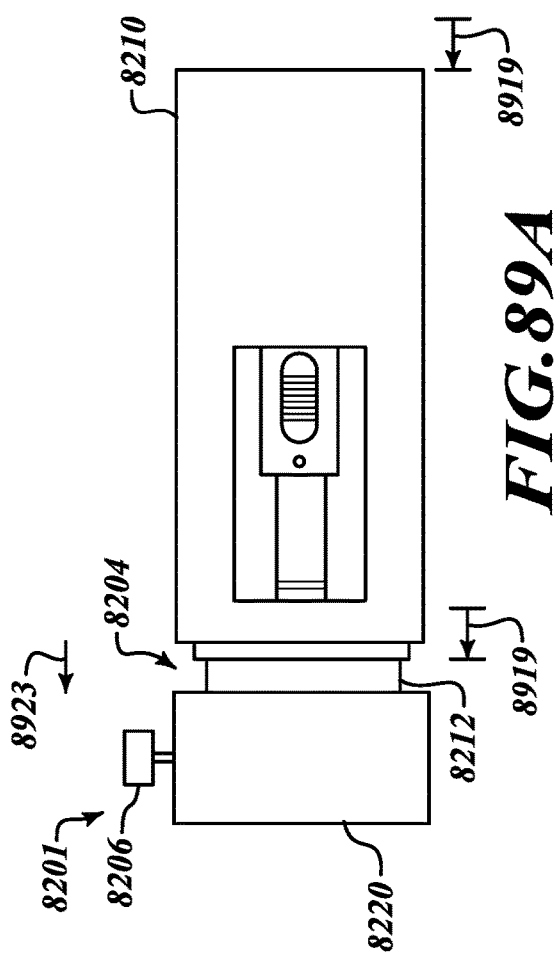

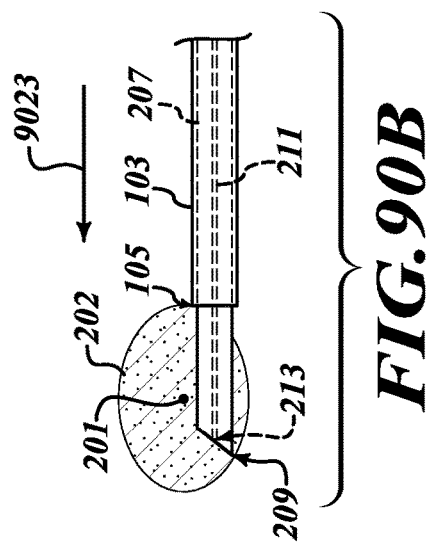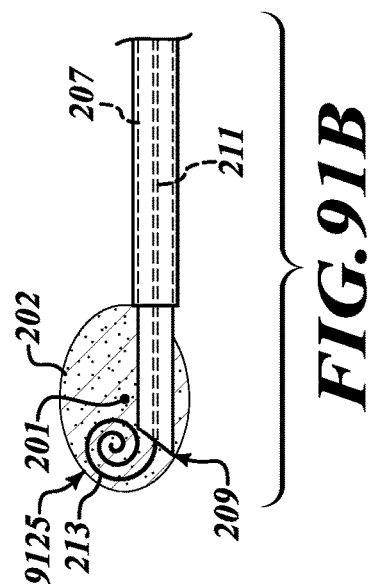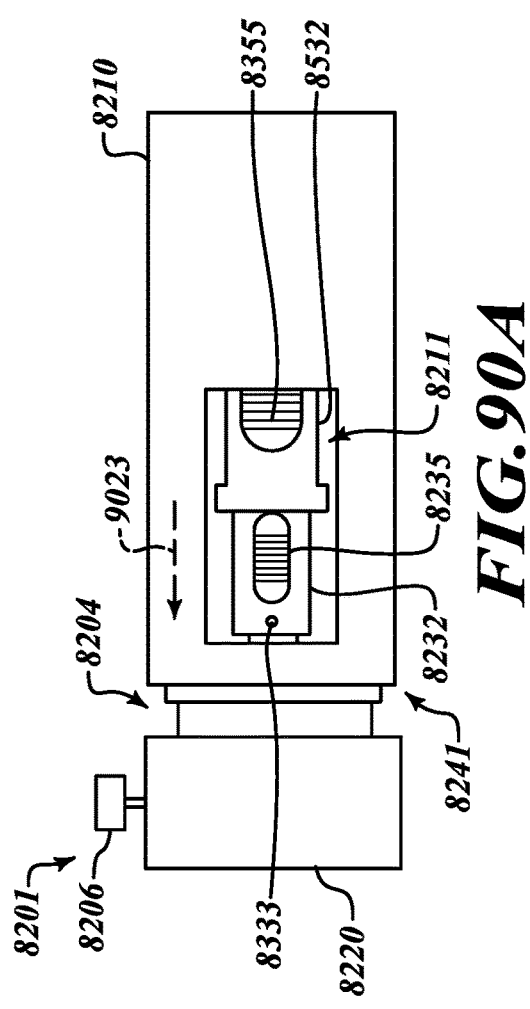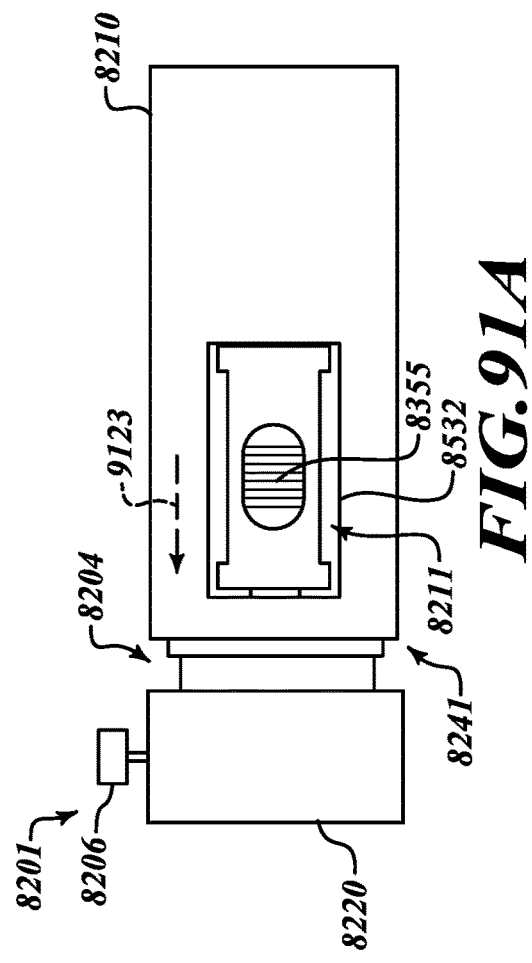

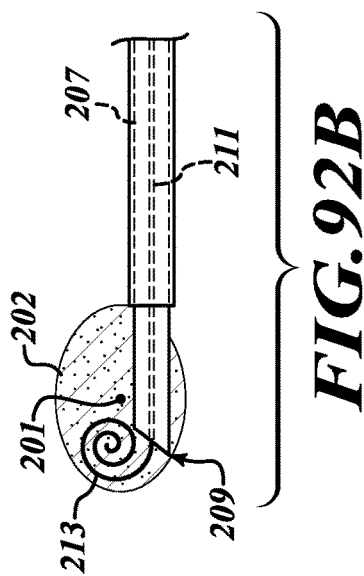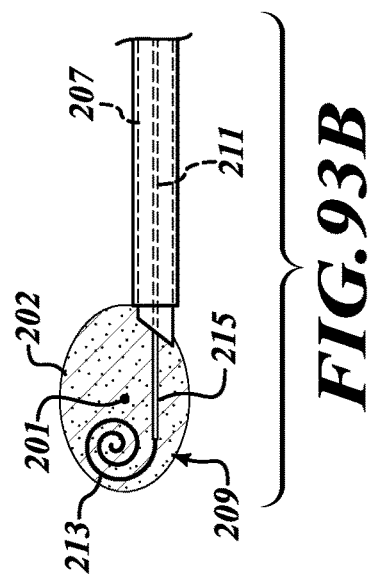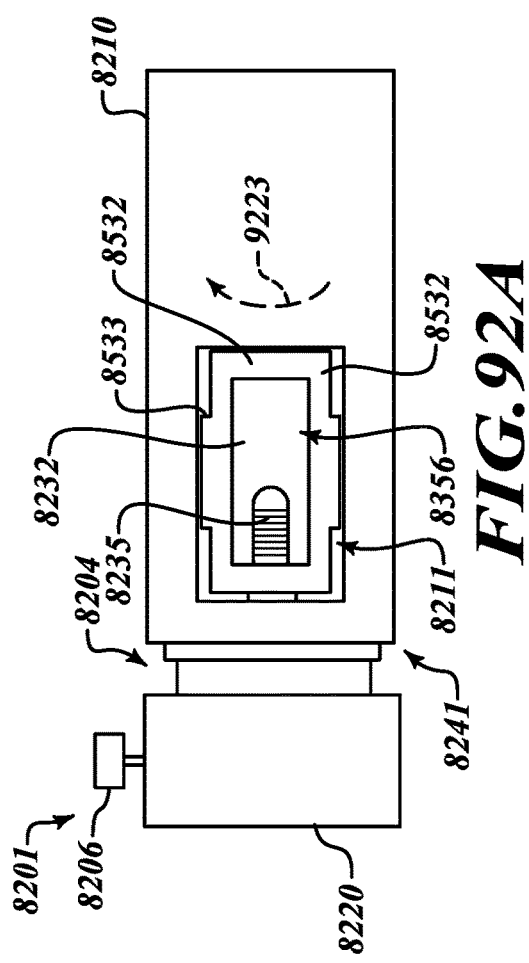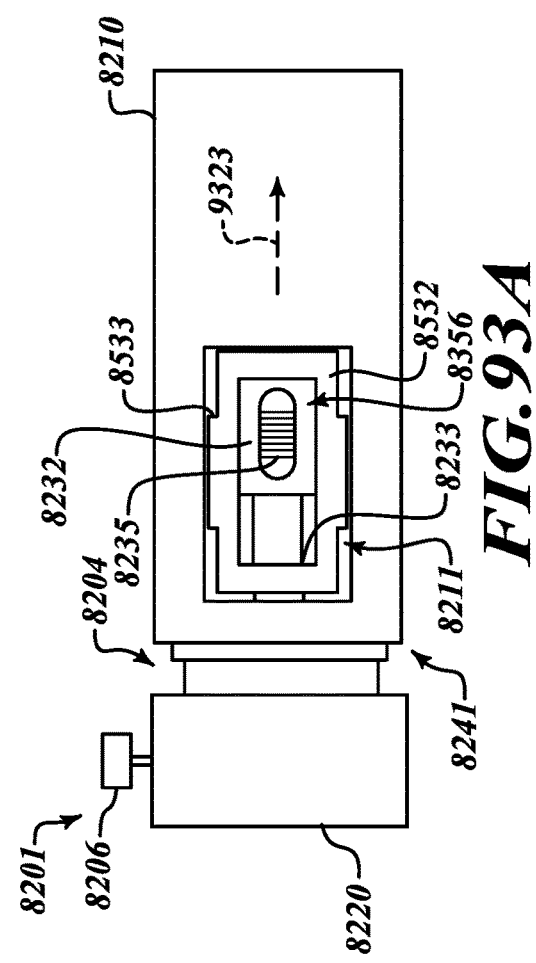

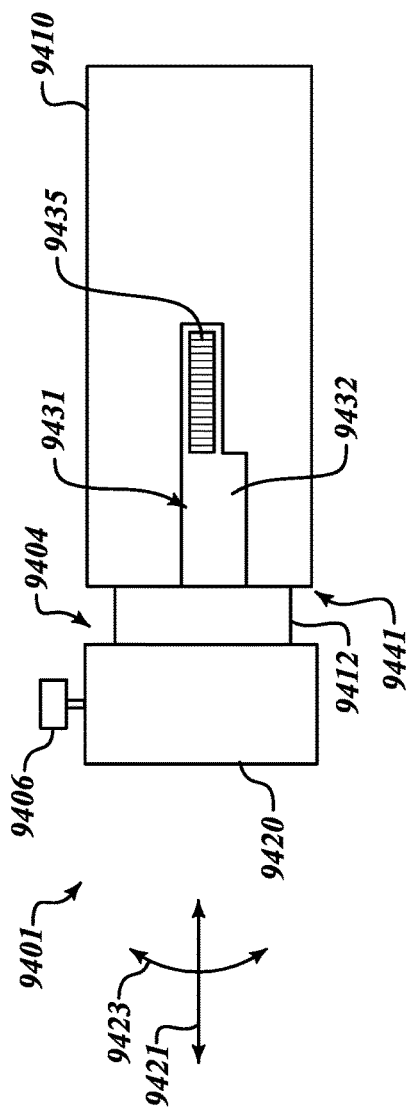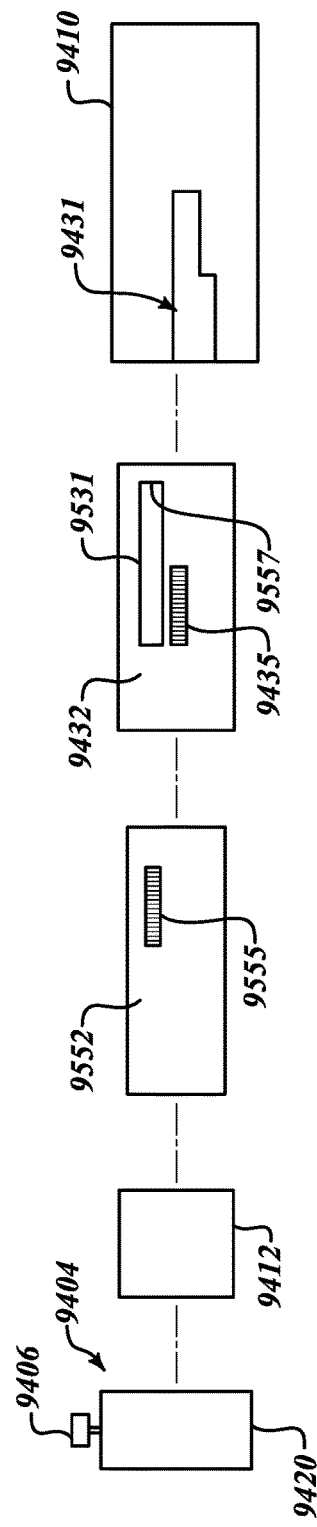

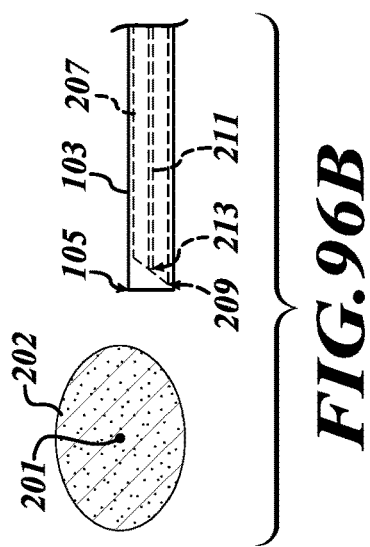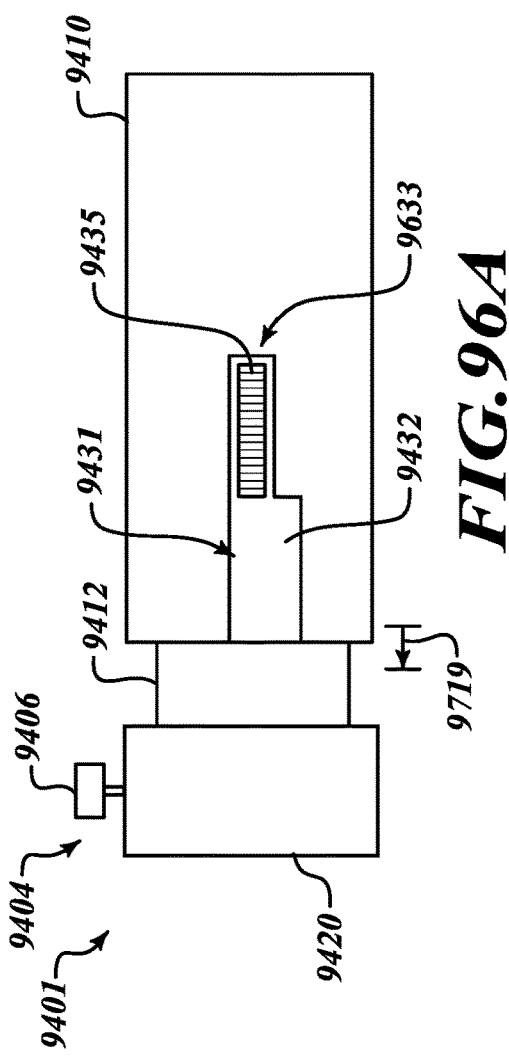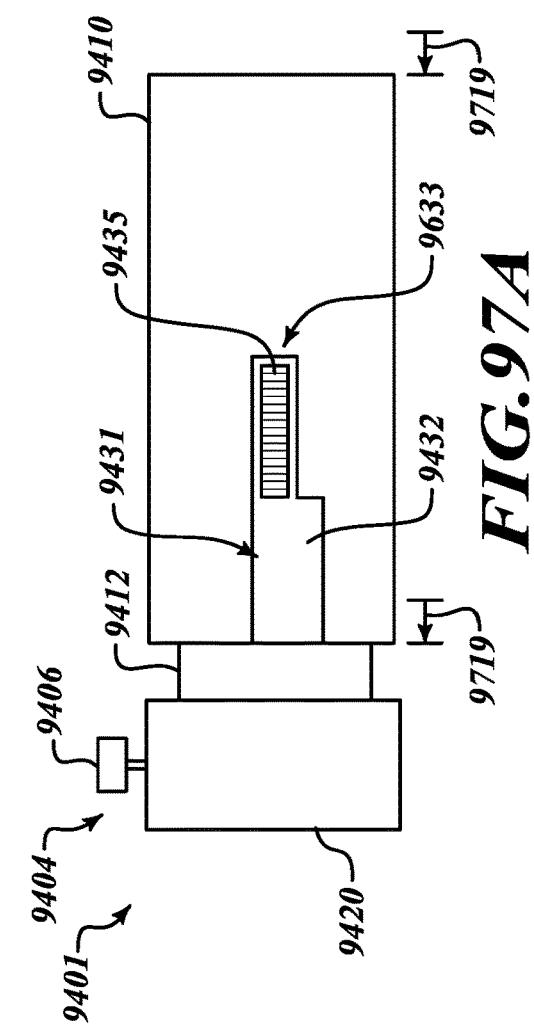

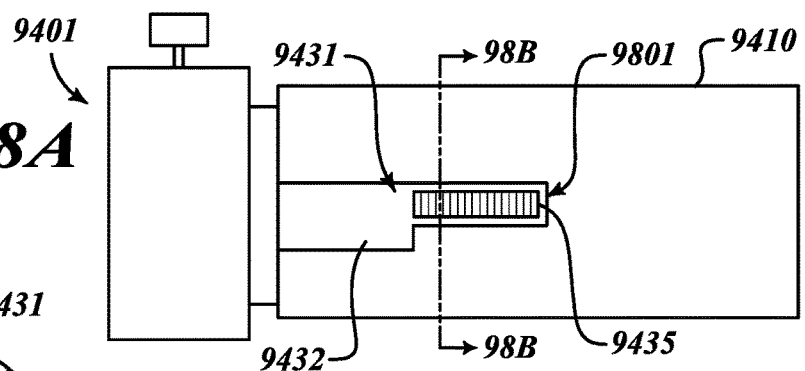
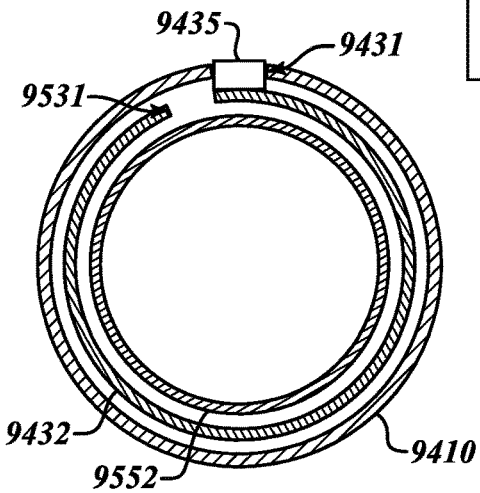
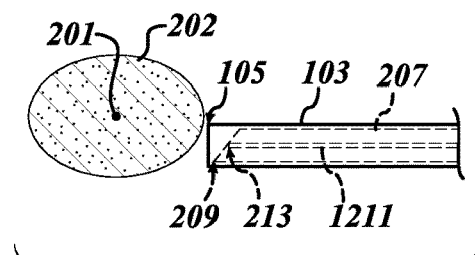
FIG.98A
FIG.98B
FIG.98C
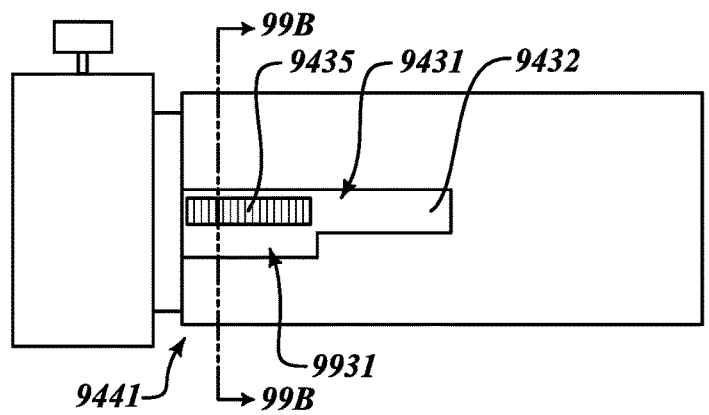
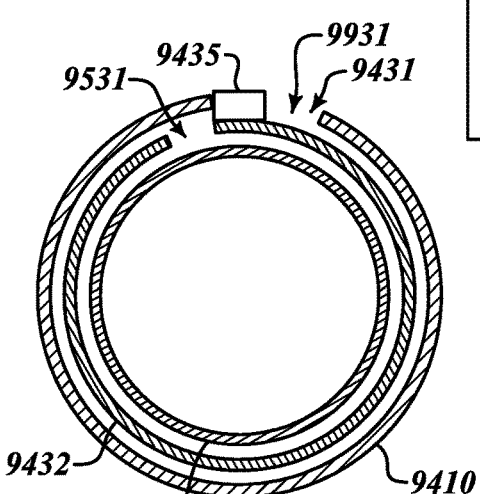
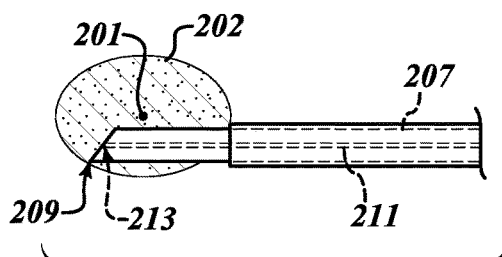
FIG.99A
FIG.99B
FIG.99C

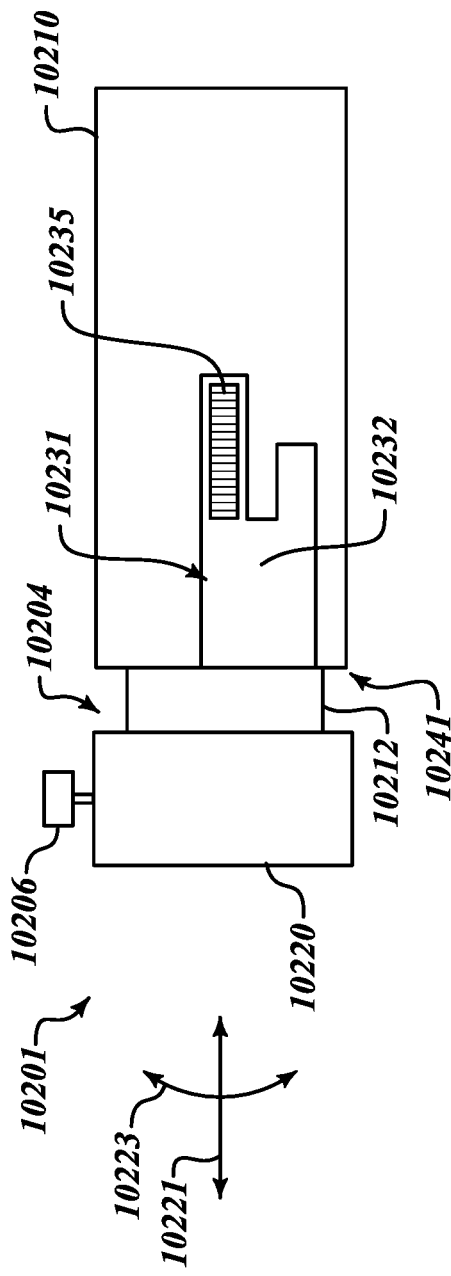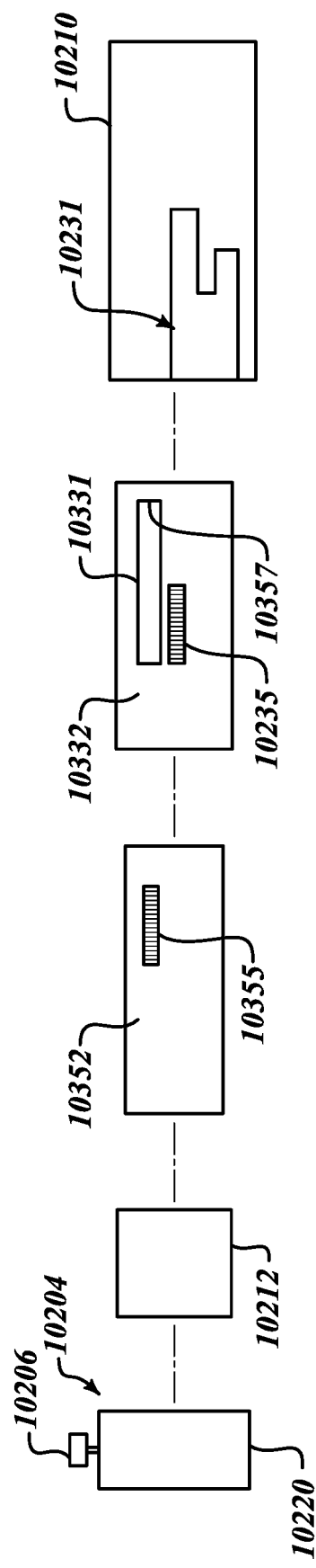

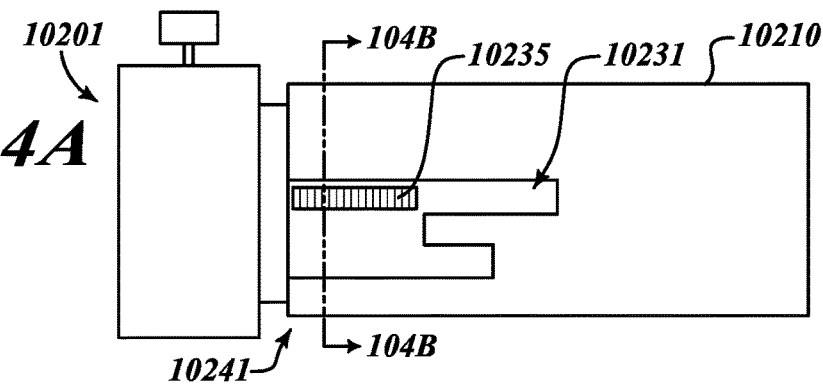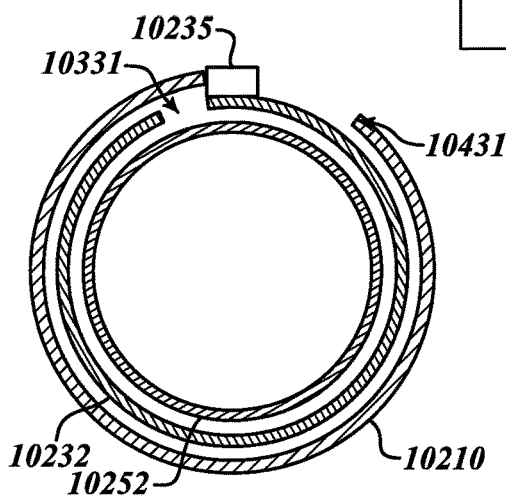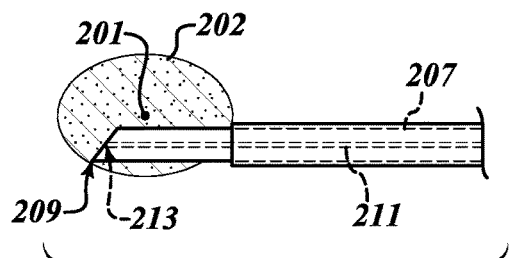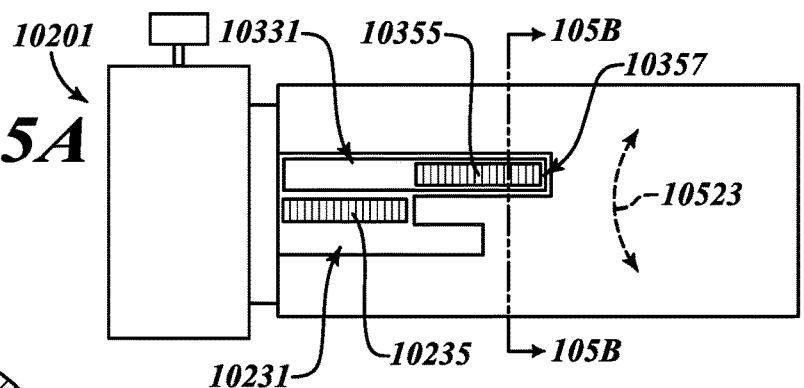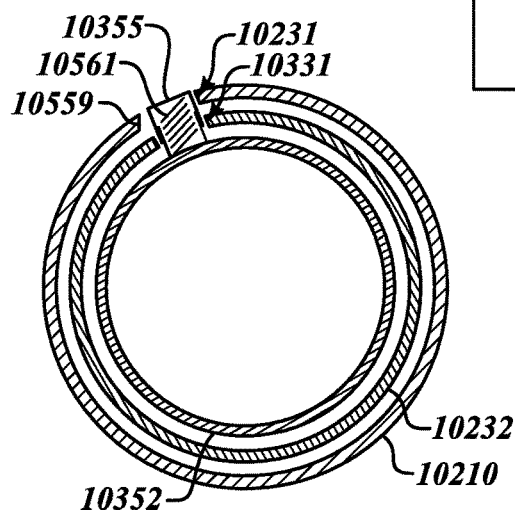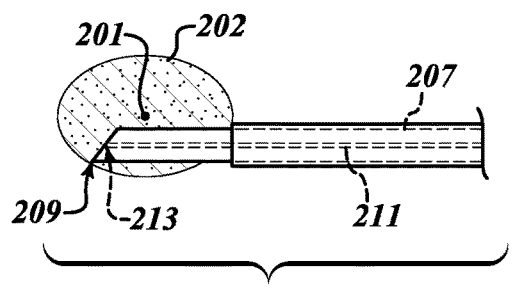

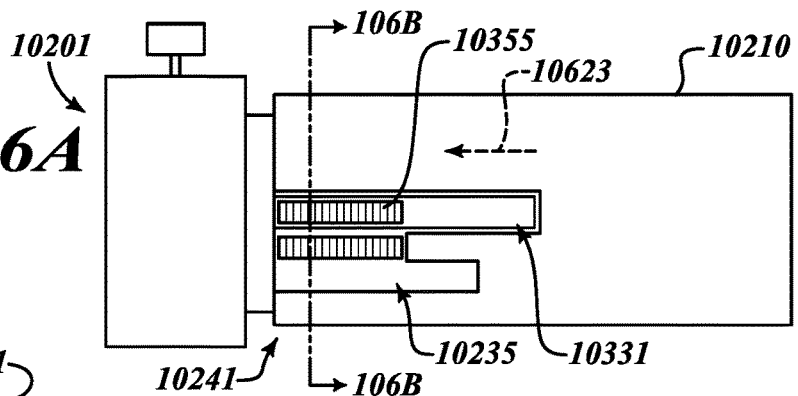
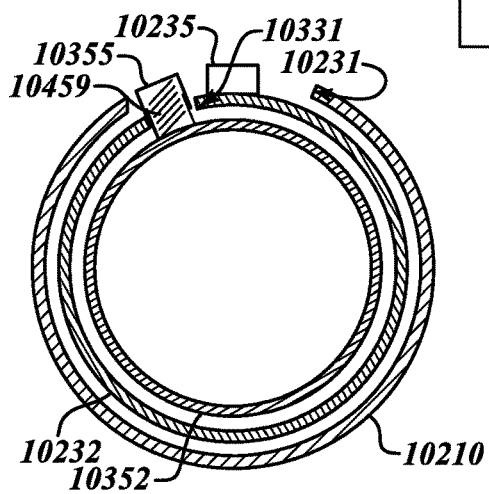
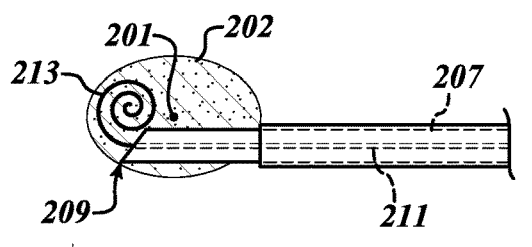
FIG.106A
FIG.106B
FIG.106C
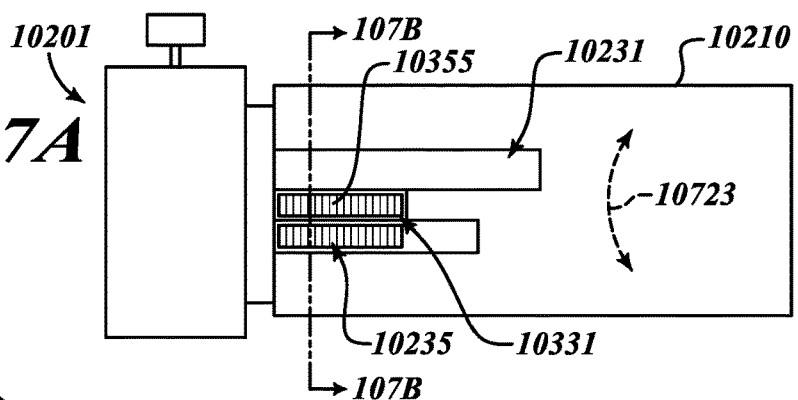
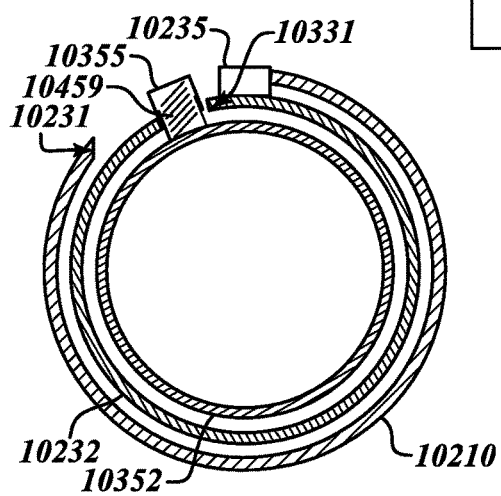
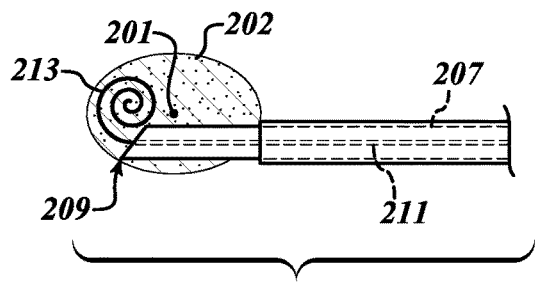
FIG.107A
FIG.107B
FIG.107C

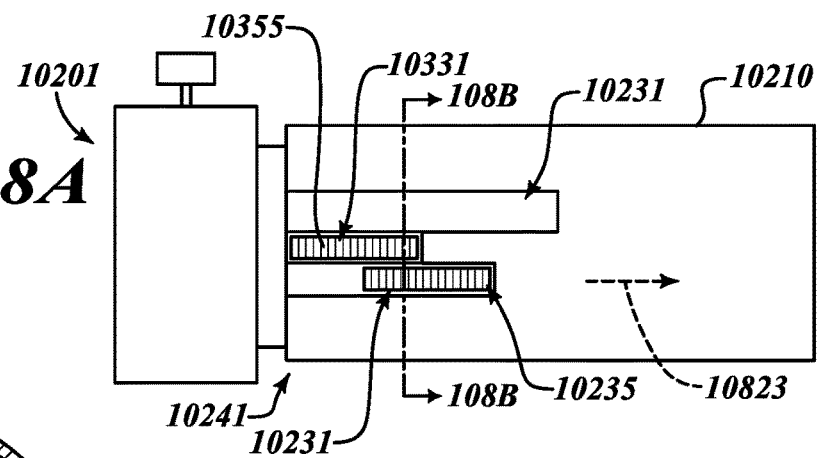
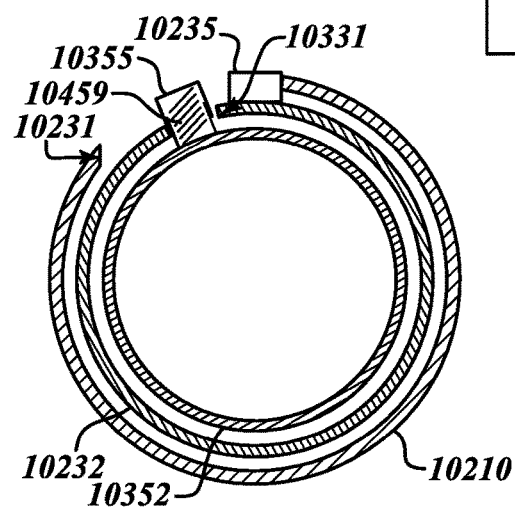
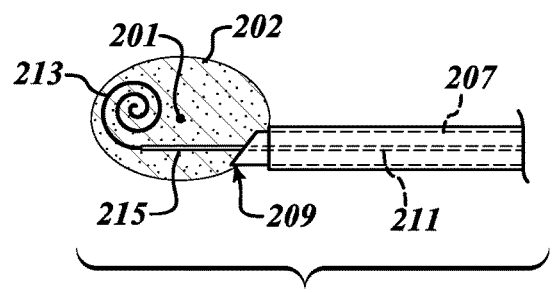
FIG.108A
FIG.108B
FIG.108C

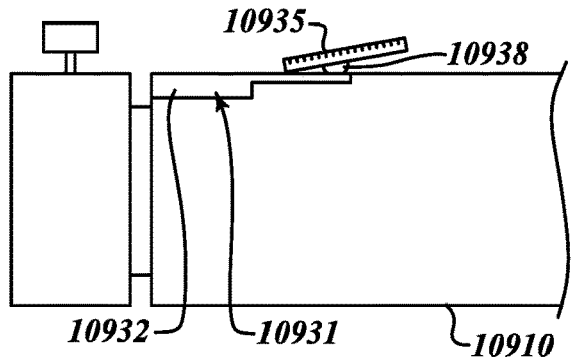 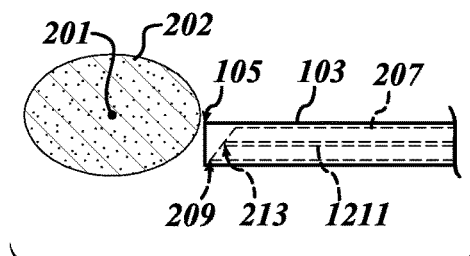
FIG.112A  FIG.112B
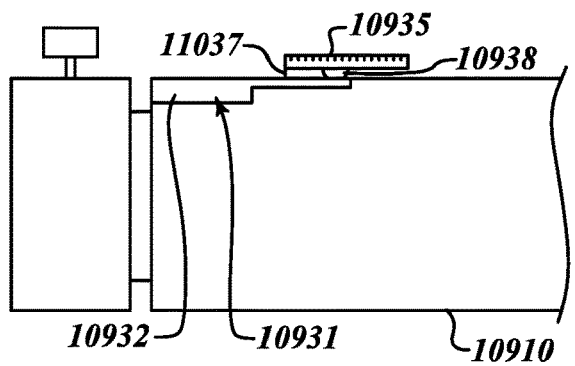 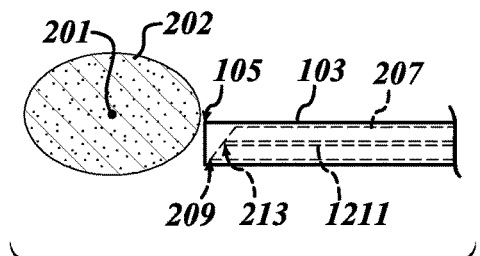
FIG.113A  FIG.113B
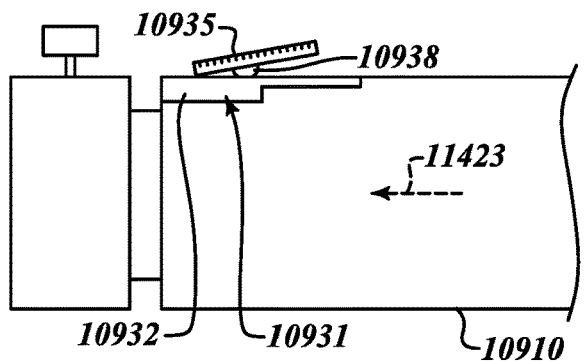 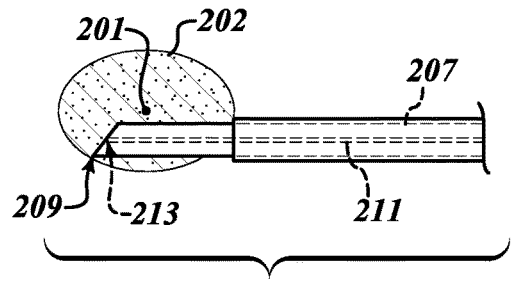
FIG.114A  FIG.114B

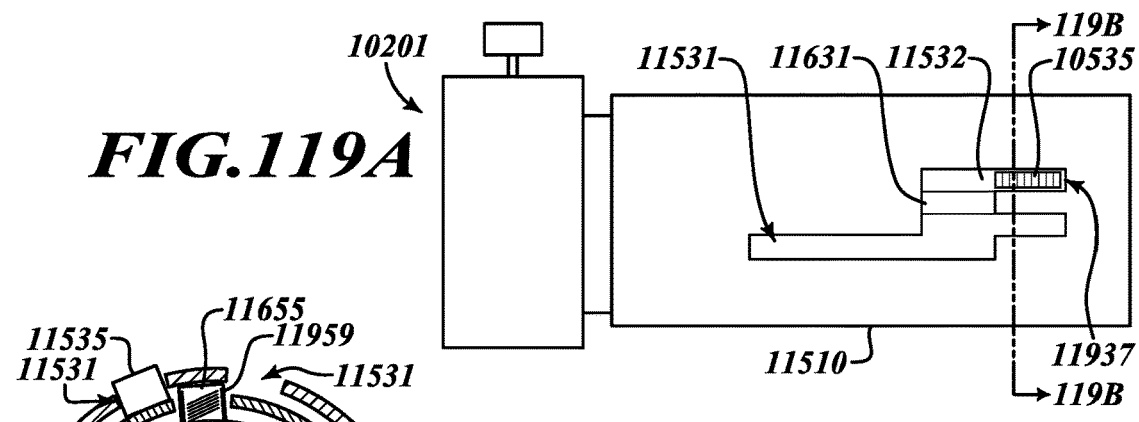
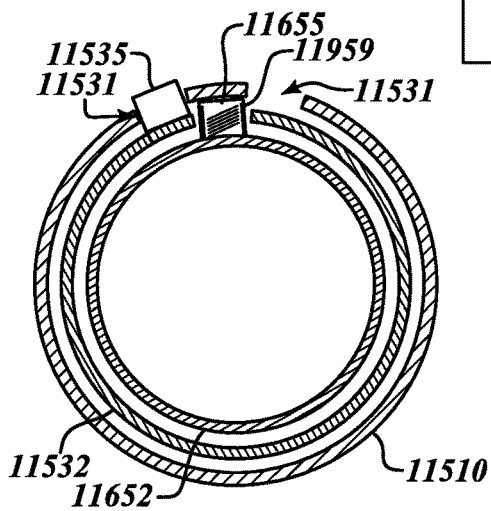
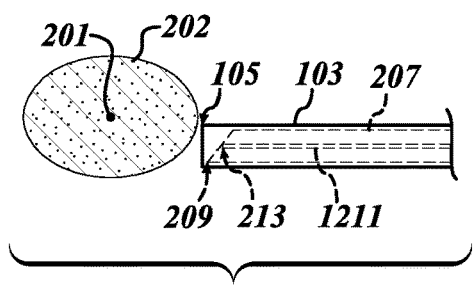
FIG.119A
FIG.119B
FIG.119C
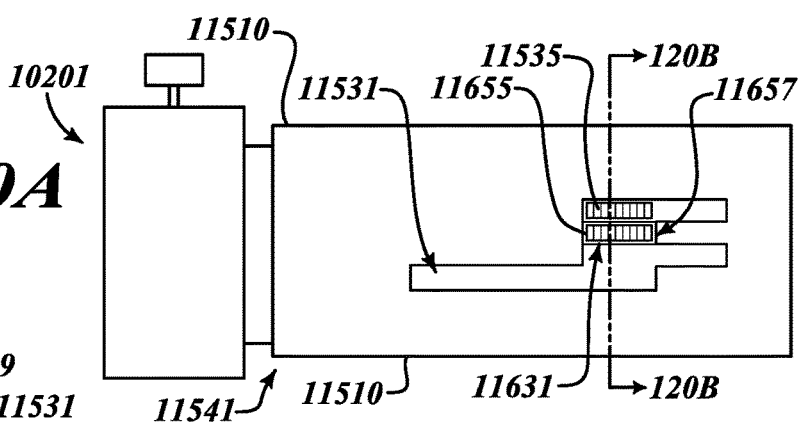
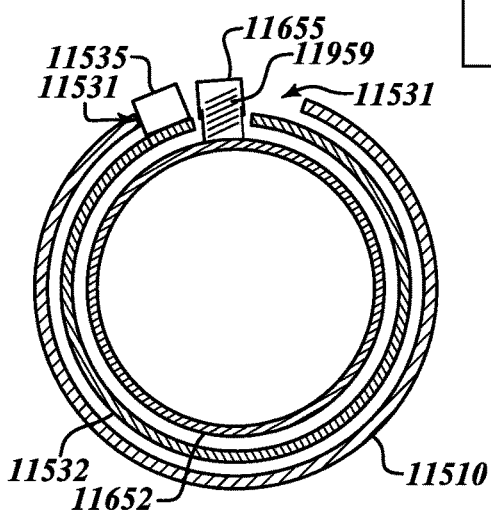
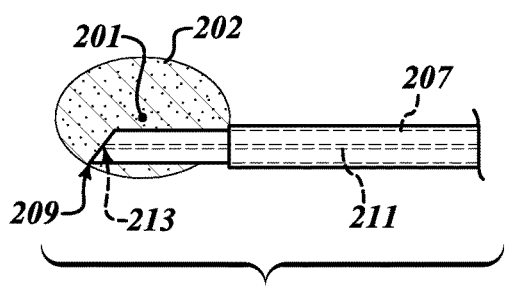
FIG.120A
FIG.120B
FIG.120C

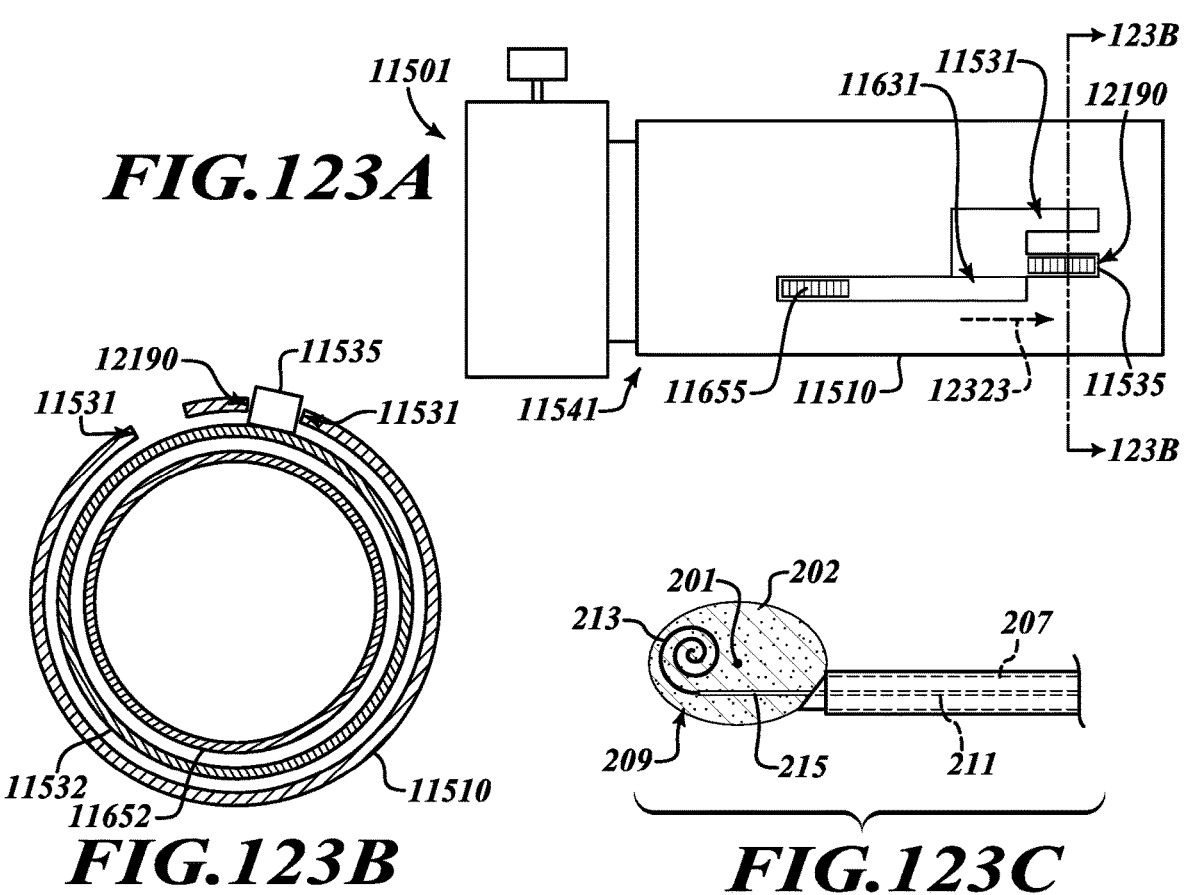

USER INTERFACE AND LOCK FEATURES FOR POSITIONING MULTIPLE COMPONENTS WITHIN A BODY

PRIORITY CLAIM

The present application is a continuation-in-part of U.S. Patent Applications bearing application Ser. Nos. 15/462,872 and 15/462,880, each entitled "USER INTERFACE AND LOCK FEATURES FOR POSITIONING MULTIPLE COMPONENTS WITHIN A BODY" and filed on Mar. 19, 2017, each of which claims the priority and benefit of U.S. Provisional Patent Application Ser. No. 62/311,226 entitled "HANDLE FOR AN ABLATION DEVICE," filed on Mar. 21, 2016.

FIELD

The present disclosure relates to a user interface and lock features for positioning multiple components within a body.

BACKGROUND

The statements in this section merely provide background information related to the present disclosure and may not constitute prior art.

Inserting and manipulating thin elements within living bodies or other objects allows for ever-improving types of analysis, diagnosis, and treatment of those bodies or objects with minimally invasive techniques. By way of two examples, endoscopic imaging and catherization treatments have enabled evaluation and treatment of numerous internal lesions without invasive surgery.

Electrosurgical techniques also provide for minimally invasive therapies by selectively applying electrical current to selected tissues. Electrosurgical techniques involve extending one or more electrodes through an orifice or a small incision to a desired location within a body, then applying a radio frequency ("RF") electric current to the electrodes to coagulate and/or ablate tissue at that location. Monopolar electrosurgical instruments only entail use of one electrode that interacts with a neutral electrode, which is likewise connected to the body of a patient. A bipolar electrosurgical instrument typically includes a user interface used for positioning two electrodes, which may include a distal electrode and a proximal electrode.

Positioning one or two electrodes at the desired location is an important part of such electrosurgical treatments. Moving and holding electrodes in place, particularly when more than one electrode has to be moved or held independently of another electrode, may present a challenge for the medical personnel directing the treatment. Because positioning one or more electrodes in place may involve adhering to an order of steps, assisting an operator in properly following a sequence also may be important.

SUMMARY

Disclosed embodiments include apparatuses for slidably moving multiple components within a body, systems for treating tissue at a reference point, and methods for moving electrodes into positions for ablative electrical treatment at a reference point.

In an illustrative embodiment, an apparatus for slidably moving multiple features relative to a sheath inserted into a body and positioned relative to a reference point includes a primary actuator configured to move a primary electrode, a secondary actuator configured to move a secondary electrode, and a control mechanism. The control mechanism is configured to selectively prevent movement of at least one of the primary actuator based on a position of the secondary actuator and of the secondary actuator based on a position of the primary actuator and lock positions of the primary actuator and the secondary actuator.

In another illustrative embodiment, a system for treating tissue at a reference point includes a controllable electrical power source configured to selectively provide electrical power between a first pole and a second pole. An electrosurgical apparatus is configured to be inserted into a body to convey a sheath containing a primary electrode electrically coupled to the first pole of the electrical power source and a secondary electrode electrically coupled to the second pole of the electrical power source to a vicinity of a reference point. A sheath actuator is configured to move the sheath relative to the reference point. A sheath lock is configured to selectively lock a position of the sheath. A primary actuator is configured to move the primary electrode. A secondary actuator is configured to move the secondary electrode. A control mechanism includes a control mechanism configured to selectively prevent movement of at least one of the primary actuator based on a position of the secondary actuator and of the secondary actuator based on a position of the primary actuator and to lock positions of the primary actuator and the secondary actuator.

In a further illustrative embodiment, a method is provided for preparing electrodes for ablative electrical treatment of tissue at a reference point. A sheath containing a primary electrode and a secondary electrode is extended, wherein the secondary electrode is contained within the primary electrode and initially coupled to move with the primary electrode. Movement of the primary electrode is unlocked, the primary electrode is moved to a first location near the reference point, and the primary electrode is locked in position at the first location. Movement of the secondary electrode is unlocked, the secondary electrode is moved to a second location near the reference point, and the secondary electrode is locked in position at the second location.

In an additional illustrative embodiment, an apparatus for slidably moving multiple features relative to a sheath inserted into a body and positioned relative to a reference point includes a primary actuator configured to move a primary electrode, a secondary actuator configured to deploy a secondary electrode by moving the secondary electrode independently of the primary electrode, and a control mechanism. The control mechanism includes a primary release configured to selectively permit movement of the primary actuator, a secondary release configured to selectively decouple the secondary actuator from the primary actuator and permit movement of the secondary actuator within a predetermined range, and an actuator interlock configured to selectively prevent activation of the primary release.

In another illustrative embodiment, a system for treating tissue at a reference point includes an electrical power source configured to selectively provide electrical power between a first pole and a second pole. An electrosurgical apparatus is configured to be inserted into a body to convey a sheath containing a primary electrode electrically coupled to the first pole of the electrical power source and a secondary electrode electrically coupled to the second pole of the electrical power source to a vicinity of a reference point. A sheath actuator is configured to move the sheath relative to the reference point and a sheath lock configured to selectively lock a position of the sheath. A primary actuator is configured to move the primary electrode. A secondary actuator is configured to deploy the secondary electrode by moving the secondary electrode independently of the primary electrode. A control mechanism includes a primary release configured to selectively permit movement of the primary actuator, a secondary release configured to selectively decouple the secondary actuator from the primary actuator and permit movement of the secondary actuator within a predetermined range, and an actuator interlock configured to selectively prevent activation of the primary release.

In a further illustrative embodiment, a method of using an apparatus to move electrodes into positions for ablative electrical treatment of tissue at a reference point includes extending a sheath toward a reference point. The sheath contains a primary electrode mechanically coupled to a primary actuator and selectively lockable by a primary release. The sheath also contains a secondary electrode mechanically coupled to a secondary actuator and lockable by a secondary release, where the secondary electrode is slidably received within the primary electrode. The primary release is activated to permit movement of the primary actuator. The primary actuator is moved to move the primary electrode to a first location relative to the reference point. The primary release is locked to lock the primary actuator to maintain the primary electrode at the first location. The secondary release is activated to decouple the secondary actuator from the primary actuator to permit movement of the secondary actuator independent of the primary actuator. The secondary actuator is moved to move the secondary electrode to a second location relative to the reference point. The secondary release is locked to lock the secondary actuator to maintain the secondary electrode at the second location.

In an additional illustrative embodiment, an apparatus for slidably moving multiple features relative to a sheath inserted into a body and positioned relative to a reference point includes a housing mechanically coupled with a primary electrode and defining a guide slot having sections transverse and parallel to an axis of the housing. A sleeve having a distal end is configured to engage an electrosurgical device and a proximal end configured to be slidably received within a first end of the housing. A latch disposed at the first end of the housing is configured to selectively enable the housing to move along the sleeve to move the primary electrode to a first location relative to the reference point. A secondary actuator is received within the housing and coupled with a secondary electrode, where the secondary actuator is configured to move independently of the primary electrode parallel to the axis of the housing. An interlock lever mechanically is coupled with the secondary actuator and extends through the guide slot. An interlock lever also includes a clamp configured to lock the secondary actuator to the sleeve when the secondary electrode reaches a second location relative to the reference point.

In another illustrative embodiment, a system for treating tissue at a reference point includes an electrical power source configured to selectively provide electrical power between a first pole and a second pole. An electrosurgical device is configured to be inserted into a body to convey a sheath containing a primary electrode electrically coupled to the first pole of the electrical power source and a secondary electrode electrically coupled to the second pole of the electrical power source to a vicinity of a reference point. A sheath actuator is configured to move the sheath relative to the reference point. A sheath lock is configured to selectively lock a position of the sheath. A housing is mechanically coupled with a primary electrode and includes a guide slot having sections transverse and parallel to an axis of the housing. A sleeve having a distal end is configured to engage a bronchoscope and a proximal end configured to be slidably received within a first end of the housing. A latch is disposed at the first end of the housing and is configured to selectively enable the housing to move along the sleeve to move the primary electrode to a first location relative to the reference point. A secondary actuator received within the housing is coupled with a secondary electrode and is configured to move independently of the primary electrode parallel to the axis of the housing. An interlock lever is mechanically coupled with the secondary actuator and extends through the guide slot, and the interlock lever further includes a clamp configured to lock the secondary actuator to the sleeve when the secondary electrode reaches a second location relative to the reference point.

In a further illustrative embodiment, a method of moving electrodes into positions for ablative electrical treatment of tissue at a reference point includes extending a sheath that contains a primary electrode that is mechanically coupled to a housing and is selectively lockable by a latch and a secondary electrode that is mechanically coupled to the secondary actuator and is lockable by an interlock lever. The secondary electrode is slidably received within the primary electrode. The latch is released to enable the housing to move the primary electrode relative to the reference point. The housing is slid to move the primary electrode to a first location relative to the reference point. The latch is secured to prevent movement of the housing relative to the sleeve. The interlock lever is moved through a series of positions in the guide slot on the housing for decoupling the secondary electrode from the primary electrode and moving the secondary electrode to a second location relative to the reference point.

In an additional embodiment, an apparatus for slidably moving multiple features relative to a sheath inserted into a body and positioned relative to a reference point includes a secondary electrode slider that is mechanically coupled with a secondary electrode and that supports a secondary actuator. A primary electrode slider is configured to slidably and rotatably receive the secondary electrode slider, the primary electrode slider being mechanically coupled with a primary electrode, supporting a primary actuator, and defining an intermediate guide slot configured to receive and engage the secondary actuator. An outer housing includes a first end facing toward the reference point. The outer housing is configured to slidably and rotatably receive the primary electrode slider and defines a first guide slot configured to receive and engage the primary actuator and a second guide slot configured to receive the secondary actuator when the secondary actuator is positioned under the second guide slot.

In another illustrative embodiment, a system for treating tissue at a reference point includes an electrical power source configured to selectively provide electrical power between a first pole and a second pole. An electrosurgical device is configured to be inserted into a body to convey a sheath containing a primary electrode electrically coupled to the first pole of the electrical power source and a secondary electrode electrically coupled to the second pole of the electrical power source to a vicinity of the reference point. A sheath actuator is configured to move the sheath relative to the reference point. A sheath lock is configured to selectively lock a position of the sheath. A secondary electrode slider is mechanically coupled with a secondary electrode and supports a secondary actuator. A primary electrode slider is configured to slidably and rotatably receive the secondary electrode slider, is mechanically coupled with a primary electrode, supports a primary actuator, and defines an intermediate guide slot configured to receive and engage the secondary actuator. An outer housing has a first end facing toward the reference point and is configured to slidably and rotatably receive the primary electrode slider. The outer housing also includes a first guide slot configured to receive and engage the primary actuator and a second guide slot configured to receive the secondary actuator when the secondary actuator is positioned under the second guide slot.

In a further illustrative embodiment, a method of moving electrodes into positions for ablative electrical treatment of tissue at a reference point includes extending a sheath, wherein the sheath contains a primary electrode and a secondary electrode slidably received within the primary electrode. An apparatus coupled with the primary electrode and the secondary electrode is deployed, wherein the apparatus includes a secondary electrode slider mechanically coupled with a secondary electrode and supporting a secondary actuator. The apparatus includes a primary electrode slider that is mechanically coupled with a primary electrode, supports a primary actuator, and defines an intermediate guide slot configured to receive and engage the secondary actuator. The apparatus also includes an outer housing having a first end, wherein the outer housing defines a first guide slot configured to receive and engage the primary actuator and a second guide slot configured to receive the secondary actuator when the secondary actuator is positioned under the second guide slot. The primary actuator is moved toward the front end of the outer housing to position the primary electrode at a first location relative to the reference point. The outer housing is rotated to expose the intermediate guide slot beneath the second guide slot. The secondary actuator is moved toward the first end of the outer housing to position the secondary electrode at a second location relative to the reference point.

In an additional illustrative embodiment, an apparatus is provided for slidably moving multiple features relative to a sheath inserted into a body and positioned relative to a reference point. A lock rod is configured to be fixed in a position relative to a reference point. A primary housing is mechanically coupled with a primary electrode. The primary housing further includes an outward-facing guide slot configured to selectively limit and enable sliding movement of a guide member. The primary housing also includes a primary lock channel configured to rotatably receive the lock rod to prevent sliding movement of the primary housing relative to the lock rod. A secondary housing is mechanically coupled with a secondary electrode. The secondary housing further includes an inner channel configured to slidably and rotatably receive the primary housing and supporting the guide member. The secondary housing also includes a secondary lock channel configured to selectively one of fixably engage and slidably engage the lock rod. Rotation of the secondary housing selectively moves the lock rod in and out of the primary lock channel and within the secondary lock channel to selectively allow and prevent sliding movement relative to the lock rod of at least one of the primary housing and the secondary housing.

In another illustrative embodiment, a system for treating tissue at a reference point includes an electrical power source configured to selectively provide electrical power to a primary electrode and a secondary electrode between a first pole and a second pole. A lock rod is configured to be fixed in a position relative to a reference point. A sheath actuator is configured to move a sheath that houses the primary electrode and the secondary electrode relative to a reference point and to set a position of the lock rod relative to the reference point. A sheath lock is configured to selectively lock a position of the sheath and the lock rod. A primary housing is mechanically coupled with the primary electrode. The primary housing further includes an outward-facing guide slot configured to selectively limit and enable sliding movement of a guide member. The primary housing also includes a primary lock channel configured to rotatably receive the lock rod to prevent sliding movement of the primary housing relative to the lock rod. A secondary housing is mechanically coupled with the secondary electrode. The secondary housing further includes an inner channel configured to slidably and rotatably receive the primary housing and supporting the guide member. The secondary housing also includes a secondary lock channel configured to selectively one of fixably engage and slidably engage the lock rod. Rotation of the secondary housing selectively moves the lock rod in and out of the primary lock channel and within the secondary lock channel to selectively allow and prevent sliding movement relative to the lock rod of at least one of the primary housing and the secondary housing.

In a further illustrative embodiment, a method is provided for using an apparatus to move electrodes into positions for ablative electrical treatment of tissue at a reference point. A sheath is extended, wherein the sheath contains a primary electrode and a secondary electrode slidably received within the primary electrode. An apparatus coupled with the primary electrode and the secondary electrode is deployed. The apparatus includes a lock rod configured to be fixed in a position relative to a reference point. The apparatus also includes a primary housing is mechanically coupled with a primary electrode. The primary housing further includes an outward-facing guide slot configured to selectively limit and enable sliding movement of a guide member. The primary housing also includes a primary lock channel configured to rotatably receive the lock rod to prevent sliding movement of the primary housing relative to the lock rod. The apparatus also includes a secondary housing mechanically coupled with a secondary electrode. The secondary housing further includes an inner channel configured to slidably and rotatably receive the primary housing and supporting the guide member. The secondary housing also includes a secondary lock channel configured to selectively one of fixably engage and slidably engage the lock rod. The secondary housing is successively slide and rotated to move the secondary housing and the primary housing to move the primary electrode and the secondary electrode to positions relative to the reference point, and the primary housing is slide to move the primary electrode.

In another illustrative embodiment, an apparatus for slidably moving multiple features relative to a sheath insertable into a body and positionable relative to a reference point includes a primary actuator configured to move a primary electrode to a first position. A secondary actuator is configured to move a secondary electrode to a second position. A shrouding device is configured to selectively prevent access to the secondary actuator until the primary actuator has been manipulated to extend the primary electrode to the first position.

In a further illustrative embodiment, a system for treating tissue at a reference point includes a controllable electrical power source configured to selectively provide electrical power between a first pole and a second pole. An electrosurgical apparatus is configured to be inserted into a body to convey a sheath that houses a primary electrode electrically coupled to the first pole of the electrical power source and a secondary electrode electrically coupled to the second pole of the electrical power source to a vicinity of a reference point. The apparatus also includes an electrode control apparatus that includes a primary actuator configured to move a primary electrode to a first position. A secondary actuator is configured to move a secondary electrode to a second position. A shrouding device is configured to selectively prevent access to the secondary actuator until the primary actuator has been manipulated to extend the primary electrode to the first position.

In an additional illustrative embodiment, a method of preparing electrodes for ablative electrical treatment of tissue at a reference point includes extending a sheath containing a primary electrode and a secondary electrode, where the secondary electrode is contained within the primary electrode and initially is coupled to move with the primary electrode. A primary actuator configured to move the primary electrode is moved to a first location near a reference point. The primary actuator is moved to move a shrouding device to permit access to a secondary actuator configured to move the secondary electrode. The secondary actuator is moved to move the second electrode to a second location near the reference point.

In another illustrative embodiment, an apparatus for slidably moving multiple features relative to a sheath insertable into a body and positionable relative to a reference point includes a shaft configured to enable slidable passage of a primary electrode and a secondary electrode therethrough. A primary actuator is coupled with the primary electrode and configured to slidably move over the shaft to move the primary electrode to a first position near a reference point. A secondary actuator is coupled with the secondary electrode and configured to slidably move over the shaft to move the secondary electrode to a second position. A shroud device is incorporated in the primary actuator and is configured to at least partially prevent access to the secondary actuator. The primary actuator is configured to slidably and rotatably move relative to the shaft, and, after the primary actuator has been moved to slidably move the primary electrode to the first position, the primary actuator is further configured to be rotated to move the shroud device to permit access to the secondary actuator.

In a further illustrative embodiment, a system for treating tissue at a reference point includes a controllable electrical power source configured to selectively provide electrical power between a first pole and a second pole. An electrosurgical apparatus is configured to be inserted into a body to convey a sheath that houses a primary electrode electrically coupled to the first pole of the electrical power source and a secondary electrode electrically coupled to the second pole of the electrical power source to a vicinity of a reference point. The system also includes an electrode control apparatus that includes a shaft configured to enable slidable passage of a primary electrode and a secondary electrode therethrough. A primary actuator is coupled with the primary electrode and configured to slidably move over the shaft to move the primary electrode to a first position near a reference point. A secondary actuator is coupled with the secondary electrode and configured to slidably move over the shaft to move the secondary electrode to a second position. A shroud device is incorporated in the primary actuator and is configured to at least partially prevent access to the secondary actuator. The primary actuator is configured to slidably and rotatably move relative to the shaft, and, after the primary actuator has been moved to slidably move the primary electrode to the first position, the primary actuator is further configured to be rotated to move the shroud device to permit access to the secondary actuator.

In an additional illustrative embodiment, a method of preparing electrodes for ablative electrical treatment of tissue at a reference point includes extending a sheath containing a primary electrode and a secondary electrode, where the secondary electrode is contained within the primary electrode and is initially coupled to move with the primary electrode. A primary actuator coupled with the primary electrode is moved to move the primary electrode to a first location near a reference point. The primary actuator is rotated to expose a secondary actuator that was previously at least partially covered by the primary actuator and coupled with the secondary electrode to permit access to a secondary actuator configured to move the secondary electrode. The secondary actuator is moved to move the second electrode to a second location near the reference point.

In another illustrative embodiment, an apparatus for slidably moving multiple features relative to a sheath insertable into a body and positionable relative to a reference point includes a primary actuator configured to move a primary electrode to a first position when a primary actuator grip is slidably moved toward a first end. A secondary actuator is configured to move a secondary electrode to a second position when a secondary actuator grip is slidably moved toward the first end. An outer handle is configured to selectively prevent access to the secondary actuator grip of the secondary actuator until the primary actuator has been manipulated to extend the primary electrode to the first position and rotated relative to the primary actuator to expose the secondary actuator.

In a further illustrative embodiment, a system for treating tissue at a reference point includes a controllable electrical power source configured to selectively provide electrical power between a first pole and a second pole. An electrosurgical apparatus is configured to be inserted into a body to convey a sheath that houses a primary electrode electrically coupled to the first pole of the electrical power source and a secondary electrode electrically coupled to the second pole of the electrical power source to a vicinity of a reference point. The system also includes an electrode control apparatus that includes a primary actuator configured to move a primary electrode to a first position when a primary actuator grip is slidably moved toward a first end. A secondary actuator is configured to move a secondary electrode to a second position when a secondary actuator grip is slidably moved toward the first end. An outer handle is configured to selectively prevent access to the secondary actuator grip of the secondary actuator until the primary actuator has been manipulated to extend the primary electrode to the first position and rotated relative to the primary actuator to expose the secondary actuator grip.

In an additional illustrative embodiment, a method of preparing electrodes for ablative electrical treatment of tissue at a reference point includes extending a sheath that houses a primary electrode and a secondary electrode, where the secondary electrode is contained within the primary electrode and initially coupled to move with the primary electrode. A primary actuator grip is slid within a channel defined in an outer handle to move a primary actuator to move the primary electrode to a first location near a reference point. The primary actuator grip is rotated to expose a secondary actuator grip within the channel to enable movement of a secondary actuator configured to move the secondary electrode. The secondary actuator grip is moved within the channel to move the second electrode to a second location near the reference point.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings:

FIGS. 7A and 8A are schematic diagrams of a sheath actuator for positioning a sheath relative to a reference point;

FIGS. 7B and 8B are schematic diagrams of positioning of distal ends of the sheath, a primary electrode, and a secondary electrode relative to a reference point corresponding to positions of the sheath actuator of FIGS. 7A and 8A, respectively;

Figure 15:
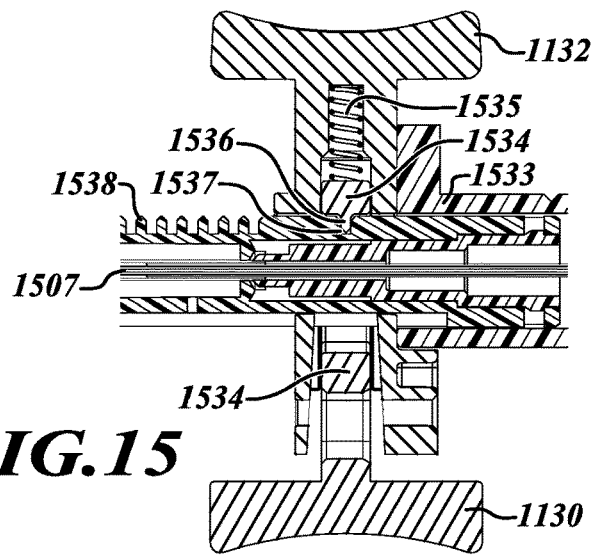
Figure 16:
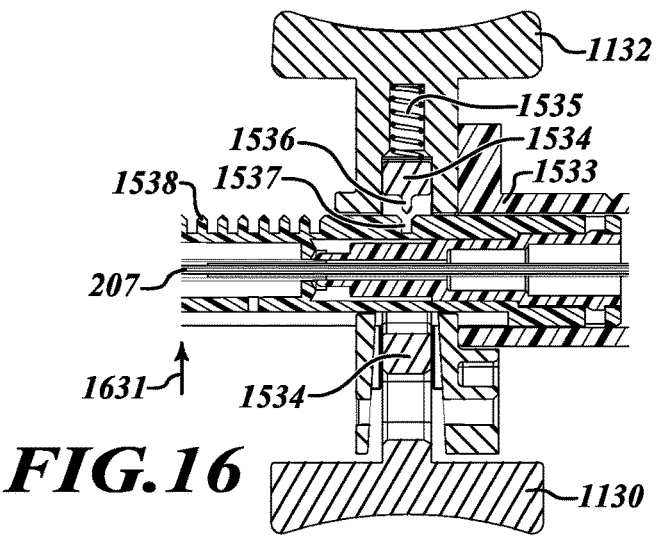
Figure 17:
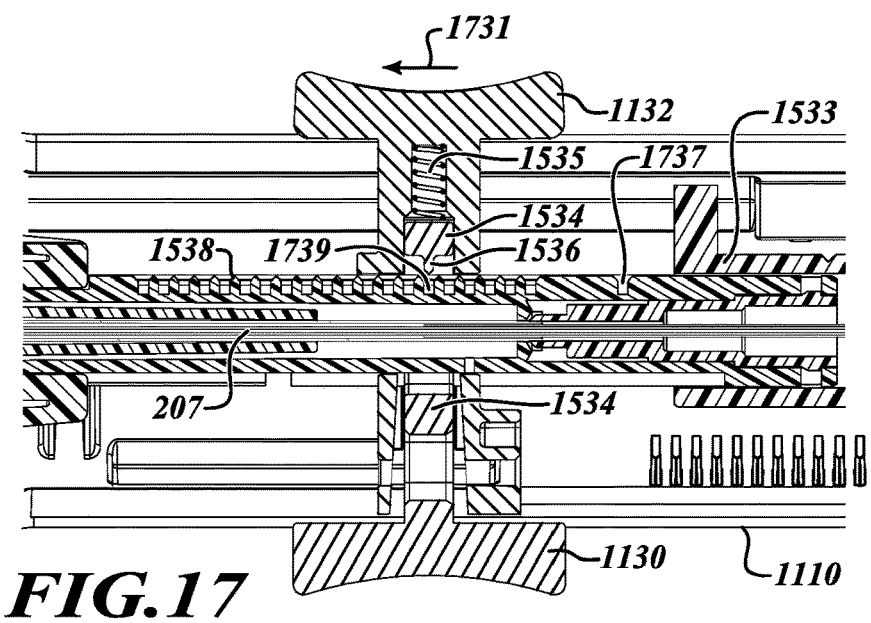
Figure 21:
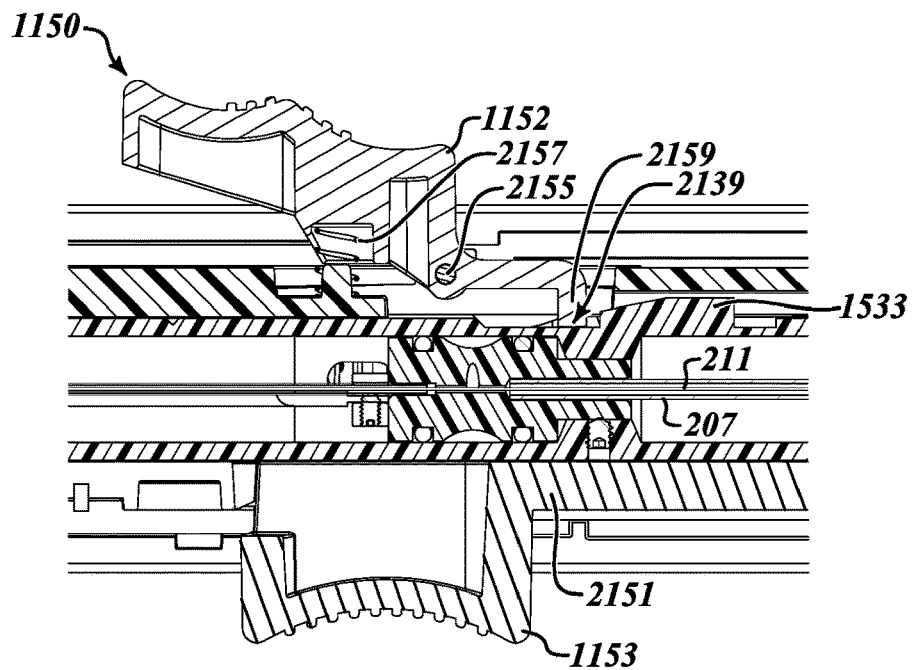
Figure 22:
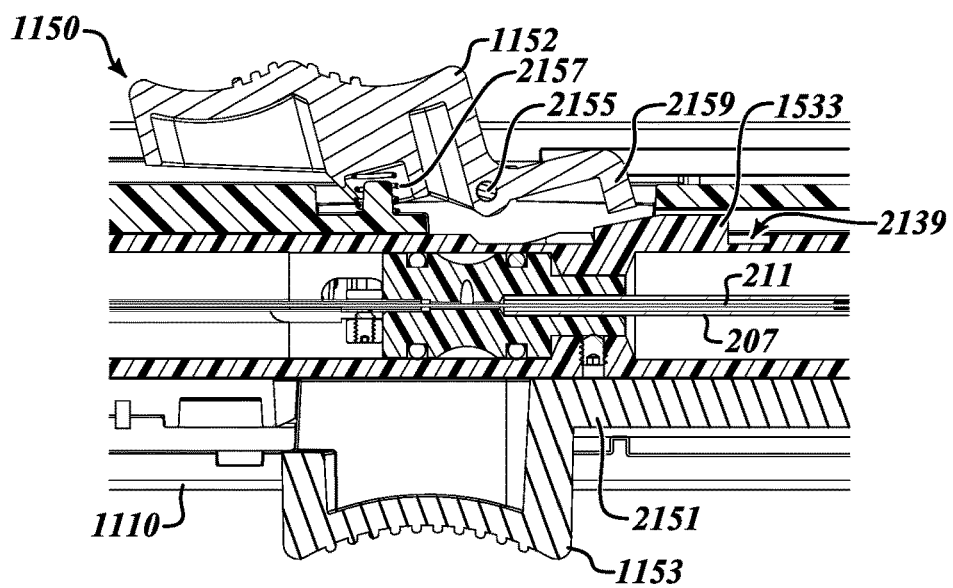
Figure 29:
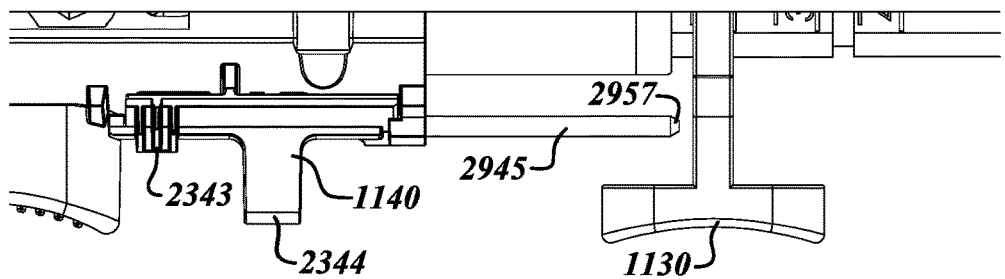
Figure 30:
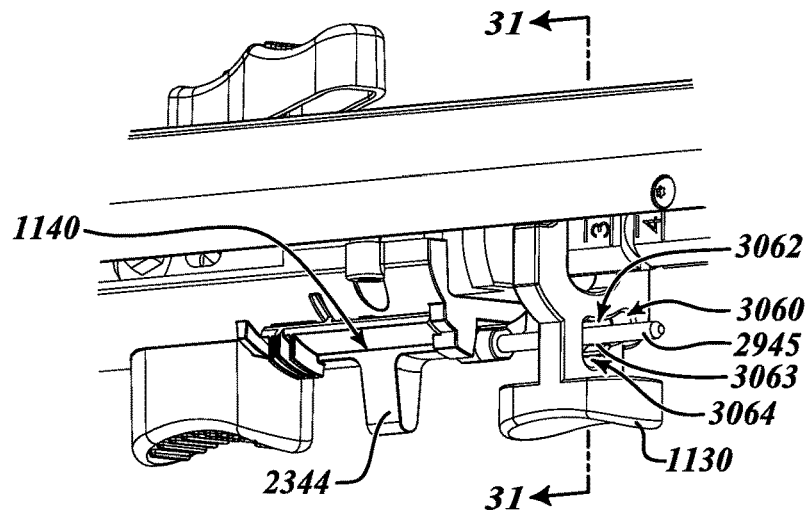
Figure 31:
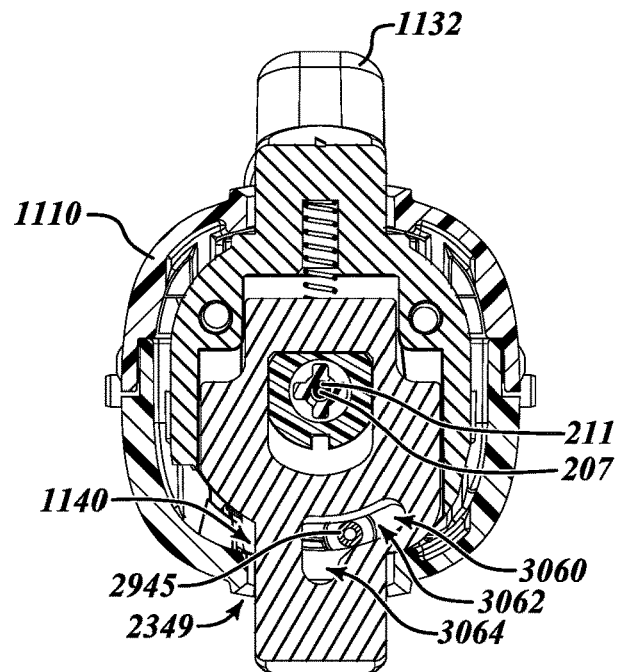
Figure 37A:
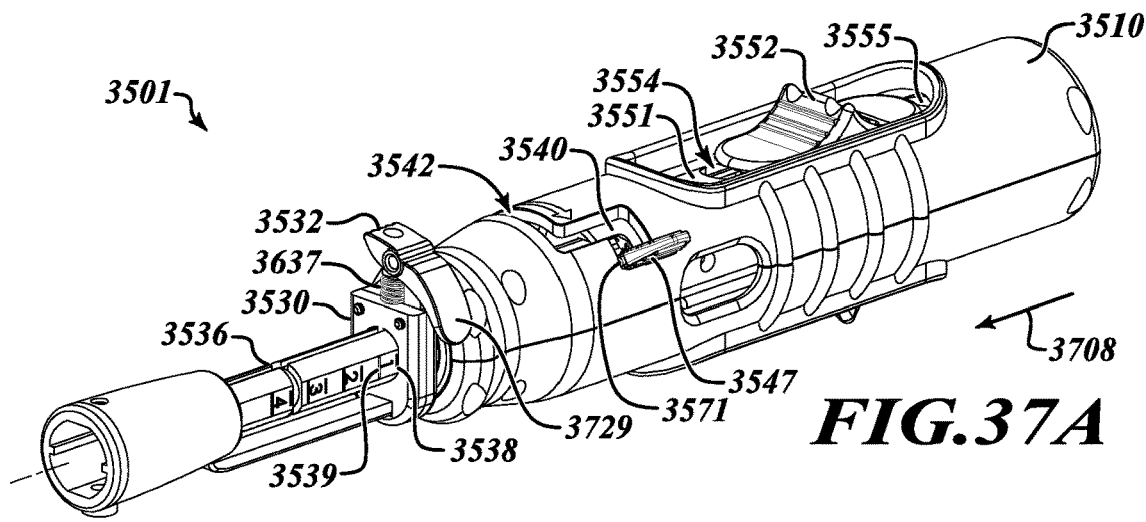
Figure 37B:
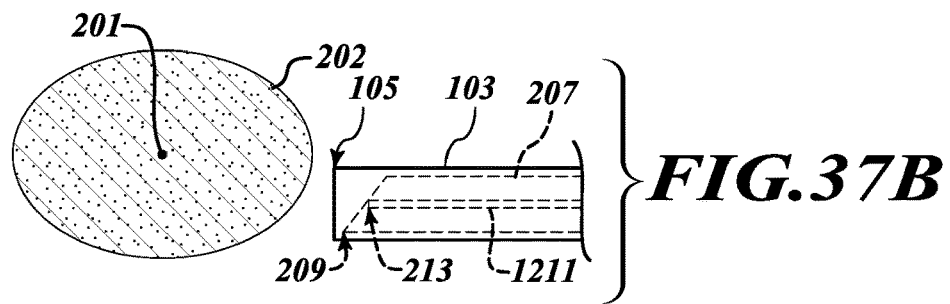
Figure 38A:
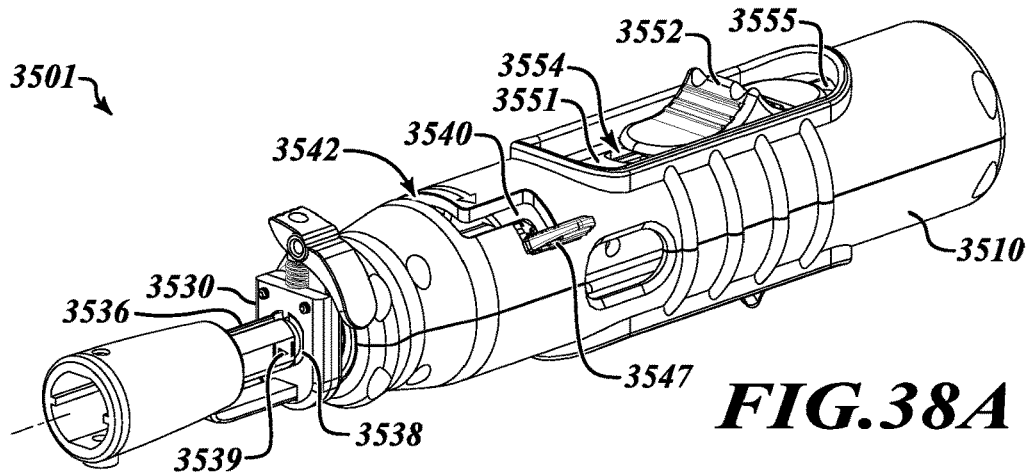
Figure 38B:
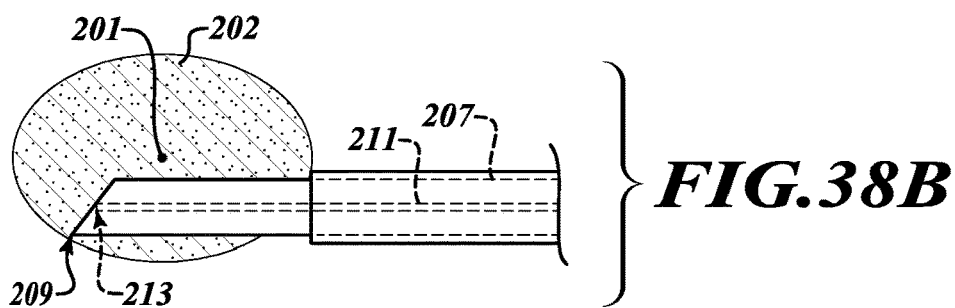
Figure 39:
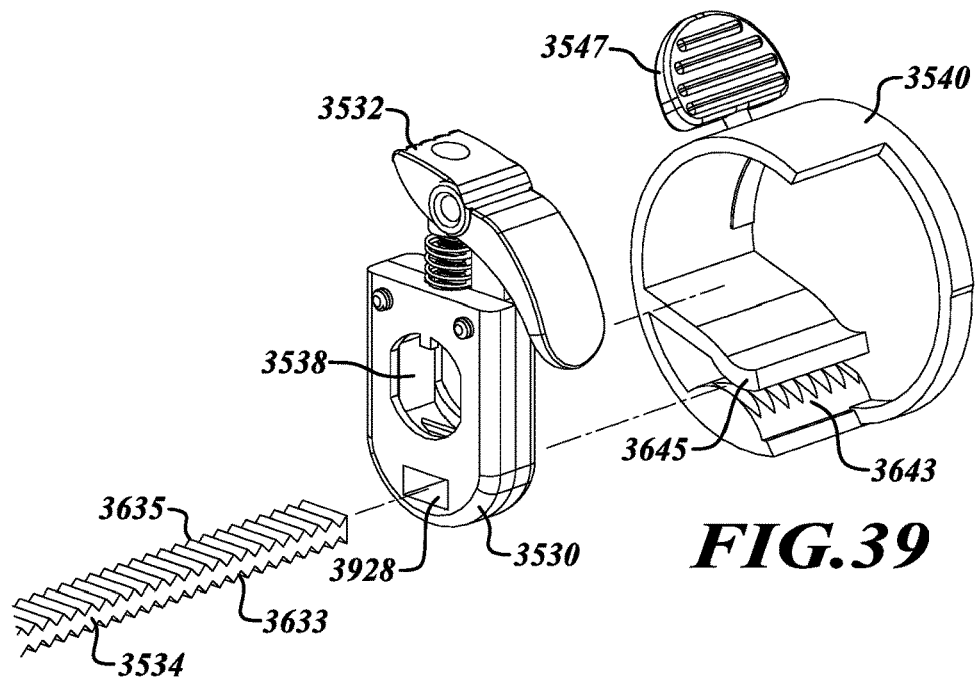
Figure 40:
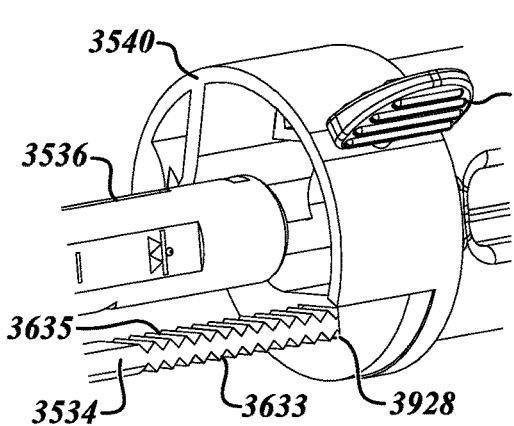
Figure 41:
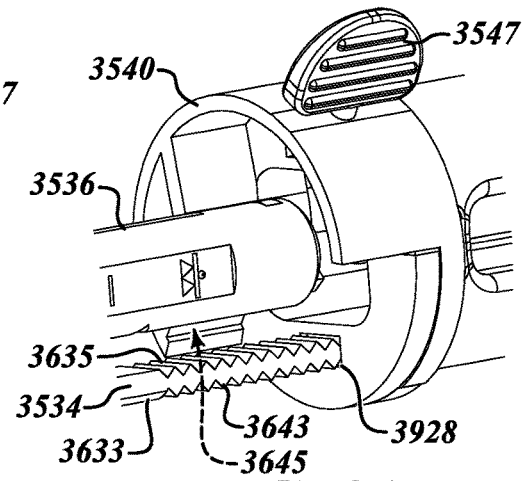
Figure 42:
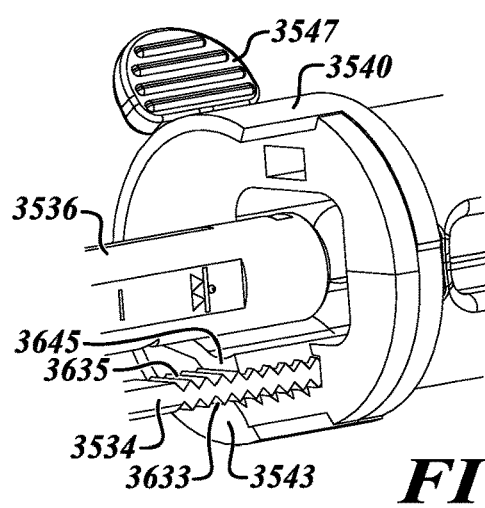
Figure 64A:
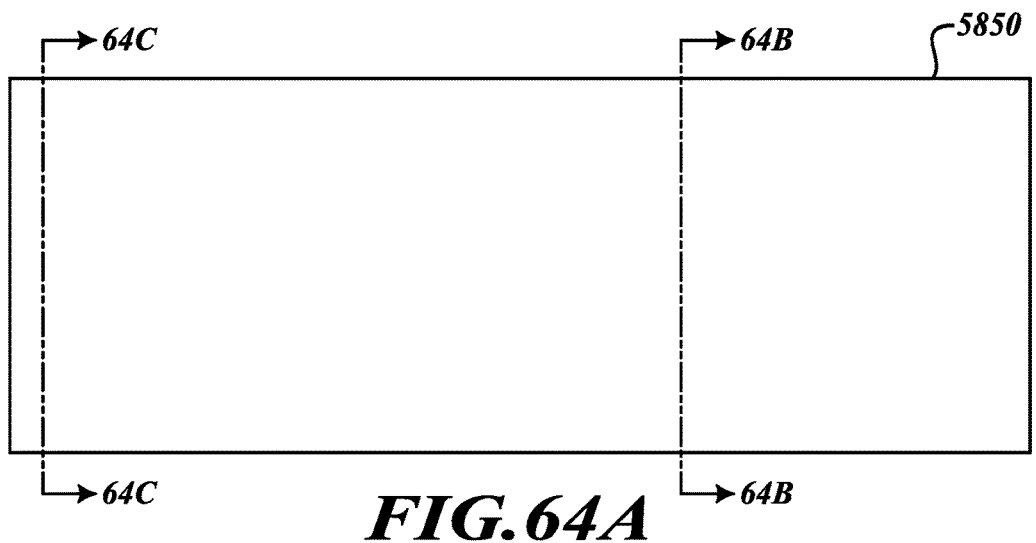
Figure 64B:
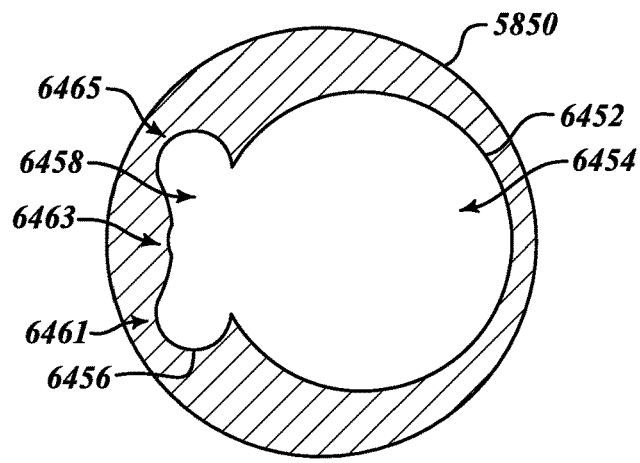
Figure 64C:
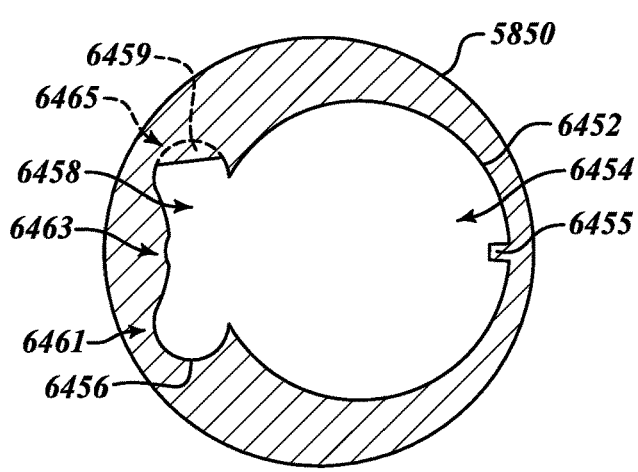
Figure 84A:
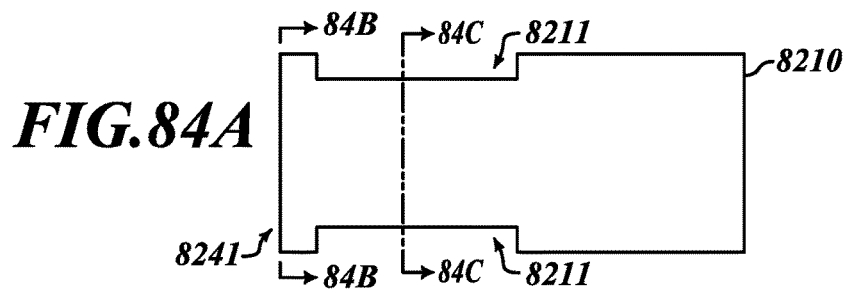
Figure 84B:
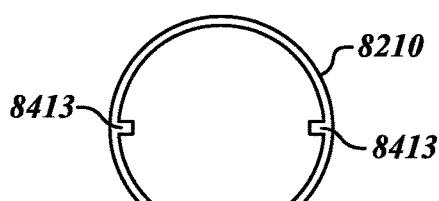
Figure 84C:
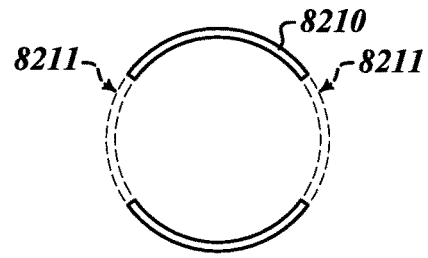
Figure 85A:
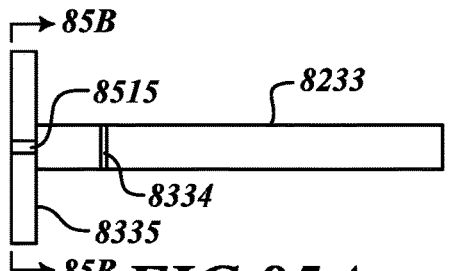
Figure 85B:
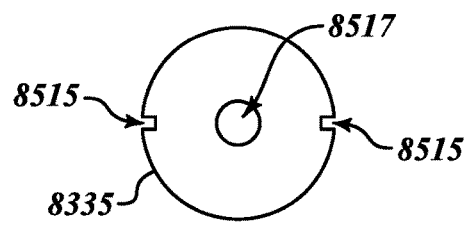
Figure 86A:
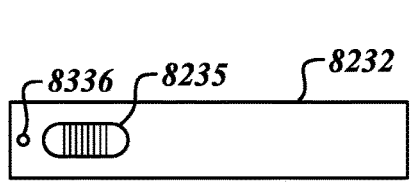
Figure 86B:
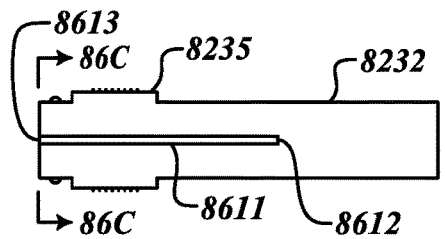
Figure 86C:
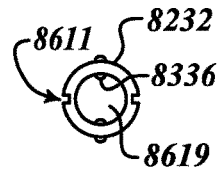
Figure 87A:
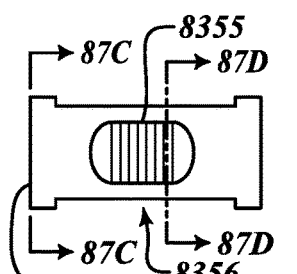
Figure 87B:
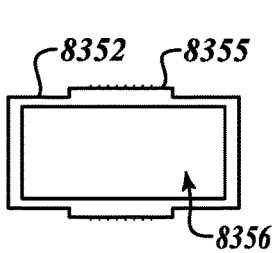
Figure 87C:
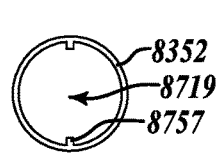
Figure 87D:
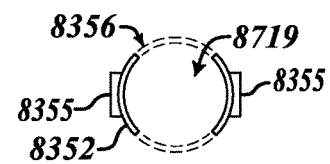
Figure 110:
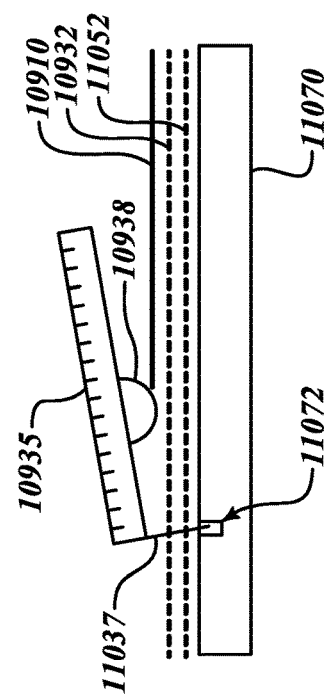
Figure 109:
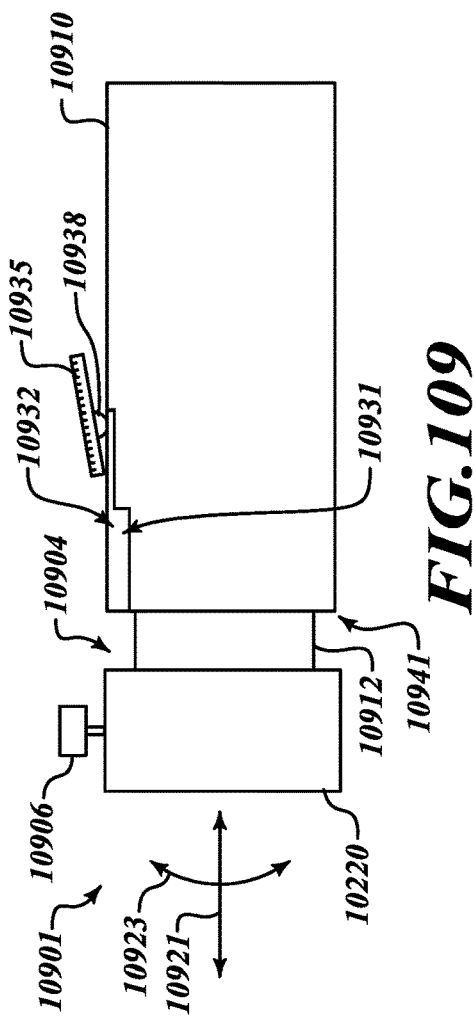
Figure 111:
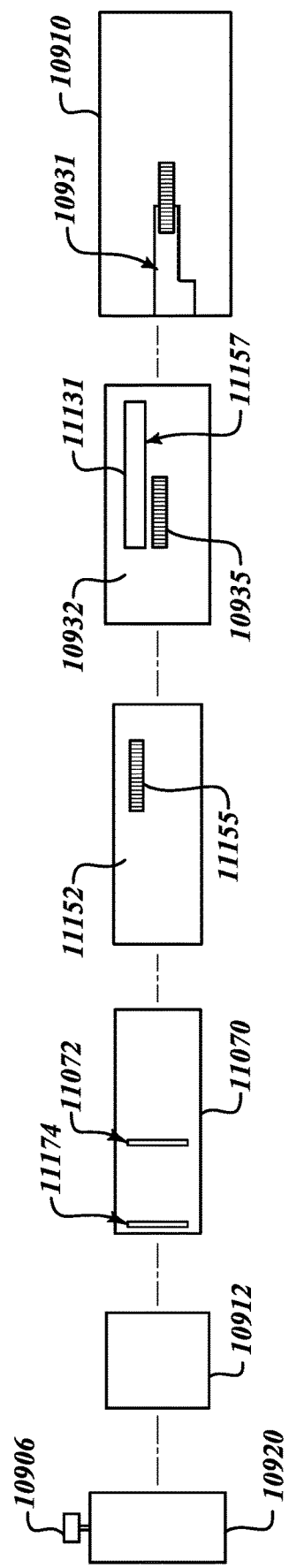
Figure 115:
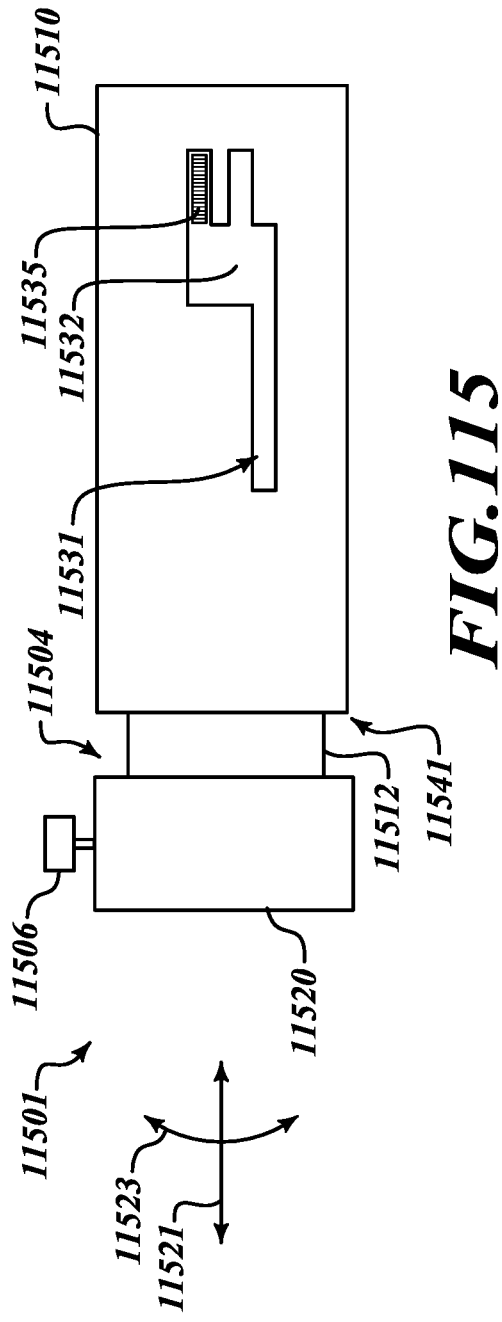
Figure 116:
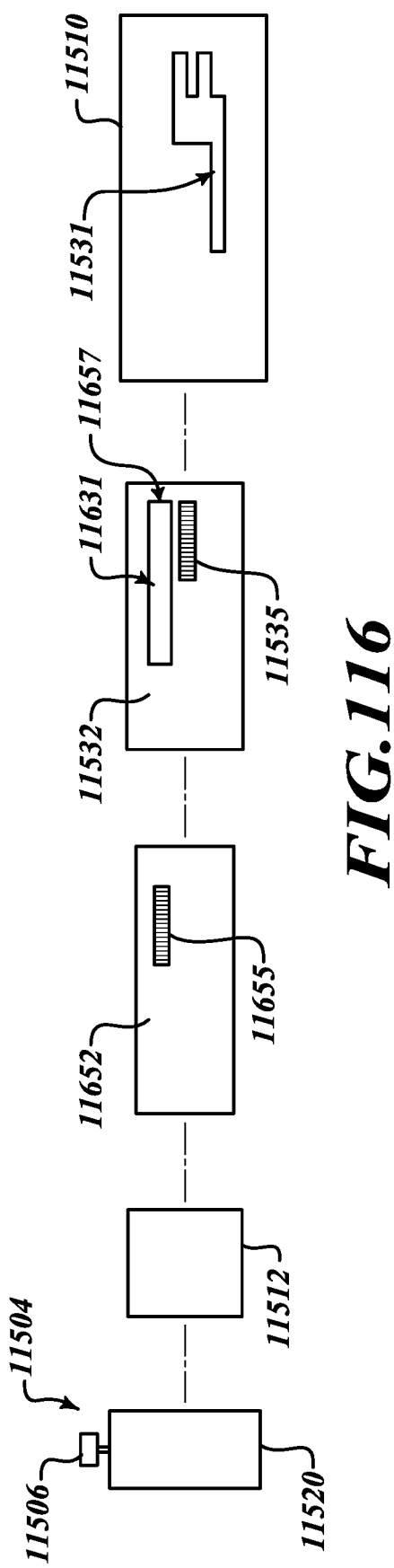
Figure 117B:
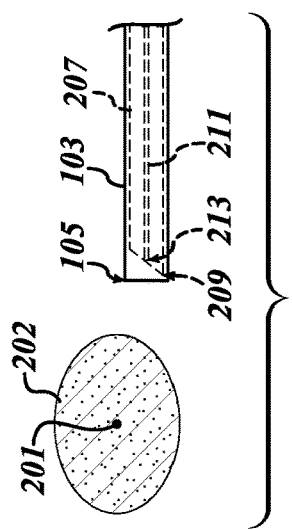
Figure 118B:
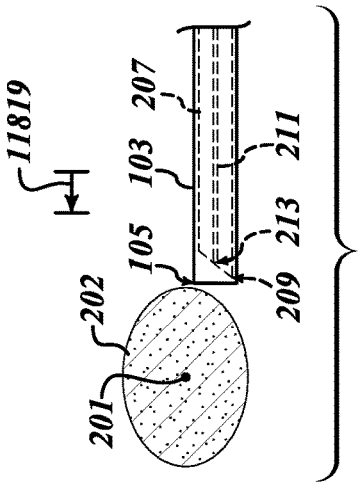
Figure 117A:
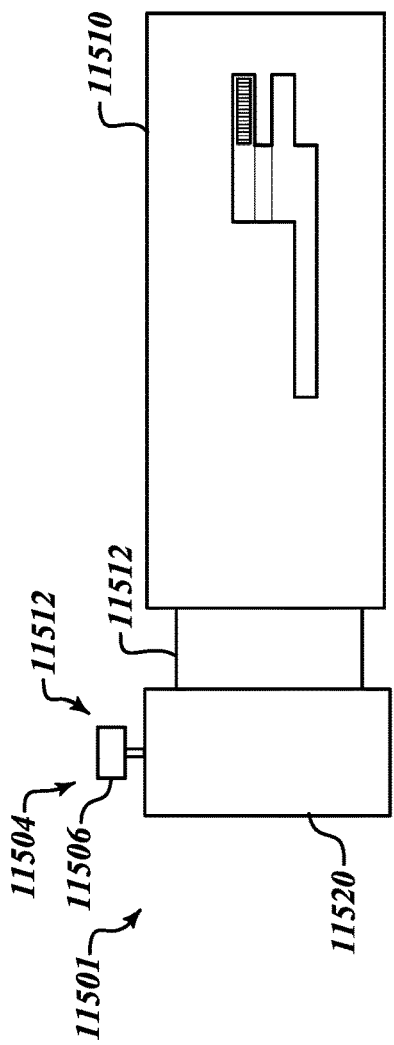
Figure 118A:
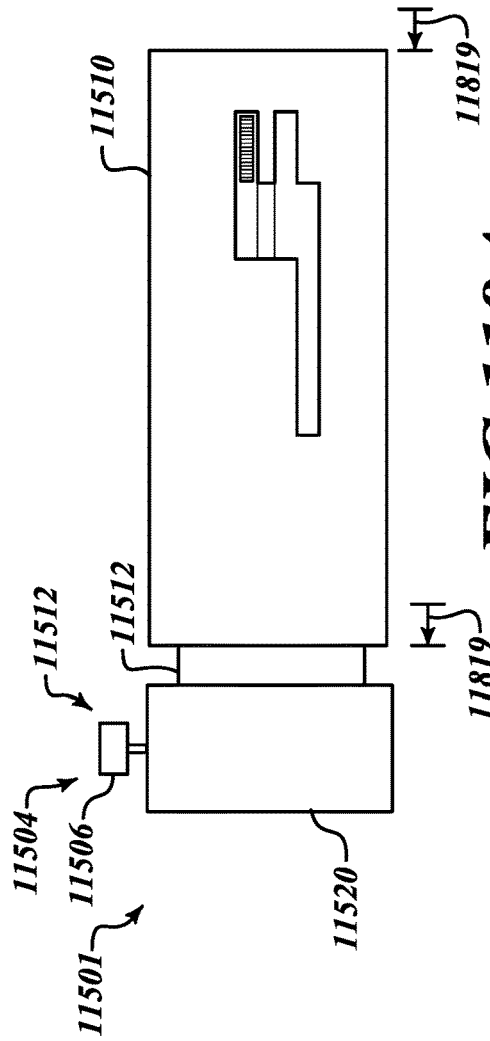
Figure 124:
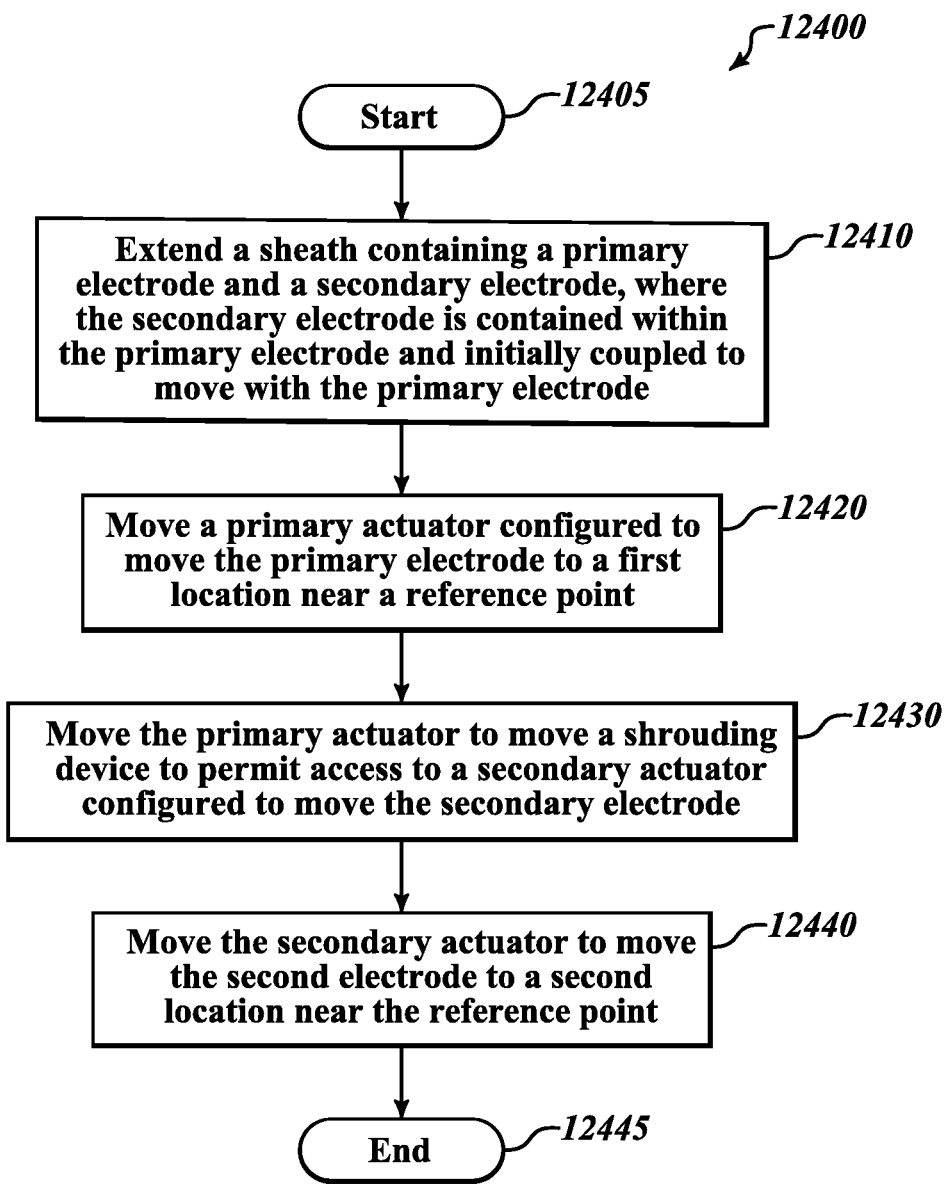
Figure 125:
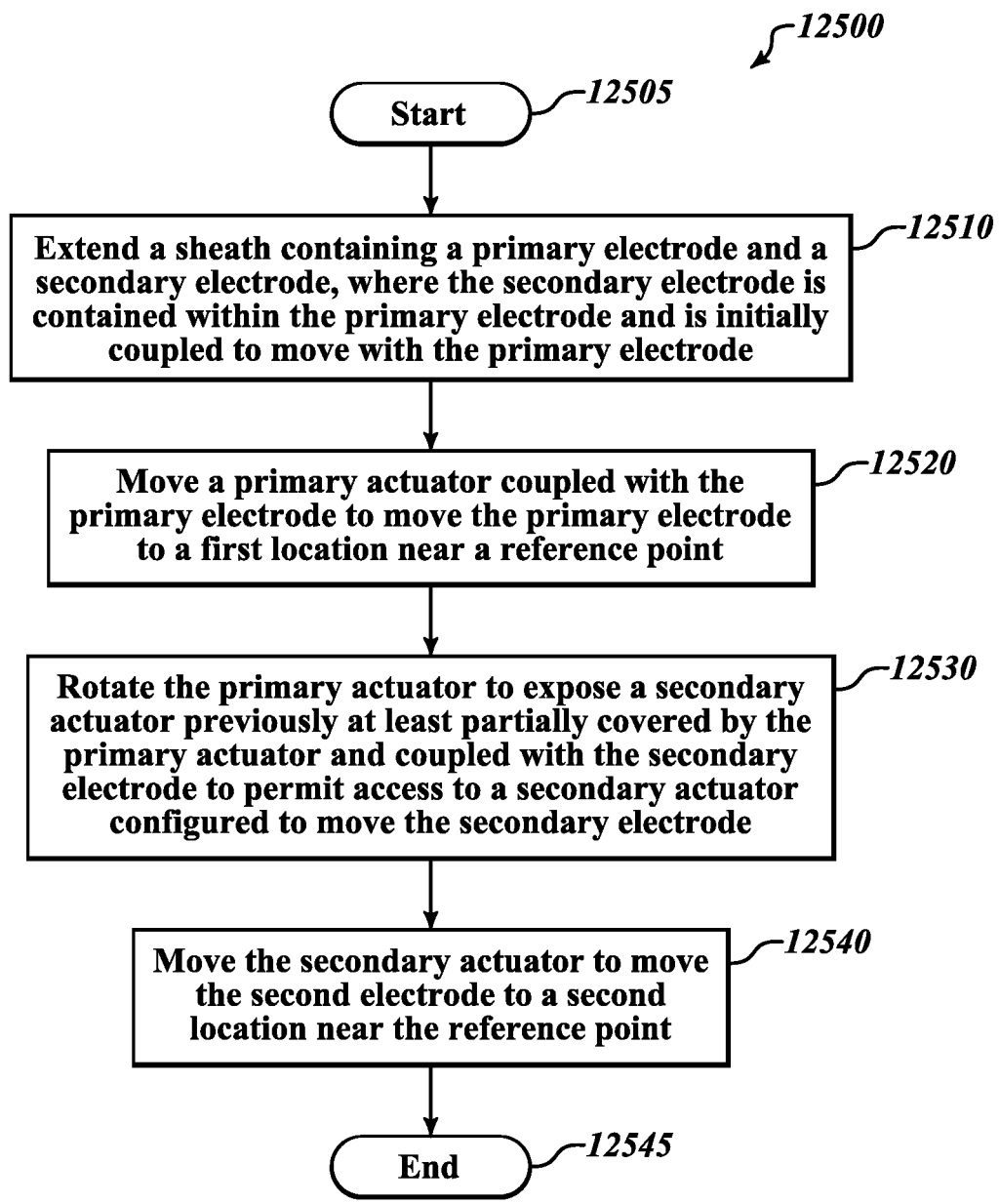
Figure 126:
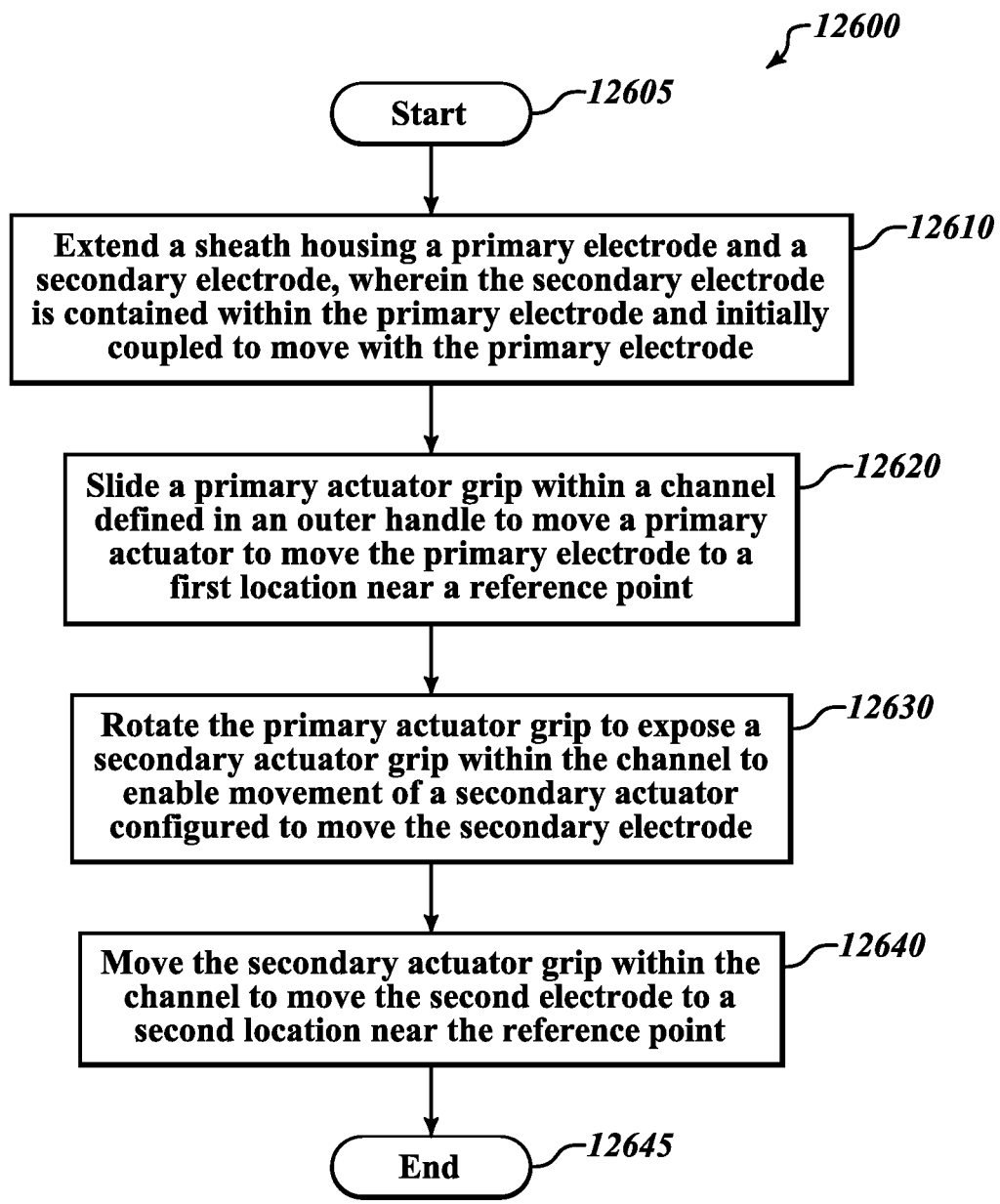

FIGS. 11, 12A, 13A, 14A, 18A, 19A, 20A, 32A, 33A, and 34A are side views of an embodiment of a user interface for positioning multiple components relative to the reference point;

FIGS. 12B, 13B, 14B, 18B, 19B, 20B, 32B, 33B, and 34B are schematic diagrams of positioning of distal ends of a sheath, primary electrode, and secondary electrode relative to a reference point corresponding to positions of the components of the user interface of FIGS. 12A, 13A, 14A, 18A, 19A, 20A, 32A, 33A, and 34A, respectively;

FIGS. 15-17 are cutaway views of the primary actuator and the primary release of the user interface of FIG. 11;

FIGS. 21 and 22 are cutaway views of the secondary actuator and the secondary release of the user interface of FIG. 11;

FIG. 23 is a partial bottom view of the user interface of FIG. 11 showing the actuator interlock in a first position;

FIG. 24 is another partial bottom view of the user interface of FIG. 11 showing the actuator interlock in the first position corresponding to the position of the actuator interlock of FIG. 23;

FIG. 25 is a cross-sectional view of the user interface of FIG. 11 showing the actuator interlock in the first position corresponding to the position of the actuator interlock of FIGS. 23 and 24;

FIG. 26 is a partial bottom view of the user interface of FIG. 11 showing the actuator interlock in a second position;

FIG. 27 is another partial bottom view of the user interface of FIG. 11 showing the actuator interlock in the second position corresponding to the position of the actuator interlock of FIG. 26;

FIG. 28 is a cross-sectional view of the user interface of FIG. 11 showing the actuator interlock in the second position corresponding to the position of the actuator interlock of FIGS. 26 and 27;

FIG. 29 is a partial cutaway side view of the user interface of FIG. 11 illustrating the actuator interlock in a second position to enable use of the primary release;

FIG. 30 is a partial cutaway perspective view of the user interface of FIG. 11 illustrating the actuator interlock in the second position to enable use of the primary release;

FIG. 31 is a cross-sectional view of the user interface of FIG. 11 showing the actuator interlock in the second position corresponding to the position of the actuator interlock of FIG. 30 to enable use of the primary release;

FIG. 35 is a perspective view of another embodiment of a user interface for positioning multiple components relative to the reference point;

FIG. 36 is an exploded view of the user interface of FIG. 35;

FIGS. 37A and 38A are perspective views of the user interface of FIG. 35 for positioning multiple components relative to the reference point;

FIGS. 37B and 38B are schematic diagrams of positioning of distal ends of a sheath, primary electrode, and secondary electrode relative to the reference point corresponding to positions of the primary release and a housing of the user interface of FIGS. 37A and 38A, respectively;

FIG. 39 is an exploded view of the latch and the interlock lever of the user interface of FIG. 35;

FIGS. 40-42 are partial perspective views of the user interface of FIG. 35 illustrating positions of the interlock lever of the user interface of FIG. 35;

FIGS. 43A, 44A, 45A, 46A, and 47A are partial top views of the user interface of FIG. 35;

FIGS. 43B, 44B, 45B, 46B, and 47B are partial side views of the user interface of FIG. 35 corresponding with the partial top views of FIGS. 43A, 44A, 45A, 46A, and 47A, respectively;

FIGS. 43C, 44C, 45C, 46C, and 47C are schematic diagrams of positioning of distal ends of the sheath, primary electrode, and secondary electrode relative to the reference point corresponding to positions of the user interface shown in FIGS. 43A-43B, 44A-44B, 45A-45B, 46A-46B, and 47A-47B, respectively;

FIG. 48 is a side view of another embodiment of a user interface for positioning multiple components relative to a reference point;

FIG. 49 is an exploded view of the user interface of FIG. 48;

FIGS. 50A and 51A are side views of the user interface of FIG. 48 being manipulated to position a sheath;

FIGS. 50B and 51B are schematic diagrams of positioning of distal ends of the sheath, primary electrode, and secondary electrode relative to a reference point corresponding to positions of the sheath actuator of FIGS. 50A and 51A, respectively;

FIGS. 52A, 53A, 54A, 55A, 56A, and 57A are side views of the user interface of FIG. 48 being used to position electrodes within a body;

FIGS. 52B, 53B, 54B, 55B, 56B, and 57B are cross-sectional views of the user interface of FIG. 48 corresponding with the side views of FIGS. 52A, 53A, 54A, 55A, 56A, and 57A, respectively;

FIGS. 52C, 53C, 54C, 55C, 56C, and 57C are schematic diagrams of positioning of distal ends of the sheath, primary electrode, and secondary electrode relative to the reference point corresponding to positions of the user interface shown in FIGS. 52A-52B, 53A-53B, 54A-54B, 55A-55B, 56A-56B, and 57A-57B, respectively;

FIG. 58 is a side view of another embodiment of a user interface for positioning multiple components relative to a reference point;

FIG. 59 is a partial cutaway view of the user interface of FIG. 58;

FIGS. 60A and 61A are side views of the user interface of FIG. 58 being manipulated to position a sheath;

FIGS. 60B and 61B are schematic diagrams of positioning of distal ends of the sheath, primary electrode, and secondary electrode relative to a reference point corresponding to positions of the sheath actuator of FIGS. 60A and 61A, respectively;

FIG. 62 is a side view of a lock rod of the user interface of FIG. 58;

FIG. 63A is a side view of a primary housing of the user interface of FIG. 58;

FIG. 63B is a bottom view of the primary housing of the user interface of FIG. 58;

FIGS. 63C and 63D are cross-sectional views of the primary housing of the user interface of FIG. 58;

FIG. 64A is a side view of the secondary housing of the user interface of FIG. 58;

FIGS. 64B and 64C are cross-sectional views of the secondary housing of the user interface of FIG. 58;

FIGS. 65A, 66A, 67A, 68A, 69A, and 70A are partial cutaway side views of the user interface of FIG. 58 being used to position electrodes within a body;

FIGS. 65B-65C, 66B-66C, 67B-67C, 68B-68C, 69B-69C, and 70B-70C are cross-sectional views of the user interface of FIG. 58 corresponding with the partial cutaway side views of FIGS. 65A, 66A, 67A, 68A, 69A, and 70A, respectively;

FIGS. 65D, 66D, 67D, 68D, 69D, and 70D are schematic diagrams of positioning of distal ends of the sheath, primary electrode, and secondary electrode relative to the reference point corresponding to positions of the user interface shown in FIGS. 65A-65C, 66A-66C, 67A-67C, 68A-68C, 69A-69C, and 70A-70C, respectively;

FIGS. 71A, 72A, 73A, 74A, 75A, and 76A are side views of the user interface of FIG. 58 being manipulated to position multiple components relative to a reference point;

FIGS. 71B, 72B, 73B, 74B, 75B, and 76B are schematic diagrams of positioning of distal ends of the sheath, primary electrode, and secondary electrode relative to the reference point corresponding to positions of the user interface shown in FIGS. 71A, 72A, 73A, 74A, 75A, and 76A, respectively;

FIGS. 77-81 are flow diagrams of illustrative methods of positioning components using a user interface;

FIG. 82 is a side view of another embodiment of a user interface for positioning multiple components relative to a reference point;

FIG. 83 is an exploded view of the user interface of FIG. 82;

FIG. 84A is a side view of an outer housing of the user interface of FIG. 82;

FIGS. 84B and 84C are cross-sectional views of the outer housing of the user interface of FIG. 82;

FIG. 85A is a side view of a shaft of the user interface of FIG. 82;

FIG. 85B is a cross-sectional view of a base of the shaft of the user interface of FIG. 82;

FIGS. 86A and 86B are side views of a primary actuator of the user interface of FIG. 82;

FIG. 86C is a cross-sectional view of the primary actuator of the user interface of FIG. 82;

FIGS. 87A and 87B are side views of the secondary actuator of the user interface of FIG. 82;

FIGS. 87C and 87D are cross-sectional views of the secondary actuator of the user interface of FIG. 82;

FIGS. 88A, 89A, 90A, 91A, 92A, and 93A are side views of the user interface of FIG. 82 being manipulated to position electrodes within a body;

FIGS. 88B, 89B, 90B, 91B, 92B, and 93B are schematic diagrams of positioning of distal ends of the sheath, primary electrode, and secondary electrode relative to a reference point corresponding to positions of the user interface of FIGS. 88A, 89A, 90A, 91A, 92A, and 93A, respectively;

FIG. 94 is a side view of another embodiment of a user interface for positioning multiple components relative to a reference point;

FIG. 95 is an exploded view of the user interface of FIG. 94;

FIGS. 96A and 97A are side views of the user interface of FIG. 94 being manipulated to position a sheath;

FIGS. 96B and 97B are schematic diagrams of positioning of distal ends of the sheath, primary electrode, and secondary electrode relative to a reference point corresponding to positions of the sheath actuator of FIGS. 96A and 97A, respectively;

FIGS. 98A, 99A, 100A, and 101A are side views of the user interface of FIG. 94 being manipulated to position electrodes within a body;

FIGS. 98B, 99B, 100B, and 101B are cross-sectional views of the user interface of FIG. 94 being manipulated to position electrodes within a body corresponding with positions of the user interface of FIGS. 98A, 99A, 100A, and 101A, respectively;

FIGS. 98C, 99C, 100C, and 101C are schematic diagrams of positioning of distal ends of the sheath, primary electrode, and secondary electrode relative to a reference point corresponding to positions of the user interface of FIGS. 98A, 99A, 100A, and 101A, respectively;

FIG. 102 is a side view of another embodiment of a user interface for positioning multiple components relative to a reference point;

FIG. 103 is an exploded view of the user interface of FIG. 102;

FIGS. 104A, 105A, 106A, 107A, and 108A are side views of the user interface of FIG. 102 being manipulated to position electrodes within a body;

FIGS. 104B, 105B, 106B, 107B, and 108B are cross-sectional views of the user interface of FIG. 102 being manipulated to position electrodes within a body corresponding with positions of the user interface of FIGS. 104A, 105A, 106A, 107A, and 108A, respectively;

FIGS. 104C, 105C, 106C, 107C, and 108C are schematic diagrams of positioning of distal ends of the sheath, primary electrode, and secondary electrode relative to a reference point corresponding to positions of the user interface of FIGS. 104A, 105A, 106A, 107A, and 108A, respectively;

FIG. 109 is a side view of another embodiment of a user interface for positioning multiple components relative to a reference point;

FIG. 110 is an enlarged partial cutaway view of a primary actuator grip of the user interface of FIG. 109;

FIG. 111 is an exploded view of the user interface of FIG. 109;

FIGS. 112A, 113A, and 114A are side views of the user interface of FIG. 109 being manipulated to position a sheath;

FIGS. 112B, 113B, and 114B are schematic diagrams of positioning of distal ends of the sheath, primary electrode, and secondary electrode relative to a reference point corresponding to positions of the sheath actuator of FIGS. 112A, 113A, and 114A, respectively;

FIG. 115 is a side view of another embodiment of a user interface for positioning multiple components relative to a reference point;

FIG. 116 is an exploded view of the user interface of FIG. 115;

FIGS. 117A and 118A are side views of the user interface of FIG. 94 being manipulated to position a sheath;

FIGS. 117B and 118B are schematic diagrams of positioning of distal ends of the sheath, primary electrode, and secondary electrode relative to a reference point corresponding to positions of the sheath actuator of FIGS. 117A and 118A, respectively;

FIGS. 119A, 120A, 121A, 122A, and 123A are side views of the user interface of FIG. 115 being manipulated to position electrodes within a body;

FIGS. 119B, 120B, 121B, 122B, and 123B are cross-sectional views of the user interface of FIG. 115 being manipulated to position electrodes within a body corresponding with positions of the user interface of FIGS. 119A, 120A, 121A, 122A, and 123A, respectively;

FIGS. 119C, 120C, 121C, 122C, and 123C are schematic diagrams of positioning of distal ends of the sheath, primary electrode, and secondary electrode relative to a reference point corresponding to positions of the user interface of FIGS. 119A, 120A, 121A, 122A, and 123A, respectively; and FIGS. 124-126 are flow diagrams of illustrative methods of positioning components using a user interface.

DETAILED DESCRIPTION

The following description is merely illustrative in nature and is not intended to limit the present disclosure, application, or uses. It will be noted that the first digit of three-digit reference numbers, the first two digits of four-digit reference numbers correspond to the first digit of one-digit figure numbers and the first two-digits of the figure numbers, respectively, in which the element first appears.

The following description explains, by way of illustration only and not of limitation, various embodiments of user interfaces to position electrodes for electrosurgical apparatuses, as well as systems including such user interfaces and methods of using the same. As will be described in detail below, electrosurgical techniques position first and second electrodes adjacent a reference point where electrical treatment, such as ablative treatment, is to be applied. For a specific example, the user interfaces and methods of their use may be used for ablating and/or coagulating tissue, removing lesions, and for performing other medical procedures within the lung.

It will be appreciated that various embodiments of user interfaces described herein may help to simplify the process of positioning the electrodes and holding the electrodes in place. As will be described below, various embodiments of the user interface accomplish the selective positioning and locking in place of the electrodes by depressing releases and sliding levers, rotating and sliding a housing, or combinations of sliding levers and rotating housings.

Figure 1:
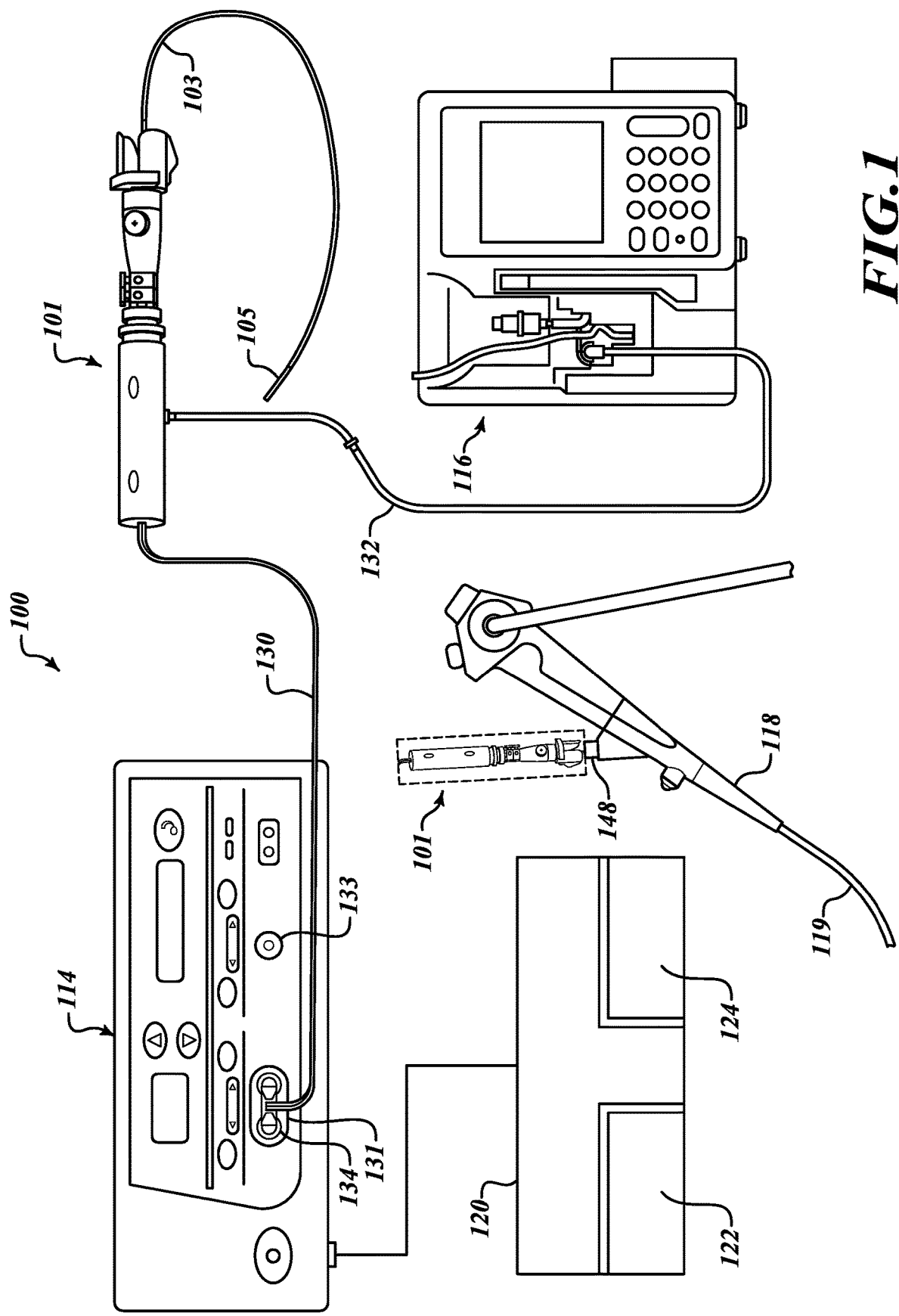
FIG. 1 is a block diagram in partial schematic form of an illustrative system for treating tissue.

Referring to FIG. 1, a system 100 is provided for treating tissue at a reference point in an anatomical region of a patient (not shown in FIG. 1). The system 100 may be a bipolar or monopolar radio frequency (RF) system, as desired, for treating tissue in a patient. Specifically, the system 100 may be employed for coagulation and/or ablation of soft tissue during percutaneous and/or endoscopic, including bronchoscopic, surgical procedures, such as, for example, partial and/or complete ablation of cancerous and/or noncancerous organ lesions. As will be further described, the tissue is treated by positioning one or more electrodes proximate the tissue to be treated and passing an electrical current through the tissue at a reference point.

In some embodiments, the system 100 includes a user interface 101, an electrosurgical radio frequency (RF) generator operating as a switchable current source 114, an infusion pump 116, and an electrosurgical instrument or apparatus, such as without limitation a bronchoscope 118. It will be appreciated that the electrosurgical instrument or apparatus may also include an endoscope or any other electrosurgical instrument as desired for a particular application. The bronchoscope 118 may be configured to receive the user interface 101 at a port 148 to enable the user interface 101 to manipulate electrodes at the reference point via the bronchoscope 118.

The user interface 101 electrically communicates with the switchable current source 114 though an electrical conductor 130. In some embodiments, the electrical conductor 130 is connected to an outlet 131 when the system is operated in a bipolar mode. The electrical conductor 130 may be coupled with the outlet 131 using an electrical connector 134 configured to electrically engage the outlet 131. In some other embodiments, the system 100 can be operated in a monopolar mode when the electrical conductor 130 is connected to a secondary outlet 133 with an adapter (not shown in FIG. 1) as desired. The user interface 101 is further connected to the infusion pump 116 with a tube 132 that facilitates the flow of liquid, for example saline solution, from the infusion pump 116 to the user interface 101.

The switchable current source 114 can be operated with the use of a foot operated unit 120 electrically connected to the switchable current source 114. The foot operated unit 120 includes a pedal 122 that instructs the switchable current source 114 to apply an electrical current to electrode(s) (described below) to cut and/or ablate tissue and a pedal 124 that instructs the generator 114 to apply a lower electrical current to the electrode(s) to coagulate tissue.

In various embodiments the bronchoscope 118 includes an insertion tube 119 that permits insertion of a sheath 103 into a body (not shown). A distal end 105 of the sheath 103 is delivered to a location near the tissue to be treated at the reference point. The sheath 103 contains and conveys the electrodes (not shown) to a desired treatment location. Positioning of the distal end 105 of the sheath 103 and the distal ends of the electrodes (not shown in FIG. 1) may be controlled by the user interface 101 received by the bronchoscope 118 at a port 148.

Referring to FIGS. 2-6, distal ends of components are positioned relative to a reference point 201 using various embodiments of a user interface. The reference point 201, for example, may be at a point within a target tissue 202 such as a lesion or any portion of tissue to be treated within a body. Given by way of illustration only and not of limitation, the illustrative embodiments of the user interface described below all are capable of positioning the components as described with reference to FIGS. 2-6, as further described with reference to each of the described embodiments. The description of FIGS. 2-6 is provided as a baseline to describe the operation of the various embodiments of the user interface.

In particular embodiments, a secondary electrode 211 is slidably received within a primary electrode 207, and the primary electrode 207 is slidably received within a sheath 203. In particular embodiments, until a user interface is manipulated to separately move the primary electrode 207 and/or the secondary electrode 211, the primary electrode 207 and the secondary electrode 211 move in concert with the sheath 203, which means that the electrodes 207 and 211 move at a same time and through a same distance as the sheath 203. As will be described below, in some instances, the secondary electrode 211 also may move in concert with the primary electrode 209 while both electrodes move independently of the sheath 103. Components contained within other components are represented with dashed lines in FIGS. 2-6.

Figure 2:
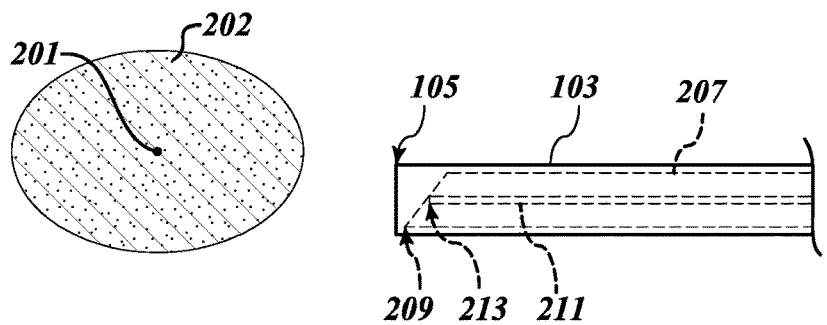
FIGS. 2-6 are schematic diagrams of positioning of distal ends of a sheath, primary electrode, and secondary electrode relative to a reference point.

Referring to FIG. 2, the sheath 203, the primary electrode 207, and the secondary electrode 211 are shown as they are positioned at an initial position relative to the reference point 201 at or near the target tissue 202. More particularly, FIG. 2 shows the components as they might be positioned upon the insertion of the sheath 203 through an insertion tube in a bronchoscope, such as the insertion tube 119 and the bronchoscope 118 of FIG. 1, before they are moved into precisely desired locations by manipulating the user interface (not shown) as further described below.

A distal end 205 of the sheath 203 is positioned close to the target tissue 202. The primary electrode 207 is slidably received within the sheath 203, with a distal end 209 of the primary electrode 207 at or near the distal end 205 of the sheath. Specifically, FIG. 2, for example, shows the distal end 209 of the primary electrode 207 positioned just short of the distal end 205 of the sheath 203. In turn, the secondary electrode 211 is slidably received within the primary electrode 207, with the distal end 213 of the secondary electrode 211 positioned just within the distal end 209 of the primary electrode 207.

Figure 3:
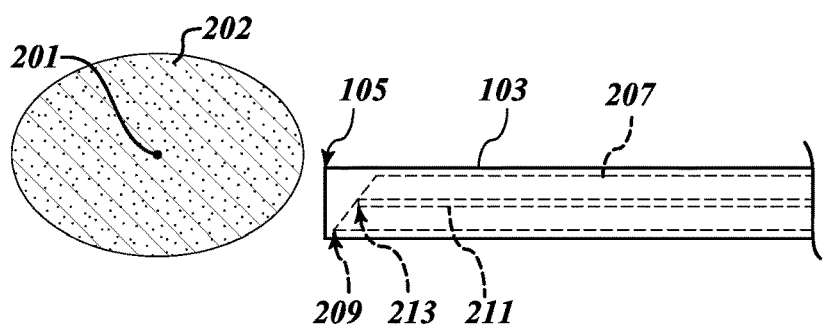

Referring to FIG. 3, the sheath 203, the primary electrode 207, and the secondary electrode 211 are shown as they are positioned once the sheath 203 has been moved closer to the reference point 201. As contrasted with FIG. 2, in FIG. 3, a distal end 205 of the sheath 203 has been moved closer to the reference point 201 at the edge of the target tissue 202. Just as in FIG. 2, because the primary electrode 207 and the secondary electrode 211 have not been separately moved through the manipulation of a user interface (not shown), the primary electrode 207 and the secondary electrode 211 have moved with the movement of the sheath 203. Thus, at the deployment position closer to the reference point 201, the distal end 209 of the primary electrode 207 remains positioned just short of the distal end 205 of the sheath 203. Similarly, the distal end 213 of the secondary electrode 211 remains positioned just within the distal end 209 of the primary electrode 207. As will be further described with reference to embodiments of a sheath lock that may be part of a user interface or used in conjunction with a user interface, once the distal end 205 of the sheath 203 has been moved to a desired location, the sheath 203 may be locked in place.

Figure 4:
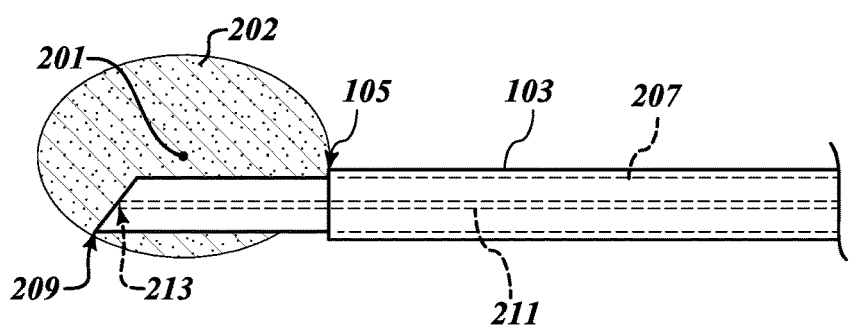

Referring to FIG. 4, the sheath 203, the primary electrode 207, and the secondary electrode 211 are shown as they are positioned once the primary electrode 207 has been extended from the sheath 203 toward the reference point 201 and into the target tissue 202. In particular embodiments, unless the user interface (not shown) is manipulated to disengage movement of the secondary electrode 211 from movement of the primary electrode 207, the secondary electrode 211 moves in concert with the primary electrode 207, with the secondary electrode 211 moving in the same direction and the same distance as the primary electrode 207. Thus, as shown in FIG. 4, the primary electrode 207 as the primary electrode 207 is extended beyond the distal end 105 of the sheath 103, and the secondary electrode 211 moves in concert with the primary electrode 207. As shown in FIG. 4, the distal end 209 of the primary electrode 207 is extended toward the reference point 201 and beyond the distal end 205 of the sheath 203. The distal end 213 of the secondary electrode 211 remains positioned just within the distal end 209 of the primary electrode 207. In particular embodiments, the primary electrode 207 is in the form of a needle, with the distal end 209 being configured to pierce tissue, such as the target tissue 202, to enable the distal end 209 of the primary electrode 207 to reach a desired position, and to be able to situate the secondary electrode 211 at a desired point.

As will be further described below, once the distal end 205 of the sheath 203 is in a desired location and locked in place, embodiments of the user interface allow the primary electrode 207 to be unlocked so that the primary electrode 207 may be moved independently of the sheath 103. As also further described below, embodiments of the user interface may keep motion of the secondary electrode 211 locked with motion of the primary electrode 207 so that the distal end 213 of the secondary electrode 211 moves in concert with the distal end 209 of the primary electrode 207. As also further described below, embodiments of a user interface permit one or both of the primary electrode 207 and the secondary electrode 211 to be fixed in position—that is, remain in place—so that one or both of the electrodes 207 and 211 are secured at a current position. Thus, for example, a position of the primary electrode 207 may be fixed while the secondary electrode 211 may be moved independently of the primary electrode 207, or a position of the secondary electrode 211 may be fixed while the primary electrode 207 may be moved independently of the secondary electrode 211. Also, both electrodes 207 and 211 may be fixed in place, for example, when treatment is administered by applying an electrical current using an electrosurgical apparatus such as that shown in the system 100 of FIG. 1.

Figure 5:
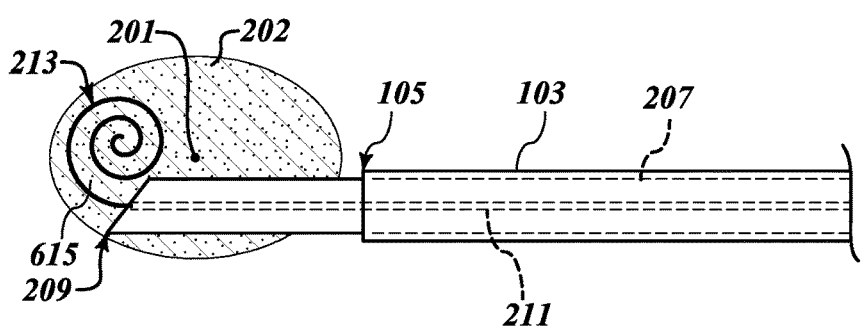

Referring to FIG. 5, the sheath 203, the primary electrode 207, and the secondary electrode 211 are shown as they are positioned once the secondary electrode 211 has been extended from the primary electrode 207. A distal end 213 of the secondary electrode 211 is deployed at a position on an opposite side of the reference point 201 and at an opposite side of the target tissue 202 from the primary electrode 207. In particular embodiments, the secondary electrode 211 is configured as coiled wire which is received within the primary electrode 207 in a straightened form. Once the user interface is manipulated to independently extend the secondary electrode 211 from the primary electrode 207, the secondary electrode 211 coils. As a result, the distal end 213 of the secondary electrode 211 corkscrews into tissue, such as the target tissue 202. The corkscrewing of the distal end 213 of the secondary electrode 211 may assist in securing the position of the distal end 213 of the secondary electrode 211 during treatment. FIG. 5 also shows insulation 215 along a length of the secondary electrode 211, but which stops short of the distal end 213 of the secondary electrode 211. The insulation 215 electrically insulates the secondary electrode 211 from the primary electrode 207 such that, when electrical current is applied to proximal ends (not shown) of the primary electrode 207 and the secondary electrode 211, the electrical current may only flow between the distal end 209 of the primary electrode 207 and the uninsulated distal end 213 of the secondary electrode 211.

Figure 6:
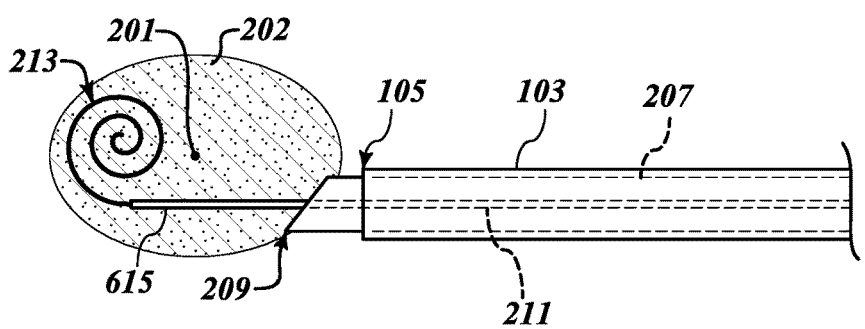

Referring to FIG. 6, the sheath 303, the primary electrode 207, and the secondary electrode 511 are shown as they are positioned once the primary electrode 207 is partially retracted away from the reference point 201 and partially retracted from the target tissue 202 and into the sheath 503.

As previously described, a needle shape of the primary electrode 207 assists in positioning the distal end 213 of the secondary electrode 211 at a desired location. Once the distal end 213 of the secondary electrode 211 has been disposed at that location, however, it may be desired to move a distal end 209 of the primary electrode 207 away from the reference point 201 to create a desirable gap between the distal end 213 of the secondary electrode 211 and the distal end 209 of the primary electrode 207 across which electrical current may be applied to treat the target tissue 202 near the reference point 201. As will be described further below, once the distal end 213 of the secondary electrode 211 has been secured at a desirable location, embodiments of the user interface (not shown in FIG. 6) permit the primary electrode 207 to be unlocked and moved independently from the secondary electrode 211 to enable the partial retraction shown in FIG. 6. Once partially retracted, embodiments of the user interface also enable the primary electrode 207 to be locked in place.

Referring to FIGS. 7A and 7B, an apparatus 700 includes an illustrative user interface 701 received at a port 748 of an electrosurgical apparatus 718, such as a bronchoscope or another minimally invasive device used for performing diagnostic or therapeutic tasks by extending a sheath or catheter into a body (not shown in FIGS. 7A and 7B). In the apparatus 700 of FIG. 7A, the user interface 701 includes a sheath actuator 704 and a sheath lock 706 configured to move the sheath 103 to a desired location to position a distal end 105 of the sheath 103 relative to the reference point 201. In some embodiments, the sheath actuator 704 may be a slidable mechanism incorporating a slidable sleeve 712 that is received within a collar 714. The slidable sleeve 712 may be locked in position at the collar 714 by the sheath lock 706. The sheath lock 706 may be a spring-loaded locking pin, a thumbscrew, or another mechanism configured to mechanically engage the slidable sleeve 712 to secure the slidable sleeve 712—and, in turn, the sheath 703—in place at a desired location.

In some embodiments, the sheath actuator 704 may be part of the user interface 701. For example, in the user interface 701 of FIG. 7A the slidable sleeve 712 is fixably engaged with an interface housing 710 at a distal end 716 of the interface housing 710. The collar 714 then may engage the port 748 on the electrosurgical apparatus 718, where movement of the slidable sleeve 712 within the collar 714 controls movement of the sheath 103. In some other embodiments, the sheath actuator 704 may, for example, be part of the electrosurgical apparatus 718. The collar 714 may be fixably joined to the port 748. The slidable sleeve 712 may be associated with the port 748 to engage the distal end 716 of the interface housing 710. In another embodiment, the slidable sleeve 712 may be fixably joined to the distal end 716 of the interface housing 710 and be configured to receivably engage the collar 714 that is fixably attached to the port 748. Any of these embodiments of the sheath actuator 704 may facilitate movement of the sheath 103 as described below.

In various embodiments the user interface 701 is mechanically coupled with a primary electrode 207 slidably received within the sheath 103, with a distal end 209 of the primary electrode 207 positioned just short of the distal end 105 of the sheath 103. The user interface 701 is also mechanically coupled with a secondary electrode 211 slidably received within the primary electrode 207, with the distal end 213 of the secondary electrode 211 positioned just within the distal end 209 of the primary electrode 207. Embodiments of the user interface 701 may be configured to secure the primary electrode 207 and the secondary electrode 211 relative to the sheath 103 so that both the primary electrode 207 and the secondary electrode 211 move in concert with the sheath 103 as the sheath is moved as described with reference to FIG. 3.

Referring to FIGS. 8A and 8B, manipulation of the sheath actuator 704 illustrates an example of how the sheath 103 may be unlocked and moved into position as previously described with reference to FIG. 3. In the configuration shown in FIGS. 8A and 8B, the sheath actuator 704 has been manipulated to enable the sheath 103 to be moved a distance 819 closer to the reference point 201 and the target tissue 202. Specifically, once the sheath lock 706 of the sheath actuator 704 is manipulated to enable movement of the slidable sleeve 712 within the collar 714, the interface housing 710 is moved the distance 819 to move the sheath 103 the same distance 819 toward the reference point 702. Once the sheath 103 has reached the desired location, the slidable sleeve 712 may be locked in position at the collar 714 by the sheath lock 706. As will be described further below, embodiments of the user interface 701 maintain the positions of the primary electrode 207 and the secondary electrode 211 relative to the sheath 103 as the sheath actuator 704 is used to move the sheath 103. Therefore, a distal end 209 of the primary electrode 207 and a distal end 213 of the secondary electrode 211 also are moved by the distance 219 toward the reference point 201.

Figure 9:
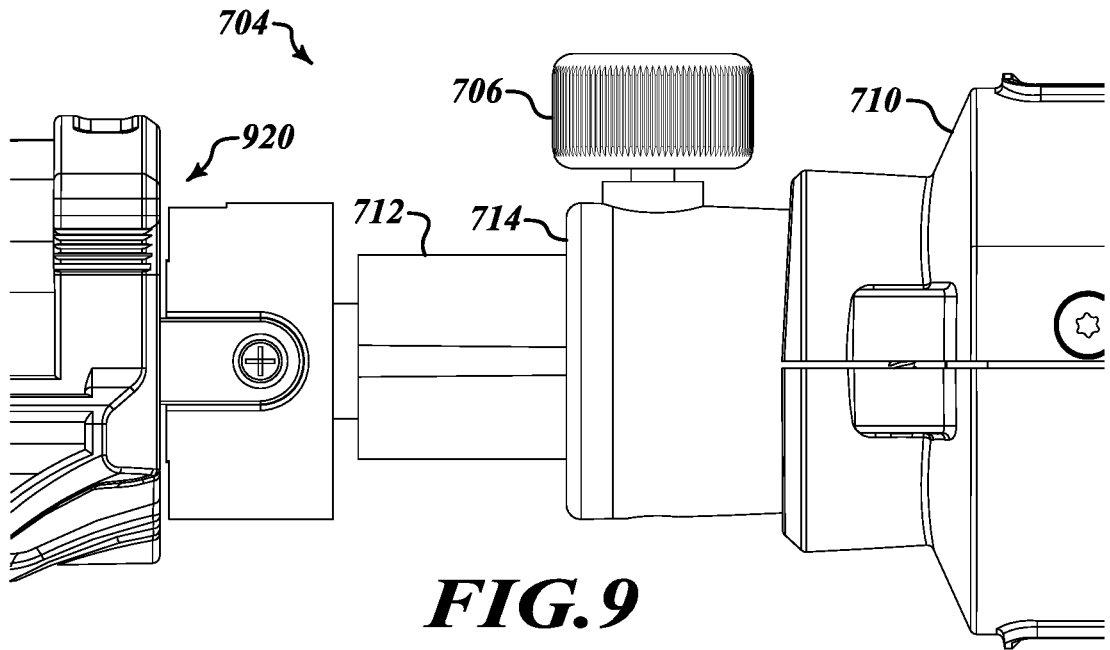
FIG. 9 is a side view of an illustrative sheath actuator and a sheath lock.

Referring to FIG. 9, an enlarged external view shows an illustrative sheath actuator 704 and a sheath lock 706 in greater detail. The sheath actuator 704 includes a slidable sleeve 712 that is fixably attached to a coupling 920 configured to engage a port (not shown in FIG. 9) of an electrosurgical apparatus (not shown in FIG. 9) such as a bronchoscope. The sheath lock 706 in the embodiment of FIG. 9 is a thumbscrew that may be loosened to permit movement of a collar 714 fixably attached to the interface housing 710 to move the sheath (not shown in FIG. 9) as previously described with reference to FIGS. 7 and 8. After the interface housing 710 has been manipulated to slide the collar 714 relative to the slidable sleeve 712 to move the sheath to a desired location, the sheath lock 706 is reengaged, such as by turning a thumbscrew, to fix the position of the sheath.

Figure 10:
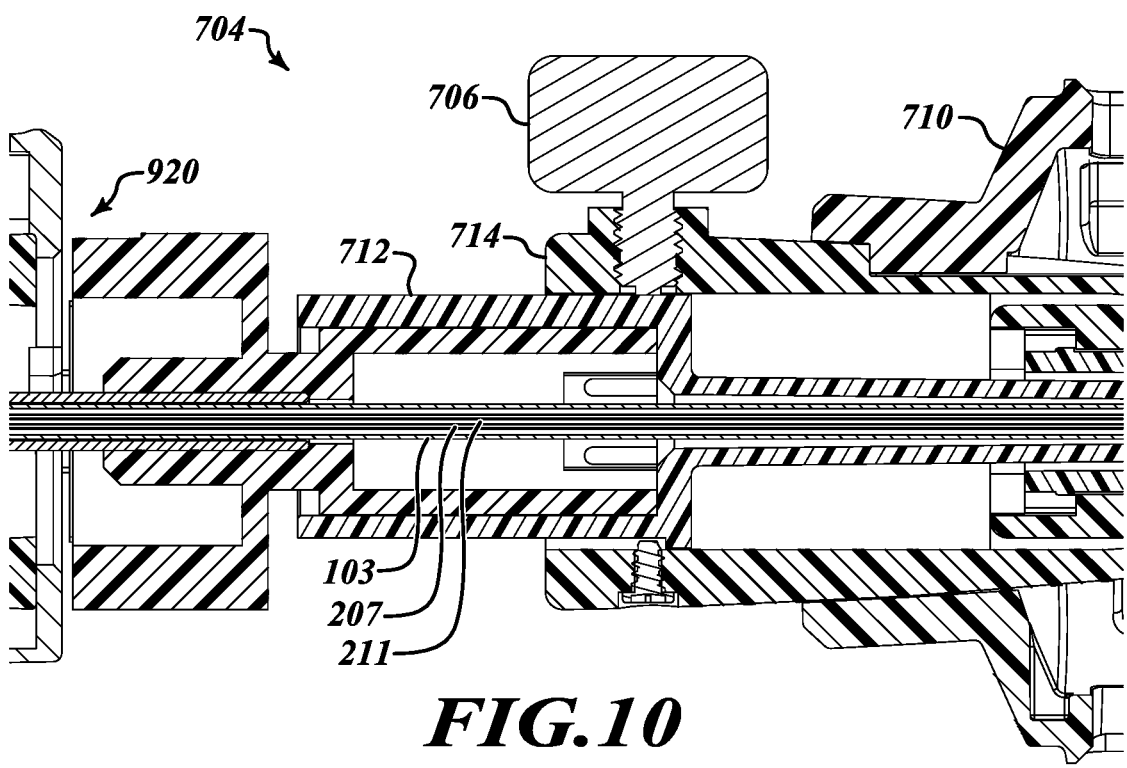
FIG. 10 is a cutaway view of the sheath actuator and sheath lock of FIG. 9.

Referring to FIG. 10, a cutaway view of the illustrative sheath actuator 704 shows internal operation of the sheath actuator 704 of FIG. 9. As previously described, the sheath actuator 704 includes the slidable sleeve 712 that is fixably attached to the coupling 920. In some embodiments the sheath lock 706 is a thumbscrew that may be loosened to permit movement of the collar 714 fixably attached to the interface housing 710 to move the sheath 103 and, in concert therewith, the primary electrode 207 and the secondary electrode 211 received within the sheath 103. After the interface housing 710 is manipulated to slide the collar 714 relative to the slidable sleeve 712 to move the sheath 103 to the desired location, the sheath lock 706 is turned to fix the position of the collar 714 relative to the slidable sleeve 712 to fix the position of the sheath 103.

Referring to FIG. 11, in some embodiments an illustrative user interface 1101 is used to position a sheath 1003, a primary electrode, and secondary electrode relative to a reference point (not shown in FIG. 11). The user interface 1101 includes components that are moved parallel with or transverse to an axis 1121 or rotated about a curve 1123 around the axis 1121, as further described below. The user interface 1101 includes a coupling 1120 and a sheath actuator 1104, including a slidable sleeve 1112 that moves within a collar 1114 fixably attached to the interface housing 1110 when released by a sheath lock 1106 to move the sheath 103, as previously described with reference to FIGS. 9 and 10. The user interface 1101 also receives leads 1122 that provides electrical connections between electrodes and a switchable current source (not shown in FIG. 11), as previously described with reference to FIG. 1. The user interface 1101, as well as other embodiments of the user interface described throughout this description, also receives a source of saline fluid (not shown) that may be passed through the sheath to facilitate the application of electrosurgical treatments. Although not expressly shown in subsequent depictions of other illustrative embodiments of the user interface described with reference to FIGS. 35-75, it will be appreciated that similar leads may be used to provide electrical connections between the electrodes and a switchable current source.

The illustrative user interface 1101 shown in FIG. 11 includes several user controls whose operation and effect are described in further detail in the following figures. A primary release 1130 extends from a lower side 1124 of the housing 1110 and is configured to unlock movement of the primary electrode (not shown) that is moved through manipulation of a primary actuator 1132 extending from an upper side 1126 of the housing 1110. The primary actuator 1132 is mechanically coupled with the primary electrode (not shown in FIG. 11) so that, when the primary actuator 1132 moves relative to the housing 1110, the primary electrode moves relative to the reference point (also not shown in FIG. 11). A depth gauge 1190 on the housing 1110 includes an indicator 1192 to indicate an insertion depth of the primary electrode beyond an end of the sheath (not shown).
electrode moves relative to the reference point (also not shown in FIG. 11). A depth gauge 1190 on the housing 1110 includes an indicator 1192 to indicate an insertion depth of the primary electrode beyond an end of the sheath (not shown).

A secondary release 1150 is integrated with a secondary actuator 1152 disposed along the upper side 1126 of the housing and is configured to unlock and control movement of the secondary electrode, respectively. The secondary actuator 1152 is fixably coupled with a secondary grip 1153 extending from the lower side 1124 of the housing 1110. The secondary actuator 1152 is mechanically coupled with the secondary electrode (not shown) so that, when the secondary actuator 1152 moves relative to the housing 1110, the secondary electrode moves relative to the reference point (not shown in FIG. 11).

An actuator interlock 1140 positioned along the lower side 1124 of the housing 1110 may restrict movement of the secondary electrode relative to the primary electrode, block use of the primary release 1130, and decouple the secondary electrode (not shown) from the primary electrode, as further described below. As will be shown below, when both the primary actuator 1132 and the secondary actuator 1152 move in concert, the actuator interlock 1140 moves in concert with the primary actuator 1132 and the secondary actuator. As will be further described below, the primary release 1130, the actuator interlock 1140, and the secondary release 1150 enable selective movement of the electrodes in concert and independently to facilitate placement of distal ends of the electrodes within a body.

Referring to FIGS. 12A and 12B, in some embodiments the user interface 1101 has an initial deployment configuration once a sheath 103 has been deployed near the reference point 201. As described with reference to FIGS. 7A-10, a sheath actuator 1104 and sheath lock 1106 have been previously engaged to position a distal end 105 of the sheath 103 at a desired location near the reference point 201, as shown in an inset view. As previously described, a primary electrode 207 is received within the sheath 103, with the distal end 209 of the primary electrode 207 initially positioned just short of the distal end 105 of the sheath 103. A secondary electrode 211 is received within the primary electrode 207, with the distal end 213 of the secondary electrode 211 positioned just short of the distal end 209 of the primary electrode 207.

Referring to FIGS. 13A and 13B, in some embodiments of the user interface 1101, the primary release 1130 is engaged to allow the primary electrode 207 to be moved. Specifically, releasing the primary release 1130 is accomplished by depressing the primary release 1130 toward the housing 1110 of the user interface in a direction 1331. Activating the primary release 1130 does not cause movement of the sheath 103 or the electrodes 207 or 211 relative to the reference point 201 as shown in the inset view of FIG. 12B, but only enables movement of the primary electrode 207 which, as further described below, may or may not also move the secondary electrode 211.

Referring to FIGS. 14A and 14B, the user interface 1101 is shown after a primary actuator 1132 has been moved a distance 1433. After the primary actuator 1132 is moved, the primary release 1130 is disengaged to allow the primary release to move in a direction 1431 away from the housing 1110 to resume its original position as shown with reference to FIG. 12A. Four actions result from the movement of the primary actuator 1132. First, as shown in the inset of FIG. 14B, movement of the primary actuator 1132 extends the primary electrode 207 beyond the distal end 105 of the sheath 103 and into the target tissue 202, thereby positioning the distal end 209 of the primary electrode 207 close to the reference point 201. Second, the secondary electrode 211 moves in concert with the primary electrode 207, with the distal end 213 of the secondary electrode 211 continuing to be positioned just short of the distal end 209 of the secondary electrode 207. Third, the concerted movement of the primary electrode 207 and the secondary electrode 211 is reflected in movements through the same distance 1433 of the actuator interlock 1140, the secondary release 1150, the secondary actuator 1152, and the secondary grip 1153. The primary actuator 1132 and the secondary actuator 1152 are mechanically linked to enable the concerted movement of the primary electrode 207 and the secondary electrode 211, as further described below. Fourth, the indicator 1192 of the depth gauge 1190 also is mechanically co15upled to the primary actuator 1132. Thus, the distance 1433 the primary actuator 1132 and the primary electrode 207 are moved is shown on the depth gauge 1190 by the indicator 1192.

Referring to FIG. 15, a primary actuator 1132 and a primary release 1130 may be used in embodiments of the user interface described with reference to FIGS. 11-14B, with the primary release 1130 in a locked position as shown in FIGS. 12A and 14.A The primary actuator 1132 is mechanically coupled with a primary electrode slider 1533 that is mechanically coupled with the primary electrode 207 to move the primary electrode 207 as previously described with reference to FIGS. 2-6 and 12-14. When the primary release 1130 is in a locked position, a lock member 1534 that extends through the inside of the primary actuator 1132 is urged by a biasing member, such as a spring 1535, to force a locking pin 1536 into a starting notch 1537 in a locking rack 1538 within a housing (not shown in FIG. 15) of the user interface of FIGS. 11-14. The locking pin 1536 forcibly engages the starting notch 1537 to prevent movement of the primary actuator 1132, thus also preventing movement of the primary electrode slider 1533 and the primary electrode 207. Thus, with the primary release 1130 in the locked position shown in FIG. 15, the primary electrode slider 1530 and the primary electrode 207 are locked at their current positions.

Referring to FIG. 16, the operation of the primary actuator 1132 and a primary release 1130 are shown with the primary release 1130 engaged to enable movement of the primary actuator 1132. When a force is applied to the primary release 1130 to move the primary actuator 1132 in a direction 1631, the primary release 1130 causes the lock member 1534 to move in the direction 1631, compressing the spring 1535 and moving the locking pin 1536 out of the starting notch 1537 to enable movement of the primary actuator 1132. In other words, pressing the primary release 1130 frees the locking pin 1536 from the starting notch 1537 of the locking rack 1538 to allow the primary actuator 1132 to move the primary electrode slider 1533.

Referring to FIG. 17, the operation of a primary actuator 1132 in moving the primary electrode slider 1533 and the primary electrode 207 is shown while the primary release 1130 remains engaged to enable movement of the primary actuator 1132. As shown with reference to FIG. 16, enabling release of the locking pin 1536 from the starting notch 1537 by the primary actuator 1132 causes the lock member 1534 to compress the spring 1535 to allow the primary actuator 1132 and, thus, the primary electrode slider 1533 and the primary electrode 207, to move in a direction 1731 relative to the housing 1110. The force applied to the primary release 1130 continues to cause the lock member 1534 to compress the spring 1535 and thus allows the locking pin 1536 to move relative to the locking rack 1538 where, if released in the position shown in FIG. 17, the locking pin 1536 would be allowed to engage a selected notch 1739 in the locking rack 1538. It should be noted that the primary release 1130 moves in concert with the primary actuator 1132 as the primary actuator 1132 is moved relative to the housing 1110. Thus, only the starting notch 1537, the locking rack 1538, and the housing 1110 remain in the same position in the embodiment of FIG. 17.

Upon release of the primary release 1130, pressure previously applied by the lock member 1534 on the spring 1535 is released. As a result, the spring 1535 presses against the lock member 1534 and, in turn, causes the locking pin 1536 to engage the selected notch 1739 in the locking rack 1538. Then, similar to the configuration shown in FIG. 15, the primary electrode slider 1530 and the primary electrode 207 are then locked at a new position relative to the housing 1110 which also would move a distal end (not shown in FIG. 15) of the primary electrode 207 in a body (also not shown in FIG. 17).

Referring to FIGS. 18A and 18B, in some embodiments the primary electrode 207 has been deployed with the distal end 209 near the reference point 201 and locked in position as shown in FIG. 14B just before the secondary release 1150 is engaged to unlock movement of the secondary electrode 211. The secondary release 1150 is integrated with the secondary actuator 1152. Specifically, the secondary release 1150 constitutes an end of the secondary actuator 1152 that may be depressed in a direction 1831 that partially rotates the secondary actuator 1152 downward toward the interface housing 1110 to disengage the secondary actuator 1152 from the primary electrode slider (not shown in FIG. 18A). Disengagement of the secondary actuator 1152 permits the secondary actuator 1152 and a fixably coupled secondary grip 1153 to be moved independently of the primary actuator 1132 to enable the secondary electrode 211 to be moved independently of the primary electrode 207 toward the reference point 102. Operation of the secondary release 1152 to disengage the secondary actuator 1150 from the primary electrode slider is further described with reference to FIGS. 21 and 22.

Referring to FIGS. 19A and 19B, in some embodiments of the user interface 1101, the secondary release 1150 may be depressed to partially rotate the secondary actuator 1152 toward the interface housing 1110 to permit movement of the secondary actuator 1152 independent of the primary actuator 1132. Although the secondary actuator 1152 is unlocked by depressing the secondary release 1150, the secondary actuator 1152 and the associated secondary grip 1153 have not yet been moved. Thus, the distal end 213 of the secondary electrode 211 has not yet been moved relative to the distal end 209 of the primary electrode 207 toward the reference point 201, as shown in the inset view.

Referring to FIGS. 20A and 20B, the secondary actuator 1152 has been moved a distance 2033 to extend the distal end 213 of the secondary electrode 211 beyond the distal end 209 of the primary electrode 207 and beyond the reference point 201. The secondary actuator 1152 is fixably engaged with a secondary grip 1153. Thus, the secondary grip 1153 also moves the distance 2033. Fixably engaging the secondary actuator 1152 with the secondary grip 1153 enables a user (not shown) to apply more force in extending the secondary electrode 211 than may be possible if the user only were able to apply force on one side of the interface housing 1110 to move the secondary actuator 1152. This may be valuable if, for example, the distal end 213 of the secondary electrode 211 were being forced into tissue (not shown) such that a coiled shape of the distal end 213 of the secondary electrode 211 may corkscrew into the tissue to anchor the distal end 213 of the secondary electrode 211 in the tissue. With the secondary actuator 1152 having been moved to extend the distal end 213 of the secondary electrode 211, the secondary release 1150 is released to lock the position of the secondary actuator 1152 and, thus, to lock the position of the secondary electrode 211.

As the secondary actuator 1152 moves through the distance 2033, the actuator interlock 1140 also moves forward by the distance 2033. The term "forward," as used in this description, describes a direction toward a coupling 1120 (FIG. 11) where the user interface engages a port of an electrosurgical apparatus, such as the port 748 of bronchoscope 718 of FIGS. 7 and 8. In the FIGURES to follow, the forward direction consistently is positioned either toward the left-hand side of the FIGURE or coming out of the FIGURE. As further described below, the forward travel of the secondary actuator 1152 and the secondary grip 1153 is arrested when the actuator interlock 1140 abuts the primary release 1130 (and, thus, the coupled primary actuator 1132) and the secondary grip 1153 (and, thus, the coupled secondary actuator 1152). In various embodiments, for example, a pin (not shown) on a forward end of the primary electrode slider 1533 may reach an end of a slot on the actuator interlock 1140 that, in turn, stops the movement of the secondary actuator 1152 and the secondary grip 1153. Thus, the actuator interlock 1140 serves to limit the travel of the secondary actuator 1152 and, thus, a length by which the distal end 213 of the secondary electrode 211 may be extended beyond the distal end 209 of the primary electrode 207. A configuration of the actuator interlock 1140 and the operation of the actuator interlock is explained with reference to FIGS. 23-31.

Referring to FIG. 21, a secondary release 1150 and a secondary actuator 1152 are shown in a locked position. When the secondary release 1150 is in a locked position, the secondary electrode 211 moves in concert with the primary electrode 207 as previously described with reference to FIGS. 12-17. As previously described, the secondary release 1150 is integrated with the secondary actuator 1152 in the embodiment of FIG. 21. The secondary actuator 1152 is rotatably mounted to a secondary electrode slider 2151 at a pivot 2155. A spring 2157 maintains the secondary release 2150 in the locked position when the secondary release 1150 is not being depressed. A secondary grip 1153 is fixably coupled to the secondary electrode slider 2151 and moves (or does not move, as the case may be) in concert with the secondary actuator 1152. When the secondary release 1150 is in the locked position, a locking arm 2159 engages a locking notch 2139 in the primary electrode slider 1533. As shown in FIG. 21, the secondary electrode 211 is in an extended position in which the primary actuator 1132 and the secondary actuator 1152 no longer move in concert.

Referring to FIG. 22, a secondary release 1150 and a secondary actuator 1152 are shown in an unlocked position. As previously described with reference to FIG. 19, the secondary release 1150 is unlocked by depressing the secondary release 1150, thereby causing the secondary actuator 1152 to deform the spring 2157 and, thus, causing the secondary actuator 1152 to rotate about the pivot 2155 into an unlocked position. With the secondary actuator 1152 rotated into the unlocked position, the locking arm 2159 is withdrawn from the locking notch 2139, thereby enabling the secondary actuator 1152 to move. Then, by applying force to the secondary actuator 1152 and/or the secondary grip 1153, an operator (not shown in FIG. 22) can extend a secondary electrode 211 independently of the primary electrode 207 as previously described with reference to FIGS. 18-20.

According to various embodiments of the present disclosure and as previously described with reference to FIGS. 4 and 12-14, it may be desirable to selectively enable the primary electrode and the secondary electrode to move in concert. However, as described with reference to FIG. 6, once the secondary electrode is deployed, it may be desirable to partially withdraw the primary electrode while maintaining the position of the secondary electrode. Referring again to FIG. 4, the distal end 209 of the primary electrode 207 may be needle-shaped in order to pierce tissue at or adjacent the reference point 201. The secondary electrode 211 is moved in concert with the primary electrode 207, thereby positioning the distal end 213 of the secondary electrode closer to the reference point 201. Referring to FIG. 5, the piercing capability provided by this illustrative configuration of the primary electrode 207 may be useful to deploy the distal end 213 of the secondary electrode 211 at a desired location relative to the reference point 201.

However, once the position of the primary electrode 207 has been exploited to deploy the distal end 213 of the secondary electrode 211, with reference to FIG. 6, it may be desirable to partially retract the distal end 209 of the primary electrode 207 to apply an electrical current over a distance between the distal end 213 of the secondary electrode 211 and the distal end 209 of the secondary electrode 207. Providing a selective degree of movement of the distal end 213 of the secondary electrode 211 independent of the primary electrode 207, as shown in FIG. 6, as well as maintaining the distal end 213 of the secondary electrode 211 when the distal end 209 of the primary electrode 207 is partially withdrawn, is controlled by the actuator interlock 1140 working in concert with the primary actuator and the secondary actuator as further described below with reference to FIGS. 23-31.

Referring to FIG. 23, the actuator interlock 1140 is shown as situated within the housing 1110 of the user interface. Specifically, the actuator interlock 1140 is positioned between the secondary grip 1153 (which moves in concert with the secondary actuator, as previously described with reference to FIGS. 18-22) and the primary release 1130 (which moves in concert with the primary actuator 1132, as previously described with reference to FIGS. 12-17). Portions of the primary release 1130, the actuator interlock 1140, and the secondary grip 1153 extend from the housing 1110 through a channel 2349 on an underside of the housing 1110. As previously described with reference to FIGS. 21 and 22, the secondary actuator 1152 engages the primary electrode slider 1533 to cause the secondary electrode slider 2151 to move in concert with the primary electrode slider 1533. The actuator interlock 1140 is sized such that, in the first position shown in FIG. 23, a second end 2341 of the actuator interlock 1140 abuts a leading end 2331 of the secondary actuator 1153 and a first end 2342 of the actuator interlock 1140 abuts a trailing edge 2354 of the secondary electrode slider 1533 such that the actuator interlock 1140 controls relative movement of the primary release 1130 (and thus the primary actuator 1132) toward the secondary grip 1153 (and thus the secondary actuator 1152) toward one another. In various embodiments, a pin (not shown) fixed to the primary electrode slider 1533 slides within a slot (not shown) within the actuator interlock 1140, and ends of the slot in the actuator interlock 1140 present hard stops that limit the travel of the pin and, corresponding, limit the travel of the secondary electrode slider 2151. Thus, the secondary actuator 1140 operates to maintain a distance between the primary release 1130 and the secondary grip 1153 while the actuator interlock 1140 is in the first position shown in FIG. 23.

The actuator interlock 1140 also features a lock bar (not shown in FIG. 23) that engages the primary release 1130, as further described with reference to FIGS. 29-31. The lock bar prevents the primary release from being engaged while the actuator interlock 1140 is in the first position, as further described below. The actuator interlock 1140 also features locking teeth 2343 configured to engage locking notches (not shown in FIG. 23) within the housing 1110 when the actuator interlock 1140 is in a second position, as further described below with reference to FIG. 24. The locking teeth 2343 operate to secure the actuator interlock 1140 in place to enable the primary actuator (not shown in FIG. 23) and the primary release 1130 to be moved independently of the secondary actuator (not shown in FIG. 23) and the secondary grip 1153 to enable the primary electrode (not shown in FIG. 23) to be partially retracted while the secondary electrode (not shown in FIG. 23) stays in place, as further described below. Finally, a lever 2344 allows an operator to engage the actuator interlock 1140 to rotate the actuator interlock 1140 between the first position and the second position, as further described below.

Referring to FIG. 24, in a first position of the actuator interlock 1140, locking teeth 2343 are situated to potentially engage locking notches 2446 in the housing 1110 to lock the secondary electrode (not shown in FIG. 24) in place. The locking notches 2446 are positioned to receive the locking teeth 2343 after the secondary actuator and the secondary grip (not shown in FIG. 24) are moved to extend the distal end of the secondary electrode (not shown in FIG. 24) as previously described. As will be appreciated and as will be further described below, when the actuator interlock 1140 is rotated from the first position shown in FIG. 24 to a second position (shown in FIGS. 26-28), the locking teeth 2343 fit within the locking notches 2446 to prevent the actuator interlock 1140 from being moved relative to the housing 1110 when, for example, the primary release 1130 is engaged and moved relative to the housing. As further described below, the use of the locking teeth 2343 to secure the position of the actuator interlock 1140 serves to lock a secondary electrode slider to prevent movement of the secondary electrode (neither of which is shown in FIG. 24), as is further described below.

Referring to FIG. 25, the actuator interlock 1140 is disposed within the housing 1110 with the actuator interlock 1140 shown in a first position. The actuator interlock 1140 rotates within the housing 1110 around a primary electrode 207 and a secondary electrode 211. A lever 2344 extending out of the housing 1110 through the channel 2349 allows a user to engage and rotate the actuator interlock 1140. As previously shown in FIGS. 18-20, the interlock lever 2344 is situated forward of a secondary actuator 1152 and a secondary grip 1153, where a forward direction is the left side of the FIGURE.

Referring to FIG. 26, the actuator interlock 1140 is shown in a second position after the secondary electrode (not shown in FIG. 26) has been deployed and before the primary electrode (not shown in FIG. 26) is partially retracted. The lever 2344 is used to rotate the actuator interlock 1140 relative to the housing 1110 so as to cause locking teeth 2343 of the actuator interlock 1140 to move into a second position within the channel 2349 where the locking teeth 2343 engage locking notches (not shown in FIG. 26) to fix the actuator interlock 1140 in place. As previously described with reference to FIG. 23, the actuator interlock 1140 maintains a distance between the primary release (not shown in FIG. 26) and the secondary grip 1153 while the actuator interlock 1140 is in the first position. However, when the actuator interlock 1140 is in the second position as shown in FIG. 26, the actuator interlock 1140 no longer prevents relative motion of the primary release 1130 (and thus the primary actuator 1132) toward the secondary grip 1153 (and thus the secondary actuator 1152). With the actuator interlock 1140 in the second position, the position of the secondary electrode slider 2151 is secured relative to the housing 1110 and, thus, may not move longitudinally relative to the housing 1110; however, the primary actuator 1132 may be moved upon engaging the primary release 1130. Thus, the primary actuator (also not shown in FIG. 26) is enabled to move independently of the secondary actuator (also not shown in FIG. 26) to allow the primary actuator to be moved toward the secondary grip 1153 to retract the primary electrode (not shown in FIG. 26) without moving the secondary electrode (not shown in FIG. 26).

Referring to FIG. 27, another view is provided of the actuator interlock 1140 in the second position to show how the locking teeth 2343 engages locking notches 2446 in the housing 1110 to lock the secondary electrode (not shown in FIG. 26) in place. The locking notches 2446 receive the locking teeth 2343 to lock the actuator interlock 1140 and to fix a position of the secondary electrode slider 2151 in place while the primary actuator 1132 and the primary electrode slider 1533 are able to move upon the primary release 1130 being engaged. Again, the lever 2344 allows a user to move the actuator interlock 1140 from the first position (shown in FIGS. 23-25) to the second position shown in FIGS. 26-28). It will be appreciated that the lever 2344, which is slidable across the channel 2349 to enable the actuator interlock 1140 to be moved into the second position, is in the nature of a swipe lock that can be swiped from the first position to the second position.

Referring to FIG. 28, in the user interface 1101 the actuator interlock 1140 has been rotated within the housing 1110 about the primary electrode 207 and the secondary electrode 211 into the second position. FIG. 28 is similar to FIG. 25 except, in FIG. 28, the actuator interlock 1140 has been rotated into the second position, whereas FIG. 25 showed the actuator interlock 1140 in the first position. The lever 2344 (extending from the actuator interlock 1140 and out of the housing 1110 through a channel 2349) has been engaged by a user to rotate the actuator interlock 1140 into the second position, as previously described with reference to FIGS. 26 and 27.

Referring to FIG. 29, another view of the actuator interlock 1140 is provided to show operation of a lock bar 2945 associated with the actuator interlock 1140. The lock bar 2945 selectively prevents movement of a primary release 1130. As previously described with reference to FIG. 5, once the primary electrode 207 is deployed with the distal end 209 at a desired location relative to the reference point 201, the primary electrode 207 remains stationary while the secondary electrode 211 is extended. The lock bar 2945 prevents the primary release 1130 from being engaged to prevent the primary actuator (not shown in FIG. 29) from being moved to prevent movement of the primary electrode while the secondary electrode (neither of which is shown in FIG. 29) is extended.

Still referring to FIG. 29, the actuator interlock 1140 is shown in the first position and is positioned before the secondary release and secondary actuator are engaged to move secondary electrode (none of which are shown in FIG. 29) independently of the primary actuator and the primary electrode (also not shown in FIG. 29) as shown in FIG. 5. In this position, a distal end 2957 of the lock bar 2945 does not engage the primary release 1130. As previously described with reference to FIGS. 12-17, the primary release 1130 and thus the primary actuator 1132 may be operated to move the primary electrode (not shown in FIG. 29) as desired. As also previously described, for example, and with reference to FIGS. 14 and 22, until the secondary release is engaged the secondary actuator and, thus, the secondary electrode move in concert with the primary actuator and the primary electrode, as previously described.

Referring to FIG. 30, with the actuator interlock 1140 in the first position, the secondary actuator (not shown in FIG. 30) and, thus, the secondary grip 1153 has been moved forward to extend the secondary electrode (not shown in FIG. 30). As a result, the actuator interlock 1140 moves forward and, thus, the lock bar 2945 extends through a lock channel 3060 in the primary release 1130. The lock channel 3060 includes a locking lobe 3062 and an open lobe 3064. When the actuator interlock 1140 is in the first position, the lock bar 2945 passes through the locking lobe 3062 of the lock channel 3060. As a result, if a user attempts to engage the primary release 1130 by depressing it as described with reference to FIG. 13, the lock bar 2945 engages a first inner surface 3063 within the locking lobe 3062, thereby preventing the primary release 1130 from being depressed. However, as further described with reference to FIG. 31, when the actuator interlock 1140 is rotated into the second position, the lock bar 2945 rotates with the actuator interlock 1140 and the lock bar 2945 moves into the open lobe 3064 where the lock bar 2945 no longer engages the first inner surface 3063 when a user attempts to depress the primary release 1130.

Referring to FIG. 31, the actuator interlock 1140 has been rotated within the housing 1110 about the primary electrode 207 and the secondary electrode 211 into the second position. With the actuator interlock 1140 rotated into the second position, the lock bar 2945 has rotated into the open lobe 3064. With the lock bar 2945 extending through the open lobe 3064, a user can depress the primary release 1130 without surfaces of the lock channel 3060 engaging the lock bar 2945. Thus, once the actuator interlock 1140 is moved into the second position, the primary release 1130 may be engaged to enable partial retraction of the primary electrode 207, as further described below.

Figure 32A:
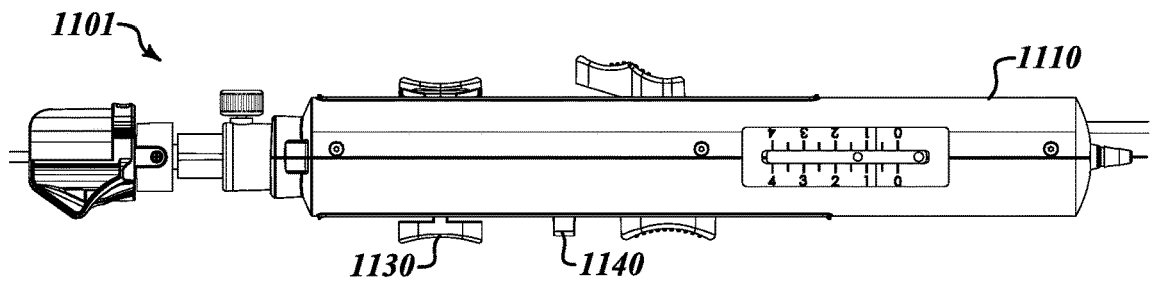
Figure 32B:
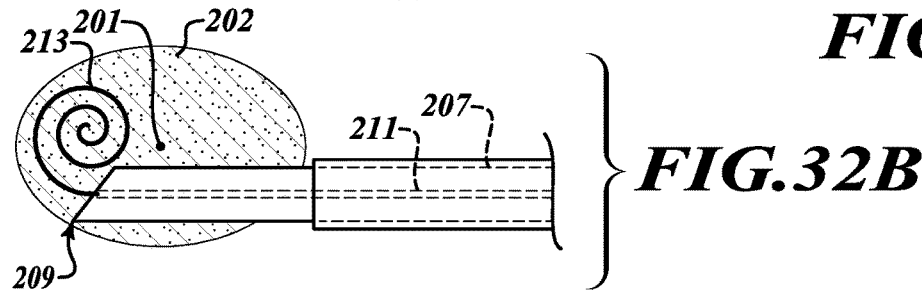

Referring to FIGS. 32A and 32B, the secondary electrode 211 has been deployed and locked in position. The distal end 213 of the secondary electrode 211 extends beyond the reference point 201, and the actuator interlock 1140 has been moved into the second position within the housing 1110 before the primary release 1130 is engaged to initiate retraction of the primary electrode 207 to withdraw the distal end 209 of the primary electrode 207 away from reference point 201. In this manner, once the secondary electrode 211 has been extended and secured in position, the primary electrode 207 may be moved to position the distal end 209 of the primary electrode 207 relative to the distal end 213 of the secondary electrode 211 to facilitate application of an electric current to provide desired treatment. As described with reference to FIGS. 29-31, once the actuator interlock 1140 is in the second position, the lock bar (not shown in FIG. 32A) does not prevent the depressing of the primary release 1130. Thus, the user interface is configured for partial withdrawal of the primary electrode 207.

Figure 33A:
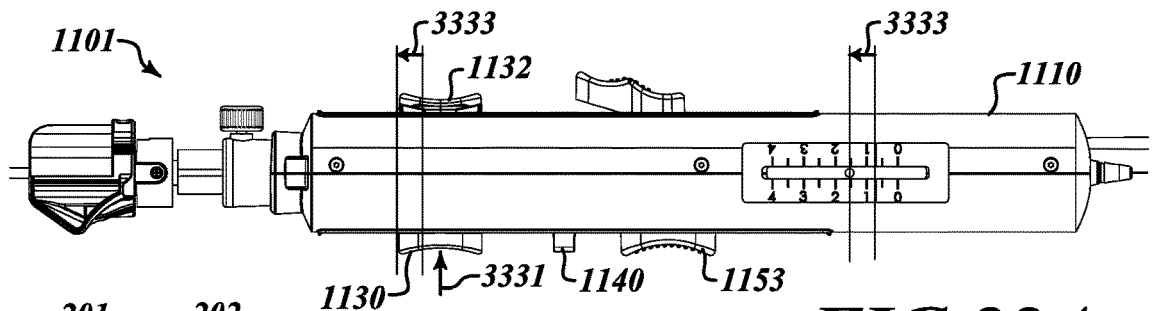
Figure 33B:
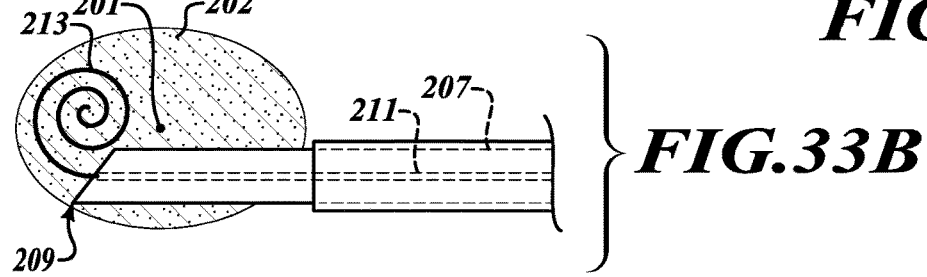

Referring to FIGS. 33A and 33, the primary release 1130 has been depressed in a direction 3331 toward the housing 1110 to release the primary actuator 1132. The primary actuator 1132 and the primary release 1130 may now be moved rearward to partially retract the distal end 209 of the primary electrode 207 away from the reference point 201. Depressing the primary release 1130 allows the primary actuator to move relative to the housing 1110 as previously described with reference to FIGS. 12A-17. As previously described with reference to FIG. 22, the previous activation of the secondary release 1150 caused the locking arm 2259 to disengage from the locking notch 2239 in the primary electrode slider 1533 so that movement of the secondary actuator 1152 and the secondary electrode slider 2151 is no longer coupled with the primary electrode slider 1533. Referring again to FIG. 33A, the actuator interlock 1140 has been rotated into the second position so as not to block relative movement between the primary release 1130 and the secondary grip 1153. Accordingly, the primary actuator 1132 and, thus, the primary electrode 207 may now be moved independently of the secondary electrode 211.

Figure 34A:
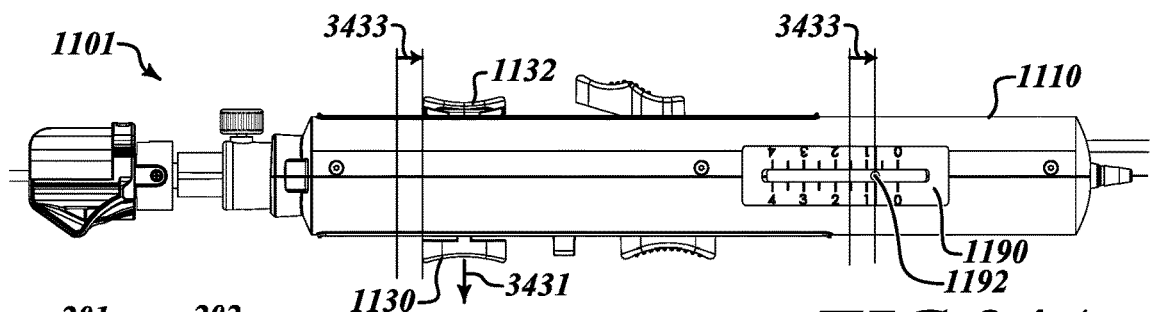
Figure 34B:
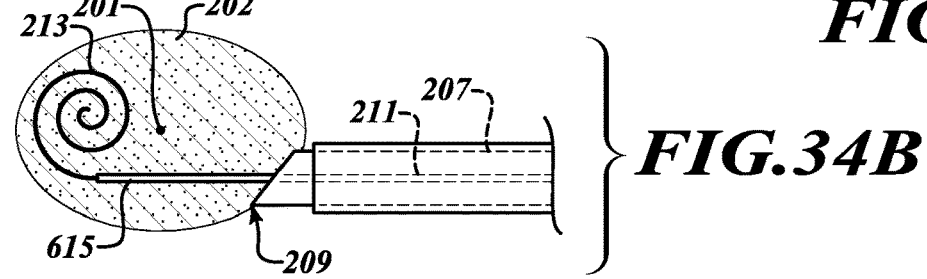

Referring to FIGS. 34A and 34B, the primary actuator 1132 has been moved a distance 3433 to retract the distal end 209 of the primary electrode 207 by that same distance 3433. The primary release 1130 is then released to travel in a direction 3431 where the primary actuator 1132 and the primary release 1130 are then locked in place relative to the housing 1110, as previously described with reference to FIGS. 14A-17. With the movement of the primary electrode 207, the indicator 1192 on the depth gauge 1190 also moves the distance 3433 to reflect the retraction of the distal end 209 of the primary electrode 207. Accordingly, in these embodiments the user interface has allowed the distal end 209 of the primary electrode 207 and the distal end 213 of the secondary electrode 211 to be positioned at desired locations proximate to the reference point 201 in preparation for application of electrical current to treat tissue at or near the reference point 201.

Referring to FIG. 35, another embodiment of a user interface 3501 may be used to position a primary electrode and a secondary electrode relative to a reference point (not shown in FIG. 35). As in previously-described embodiments, in these embodiments the user interface 3501 includes components that are moved parallel with or transverse to an axis 3521 or rotated along a curve 3523 around the axis 3521, as further described below. In such embodiments, the user interface 3501 includes a coupling 3520 configured to engage an electrosurgical apparatus, such as a bronchoscope (not shown in FIG. 35). By way of contrast to previous embodiments of the user interface, these embodiments of the user interface 3501 do not include a sheath actuator. However, a sheath actuator, like the sheath actuator described in connection with previous embodiments and as described with reference to FIGS. 7-11, may be added to these embodiments of the user interface 3501. Alternatively, the sheath actuator may be integrated with the electrosurgical apparatus as previously described with reference to FIG. 7. Also, although not shown in FIG. 35, like the previous embodiments of the user interface 1101 of FIGS. 11-24, leads from a switchable current source are received at the user interface 3501 and a sheath containing primary and secondary electrodes (not shown in FIG. 35) extend from the coupling 3520.

The user interface 3501 includes several user controls whose operation and effect are described in further detail in the following figures. A primary release 3530 coupled to the housing 3510 at a first end 3541 of the housing 3510 is configured unlock movement of the primary electrode (not shown in FIG. 35). The primary release 3530 includes a release lever 3532 and a release spring 3533 to bias the release lever 3532 in a locked position. The primary release 3530 engages a slidable shaft 3536 that is slidably received within a forward opening 3538 in the primary release 3530. The slidable shaft 3536 is fixably coupled to the coupling 3520. The slidable shaft 3536 is configured to move back and forth along the axis 3521. The slidable shaft 3536 is fixably coupled to a depth setter rod 3534 in the nature of a geared rack. As explained further below, the depth setter rod 3534 is engaged by the actuator interlock 3540 to selectively secure a position of the slidable shaft 3536 and, as a result, the position of the primary electrode.

The slidable shaft 3536 includes depth indicia 3539 that may be read at the forward opening 3538 to determine a position of the primary electrode (not shown). It will be appreciated that the depth indicia 3539 are read at the forward opening 3538 in a similar fashion, with reference to FIG. 11, to reading of the indicator 1192 on the depth gauge 1190 to determine a position of the primary electrode (not shown in FIG. 35). As will be further described below, the primary electrode is fixably coupled to the housing 3510 such that sliding the housing 3510 relative to the slidable shaft 3536 controls a position of the primary electrode. In other words, in contrast with previous embodiments of the user interface of FIG. 11 (which included a separate primary actuator 1132), the housing of the user interface 3501 itself acts as a primary actuator for the primary electrode. The housing 3510 is moved forward and back along the axis 3521 to extend and retract, respectively, the primary electrode, as further described below.

A secondary actuator 3552 is fixably coupled to a secondary electrode slider (not shown in FIG. 35), as will be described with reference to FIG. 36. Sliding the secondary actuator 3552 within the secondary channel 3554 channel permits movement of the secondary electrode (not shown in FIG. 35). The secondary actuator 3552 is selectively locked and unlocked relative to the housing 3510 (and, thus, relative to the primary electrode whose movement is controlled by movement of the housing 3510) by an interlock lever 3540 that is secured to the secondary electrode slider 3551. The interlock lever 3540 moves within a guide slot 3542 along the axis 3521 and along a curve 3523 around the axis 3521. A position of the interlock lever 3540 relative to the guide slot 3542 controls the locking and unlocking of the secondary actuator 3550 and, thus, of the secondary electrode, as further described below. In the initial configuration shown in FIG. 35, a lever end 3547 is situated at a first position 3571 within the guide slot 3542, which secures the secondary actuator 3552 at a second end 3555 of the secondary channel 3554. In an illustrative embodiment, guide indicia 3543 may be included on the housing 3510 near the guide slot 3542 to direct a user in moving the interlock lever 3540 to control operation of the secondary actuator 3550. As also described further below, in other configurations the depth setter rod 3534 may be engaged by the interlock lever 3540 to selectively lock the position of the primary electrode (not shown in FIG. 35).

Referring to FIG. 36, an exploded view of the user interface 3501 of FIG. 35 further details the composition and operation of the user interface 3501. As already described with reference to FIG. 35, the user interface 3501 includes a coupling 3520 fixably coupled to an end of the slidable shaft 3536. The slidable shaft 3536, which is fixably coupled with the depth setter rod 3534, is slidably received within the forward opening 3538 of the primary release 3530. The release lever 3532 selectively releases the slidable shaft 3536 to move relative to the forward opening 3538 and is biased in a locked position by a spring 3637 coupled between the primary release 3530 and the release lever 3532. The primary release 3530 is fixably coupled to the housing 3510. Beyond the primary release 3530, the slidable shaft 3536 is slidably received within an opening 3655 in a secondary electrode slider 3551.

The secondary electrode slider 3551 is fixably coupled to the secondary actuator 3552, which slidably moves within the secondary actuator channel 3554. Similarly, on an underside of the housing 3510, a secondary grip 3653 is coupled to an underside of the secondary electrode slider 3551 and extends through an additional channel 3655 in the housing 3510. As previously described with reference to previous embodiments of the user interface, providing both the secondary actuator 3552 and the secondary grip 3653 may allow a user to apply force as needed to cause the secondary electrode (not shown in FIG. 36) to pierce tissue as desired for a particular application. When the secondary electrode slider 3551 is slidably received within the housing 3510, electrodes (not shown in FIG. 36) may extend through a forward opening 3641 in the housing 3510.

In the exploded diagram of FIG. 36, additional aspects of the depth setter rod 3534 and the interlock lever 3540 are shown to further describe the configuration of the user interface 3501. The interlock lever 3640 is secured to the secondary electrode slider 3551. The interlock lever 3540 is configured to engage the depth setter rod 3534. Specifically, in an illustrative embodiment, the depth setter rod 3534 includes a lower-geared surface 3633 and an upper-geared surface 3635. Correspondingly, the interlock lever 3540 includes a lower-geared lock 3643 and an upper-geared lock 3645. When a user manipulates the lever end 3547, the interlock lever 3540 may be rotated to cause the lower-geared lock 3643 to engage the lower-geared surface 3633 of the depth setter rod 3534 and to cause the upper-geared lock 3645 to engage the upper-geared surface 3635 of the depth setter rod 3534. In an illustrative embodiment, the lower-geared lock 3643 and the upper-geared lock 3645 are flexible members configured to rotate over and engage the lower-geared surface 3633 and the upper-geared surface 3635, as further described below. The lower-geared lock 3643 and the upper-geared lock 3645 flex when rotated over the lower-geared surface 3633 and the upper-geared surface 3635 of the depth setter rod 3534, which applies pressure to the lower-geared surface 3633 and the upper-geared surface 3635 of the depth setter rod 3534. The pressure thus applied secures the interlock lever 3540 from being moved relative to the depth setter rod 3534 until the interlock lever 3540 is rotated to disengage the lower-geared lock 3643 and the upper-geared lock 3645 from the lower-geared surface 3633 and the upper-geared surface 3635 of the depth setter rod 3534. When the lower-geared lock 3643 and the upper-geared lock 3645 of the interlock lever 3540 engage the lower-geared surface 3633 and the upper-geared surface 3635, respectively, of the depth setter rod 3534, the slidable sleeve 3536 is secured relative to the depth setter rod 3534 and thus moves in concert with the interlock lever 3540. Accordingly, motion of the slidable sleeve 3536 is then limited to movement permitted by guide slot 3542 which engages the interlock lever 3540, as described further below.

Referring to FIGS. 37A and 37B, the user interface 3501 is shown in a first configuration prior to extension of the primary electrode 207 beyond the distal end 105 of the sheath 103 proximate to the reference point 201, as shown in the inset view. As previously described, the user interface 3501 does not include a sheath actuator to position the sheath 103, although the same may be added to the user interface, for example, at the coupling 3520, or may be included within the electrosurgical apparatus (not shown in FIG. 37A).

In various configurations of the user interface 3501, the slidable shaft 3536 is fully extended from the primary release 3530, corresponding with the distal end 209 of the primary electrode 207 resting within the distal end 105 of the sheath 103. The secondary actuator 3552 is positioned at a rear end 3555 of the secondary channel 3554 in the housing 3510, corresponding with a distal end 213 of a secondary electrode 211 resting within the distal end 209 of the primary electrode 207, prior to deployment of the secondary electrode 211 as previously described with reference to the previous embodiments of the user interface 3501. The interlock lever 3540 also is in an initial position with a lever end 3547 being positioned at a first end 3571 of the guide slot 3542 to secure the secondary actuator 3552 in place at the second end 3555 of the secondary channel 3554.

Deployment of the primary electrode 207 and the secondary electrode 211 begins with a user engaging the primary release 3530. In an illustrative embodiment, the primary release 3530 is engaged by depressing a distal end 3729 of the release lever 3532 to deform the release spring 3637 and to permit movement of the slidable shaft 3536. To extend the primary electrode 207, with the primary release 3530 thus engaged, the housing 3510 is moved in a direction 3708 along the slideable shaft 3536. Whether the desired location has been reached may be determined by reading the depth indicia 3539 on the slideable shaft 3536 at the forward opening 3538 in the primary release 3530. Once the housing 3510 has moved along the slidable shaft 3536 to move the primary electrode 3507 to a desired location, the distal end 3535 of the release lever 3532 is released, thereby allowing the release spring 3637 to return to an undeformed state and locking the slidable shaft 3536 in place relative to the primary release 3530. The primary release 3530 is configured to apply mechanical pressure to slideable shaft 3536 such that, before the distal end 3729 of the release lever 3532 is depressed to engage the primary release 3530, the primary release 3530 and the rest of the user interface 3501 cannot be moved relative to the slidable shaft 3536. Correspondingly, once the distal end distal end 3729 of the release lever 3532 is released to disengage the primary release 3530, the primary release 3530 and the rest of the user interface 3501 cannot be moved relative to the slidable shaft 3536, securing the position of the primary electrode 207, as further described herein.

Referring to FIGS. 38A and 38B, the distal end 209 of the primary electrode 207 has been extended to a desired location proximate to the reference point 201 in a manner as described with reference to FIGS. 37A and 37B. The movement of the housing 3510 relative to the slidable shaft 3536 shown in FIG. 38A has caused the distal end 209 of the primary electrode 207 to move to a desired location proximate to the reference point 201. That the desired location has been reached may be verified by reading the depth indicia 3639 on the slideable shaft 3536 at the forward opening 3538 in the primary release 3530. Also, because the interlock lever 3540 has secured the secondary actuator 3552 at the second end 3555 of the secondary channel 3554, movement of the housing 3510 also causes the secondary actuator 3552 to move the secondary electrode 211 in concert with the movement of the primary electrode 207, with the distal end 213 of the secondary electrode 211 remaining positioned inside the distal end 209 of the primary electrode 207.

Referring to FIG. 39, the interlock level 3540 engages the depth setter rod 3534 to lock a position of the secondary actuator (not shown in FIG. 39). As previously described, the primary release 3530 controls the passage of the slideable shaft (not shown in FIG. 39) through the forward opening 3538 to control positioning of the primary electrode (also not shown in FIG. 39). In addition to the forward opening 3538, a rod opening 3928 separately and slidably receives the depth setter rod 3534 as the slidable shaft is moved through the primary release 3530.

The depth setter rod 3534, as previously described, includes the lower-geared surface 3633 and the upper-geared surface 3635 that are selectively engaged by the lower-geared lock 3643 and the upper-geared lock 3645, respectively, of the interlock lever 3540. The lever end 3547 allows a user to rotate the interlock lever 3540 to cause the geared locks 3643 and 3645 to engage the geared surfaces 3633 and 3635, respectively.

Referring to FIG. 40, the interlock lever 3740 may be positioned so that the lower-geared lock and the upper-geared lock (both of which are behind the slidable shaft 3536 and, thus, are not shown in FIG. 40) slide through the rod opening 3928 without the lower-geared lock and the upper-geared lock (both not shown in FIG. 40) engaging the lower-geared surface 3633 and the upper-geared surface 3635 of the depth setter rod 3534. In this configuration, movement of the primary electrode and the secondary electrode (both not shown in FIG. 40) are controlled by release of the primary release and the housing both (not shown in FIG. 40) as previously described with reference to FIGS. 37 and 38. The position of the lever end 3547 corresponds generally with that of the lever end being at a first, second, or third position within the guide slot (not shown in FIG. 40) further described below in which the lower-geared lock and the upper-geared lock do not secure the secondary electrode slider (also not shown in FIG. 40) to the depth setter rod 3534. A user may engage the lever end 4047 to rotate the interlock lever 3540 in a direction that will lead the lower- and upper-geared locks toward the lower-geared surface 3633 and the upper-geared surface 3635, respectively, of the depth setter rod 3534, as further described below.

Referring to FIG. 41, the interlock lever 3540 has been rotated by user manipulation of the lever end 3547 so that the lower-geared lock 3643 and the upper-geared lock 3645 of the interlock lever 3540 begin to engage the lower-geared surface 3633 and the upper-geared surface 3635 of the depth setter rod 3534 forward of the rod opening 3928. As previously described, in an illustrative embodiment, the lower-geared lock 3643 and the upper-geared lock 3645 of the interlock lever 3540 are flexible so that they may deform slightly in order to engage the depth setter rod 3534. Thus, the position of the lever end 3547 corresponds generally with that of the lever end 3547 being moved between a third position within the guide slot toward a fourth position within the guide slot (not shown in FIG. 40) further described below in which the lower-geared lock and the upper-geared lock do not yet secure the secondary electrode slider (also not shown in FIG. 40) to the depth setter rod 3534, as further described below.

Referring to FIG. 42, the interlock lever 43540 has been further rotated by user manipulation of the lever end 3547 into a locked position in which the lower-geared lock 3643 and the upper-geared lock 3645 of the interlock lever 3540 engage the lower-geared surface 3633 and the upper-geared surface 3635, respectively, of the depth setter rod 3534 forward of the rod opening 3928. In a locked position, corresponding with the lever end 3547 being within a fourth or fifth position within the guide slot (not shown in FIG. 42) further described below in which the lower-geared lock 3643 and the upper-geared lock 3645 secure the interlock lever 3540 to the depth setter rod 3534. In this position, even if the housing and thus the primary electrode (neither of which are shown in FIG. 42) are moved, the secondary actuator 3540 maintains the position of the secondary actuator (not shown in FIG. 42). The function of the interlock lever 3540 in positioning the primary and secondary electrodes is further described below.

In FIGS. 43A-47C, side and top views of the second embodiment of the user interface are shown, along with inset views to show positions of the electrodes corresponding to the configuration of the user interface. In FIGS. 43A-47C, it should be appreciated that the lever end 3547 of the interlock lever 3540 provides a visible and tactile indicator of a phase in which the user interface 3501 operates, for example, such as in extending the secondary electrode 211 or retracting the primary electrode 207.

Referring to FIGS. 43A-43C, the user interface 3501 is shown with the primary electrode 207 extended before any steps have been taken to extend the secondary electrode 211. The primary release 3530 is in a locked position to secure the housing 3510 relative to the slideable shaft 3536. As a result, the distal end 209 of the primary electrode 207 is fixed in position proximate to the reference point 201. The interlock lever 3540 is in an initial locked position as indicated by the lever end 3547 of the interlock lever 3540 being disposed in the first position 3571 of the guide slot 3542. In this position, the lower-geared lock and the upper-geared lock (not shown in FIGS. 43A and 43B) of the interlock lever 3540 do not engage the depth setter rod 3534. However, with the lever end 3547 at the first position 3571, the interlock lever 3540 is restrained from moving along the axis 3521 (FIG. 35) and thus holds prevents the secondary actuator 3552 and the secondary electrode slider 3551 in place within the secondary channel 3554. Thus, because the primary electrode 207 is fixed in position and because the secondary electrode slider 3551 is locked in position, the distal end 213 of the secondary electrode 211 is also locked in position relative to the reference point 201.

Referring to FIGS. 44A-44C, the user interface 3501 is shown with the primary electrode 207 extended and the actuator interlock 3540 manipulated to unlock movement of the secondary electrode 211. The primary release 3530 remains in a locked position to secure the housing 2510 relative to the slideable shaft 3536. As a result, the distal end 209 of the primary electrode 207 remains fixed in position proximate to the reference point 302. The interlock lever 3540 is moved to a second position as indicated by the lever end 3547 of the interlock lever 3740 having been moved to the second position 4473 of the guide slot 3542. In this position, as in the position described with reference to FIGS. 44A-44C, the lower-geared lock and the upper-geared lock (not shown in FIGS. 44A and 44B) of the interlock lever 3540 still do not engage the depth setter rod 3534. However, with the lever end 3547 at the second position 4473, the interlock lever 3540 is no longer restrained from moving along the axis 3521 (FIG. 35) within the secondary channel 3554. The lever end 3547 thus may engage in limited movement within the guide slot 3542. Thus, the secondary actuator 3552 and the secondary slider 3551 also may engage in limited movement within the secondary channel 3554 to move the secondary electrode 211 toward the reference point 201. With the primary electrode 207 thus fixed in position, the distal end 213 of the secondary electrode 211 may be moved toward the reference point 201 independently of the primary electrode 207.

Referring to FIGS. 45A-45C, the primary release 3530 remains in a locked position and the secondary electrode 211 has been extended. As a result, the distal end 209 of the primary electrode 207 remains fixed in position proximate to the reference point 201. The interlock lever 3540 is moved to a third position as indicated by the lever end 3547 of the interlock lever 3540 being disposed in the third position 4575 of the guide slot 3542. In this position, as in the position described with reference to FIGS. 44A-44C, the lower-geared lock and the upper-geared lock (not shown in FIGS. 45A and 45B) of the interlock lever 3540 still do not engage the depth setter rod 3534. The lever end 3547 moves to the third position 4575 within the guide slot 3542 as a user moves the secondary actuator 3552 to move the secondary electrode slider 3551 within the secondary channel 3554. The movement of the secondary actuator 3552 moves the distal end 213 of the secondary electrode 211 to a desired position beyond the reference point 201 while the distal end 209 of the primary electrode 207 remains fixed in position. Insulation 515 on the secondary electrode 211 electrically isolates the distal end 213 of the secondary electrode 211 from the distal end 209 of the primary electrode 207, as previously described.

Referring to FIGS. 46A-46C, the primary release 3530 remains in a locked position to secure the housing 3510 relative to the slideable shaft 3536 and the actuator interlock 3540 has been manipulated to lock the movement of the secondary electrode 211. As a result, the distal end 209 of the primary electrode 207 remains fixed in position proximate to the reference point 201. The interlock lever 3540 is moved to a fourth position 4677 by a user having moved the lever end 3547 of the interlock lever 3540 to the fourth position 4677 of the guide slot 3542. In this position, as described with reference to FIG. 42, the lower-geared lock 3643 and the upper-geared lock 3645 of the interlock lever 3540 engage the lower-geared surface 3633 and the upper-geared surface 3635, respectively, of the depth setter rod 3534. Thus, with the lever end 3547 in the fourth position 4677 of the guide slot 3542, the interlock lever 3540 and, thus, the secondary electrode slider 3551 and the secondary actuator 3552 are locked in position with respect to the depth setter rod 3534. Accordingly, both the distal end 209 of the primary electrode 207 and distal end 213 of the secondary electrode 211 are locked in place relative to the reference point 201.

Referring to FIGS. 47A-47C, the primary release 3530 has been engaged to unlock the position of the housing 3510 relative to the slideable shaft 3536 and the housing 3510 has been moved in a direction 4781 to partially retract the distal end 309 of the primary electrode 207. As a result, the distal end 209 of the primary electrode 207 is partially withdrawn from the reference point 201 toward the distal end 105 of the sheath 103. The interlock lever 3540 is moved to a fifth position by the movement of the housing 3510, with the lever end 3547 of the interlock lever 3540 to the fifth position 4779 of the guide slot 3542. In this position, as described with reference to FIG. 42, the lower-geared lock 3643 and the upper-geared lock 3645 of the interlock lever 3540 continue to engage the lower-geared surface 3633 and the upper-geared surface 3635, respectively, of the depth setter rod 3534. Thus, with the lever end 3547 in the fourth position 4779 of the guide slot 3542, the interlock lever 3540 and, thus, the secondary electrode slider 3551 and the secondary actuator 3552 remain locked in position with respect to the depth setter rod 3534. The movement of the housing 3510 causes the secondary electrode slider 3551 and the secondary actuator 3552 to move to forward in the secondary channel 3554 to allow the secondary electrode slider 3551 to remain locked in position relative to the depth setter rod 3534 while the housing 3510 is moved in the direction 4781. In this manner, once the secondary electrode 211 has been extended and secured in position, the primary electrode 207 may be moved to position the distal end 209 of the primary electrode 207 relative to the distal end 213 of the secondary electrode 211 to facilitate application of an electric current to provide desired treatment. Accordingly, these embodiments of the user interface have allowed the distal end 209 of the primary electrode 207 and the distal end 213 of the secondary electrode 211 to be positioned at desired locations proximate to the reference point 201 in preparation for application of electrical current to treat tissue at or near the reference point 201.

Referring to FIG. 48, another embodiment of the user interface 4801 is shown for positioning electrodes. The user interface 4801 includes components that are moved parallel along an axis 4821 or rotated along a curve 4823 around the axis 4821, as further described below. As also further described below, the user interface 4801 generally is controlled by sliding the outer housing 4810 along the axis 4821, by sliding actuators extending through the outer housing 4810 at a first end 4841 of the outer housing 4810, and by rotating the outer housing around the axis 4821.

The user interface 4801 includes a coupling 4820 to engage a port on an electrosurgical apparatus, such as a bronchoscope, as described with reference to FIGS. 1, 7, and 8. The user interface 4801 also includes a sheath actuator 4804 to position a sheath (not shown in FIG. 48) as previously described with reference to FIGS. 7-11. The sheath actuator 4804 includes a slidable sleeve 4812 and a sheath lock 4806 to engage the slidable sleeve 4812 and secure the slidable sleeve 4812 in place, as described further below. It will be appreciated that, as described with reference to FIG. 35 and regarding another embodiment of the user interface 3501, a sheath actuator may be part of the bronchoscope or a separate device inserted between the user interface 4801 and the bronchoscope (not shown in FIG. 48).

The user interface 4801 includes an outer housing 4810 configured to enable manipulation of the electrodes. The outer sheath 4810 includes a first guide slot 4831 configured to receive and direct movements of a primary actuator 4832 that extends up through the first guide slot 4831. The outer housing 4810 also includes a second guide slot 4851 configured to receive a secondary actuator (not shown in FIG. 48). As is further described below, rotation of the outer housing 4810 along the curve 4823 about the axis 4821 exposes and introduces the secondary actuator into the second guide slot 4851. When the secondary actuator is received through the second guide slot 4851, the secondary actuator may be secured in place with a slidable actuator lock 4859, the operation of which is further described below. Also, although not shown in FIG. 48, as in embodiments shown in FIGS. 1 and 11, leads from a switchable current source are received at the user interface 4801 and a sheath containing primary and secondary electrodes extends from the user interface 4801 via the coupling 4820.

Referring to FIG. 49, the outer housing 4810 includes the first guide slot 4831 to engage the primary actuator 4832. The primary actuator 4832 extends from a primary electrode slider 4914, as described further below. The primary actuator 4832 extends upwardly through the first guide slot 4831 in the outer housing 4810. By sliding the primary actuator 4832 through the first guide slot 4831, a user may extend, lock, and partially retract the primary electrode (not shown in FIG. 49). The outer housing 4810 also includes the second guide slot 4851 that is configured to receive the secondary actuator 4952 and which extends from the secondary electrode slider 4916 through an intermediate guide slot 4933 in the primary electrode slider 4914, as further described below. A ramp 4957 adjacent a second end 4958 of the second guide slot 4851 and on an underside of the outer housing 4810 engages and subverts the secondary actuator 4852 when it is desired to retract the secondary electrode, as will be described further below.

The second guide slot 4851 in the outer housing 4810 is configured to receive the secondary actuator 4952 when, as further described below, rotation of the outer housing 4810 along the curve 4823 about the axis 4821 (FIG. 48) exposes and introduces the secondary actuator 4952 into the second guide slot 4851. When the secondary actuator is received through the second guide slot 4851, the secondary actuator may be secured in place with a slidable actuator lock 4859, the operation of which is further described below.

The primary electrode slider 4914 is longitudinally fixable to the primary electrode (not shown in FIG. 49) such that longitudinal movement of the primary electrode slider 4914 extends and retracts the primary electrode without twisting the primary electrode. The primary electrode slider 4914 is slidably and rotatably received within the outer housing 4810. The primary actuator 4832 extends outwardly from the primary electrode slider 4914 so that it extends upwardly through the outer housing 4810. The primary electrode slider 4914 also includes an intermediate guide slot 4933 configured to receive the secondary actuator 4952 extending from the secondary electrode slider 4916.

The secondary electrode slider 4916 is longitudinally fixable to the secondary electrode (not shown in FIG. 49) such that longitudinal movement of the secondary electrode slider 4916 extends and retracts the secondary electrode without twisting the secondary electrode. The secondary electrode slider 4916 is slidably received within the primary electrode slider 4914. The secondary actuator 4952 extends outwardly from the secondary electrode slider 4916 is receivable through the intermediate guide slot 4933 in the primary electrode slider 4914. In an illustrative embodiment, the secondary actuator 4952 is spring-loaded or similarly extendable such that, when the outer housing 4810 is rotated such that the second guide slot 4851 overlaps the intermediate guide slot 4933 in the primary electrode slider 4914, the secondary actuator 4952 extends upward through the second guide slot 4851. In another illustrative embodiment, when the outer housing 4810 is rotated to move the second guide slot 4851 so that it no longer overlaps the intermediate guide slot 4933 in the primary electrode slider 4914, the ramp 4959 engages and compresses the secondary actuator 4952 to fit beneath the outer housing 4810.

The sheath actuator 4804 includes a slidable sleeve 4812 fixably coupled to the sheath (not shown) and slidably received within the coupling 4820 and securable with the sheath lock 4806. Operation of the sheath actuator 4804 is further described with reference to FIGS. 50 and 51. In an illustrative embodiment, the slidable sleeve 4812 may be fixably coupled to the outer housing 4810, such that movement of the electrodes (not shown in FIG. 49) made by using the user interface 4810 moves the electrodes relative to the sheath.

Referring to FIGS. 50A and 50B and as used in conjunction with a user interface 4801, the sheath actuator 4804 controls a position of the sheath 103. Specifically, a position of the sheath 103 is controlled by sliding the slidable sleeve 4812 within the coupling 4820 and securing the sheath 103 at the desired location by securing the slidable sleeve 4812 with the sheath lock 4806. The sheath actuator 4804 may operate similarly to the sheath lock 706 of FIG. 9, as previously described. The slidable sleeve 4812 is fixably mounted to the outer housing 4810 and is slidably received within the coupling 4820. When the slidable sleeve 4812 is situated to position the sheath 103 containing the electrodes 207 and 211 at a desired location, the sheath lock 4806 is locked to secure the slidable sleeve 4812 in place. The sheath lock 4806 may be a spring-loaded lock, a thumbscrew, or another similar mechanism as previously described with reference to FIGS. 7-10 to secure the slidable sleeve 4812 in place to secure the position of the sheath 103.

As previously described and as shown in the inset view, in illustrative embodiments the secondary electrode 211 is received within the primary electrode, with a distal end 213 of the secondary electrode 211 initially resting just within the distal end 209 of the primary electrode 207. In turn, the distal end 209 of the primary electrode 207 rests just within the distal end 105 of the sheath 103. Before the sheath actuator 4804 is used to position the distal end 105 of the sheath 103 near the reference point 201, the distal end of the sheath 103 may initially rest at a position away from or immediately adjacent to the reference point 201.

Referring to FIGS. 51A and 51B and as used in conjunction with a user interface 4801, the sheath actuator 4804 is used to move the distal end 105 of the sheath 103 to a position closer to the reference point 201 as shown in the inset view. A relative movement of the outer housing 4810 toward the coupling 4820 by a distance 5019 moves the distal end 105 of the sheath 103 a corresponding distance to move the distal end 105 of the sheath 103 closer to the reference point 201. In turn, the distal end 209 of the primary electrode 207 and the distal end 213 of the secondary electrode 211 are also moved closer to the reference point 201. The relative movement of the outer housing 4810 toward the coupling 4820 is accomplished by the slidable sleeve 4812 being at least partially received within the coupling 5120 and then secured with the sheath lock 4806, as previously described.

FIGS. 52A-57C show how the user interface 4801 moves the electrodes 207 and 211 based on manipulation of the user interface 4801. Referring to FIG. 52A with regard to the user interface 4801, the primary actuator 4832 extends from the primary slider 4914 through the first guide slot 4831 of the outer housing 4810 and is situated at a first position 5233 within the first guide slot 4831 (as shown in the cross-sectional view taken along line A-A and in the top-down view). Correspondingly, as shown in the inset view, in an initial position the distal end 209 of the primary electrode 207 remains positioned within a distal end 105 of the sheath 103, with the distal end 105 of the sheath 103 having been positioned proximate the reference point 201. The distal end 213 of the secondary electrode 211 remains positioned within the distal end 209 of the primary electrode 207.

It should be noted that the secondary actuator 4952 and the intermediate guide slot 4933 are not yet exposed within the second guide slot 4851 in the outer housing 4810 and, thus, are represented by dashed lines in the top-down view. As will be appreciated, manipulation of the outer housing 4810 and the primary actuator 4832 brings the secondary actuator 4952 and the intermediate guide slot 4934 beneath the second guide slot 4851 in the outer housing 4810 where the secondary actuator 4952 may be subsequently engaged by a user.

It should also be noted that the primary actuator 4832 is fixably coupled to the primary electrode slider 4914 and the secondary actuator 4952 is fixably coupled to the secondary electrode slider 4916. Accordingly, linear or rotational movement of the primary actuator 4832 results in a corresponding movement of the primary electrode slider 4914 to move the primary electrode 5207. Correspondingly, linear or rotational movement of the secondary actuator 4852 results in a corresponding movement of the secondary electrode slider 4916 to move the secondary electrode 211. Thus, it should be understood that movement of the primary actuator 4832 may be regarded as causing movement of the primary electrode 207 and movement of the secondary actuator 4952 may be regarded as causing movement of the secondary electrode 211 without associated movement of the respective electrode slider being expressly described.

Referring to FIGS. 53A-53C, the primary actuator 4832 (extending through the first guide slot 4831 of the outer housing 4810 of the user interface 4801) has been moved by a user (not shown) to a second position 5335 within the first guide slot 4831 as shown in the cross-sectional view taken along line B-B and in the top-down view. The user may, for example, push the primary actuator 4832 forward to slide the primary actuator 4832 through the first guide slot 4831 to the second position 5335. Correspondingly, as shown in the inset view, in a second position, the distal end 209 of the primary electrode 207 extends beyond the distal end 105 of the sheath 103 toward the reference point 201 within the target tissue 202. The distal end 213 of the secondary electrode 211 remains positioned within the distal end 209 of the primary electrode 207.

The secondary actuator 4952 (extending through the intermediate guide slot 4934 of the primary electrode slider 4914 and the intermediate guide slot 4934 of the primary electrode slider 4914) are not yet exposed within the second guide slot 4851 in the outer housing 4810 and, thus, continue to be represented by dashed lines in the top-down view. However, it should be appreciated that, with movement of the primary actuator 4832 to the second position 5335 in the first guide slot 4831 brings the intermediate guide slot 4934 parallel with the second guide slot 4951 in the outer housing 4810. As described with reference to FIGS. 54A-54C, relative rotation of the primary actuator 4832 across the first guide slot 4831 brings the secondary actuator 4952 and the intermediate guide slot 4934 beneath the second guide slot 4951 in the outer housing 4810 where the secondary actuator 4952 may be subsequently engaged by a user.

Referring to FIGS. 54A-54C, the primary actuator 4832 (extending through the first guide slot 4831 of the outer housing 4810 of the user interface 4801) has been moved by the user (not shown) to a third position 5437 within the first guide slot 4831 as shown in the cross-sectional view taken along line C-C and in the top-down view. The user may, for example, rotate the primary actuator 4832 laterally while the primary electrode slider 4914 and the secondary electrode slider 4916 remain rotationally stationary to slide the primary actuator 4832 within the first guide slot 4831 to the third position 5437. As shown in the inset view, the relative position of the electrodes 207 and 211 has not changed. The distal end 209 of the primary electrode 207 remains extended beyond the distal end 105 of the sheath 103 near the reference point 201, as shown in FIG. 53C. Similarly, the distal end 213 of the secondary electrode 211 remains positioned within the distal end 209 of the primary electrode 207.

However, with movement of the primary actuator 4832 to the third position 5437, the secondary actuator 4952 extends through the intermediate guide slot 4934 of the primary electrode slider 4914 and now extends through the second guide slot 4851 in the outer housing 5810 of the user interface 4801. The intermediate guide slot 4934 in the primary electrode slider 4914 is overlapped by the second guide slot 4851 in the outer housing 4810. In this position, the secondary actuator 4952 rests at a first position 5453 within the second guide slot 4851. The secondary actuator 4952 may now be engaged by a user to extend the secondary electrode 211, as described with reference to FIGS. 55A-55C.

Referring to FIGS. 55A-55C, the secondary actuator 4952 extends through the first guide slot 4851 in outer housing 4810 of the user interface 4801 and is moved from the first location 5453 to a second location 5555 in the second guide slot 4851. At the second location 5555, the secondary actuator 4952 is now situated adjacent to the slidable actuator lock 4859, the operation of which is further described with reference to FIG. 56. The primary actuator 4832 extends through the first guide slot 4831 of the outer housing 4810 and remains at the third position 5437 within the first guide slot 4831. A user (not shown), for example, may push the secondary actuator 4952 to move the secondary actuator 4952 from the first position 5453 to the second position 5555 in the second guide slot 4851.

As shown in the inset view, with movement of the secondary actuator 4952, the distal end 213 of the secondary electrode 211 is extended beyond the distal end 209 of the primary electrode 207 to a location beyond the reference point 201. Electrical insulation 515 electrically isolates all but the distal end 213 of the secondary electrode 211 from the primary electrode 207. By contrast, with movement of the primary actuator 4832 toward the reference point 201 being limited by the first guide slot 4831, the distal end 209 of the primary electrode 207 remains in the same position as shown in FIG. 54C.

Referring to FIGS. 56A-56C, the secondary actuator 4952 extends through the intermediate guide slot 4934 in the primary electrode slider 4914 and is secured in place by the slidable actuator lock 4859. As previously described with reference to other embodiments of the user interface, once the distal end 213 of the secondary electrode 211 is extended to a desired location opposite the reference point 201 from the distal end 209 of the primary electrode 207, it may be desirable to maintain the secondary electrode 211 in place while the distal end 209 of the primary electrode 207 is partially withdrawn. Because the secondary electrode 211 extends through the primary electrode 209, withdrawal of the primary electrode 209 may apply force to the secondary electrode 211 that, potentially, could cause the distal end 213 of the secondary electrode 211 to retract. The slidable actuator lock 4859, however, may help prevent the secondary actuator 4952 from moving within the second guide slot 4851, thereby helping hold the distal end 213 of the secondary electrode 211 in place.

The slidable actuator lock 4859 slides across the second guide slot 4851 from a base 5669 and engages the secondary actuator 4952 to prevent the secondary actuator 4952 from moving from the second location 5555 in the second guide slot 4851. As a result, when the primary actuator 4832 is engaged to retract the primary electrode 207 as described with reference to FIGS. 57A-57C, the secondary actuator 4952 and, thus, the secondary electrode 211, remain in place.

Referring to FIGS. 57A-57C, with the secondary actuator 4952 secured at the second location 5555 in the second guide slot 4851 by the slidable actuator lock 4859, the primary actuator 4832 is engaged by a user (not shown) to partially retract the distal end 209 of the primary electrode 207. Specifically, the primary actuator 4832 (that extends from the primary slider 4914 through the first guide slot 4831 of the outer housing 4810 of the user interface 4801) has been moved by the user (not shown) to a fourth position 5739 within the first guide slot 4831 as shown in the top-down view and in the cross-sectional view taken along line E-E. The user may, for example, push the primary actuator 4832 to slide the primary actuator 4832 through the first guide slot 4831 to the fourth position 5739. As shown in the inset view, the position of the distal end 213 of the secondary electrode 211 remains unchanged relative to the reference point 201, because the secondary actuator 4952 is held in place by the slidable actuator lock 4859 at the second position 5555 in the second guide slot 4851. However, as shown in FIG. 57C, the distal end 209 of the primary electrode 207 has been partially retracted nearer to the distal end 105 of the sheath 103. In this manner, once the secondary electrode 211 has been extended and secured in position, the primary electrode 207 may be moved to position the distal end 209 of the primary electrode 207 relative to the distal end 213 of the secondary electrode 211 to facilitate application of an electric current to provide desired treatment.

The following pertains to removal of the device. Due to the primary actuator 4832 being located at the fourth position 5739 in the first guide slot 4831, the primary electrode 207 cannot be retracted until the primary actuator 4832 is moved to the third position 5437 within the first guide slot 4831, the slidable actuator lock 4859 unlocks the secondary actuator 4952 and the secondary actuator 4952 is retracted to the first position 5453 within the second guide slot 4851. Thus, accidental retraction of the primary electrode 207 cannot occur while the secondary electrode 211 is in the extended position.

Referring to FIG. 58, in another embodiment a user interface 5801 is provided for positioning electrodes conveyed by a sheath at a desired location at or near a reference point (none of which are shown in FIG. 58). The user interface 5801 includes a sheath actuator 5804, a primary housing 5830, a secondary housing 5850, and a lock rod 5870. As will be described in detail below, movement of the electrodes is accomplished by using the sheath actuator 5804 to position a sheath and to set a position of the lock rod 5870, rotating the secondary housing 5850 along a curve 5823 around an axis 5821 of the user interface 5801, and sliding the primary housing 5850 along the axis 5821. The primary housing 5830 is mechanically secured to a primary electrode (not shown in FIG. 58) such that sliding the primary housing 5830 slides the primary electrode. Similarly, the secondary housing 5850 is mechanically secured to a secondary electrode (not shown in FIG. 58) such that sliding the secondary housing 5850 slides the secondary electrode. By contrast with previous embodiments described with reference to FIGS. 11-57, the user interface 5801 does not include actuators or levers used to manipulate the position of the electrodes. Instead, manipulation of the electrodes is performed by sliding and rotating the secondary housing 5850 and sliding the primary housing 5830, as further described below.

Referring to FIG. 59, in a particular embodiment, the coupling 5820 is configured to engage a port on an electrosurgical apparatus, such as a bronchoscope, as described with reference to FIGS. 1, 7, and 8. The coupling 5820 slidably receives the primary housing 5830 and the lock bar 5870. Once the sheath (not shown in FIG. 59) is disposed at a desired location relative to the reference point (also not shown in FIG. 59), a sheath lock 5806 may be used to fix the sheath in place and also to fix a position of the lock bar 5870 relative to the reference point. The primary housing 5830 and the lock bar 5870 also are slidably and rotatably received within the secondary housing 5850. As described in detail below, the sliding and rotation of the primary housing 5830 and the lock bar 5870 relative to the secondary housing 5850 controls the relative movement and fixing of positions of the primary housing 5830 and the secondary housing 5850 and, thus, the relative movement and fixing positions of the primary and secondary electrode, respectively.

Referring to FIGS. 60A and 60B, operation of the sheath actuator 5804 is described to explain positioning of the sheath 105 and the lock bar 5870. As further described below, in an initial configuration, sliding of the secondary housing 5850 also slides the primary housing 5830. Thus, sliding the secondary housing 5850 slides the primary housing 5830 relative to the coupling 5820.

Referring to FIGS. 61A and 61B, movement of the secondary housing 5850 through the distance 6019 results in the primary housing 5830 advancing through the distance 6019 into the coupling 5820. Correspondingly, the sheath 103 advances into the body to move the distal end 105 of the sheath 103 toward the reference point 202. In this configuration, movement of the secondary housing 5850 also causes the distal end 209 of the primary electrode 207 (which rests within the distal end 105 of the sheath 103) and the distal end 213 of the secondary electrode 211 (which rests within the distal end 209 of the primary electrode 207) to be correspondingly advanced toward the reference point. Once the distal end 105 of the sheath 103 reaches a desired location relative to the reference point 202, the sheath lock 5806 may be used to lock the sheath 103 in place. In a particular embodiment, the sheath lock 5806 also may lock a position of the lock rod 5870, which thereby fixes a reference position for positioning of the primary housing 5830 and the secondary housing 5850, as will be further described below.

FIGS. 62-64C illustrate components of the user interface 5801. Referring to FIG. 62, the lock rod 5870 includes a positioning section 6271 and a locking section 6273. The positioning section 6271 may be received and secured, for example, in the coupling 5820 as previously described to fix a position of the lock rod. The locking section 6273 supports a plurality of outwardly-extending teeth 6275 which are engaged by one or more inward facing teeth supported by the primary housing 5830 and the secondary housing 5850, as further described below, to facilitate locking positions of the housings 5830 and 5850 to prevent them from sliding along the lock rod 5870.

Referring to FIG. 63A, a first side of the primary housing 5830 is shown. In a particular embodiment, the primary housing 5830 is generally cylindrical in shape to permit sliding and rotating within a chamber within the secondary housing 5850, as further described with reference to FIGS. 64A-70C. The primary housing 5830 includes an outward-facing guide slot 6333 configured to receive a guide member (not shown in FIG. 63A) extending inwardly from a secondary housing 5850. The engagement of the guide member with the guide slot 6333 controls relative movement of the primary housing 5830 and the secondary housing 5850, as further described below.

Referring to FIG. 63B, a second side of the primary housing 5830 is shown. In a particular embodiment, the primary housing 5830 includes a primary lock channel 6335 that is configured to receive the lock rod 5870. Within the primary lock channel 6335, one or more inwardly-facing teeth 6337 are configured to engage the teeth 6275 extending from the lock rod 5870 to prevent the primary housing 5830 from sliding relative to the lock rod 5870 when the lock rod 5870 is received within the primary lock channel.

Referring to FIG. 63C, a cross-sectional view of the primary housing 5830 shows the guide slot 6333 and the primary lock channel 6335. At the point along the primary housing 5830 where the cross-sectional view of FIG. 64C is taken, the guide slot 6333 enables sliding of the guide member (not shown) within the guide slot 6333 because, with reference to FIG. 63A, there are no transverse sides of the guide slot 6333 at this location to block sliding of the guide member. The primary lock channel 6335 includes a groove configured to receive the lock bar 5870. It should be noted that the primary housing 5830 defines an open core 6334 through which the primary electrode, the secondary electrode, the sheath, or other apparatuses (none of which are shown in FIG. 63C) may extend or may be received.

Referring to FIG. 63D, another cross-sectional view of the primary housing 5830 shows the guide slot 6333 and the primary lock channel 6335. At the point along the primary housing 5830 where the cross-sectional view of FIG. 64D is taken, the guide slot 6333 enables rotating of the guide member (not shown) across the guide slot 6333, although, with reference to FIG. 63A, adjacent transverse sides may block sliding of the guide member. Within the primary lock channel 6335, the one or more teeth 6337 extend to engage the teeth 6275 on the lock bar 5870 when it is received within the primary lock channel 6335 to prevent the primary housing 5830 from sliding along the lock bar 5870.

Referring to FIG. 64A, a side view of the secondary housing 5850 is shown. As previously stated, in contrast to the embodiment of the user interface 4801 of FIGS. 48-57, the secondary housing 5850, which is an outer housing, does not support levers, separate actuators, or openings through which such levels and separate actuators extend. Instead, the secondary housing 5850 in and of itself is an actuator to be engaged by a user to manipulate positions of electrodes (not shown in FIG. 64A). In the illustrated embodiment, the secondary housing 5850 is shown to have a cylindrical outer shape, but the secondary housing 5850 may support knurled grips or feature a different outer shape that may be desirable for holding or manipulating the user interface.

Referring to FIGS. 64B and 64C, cross-sectional views of the secondary housing 5850 show an inner channel 6454 defined by an inner wall 6452 that is configured to slidably and rotatably receive the primary housing 5830. A secondary lock channel 6458 defined by a secondary channel wall 6456 is configured to receive the lock bar 5870 which, as described below, may slide within the secondary lock channel 6458 or be moved across the secondary lock channel 6458 by the rotation of the secondary housing 5850 to selectively reposition the lock bar 5870.

The secondary channel 6458 includes three lobes which control relative movement of the housings 5830 and 5850 relative to the lock bar 5870 as described in detail with reference 65A-65C, 66A-66C, 67A-67C, 68A-68C, 69A-69C, and 70A-70C. With the lock bar 5870 in a first lobe 6461, the primary housing 5830 and the secondary housing 5850 may slide freely relative to the lock bar 5870. With the lock bar 5870 in a second lobe 6463, the secondary channel wall 6456 presses against the lock rod 5870, causing the lock rod 5870 to engage the teeth 6337 in the primary lock channel 6335 of the primary housing 5830, thereby preventing the primary housing 5830 from sliding relative to the lock rod 5870. However, with the lock rod 5870 in the second lobe 6463, the secondary housing 5850 remains free to slide relative to the lock bar 5870. In a third lobe 6465, one or more inward-facing teeth 6459 configured to engage the outward-facing teeth 6275 extending from the lock bar 5870. Thus, with the lock bar 5870 in the third lobe 6465, the secondary housing 5850 is blocked from sliding relative to the lock bar 5870. However, when the lock bar 5870 is in the third lobe 6465, the teeth 6337 in the primary lock channel 6335 of the primary housing 5830 no longer engage the lock rod 5870, so the primary housing 5830 is free to slide relative to the lock bar 5870.

Referring again to FIG. 64C, an inwardly-extending guide member 6455 is configured to be received within the guide slot 6333 of the primary housing 5830 described with reference to FIGS. 63A and 63C. Engagement of the guide member 6455 with the guide slot 6333 controls relative movement of the primary housing 5830 and the secondary housing 5850, as further described below.

Referring to FIG. 65A, a side view of the user interface 5801 is shown in an initial configuration for extending both the primary electrode 207 and the secondary electrode 211 (FIG. 65D). FIGS. 65A-70D are used to illustrate how movement of the user interface 5801 is used to control positions of the distal end 209 of the primary electrode 207 and the distal end 213 of the secondary electrode 211 within a body. Specifically, sliding and rotating of the outer, secondary housing 5850 and sliding of the inner, primary housing 5830 positions the electrodes 207 and 211 relative to reference point 202. It should be noted that in the side views of the user interface 5801 of FIGS. 65A, 66A, 67A, 68A, 69A, and 70A, the coupling 5820 and the secondary housing 5850 are shown in cutaway views (represented by dashed lines) to show the relative movement of the primary housing 5830 relative to the coupling 5820 and the secondary housing 5850. Also, in the views of FIGS. 65A, 66A, 67A, 68A, 69A, and 70A, the lock rod 5870 would be positioned behind the user interface and, thus, is not shown in FIGS. 65A, 66A, 67A, 68A, 69A, and 70A. However, the lock bar 5870 and its engagement with the primary housing 5830 and the secondary housing 5850 are shown in the cross-sectional views, such as shown in the cross-sectional views of FIGS. 65B and 65C. Movement of the electrodes 207 and 211 relative to the reference point is shown in the corresponding inset views, such as shown in FIG. 65D.

Referring again to FIG. 65A, in the initial configuration for extending both the primary electrode 207 and the secondary electrode 211, the guide member 6455 is received in a first transverse guide segment 6541 of the guide slot 6333 of the secondary housing 5850 (FIG. 65D). With the guide member 6455 of the secondary housing 5850 engaged in the first transverse guide segment 6541 of the guide slot 6333 of the primary housing 5830, the housings 5830 and 5850 can only be moved in concert along the axis 5821 (FIG. 58) of the user interface 5801.

Referring to FIGS. 65B and 65C, with the guide member 6455 in the first transverse guide segment 6541 of the guide slot 6333, the lock rod 5870 is received in a first lobe 6561 of the secondary lock channel 6458. When received in the first lobe 6561 of the secondary lock channel 6458, neither the teeth 6459 in the secondary lock channel 6458 of the secondary housing 5850 nor the teeth 6337 in the primary lock channel 6335 engage the lock rod 5870. Thus, both the primary housing 5830 and the secondary housing 5850 may slide freely relative to the lock rod 5870, although, as previously described, the engagement of the guide member 6455 with the guide slot 6333 cause the primary housing 5830 and the secondary housing 5850 to move in concert (i.e., to move simultaneously through the same distance).

Referring to FIG. 66A, a side view of the user interface 5801 is shown in a second configuration once the distal end 209 of the primary electrode 207 and the distal end 213 of the secondary electrode 211 have been extended into the reference point 201 as shown in FIG. 66D. As described with reference to FIG. 65A, engagement of the guide member 6455 with the guide slot 6333 of the secondary housing 5850 causes the primary housing 5830 and the secondary housing 5850 to move in concert through a distance 6691. As shown in FIGS. 66B and 66C, and as previously explained with reference to FIGS. 65B and 66C, the lock rod 5870 is in the first lobe 6461 of the secondary lock channel 6456 where it does not engage the teeth 6459 in the secondary lock channel 6458 of the secondary housing 5850 or the teeth 6337 in the primary lock channel 6335, enabling the primary housing 5830 and the secondary housing 5850 to slide freely relative to the lock rod 5870.

Referring to FIG. 67A, the secondary housing 5850 is rotated in a direction 6793 to move the guide member 6455 into a second segment 6743 of the guide slot 6333. With the guide member 6455 in the second segment 6743 of the guide slot 6333, the secondary housing 5850 is free to move relative to the primary housing 5830. However, the guide slot 6333 blocks further rotation of the guide member 6455 in the direction 6793.

Referring to FIGS. 67B and 67C, it can be seen that the rotation of the secondary housing 5850 results in the lock rod 5870 moving into the second lobe 6463 of the secondary lock channel 6458 where the secondary channel wall 6456 impinges upon the lock rod 5870 so that the lock rod 5870 engages the teeth 6337 in the primary lock channel 6335 of the primary housing 5830, thus preventing the primary housing 5830 from sliding relative to the lock rod 5870. However, with the lock rod 5870 in the second lobe 6463, the secondary housing 5850 remains free to slide relative to the lock rod 5870. Referring to FIG. 67D, it can be seen that the rotation of the secondary housing 5850 does not result in movement of the electrodes 207 and 211.

Referring to FIG. 68A, the secondary housing 5850 is slidably moved through a distance 6891, independently of the primary housing 5830, to extend the distal end 213 of the secondary electrode 211 to an opposing side of the reference point 202 from the distal end 209 of the primary electrode 207. The guide member 5455 now extends into a third segment 6845 of the guide slot 6333 where the guide member 6455 is limited from further sliding in the direction of the distance 6891, but is free to move across the guide slot 6333 to permit rotation of the secondary housing 5850 relative to the primary housing 5830.

Referring to FIGS. 68B and 68C, it can be seen that the lock rod 5870 remains in the second lobe 6463 of the secondary lock channel 6458. Thus, the secondary channel wall 6456 continues to impinge upon the lock rod 5870 so that the lock rod 5870 engages the teeth 6337 in the primary lock channel 6335 of the primary housing 5830, thus continuing to prevent the primary housing 5830 from sliding relative to the lock rod 5870. With the lock rod 5870 remaining in the second lobe 6463, the secondary housing 5850 continues to be free to slide relative to the lock rod 5870.

Referring to FIG. 69A, the secondary housing 5850 is rotated in a direction 6993. The guide member 5455 now extends into a fourth segment 6947 of the guide slot 6333 where the guide member 6455 is limited from further rotating in the direction 6993, but now permits relative sliding movement of the primary housing 5830 relative to the secondary housing 5850.

Referring to FIGS. 69B and 69C, it can be seen that the lock rod 5870 moves into the third lobe 6465 of the secondary lock channel 6458. As a result, the lock rod 5870 no longer engages the teeth 6337 in the primary lock channel 6335 of the primary housing 5830, enabling the primary housing 5830 to slide relative to the lock bar 5870. However, with rotation of the secondary housing 5850 causing the lock bar 5870 to be received into the third lobe 6465 of the secondary lock channel 6458, the teeth 6459 extending from the secondary housing 5850 now engage the lock rod 5870, thereby preventing sliding movement of the secondary housing 5850 relative to the lock rod 5870. Referring to FIG. 69D, it should be noted that the rotation of the secondary housing 5850 again results in no movement of the electrodes 207 and 211.

Referring to FIG. 70A, the primary housing 5830 is moved through a distance 7091 to partially retract the primary housing 5830 within the secondary housing 5850 to partially retract the distal end 209 of the primary electrode 207 away from the distal end 213 of the secondary electrode 211 as shown in FIG. 70D. The primary housing 5830 is free to slide relative to the lock rod 5870. As previously described with reference to FIGS. 69B and 69C and as shown in FIGS. 70B and 70C, the rotation of the secondary housing 5850 caused the lock rod 5870 to be rotated into the third lobe 6465 of the secondary lock channel 6458 in the secondary housing 5850. As a result, the lock rod 5870 was moved away and disengaged from the teeth 6337 in the primary lock channel 6355 of the primary housing 5830. With the lock rod 5870 in the third lobe 6465 of the secondary lock channel 6458 of the secondary housing 5850, the lock rod 5870 engages the teeth 6459 in the third lobe 6465 of the secondary lock channel 6458 of the secondary housing 5850, thereby preventing the secondary housing 5850 from sliding relative to the lock bar 5870. In this manner, once the secondary electrode 211 has been extended and secured in position, the primary electrode 207 may be moved to position the distal end 209 of the primary electrode 207 relative to the distal end 213 of the secondary electrode 211 to facilitate application of an electric current to provide desired treatment.

It will be appreciated that the illustrative embodiment of the user interface described with reference to FIGS. 62-70D describe significant detail in the structure and operation of the user interface 5801, but has set forth relatively simple manipulation—of only the secondary housing 5850 to position the electrodes 207 and 211 until the primary housing 5830 is retracted in a final step. In furtherance thereof, FIGS. 71A-76B are provided to illustrate operation of the embodiment of the user interface described with reference to FIGS. 62-70D.

Figure 71A:
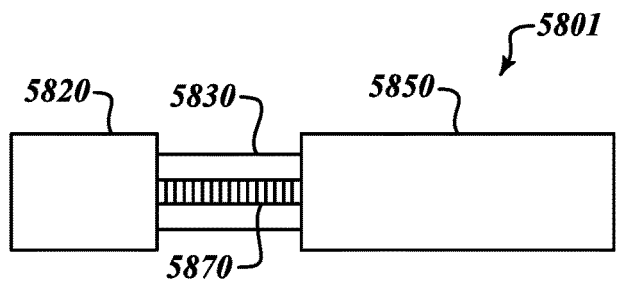
Figure 71B:
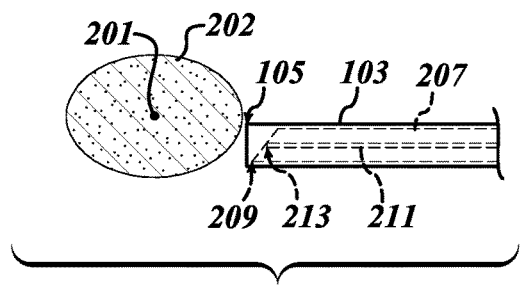

Referring to FIG. 71A, the user interface 5801 is shown in readiness for deployment of the electrodes 207 and 211 in the vicinity of the reference point 202. As shown in FIG. 71B, the distal end 209 of the primary electrode 207 rests inside the distal end 105 of the sheath 103 and the distal end 213 of the secondary electrode 211 rests inside the distal end 209 of the primary electrode 207.

Figure 72A:
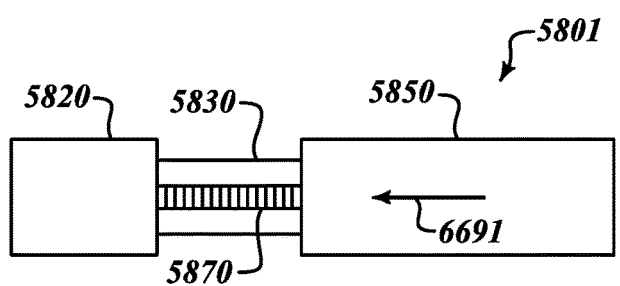
Figure 72B:
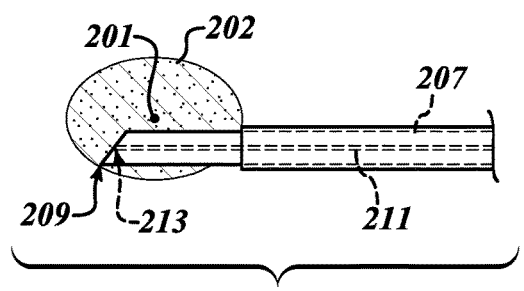

Referring to FIG. 72A, the user interface 5801 is shown with the secondary housing 5850 and the primary housing 5830 moved in the direction 6691 to, as shown in FIG. 72B, simultaneously extend the distal end 209 of the primary electrode 207 and the distal end 213 of the secondary electrode 211 into the reference point 202, as previously described with reference to FIGS. 66A-66D.

Figure 73A:
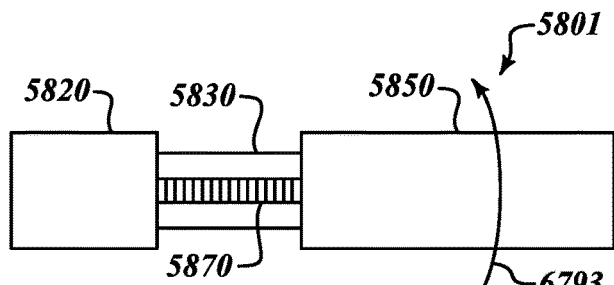
Figure 73B:
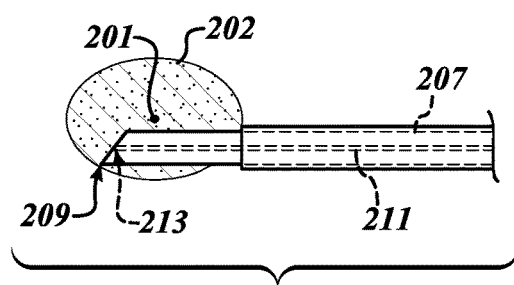

Referring to FIG. 73A, the user interface 5801 is shown with the secondary housing 5850 rotated in the direction 6793 to, as shown in FIG. 73B, secure the primary electrode 207 from being moved relative to the reference point 202. The primary electrode 207 is thus secured in place while, the secondary housing 5850 is remains free to slide, as previously described with reference to FIGS. 67A-67D.

Figure 74A:
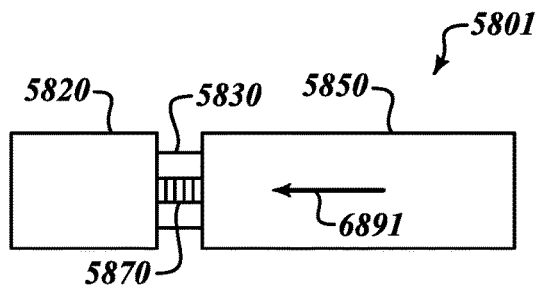
Figure 74B:
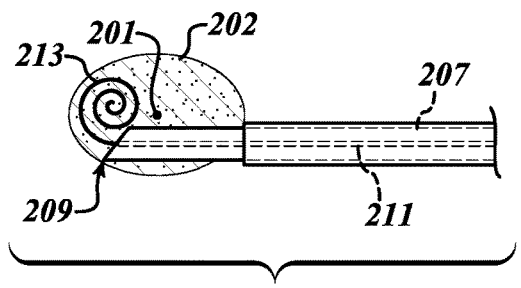

Referring to FIG. 74A, the user interface 5801 is shown with the secondary housing 5850 moved in the direction 6891 to, as shown in FIG. 74B, extend the distal end 213 of the secondary electrode 211 across the reference point 202, as previously described with reference to FIGS. 68A-68D.

Figure 75A:
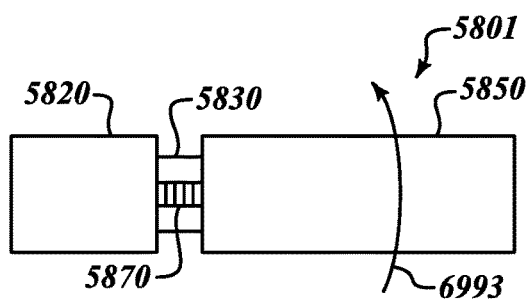
Figure 75B:
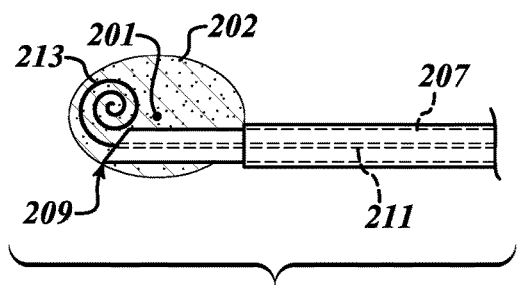

Referring to FIG. 75A, the user interface 5801 is shown with the secondary housing 5810 rotated in the direction 6993 to, as shown in FIG. 75B, secure the distal end 213 of the secondary electrode 211 in place across the reference point 202 while preparing for the partial retraction of the distal end 209 of the primary electrode 207, as previously described with reference to FIGS. 69A-69D.

Figure 76A:
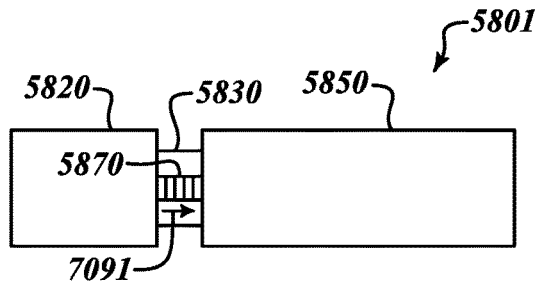
Figure 76B:
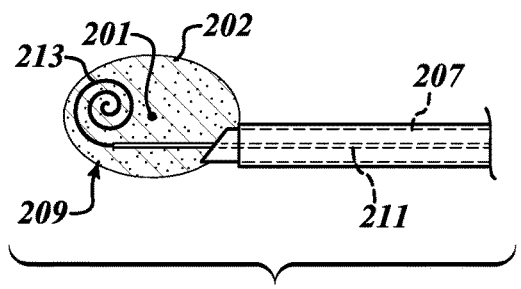

Referring to FIG. 76A, the user interface 5801 is shown with the primary housing 5830 moved in the direction 7091 as previously described with reference to FIGS. 70A-70D to partially retract the distal end 209 of the primary electrode 207. As shown in FIG. 76B, the distal end 209 of the primary electrode 207 is thus partially withdrawn from the reference point 202 while leaving the distal end 213 of the secondary electrode 211 in place, thereby readying the electrodes 207 and 211 for administration of treatment.

Figure 77:
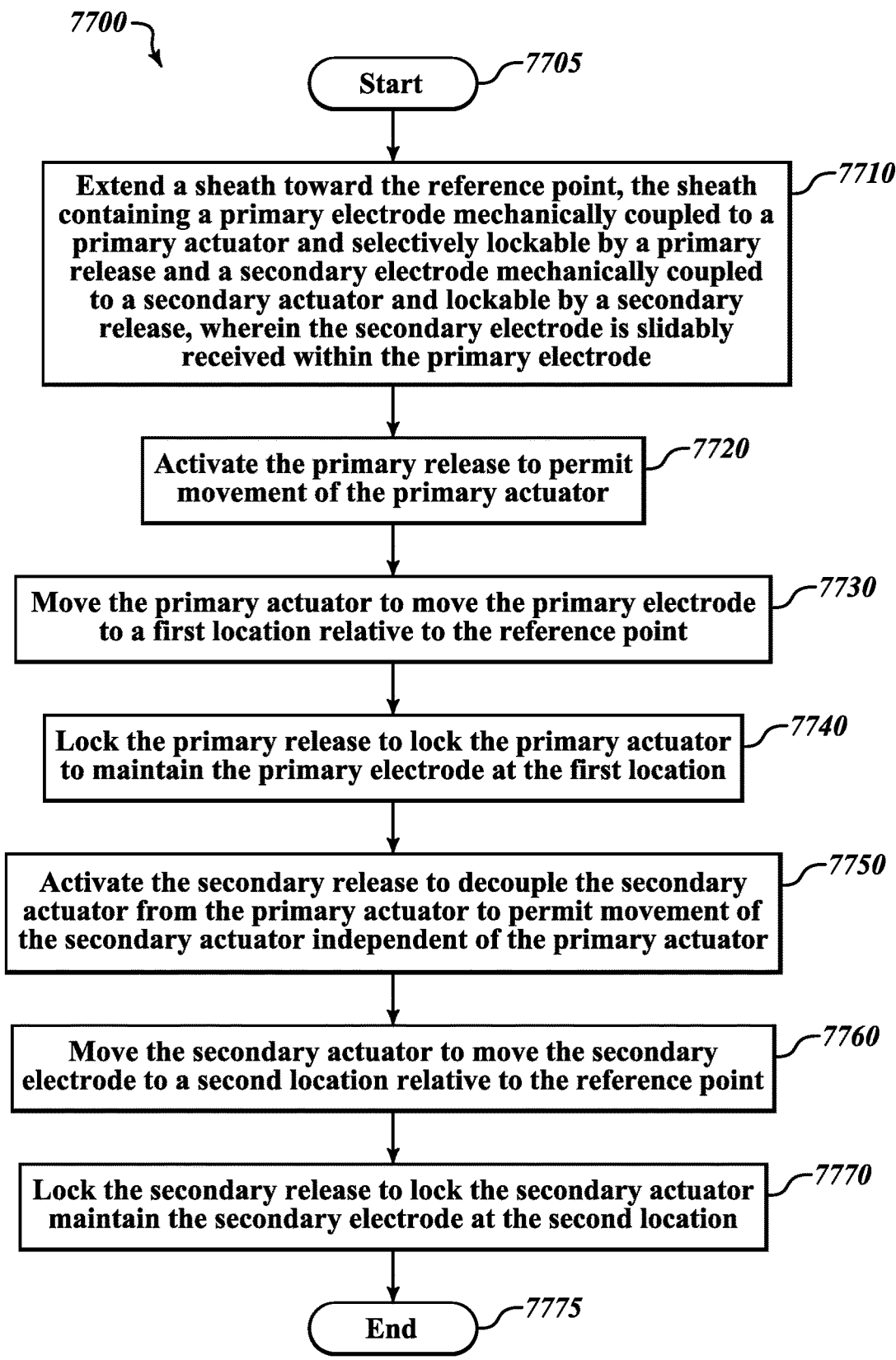

Referring to FIG. 77, an illustrative method 7700 of positioning electrodes for treatment is provided. The method 7700 starts at a block 7705. At a block 7710, a sheath containing a primary electrode and a secondary electrode is extended, where the secondary electrode is contained within the primary electrode and initially coupled to move with the primary electrode as previously described, for example, with reference to FIGS. 8, 51, and 61. At a block 7720, the primary electrode is moved to a first location near a reference point as previously described, for example, with reference to FIGS. 14, 38, 53, and 64. At a block 7730, the primary electrode is locked in position at the first location as previously described, for example, with reference to FIGS. 14, 38, 54, and 65. At a block 7740, movement of the secondary electrode (independent of the primary electrode) is unlocked as previously described, for example, with reference to FIGS. 19, 44, 54, and 65. At a block 7750, the secondary electrode is moves to a second location near the reference point as previously described, for example, with reference to FIGS. 20, 45, 55, and 66. At a block 7760, the secondary electrode is locked in position at the second position as previously described, for example, with reference to FIGS. 26, 46, 55, and 68. The method 7700 ends at a block 7765, with the electrodes now positioned for the administration of treatment.

Figure 78:
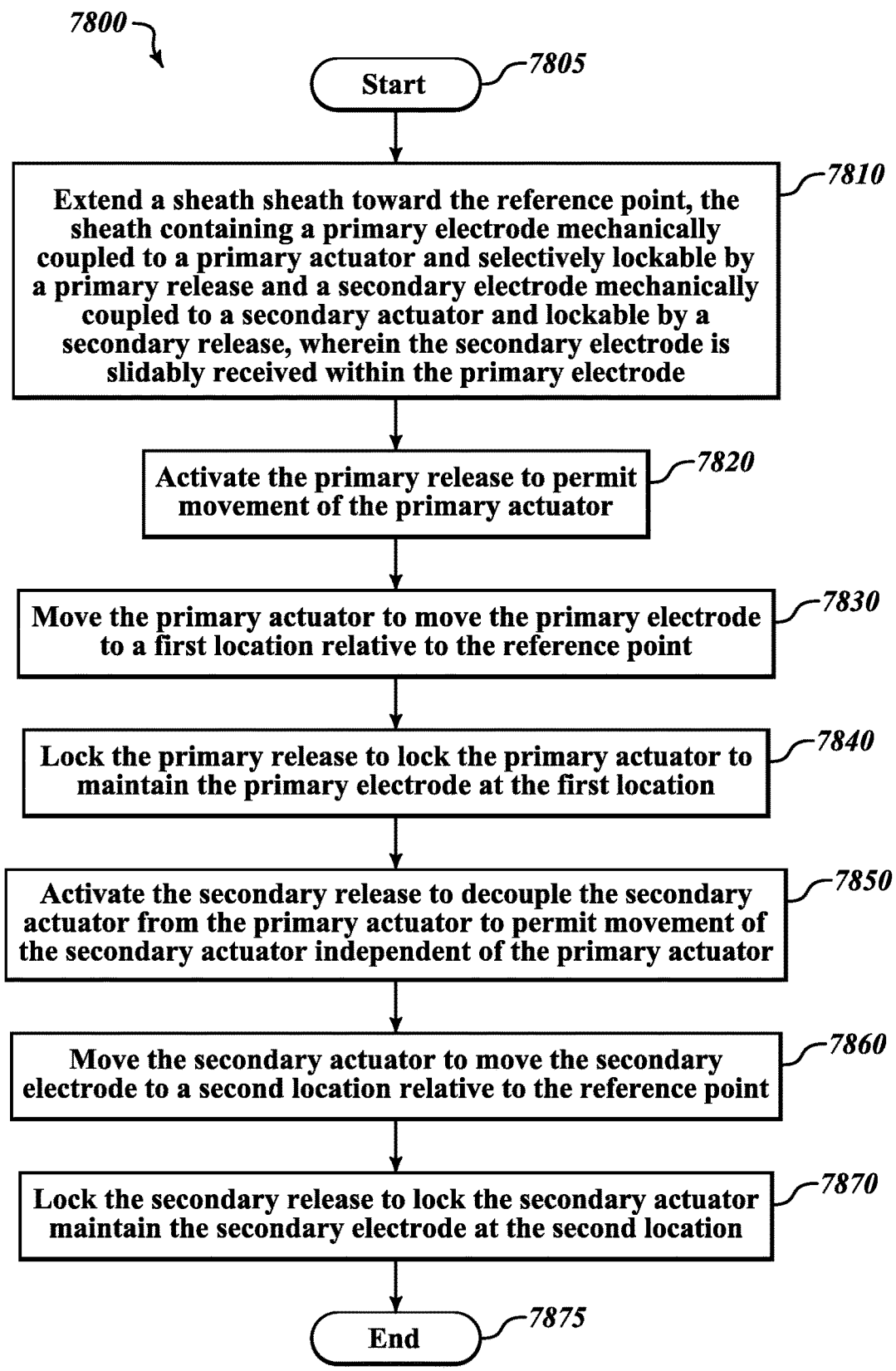

Referring to FIG. 78, an illustrative method 7800 of positioning electrodes for treatment is provided. The method 7800 relates to the use of a user interface as previously described, for example, with reference to FIGS. 11-34.

The method 7800 starts at a block 7805. At a block 7810, a sheath is extended toward a reference point, the sheath containing a primary electrode mechanically coupled to a primary actuator and selectively lockable by a primary release and a secondary electrode mechanically coupled to a secondary actuator and lockable by a secondary release, wherein the secondary electrode is slidably received within the primary electrode. At a block 7820, the primary release is activated to permit movement of the primary actuator as previously described, for example, with reference to FIG. 13. At a block 7830, the primary actuator is moved to move the primary electrode to a first location relative to the reference point as previously described, for example, with reference to FIG. 13. At a block 7840, the primary release is locked to lock the primary actuator to maintain the primary electrode at the first location as previously described, for example, with reference to FIG. 14.

At a block 7850, the secondary release is activated to decouple the secondary actuator from the primary actuator to permit movement of the secondary actuator independent of the primary actuator as previously described, for example, with reference to FIG. 19. At a block 7860, the secondary actuator is moved to move the secondary electrode to a second location relative to the reference point as previously described, for example, with reference to FIG. 20. At a block 7870, the secondary release is locked to lock the secondary actuator to maintain the secondary electrode at the second location as previously described, for example, with reference to FIG. 20. The method 7800 ends at a block 7875, with the electrodes now positioned for the administration of treatment.

Figure 79:
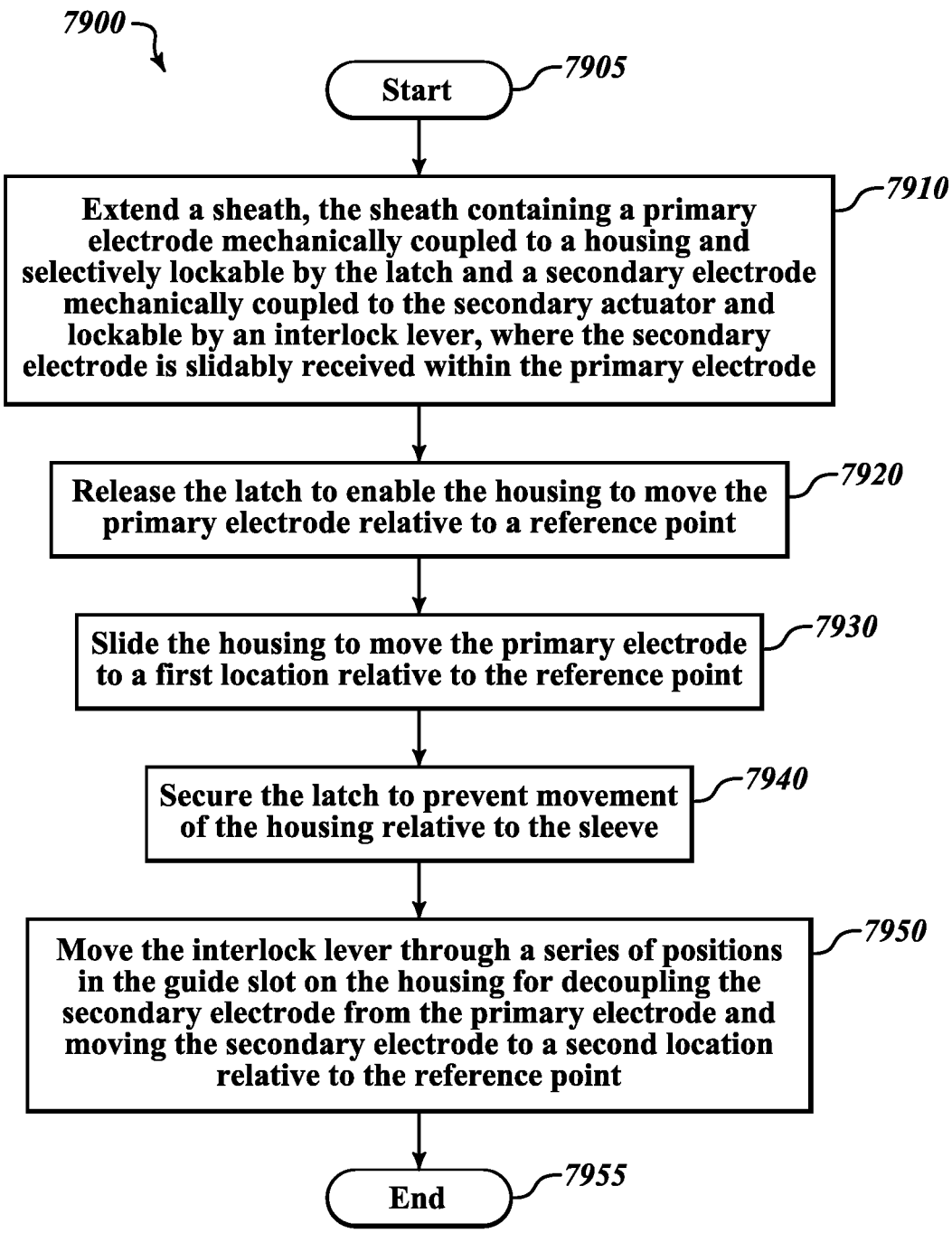

Referring to FIG. 79, an illustrative method 7900 of positioning electrodes for treatment is provided. The method 7900 relates to the use of a user interface as previously described, for example, with reference to FIGS. 35-47.

The method 7900 starts at a block 7905. At a block 7910, a sheath is extended, with the sheath containing a primary electrode mechanically coupled to a housing and selectively lockable by the latch and a secondary electrode mechanically coupled to the secondary actuator and lockable by an interlock lever, where the secondary electrode is slidably received within the primary electrode. At a block 7920, the latch is released to enable the housing to move the primary electrode relative to a reference point as previously described, for example, with reference to FIG. 38. At a block 7930, the housing is slid to move the primary electrode to a first location relative to the reference point as previously described, for example, with reference to FIG. 38. At a block 7940, the latch is secured to prevent movement of the housing relative to the sleeve as previously described, for example, with reference to FIG. 38. At a block 7950, the interlock lever is moved through a series of positions in the guide slot on the housing for decoupling the secondary electrode from the primary electrode and moving the secondary electrode to a second location relative to the reference point as previously described, for example, with reference to FIGS. 44-46. The method 7900 ends at a block 7955, with the electrodes now positioned for the administration of treatment.

Figure 80:
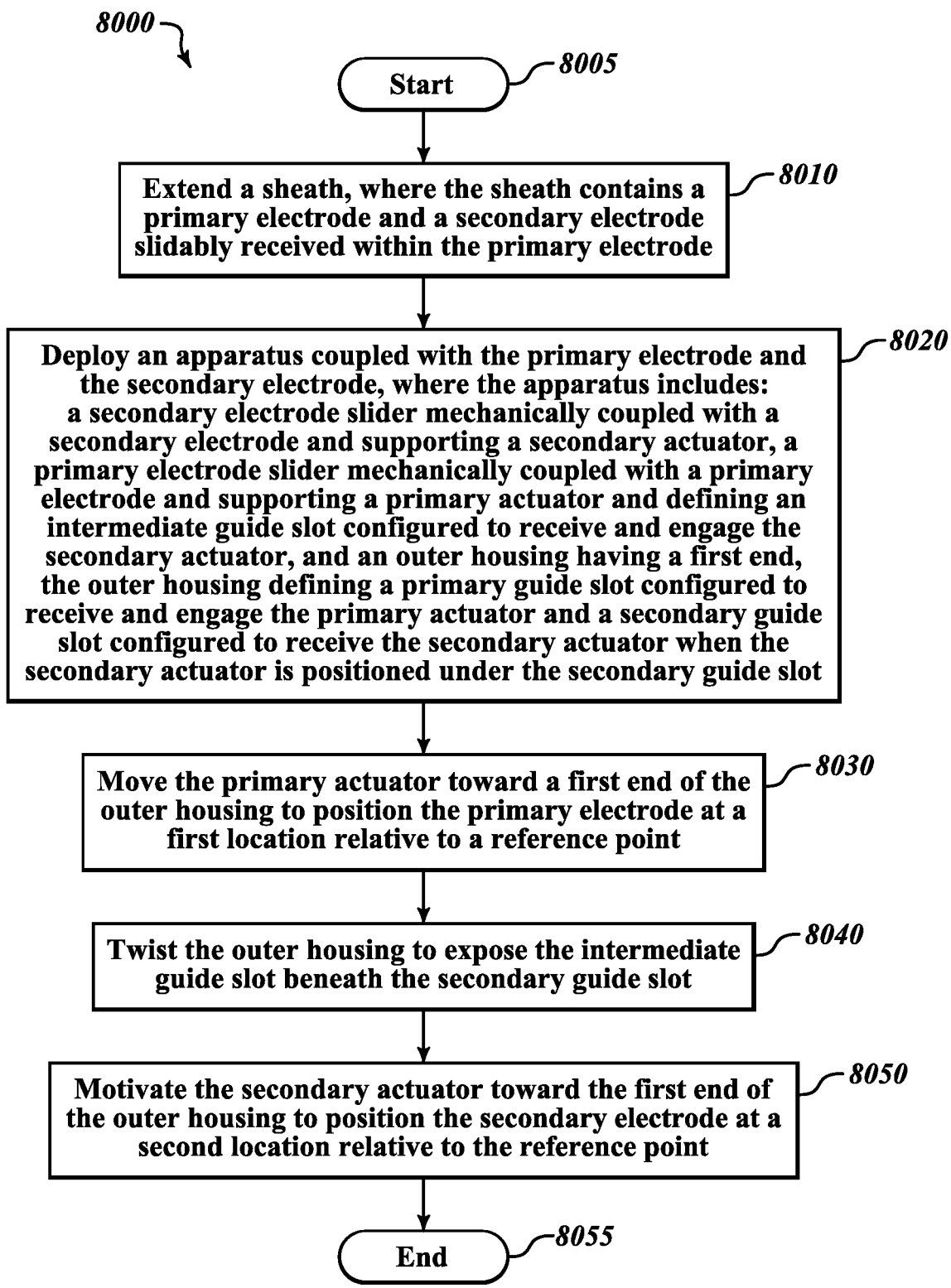

Referring to FIG. 80, an illustrative method 8000 of positioning electrodes for treatment is provided. The method 8000 relates to the use of a user interface as previously described, for example, with reference to FIGS. 48-57.

The method 8000 starts at a block 8005. At a block 8010, a sheath is extended, where the sheath contains a primary electrode and a secondary electrode slidably received within the primary electrode as previously described, for example, with reference to FIG. 51.

At a block 8020, an apparatus coupled with the primary electrode and the secondary electrode is deployed. The apparatus includes a secondary electrode slider mechanically coupled with a secondary electrode and supporting a secondary actuator. The apparatus also includes a primary electrode slider mechanically coupled with a primary electrode and supporting a primary actuator, and also defining an intermediate guide slot configured to receive and engage the secondary actuator. The apparatus also includes an outer housing having a first end, with the outer housing defining a primary guide slot configured to receive and engage the primary actuator and a secondary guide slot configured to receive the secondary actuator when the secondary actuator is positioned under the secondary guide slot, all as previously described, for example, with reference to FIGS. 48-57.

At a block 8030, the primary actuator is moved toward the front end of the outer housing to position the primary electrode at a first location relative to the reference point as previously described, for example, with reference to FIG. 53. At a block 8040, the outer housing is rotated to expose the intermediate guide slot beneath the second guide slot as previously described, for example, with reference to FIG. 54. At a block 8050, the secondary actuator is moved toward the front end of the outer housing to position the secondary electrode at a second location relative to the reference point as previously described, for example, with reference to FIG. 55. The method 8000 ends at a block 8055, with the electrodes now positioned for the administration of treatment.

Figure 81:
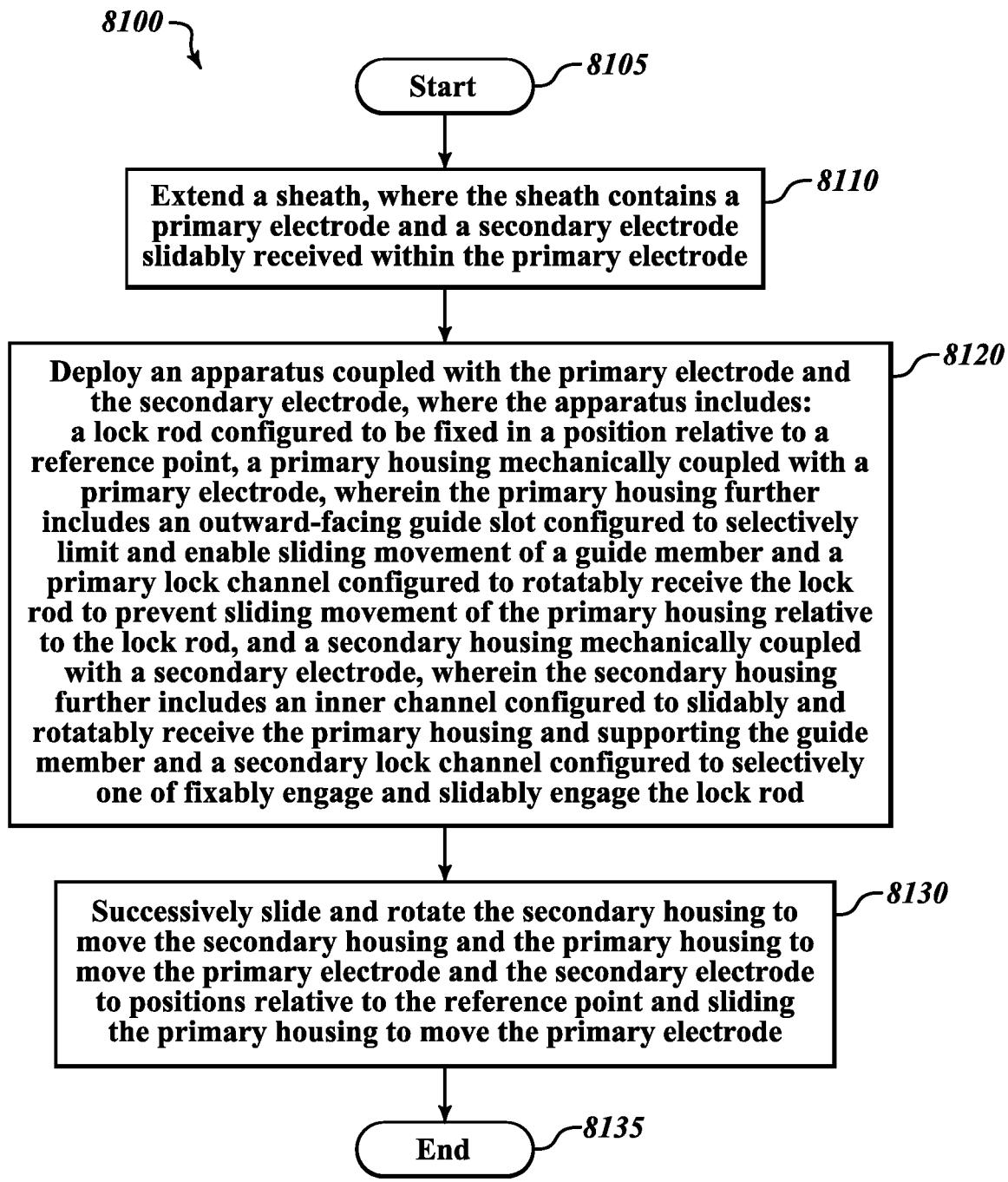

Referring to FIG. 81, an illustrative method 8100 of positioning electrodes for treatment is provided. The method 8100 relates to the use of a user interface as previously described, for example, with reference to FIGS. 58-76.

The method 8100 starts at a block 8105. At a block 8010, a sheath is extended, where the sheath contains a primary electrode and a secondary electrode slidably received within the primary electrode as previously described, for example, with reference to FIG. 61.

At a block 8120, an apparatus coupled with the primary electrode and the secondary electrode is deployed. The apparatus includes a secondary electrode slider mechanically coupled with a secondary electrode and supporting a secondary actuator. The apparatus includes a lock rod configured to be fixed in a position relative to a reference point. The apparatus also includes a primary housing mechanically coupled with a primary electrode. The primary housing also includes an outward-facing guide slot configured to selectively limit and enable sliding movement of a guide member and a primary lock channel configured to rotatably receive the lock rod to prevent sliding movement of the primary housing relative to the lock rod. The apparatus further includes a secondary housing mechanically coupled with a secondary electrode. The secondary housing further includes an inner channel configured to slidably and rotatably receive the primary housing and supporting the guide member. The secondary housing also includes a secondary lock channel configured to selectively one of fixably engage and slidably engage the lock rod.

At a block 8130, the secondary housing is successively slide and rotated to move the secondary housing and the primary housing to move the primary electrode and the secondary electrode to positions relative to the reference point and the primary housing is slide to move the primary electrode, for example, with reference to FIGS. 65A-76. The method 8000 ends at a block 8035, with the electrodes now positioned for the administration of treatment.

Referring to FIG. 82, another embodiment of the user interface 8201 for positioning electrodes is shown. The user interface 8201 includes components that are moved parallel along an axis 8221 or rotated along a curve 8223 around the axis 8221, as further described below. As also further described below, the user interface 8201 generally is controlled by moving actuators, such as the primary actuator 8232, by engaging a primary actuator grip 8235 through a first access opening 8211 defined in the outer housing 8210. The primary actuator 8232 may be moved along the axis 8221 by engaging and manipulating the primary actuator grip 8235 and sliding the primary actuator grip 8235 along the axis 8221 toward a first end 8241 of the housing 8210. The primary actuator 8232 slides along a shaft 8233 that extends along the axis 8221. The shaft 8233 may be coupled to the outer housing 8210 at a base 8234. The shaft 8233 is hollow to receive and permit sliding of electrodes (not shown in FIG. 82) therethrough. As further described below, once the primary actuator 8232 is moved to a position where the primary electrode is extended, the primary actuator 8232 may be rotated around the axis 8221 to provide access to the secondary actuator (not shown in FIG. 82). By shrouding the secondary electrode actuator, the primary actuator 8232 prevents the secondary electrode actuator from being moved to extend the secondary electrode before it is desired to do so. The structure and operation of these components are further described below.

The user interface 8201 includes a coupling 8220 to engage a port on an electrosurgical apparatus, such as a bronchoscope, as described with reference to FIGS. 1, 7, and 8. The user interface 8201 also includes a sheath actuator 8204 to position a sheath (not shown in FIG. 82) as previously described with reference to FIGS. 7-11. The sheath actuator 8204 includes a slidable sleeve 8212 and a sheath lock 8206 to engage the slidable sleeve 8212 and secure the slidable sleeve 8212 in place at the first end 8241 of the housing 8210 of the user interface 8201, as described further below. It will be appreciated that, as described with reference to FIG. 35 regarding another embodiment of the user interface 3501, a sheath actuator may be part of the bronchoscope or a separate device inserted between the user interface 8201 and the bronchoscope (not shown in FIG. 82). Thus, the sheath actuator 8204 may not be a part of the user interface 8201. Also, although not shown in FIG. 82, as in embodiments shown in FIGS. 1 and 11, leads from a switchable current source are received at the user interface 8201 and a sheath containing primary and secondary electrodes extends from the user interface 8201 via the coupling 8220.

Referring to FIG. 83, the user interface 8201 of FIG. 82 includes a number of components, including the outer housing 8210, the primary actuator 8232, the shaft 8233, a secondary actuator 8352, and components of the sheath actuator 8204, including the slidable sleeve 8212, the sheath lock 8206, and the coupling 8220. As previously described, the first access opening 8211 defined in the outer housing 8210 permits access to the primary actuator 8232 and the second actuator 8352, the operation of which will be further described below.

The primary actuator 8232, which may be manipulated by a user engaging the primary actuator grip 8235, slides along the shaft 8233 which ends at the base 8234 that may be secured to the outer housing 8210 as further described below with reference to FIGS. 85A and 85B. The primary actuator 8232 is fixably engaged with a primary electrode (not shown in FIG. 83) so that movement of the primary actuator 8232 moves the primary electrode. The primary electrode may slide through the shaft 8233 along which the primary actuator 8232 slides. In some embodiments, the shaft 8233 includes a channel 8334 that receives locking studs 8336 configured to compressibly extend inwardly from the primary actuator 8232 toward the shaft 8233. The engagement of the locking studs 8336 with the channel 8334 may secure the primary actuator 8232 in place relative to the shaft 8233 along the axis 8221 once the primary actuator 8232 is moved to place the primary electrode (not shown in FIG. 83) at a desired position. In some embodiments, the locking studs 8336 may be released from the channel 8334 by exerting an additional force on the primary actuator 8232 along the axis 8221, beyond the force that may be required to slide the primary actuator 8232 along the shaft 8233 when the locking studs 8336 are not engaged with the channel 8334.

The secondary actuator 8352 is fixably engaged with a secondary electrode (not shown in FIG. 83) and causes the secondary electrode to slide through the shaft 8233. The secondary actuator 8352 includes a secondary actuator grip 8355 that enables a user to slide and/or rotate the secondary actuator 8352, as described further below. The secondary actuator 8352 is configured to slide relative to the primary actuator 8232 just as the primary actuator 8232 slides along the shaft 8233. The secondary actuator 8352 may slide along the primary actuator 8232 along the axis 8221 and/or rotate along the curve 8232 around the axis 8221. As described further below, the secondary actuator 8352 defines a second access opening 8356 so that, after rotating the secondary actuator 8352, a user may engage the primary actuator 8232 through the second access opening 8355. Before it is rotated, the secondary actuator 8352 thus may act as a shroud to prevent access to the primary actuator 8232 when the secondary actuator 8352 is being positioned, thereby assisting a user in following a desired sequence of moving the electrodes, as described further below.

Referring to FIG. 84A, in various embodiments there may be a single first access opening 8211 on one side of the outer housing 8210, or there may be multiple first access openings 8211 at two or more places around the periphery of the outer housing 8201. For example, the outer housing 8410 of FIG. 84A includes two first access openings 8211 on opposing faces of the outer housing 8410.

Referring to FIG. 84B, in various embodiments the outer housing is generally hollow to receive the shaft 8233, the primary actuator 8232, and the secondary actuator 8352. As also shown in FIG. 84B, a plurality of tabs 8413 are configured to engage notches in the base 8335 of the shaft 8233, as further described below with reference to FIGS. 85A and 85B. Referring to FIG. 84C, in various embodiments the first access openings 8211 are defined by the outer housing 8210.

Referring to FIG. 85A, the shaft 8233 and its base 8335 are shown in greater detail than in FIG. 83. The channel 8334 (along the shaft 8233) receives the locking studs 8336 (not shown in FIG. 85A) which extend inwardly from the primary actuator 8232 (also not shown in FIG. 85A). Complementary notches 8515 are sized and positioned to receive the tabs 8413 (FIG. 84B) of the outer housing 8410. The shaft 8233 defines a channel 8517 through which the electrodes (not shown) coupled with the primary actuator 8232 and the secondary actuator 8352 may slide.

Referring to FIG. 86A, the primary actuator 8232 supports the primary actuator grip 8235 and the locking studs 8336 that are configured to engage the channel 8334 of the shaft 8233 (FIGS. 82, 83, and 85A). Referring to FIG. 86B, in various embodiments multiple primary actuator grips 8235 may extend from the primary actuator 8232. In the example of FIG. 86A, two primary actuator grips 8235 extend from opposing sides of the primary actuator 8232. Having two primary actuator grips 8235 extending from opposing sides of the primary actuator 8232, for example, would allow a user to manipulate the primary actuator from two sides of the user interface if there are two first access openings 8211 defined in opposing sides of the outer housing 8210, such as shown in the example of FIGS. 84A and 84C, and two second access openings 8356 defined in opposing sides of the secondary actuator 8352.

Still referring to FIG. 86B, the primary actuator 8232 also may include grooves 8611 configured to receive guide projections extending inwardly from the secondary actuator 8352, as further described below. Referring to FIG. 86C, in some embodiments the grooves 8611 may be formed in two opposing sides of the primary actuator 8232 as shown. In various embodiments the locking studs 8336 extend inwardly from the primary actuator 8232 into a primary actuator channel 8619 that is configured to enable the primary actuator 8232 to slide along the shaft 8233.

Referring to FIG. 87A, a detailed view of the secondary actuator 8352 is shown. The secondary actuator 8352 includes the secondary actuator grip 8355 and, in the example shown, a pair of second access openings 8356. Referring to FIG. 87B, in various embodiments multiple secondary actuator grips 8355 may extend from the secondary actuator 8352. In the example of FIG. 87B, two secondary actuator grips 8355 extend from opposing sides of the secondary actuator 8352. Having two secondary actuator grips 8355 extending from opposing sides of the secondary actuator 8352, for example, would allow a user to manipulate the secondary actuator 8352 from two sides of the user interface if there are two first access openings 8211 in opposing sides of the outer housing 8210, such as shown in the example of FIG. 84A. Correspondingly, a pair of second access openings 8356 are defined in the secondary actuator 8352 that, for example, would enable a user to engage a pair of primary actuator grips 8235 through the pair of second access openings 8356.

Referring to FIG. 87C, in various embodiments the secondary actuator 8352 also may include tabs 8757 inwardly extending into a hollow channel 8719 of the secondary actuator 8352. The tabs are configured to slidably engage the grooves 8611 in the primary actuator 8232. It will be appreciated that the grooves 8611 in the primary actuator 8432 extend only part of the length of the primary actuator 8432. As a result, with the tabs 8757 on the secondary actuator 8352 received into the grooves 8611 on the primary actuator 8232, when the tabs 8757 are at a closed end 8612 of the grooves 8611, movement of the primary actuator 8232 toward an open end 8613 of the grooves 8611 may pull the secondary actuator 8352 with the primary actuator 8232. The engagement of the tabs 8757 with the grooves 8611 thus may cause the primary actuator 8232 to cause the secondary actuator 8352 to move in concert with the primary actuator 8232 and, thus, cause the secondary electrode to move in concert with the primary electrode, as further described below with reference to FIG. 90A.

Referring to FIG. 87D, in various embodiments the secondary actuator grips 8355 extend from sides of the secondary actuator 8352 at a ninety-degree offset to the second access openings 8356 formed in the secondary actuator 8532.

Referring to FIGS. 88A, 88B, 89A, and 89A, operation of the sheath actuator 8204 is depicted. The operation of the sheath actuator 8204 of the user interface 8201 is similar to that of the sheath actuator 4804 of the user interface 4801 of FIGS. 50A, 50B, 51C, and 51D, as previously described. Referring to FIGS. 88A and 88B and as used in conjunction with a user interface 8201, the sheath actuator 8204 controls a position of the sheath 103. Specifically, a position of the sheath 103 is controlled by sliding the slidable sleeve 8212 within the coupling 8220 and securing the sheath 103 at the desired location by securing the slidable sleeve 8212 with the sheath lock 8206. The sheath actuator 8204 may operate similarly to the sheath lock 706 of FIG. 9, as previously described. The slidable sleeve 8212 is fixably mounted to the outer housing 8210 and is slidably received within the coupling 8220. When the slidable sleeve 8212 is situated to position the sheath 103 containing the electrodes 207 and 211 at a desired location, the sheath lock 8206 is locked to secure the slidable sleeve 8212 in place. The sheath lock 8206 may be a spring-loaded lock, a thumbscrew, or another similar mechanism as previously described with reference to FIGS. 7-10 to secure the slidable sleeve 8212 in place to secure the position of the sheath 103.

As previously described and as shown in the FIG. 88B, in illustrative embodiments the secondary electrode 211 is received within the primary electrode, with a distal end 213 of the secondary electrode 211 initially resting just within the distal end 209 of the primary electrode 207. In turn, the distal end 209 of the primary electrode 207 rests just within the distal end 105 of the sheath 103. Before the sheath actuator 8204 is used to position the distal end 105 of the sheath 103 near the reference point 201, the distal end of the sheath 103 may initially rest at a position away from or immediately adjacent to the reference point 201.

Referring to FIGS. 89A and 89B and as used in conjunction with a user interface 8201, the sheath actuator 8204 is used to move the distal end 105 of the sheath 103 to a position closer to the reference point 201 as shown in FIG. 89B. A relative movement of the outer housing 8210 toward the coupling 8220 by a distance 8919 moves the distal end 105 of the sheath 103 a corresponding distance to move the distal end 105 of the sheath 103 closer to the reference point 201. In turn, the distal end 209 of the primary electrode 207 and the distal end 213 of the secondary electrode 211 are also moved closer to the reference point 201. The relative movement of the outer housing 8210 toward the coupling 8220 is accomplished by the slidable sleeve 8212 being at least partially received within the coupling 8220 and then secured with the sheath lock 8206, as previously described. As shown in FIG. 89B, the distal end 209 of the primary electrode 207 remains positioned within a distal end 105 of the sheath 103, with the distal end 105 of the sheath 103 having been positioned proximate the reference point 201. The distal end 213 of the secondary electrode 211 remains positioned within the distal end 209 of the primary electrode 207.

FIGS. 90A, 90B, 91A, and 91B show how the user interface 8201 moves the electrodes 207 and 211 based on manipulation of the user interface 8201. Referring to FIG. 90A, the primary actuator 8232 is advanced toward the first end 8241 of the outer housing 8210, such as by a user engaging the primary actuator grip 8235 and sliding it in a direction 9023. As previously described with reference to FIG. 87C, the tabs 8757 on the secondary actuator 8352 engage the grooves 8611 on the primary actuator 8232. Thus, the movement of the primary actuator 8232 toward the first end 8241 of the outer housing 8210 also advances the secondary actuator 8352, as shown in FIG. 90A. As a result, after extension of the primary electrode caused by the movement of the primary actuator 8232, the secondary actuator 8352 is drawn into the first access opening 8211 where the secondary actuator grip 8355 may be engaged by a user to move the secondary actuator 8352. The outer housing 8210 thus shrouds the secondary actuator 8352 until the primary actuator 8232 is moved into a position appropriate for movement of the secondary actuator 8352. Also, in some embodiments, once the primary actuator 8232 has been moved forward, the locking studs 8333 engage the channel 8334 in the shaft 8333 (not shown in FIG. 90A), thereby holding the primary actuator 8232 (and the primary electrode) in place.

Referring to FIG. 90B, the movement of the primary actuator 8232 and the concerted movement of the secondary actuator 8352 shown in FIG. 90A results in concerted movement of the primary electrode 207 and the secondary electrode 211, moving in concert the distal ends 209 and 213, respectively, beyond the distal end 105 of the sheath 103. In the example of FIG. 90B, the primary electrode 207 and the secondary electrode 211 contained therein pierce the target tissue 202 near the reference point 201.

Referring to FIG. 91A, the secondary actuator 8352 is advanced toward the first end 8241 of the outer housing 8210 in a direction 9123. The secondary actuator 8352 passes over the primary actuator 8232 within the outer housing 8210. As will be recalled, the engagement of the tabs 8757 with the grooves 8611 on the primary actuator 8232 caused the forward movement of the primary actuator 8232 shown in FIG. 90A to draw the secondary actuator 8352 forward in concert. However, because the tabs 8757 in the secondary actuator can move independently in the grooves 8611 toward the open ends 8613, the secondary actuator 8352 may move toward the first end 8241 of the outer housing 8210 independently of the primary actuator 8232.

Referring to FIG. 91B, the movement of the secondary actuator 8352 results in movement of the secondary electrode 211 independently of the primary electrode 207. As previously described, when the distal end 213 of the secondary electrode 211 extends beyond the distal end 209 of the primary electrode 207, the secondary electrode coils, thereby augering into the target tissue 202.

Referring to FIG. 92A, now that the secondary electrode 211 (FIG. 91B) has been extended, the secondary actuator 8352 may be manipulated to unshroud the primary actuator 8232 to enable further manipulation of the primary actuator 8232 and, thus, the primary electrode 207. With the secondary actuator 8352 advanced, the tabs 8757 (which extend inwardly from the secondary actuator 8352) pass out of the grooves 8611 on the primary actuator 8232, thereby allowing the secondary actuator 8352 to be rotated relative to the primary actuator 8232 as shown in FIG. 92A. The secondary actuator 8352 is rotated along a curve 9223, presenting the second access opening 8355 defined by the secondary actuator 8232 and exposing the primary actuator 8232 and the primary actuator grip 8235.

Referring to FIG. 92B, the rotation of the secondary electrode actuator 8352 does not move either the primary electrode 207 or the secondary electrode 211. The rotation of the secondary actuator 8352 merely prepares the user interface 8201 for a next step in positioning the electrodes 207 and 211. The rotation of the secondary actuator 8352 unshrouds the primary actuator 8232 for its next movement.

Referring to FIG. 93A, the primary actuator 8232 is moved in a direction 9323 away from the first end 8241 of the outer housing 8210 to cause a partial retraction of the primary electrode 207. A user may engage the primary actuator grip 8235 through the second access opening 8355 to manipulate the primary actuator 8232. Some additional force may have to be applied to the primary actuator grip 8235 to cause the locking studs (not shown in FIG. 93A) to be withdrawn from the channel 8334 in the shaft 8333 to enable the primary actuator 8232 to move over the shaft 8333.

Referring to FIG. 93B, the movement of the primary actuator 8232 results in a partial retraction of the primary electrode 207 without commensurate movement of the secondary electrode 211. Thus, the distal end 213 of the secondary electrode 211 remains coiled in the target tissue 202 where the distal end 213 of the secondary electrode 211 was positioned at the end of the step described with reference to FIGS. 91A and 91B. However, the distal end 209 of the primary electrode 207 is moved away from the distal end 213 of the secondary electrode 211, exposing an insulated section 215 of the primary electrode 211 and creating two, electrically separated contacts with the distal ends 209 and 213 of the electrodes 207 and 211 being separated by the insulation 215.

Referring to FIG. 94, another embodiment of the user interface 9401 for positioning electrodes is shown. The user interface 9401 includes components that are moved parallel with an axis 9421 or rotated along a curve 9423 around the axis 9421, as further described below. As also further described below, the user interface 9401 generally is controlled by moving actuators, such as the primary actuator 9432, by engaging a primary actuator grip 9435 that extends from a first channel 9431 defined in an outer housing 9410. The primary actuator 9432 may be moved along the axis 9421 by engaging and manipulating the primary actuator grip 9435 and sliding the primary actuator grip 9435 along the axis 9421 toward a first end 9441 of the housing 9410. As further described below, once the primary actuator 9432 is moved to a position where the primary electrode is extended, the primary actuator 9432 may be rotated around the axis 9421 to provide access to the secondary actuator (not shown in FIG. 94). By shrouding the secondary electrode actuator, the outer housing 9410 prevents the secondary electrode actuator from being moved to extend the secondary electrode before it is desired to do so. The structure and operation of these components are further described below.

The user interface 9401 includes a coupling 9420 to engage a port on an electrosurgical apparatus, such as a bronchoscope, as described with reference to FIGS. 1, 7, and 8. The user interface 9401 also includes a sheath actuator 9404 to position a sheath (not shown in FIG. 94) as previously described with reference to FIGS. 7-11. The sheath actuator 9404 includes a slidable sleeve 9412 and a sheath lock 9406 to engage the slidable sleeve 9412 and secure the slidable sleeve 9412 in place at the first end 9441 of the housing 9410 of the user interface 9401, as described further below. It will be appreciated that, as described with reference to FIG. 35 regarding another embodiment of the user interface 3501, a sheath actuator may be part of the bronchoscope or a separate device inserted between the user interface 9401 and the bronchoscope (not shown in FIG. 94). Thus, the sheath actuator 9404 may not be a part of the user interface 9401. Also, although not shown in FIG. 94, as in embodiments shown in FIGS. 1 and 11, leads from a switchable current source are received at the user interface 9401 and a sheath (that contains primary and secondary electrodes) extends from the user interface 9401 via the coupling 9420.

Referring to FIG. 95, the user interface 9401 includes a number of components, including the outer housing 9410, the primary actuator 9432, a secondary actuator 9552, and components of the sheath actuator 9404, including the slidable sleeve 9412, the sheath lock 9406, and the coupling 9420. Movement of the primary actuator 9432 provides access to the secondary actuator 9552 and a secondary actuator grip 9555 when the primary actuator 9432 has been positioned as desired.

The primary actuator 9432, which may be manipulated by a user engaging the primary actuator grip 9435, slides and rotates within the outer housing 9410 as further described below with reference to FIGS. 99A and 100A. The primary actuator 9432 is fixably engaged with a primary electrode (not shown in FIG. 95) so that movement of the primary actuator 9432 moves the primary electrode. The secondary actuator 9552 is fixably engaged with a secondary electrode (not shown in FIG. 95) and causes the secondary electrode to move. The secondary actuator 9552 includes a secondary actuator grip 9555 that enables a user to slide the secondary actuator 9552, as described further below.

The secondary actuator grip 9555 moves within a second channel 9531 in the primary actuator 9432. As a result, and as will be further described below, only when the primary actuator 9432 has been moved to position the primary electrode at a desired location can the primary actuator 9432 be further moved to expose the second channel 9531 and the secondary actuator grip 9555. Thus, the secondary actuator 9552 can only be moved once the primary actuator 9432 has been moved to a prerequisite position, with the outer housing 9410 shrouding the secondary electrode actuator 9532 until a preceding step to be performed with the primary actuator 9432 is first accomplished.

Referring to FIGS. 96A, 96B, 97A, and 97B, operation of the sheath actuator 9404 is depicted. The operation of the sheath actuator 9404 of the user interface 9401 is very similar to that of the sheath actuator 8204 of the user interface 8201 of FIGS. 88A, 89A, 90A, and 90B and other sheath actuators, as previously described. Referring to FIGS. 96A and 96B and as used in conjunction with a user interface 9401, the sheath actuator 9404 controls a position of the sheath 103. Specifically, a position of the sheath 103 is controlled by sliding the slidable sleeve 9412 within the coupling 9420 and securing the sheath 103 at the desired location by securing the slidable sleeve 9412 with the sheath lock 9406. The sheath actuator 9404 may operate similarly to the sheath lock 706 of FIG. 9, as previously described. The slidable sleeve 9412 is fixably mounted to the outer housing 9410 and is slidably received within the coupling 9420. When the slidable sleeve 9412 is situated to position the sheath 103 containing the electrodes 207 and 211 at a desired location, the sheath lock 9406 is locked to secure the slidable sleeve 9412 in place. The sheath lock 9406 may be a spring-loaded lock, a thumbscrew, or another similar mechanism as previously described with reference to FIGS. 7-10 to secure the slidable sleeve 9412 in place to secure the position of the sheath 103.

As previously described and as shown in FIG. 96B, in illustrative embodiments the secondary electrode 211 is received within the primary electrode, with a distal end 213 of the secondary electrode 211 initially resting just within the distal end 209 of the primary electrode 207. In turn, the distal end 209 of the primary electrode 207 rests just within the distal end 105 of the sheath 103. Before the sheath actuator 8204 is used to position the distal end 105 of the sheath 103 near the reference point 201, the distal end of the sheath 103 may initially rest at a position away from or immediately adjacent to the reference point 201.

Referring to FIGS. 97A and 97B and as used in conjunction with a user interface 9401, the sheath actuator 9404 is used to move the distal end 105 of the sheath 103 to a position closer to the reference point 201 as shown in FIG. 97B. A relative movement of the outer housing 9410 toward the coupling 9420 by a distance 9719 moves the distal end 105 of the sheath 103 a corresponding distance to move the distal end 105 of the sheath 103 closer to the reference point 201. In turn, the distal end 209 of the primary electrode 207 and the distal end 213 of the secondary electrode 211 are also moved closer to the reference point 201. The relative movement of the outer housing 9410 toward the coupling 9420 is accomplished by the slidable sleeve 9412 being at least partially received within the coupling 9420 and then secured with the sheath lock 9406, as previously described. As shown in FIG. 97B, the distal end 209 of the primary electrode 207 remains positioned within a distal end 105 of the sheath 103, with the distal end 105 of the sheath 103 having been positioned proximate the reference point 201. The distal end 213 of the secondary electrode 211 remains positioned within the distal end 209 of the primary electrode 207.

FIGS. 98A-101C show how the user interface 9401 moves the electrodes 207 and 211 based on manipulation of the user interface 4801. Referring to FIG. 98A with regard to the user interface 9401, the primary actuator grip 9435 extends from the primary actuator 9432 upward through the first channel 9431 of the outer housing 9410 and is situated at an initial position at a rear end 9801 within the first channel 9431. Referring to FIG. 98B, the primary actuator grip 9435 extends from the primary actuator 9432 through the first channel 9431 in the outer housing 9410. At the point of the cross-section, the secondary channel 9531 remains shrouded by the outer housing 9410. Also, with the primary actuator 9432 in an initial position, as shown in FIG. 98C, the distal end 209 of the primary electrode 207 remains positioned within a distal end 105 of the sheath 103, with the distal end 105 of the sheath 103 having been positioned proximate the reference point 201. The distal end 213 of the secondary electrode 211 remains positioned within the distal end 209 of the primary electrode 207.

Referring to FIG. 99A, the primary actuator 9432 is moved to extend the primary electrode 207, such as by the user engaging the primary electrode grip 9435 and sliding toward the first end 9441 of the outer housing 9410. Referring to FIG. 99B, the primary actuator grip 9435 extends from the primary actuator 9432 through the first channel 9431 in the outer housing 9410. Also, as in FIG. 98B, the secondary channel 9531 remains shrouded by the outer housing 9410.

Referring to FIG. 99C, the distal end 209 of the primary electrode 207 is extended beyond the distal end 105 of the sheath 103, with the distal end 209 piercing the target tissue 202 near the reference point 201. The distal end 213 of the secondary electrode 211 remains positioned within the distal end 209 of the primary electrode 207. The secondary electrode 211 moves with primary electrode 207 because, as shown in FIG. 100A, the secondary actuator grip 9555 initially rests at a rearward end 9557 (FIG. 95) of the secondary channel 9531. Thus, the movement of the primary actuator 9432 toward the first end 9441 of the outer housing 9410 also moves the secondary actuator 9552 toward the first end 9441 of the outer housing 9410. This concerted movement of the primary actuator 9432 and the secondary actuator 9552 results in the concerted movement of the primary electrode 207 and the secondary electrode 211.

Figure 100A:
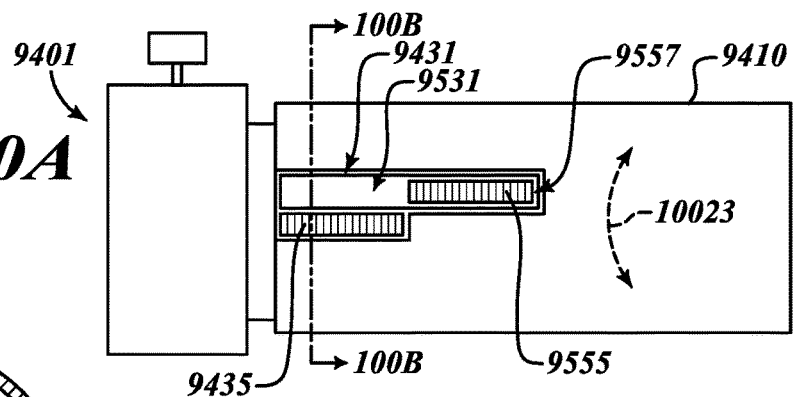

Referring to FIG. 100A, the primary actuator 9432 is rotated along a curve 10023. The movement of the primary actuator 9432 relative to the outer housing 9410 results in exposure of the secondary channel 9531 in the primary actuator 9432 and the secondary actuator grip 9555. As previously described, the secondary actuator grip 9555 rests at a rearward edge 9557 of the secondary channel 9531, so that the sliding movement of the primary actuator 9432 to extend the primary electrode 207 described with reference to FIGS. 99A and 99C also results in the sliding movement of the secondary electrode 211. Now, with the primary electrode 207 extended as described with reference to FIG. 99C, the secondary actuator grip 9555 is exposed so that the secondary electrode 211 may be separately extended, as further described below with reference to FIGS. 101A-101C.

Figure 100B:
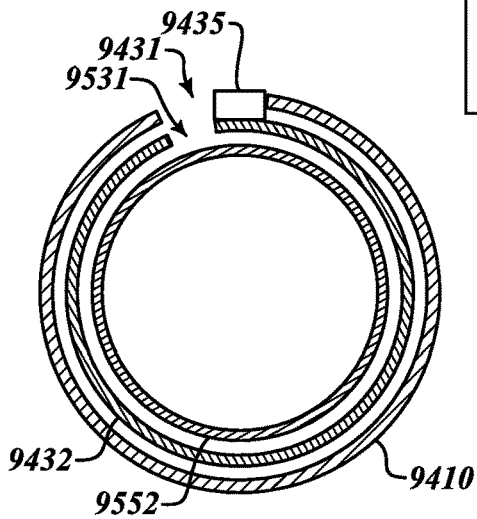
Figure 100C:
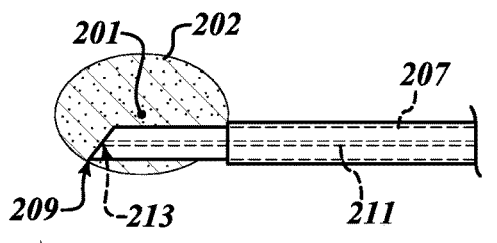

Referring to FIG. 100B, the primary actuator grip 9435 has been moved across the first channel 9431 and the secondary channel 9531 (which is defined by the primary actuator 9432 and unshrouded by the primary actuator 9432 being moved relative to the outer housing 9410). Referring to FIG. 100C, the distal end 213 of the secondary electrode 211 remains positioned within the distal end 209 of the primary electrode 207 at the positions to which the distal ends 209 and 213 were positioned at shown in FIG. 99C. The rotational movement of the primary actuator grip 9435 thus unshrouds the secondary actuator grip 9555 and the secondary channel 9531 for a next step, but does not result in movement of the electrodes 207 and 211.

Figure 101A:
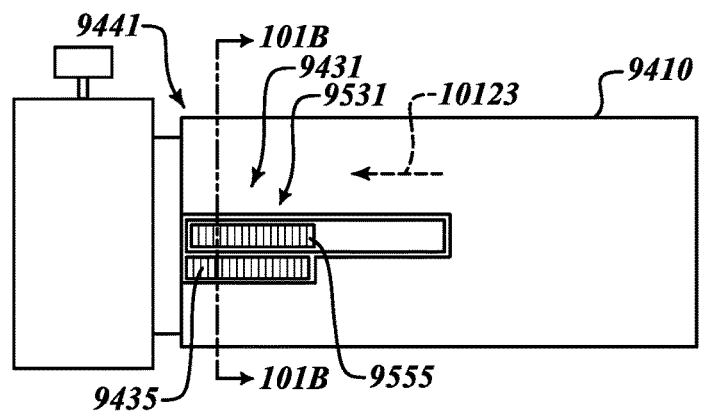
Figure 101B:
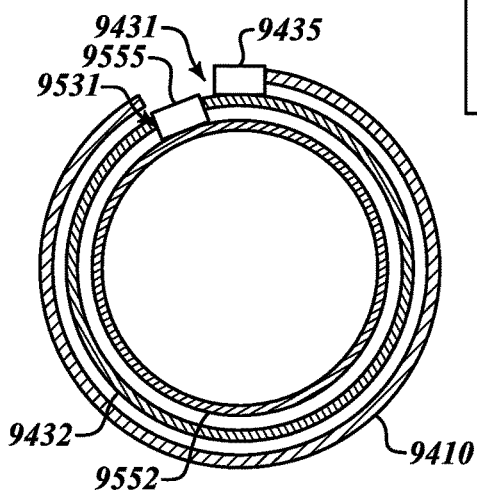
Figure 101C:
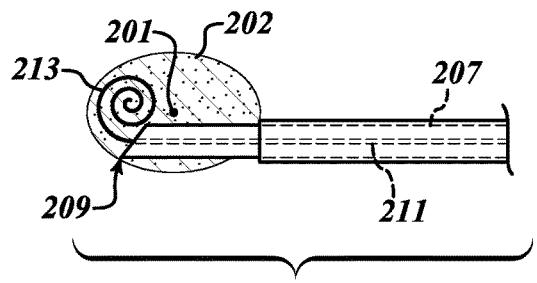

Referring to FIG. 101A, the secondary actuator 9552 is advanced toward the first end 9441 of the outer housing 9410 in a direction 9123, such as by a user sliding the secondary actuator grip 9555 toward the first end 9441 of the outer housing 9410. Referring to FIG. 101B, the secondary actuator grip 9555 is advanced to a position within the secondary channel 9531 and the primary channel 9431 alongside the primary actuator grip 9435. Referring to FIG. 101C, the distal end 213 of the secondary electrode 211 is in its extended position beyond the distal end 209 of the primary electrode 207, where the distal end 213 of secondary electrode 211 augers into the target tissue 202, as previously described with reference to other embodiments.

Referring to FIG. 102, another embodiment of the user interface 10201 for positioning electrodes is shown. The user interface 10201 includes components that are moved parallel with an axis 10221 or rotated along a curve 10223 around the axis 10221, as further described below. As also further described below, the user interface 10201 generally is controlled by moving actuators, such as the primary actuator 10232, by engaging a primary actuator grip 10235 that extends from a first channel 10231 defined in an outer housing 10210. The primary actuator 10232 may be moved along the axis 10221 by engaging and manipulating the primary actuator grip 10235 and sliding the primary actuator grip 10235 along the axis 10221 toward a first end 10241 of the housing 10210. As further described below, once the primary actuator 10232 is moved to a position where the primary electrode is extended, the primary actuator 10232 may be rotated around the axis 10221 to provide access to the secondary actuator (not shown in FIG. 102). By shrouding the secondary electrode actuator, the outer housing 10210 prevents the secondary electrode actuator from being moved to extend the secondary electrode before it is desired to do so.

Although the embodiment of the user interface 10201 has some similarities with the user interface 9401 of FIGS. 94-101C, the user interface 10201 includes features that permit further movement of the primary actuator 10232. The structure of these components and operation of these features are further described below.

The user interface 10201 includes a coupling 10220 to engage a port on an electrosurgical apparatus, such as a bronchoscope, as described with reference to FIGS. 1, 7, and 8. In various embodiments the user interface 10201 also includes a sheath actuator 10204 configured to position a sheath (not shown in FIG. 102) as previously described with reference to FIGS. 7-11. The sheath actuator 10204 includes a slidable sleeve 10212 and a sheath lock 10206 configured to engage the slidable sleeve 10212 and secure the slidable sleeve 10212 in place at the first end 10241 of the housing 10210, as described further below. It will be appreciated that, as described with reference to FIG. 35 regarding another embodiment of the user interface 3501, a sheath actuator may be part of the bronchoscope or a separate device inserted between the user interface 10201 and the bronchoscope (not shown in FIG. 102). Thus, in some embodiments the sheath actuator 10204 may not be a part of the user interface 10201. Also, although not shown in FIG. 102, as in embodiments shown in FIGS. 1 and 11, leads from a switchable current source are received at the user interface 10201 and a sheath (that contains primary and secondary electrodes) extends from the user interface 10201 via the coupling 10220.

Referring to FIG. 103, the user interface 10201 includes a number of components, including the outer housing 10210, the primary actuator 10232, a secondary actuator 10352, and components of the sheath actuator 10204, including the slidable sleeve 10212, the sheath lock 10206, and the coupling 10220. Movement of the primary actuator 10232 provides access to the secondary actuator 10352 and a secondary actuator grip 10355 when the primary actuator 10232 has been positioned as desired. Operation of the sheath actuator 10204 and its components is the same as the operation of the sheath actuator 9404 as previously described with reference to FIGS. 96A, 96B, 97A, and 97B.

The primary actuator 10232, which may be manipulated by a user engaging the primary actuator grip 10235, slides and rotates within the outer housing 10210 as further described below with reference to FIGS. 104A, 105A, 107A, and 108A. The primary actuator 10232 is engaged with a primary electrode (not shown in FIG. 103) so that movement of the primary actuator 10232 moves the primary electrode. The secondary actuator 10352 is engaged with a secondary electrode (not shown in FIG. 103) and causes the secondary electrode to move. The secondary actuator 10352 includes a secondary actuator grip 10355 that enables a user to slide the secondary actuator 10352, as described further below.

The secondary actuator grip 10355 moves within a second channel 10331 in the primary actuator 10232. As a result, and as will be further described below, only when the primary actuator 10232 has been moved to position the primary electrode at a desired location can the primary actuator 10232 be further moved to expose the second channel 10331 and the secondary actuator grip 10355. Thus, the secondary actuator 10352 can only be moved once the primary actuator 10232 has been moved to a prerequisite position, with the outer housing 10210 shrouding the secondary electrode actuator 10332 until a preceding step to be performed with the primary actuator 10232 is first accomplished. As will be further described below, the primary actuator 10232 is first moved and then rotated in order to unshroud the secondary actuator grip 10355 to enable movement of the secondary actuator 10332.

As previously described with reference to FIG. 102, operation of the user interface 10201 shares similarities with the user interface 9401 of FIGS. 94-101C. Accordingly, FIGS. 104A and 104C show the user interface 10201 as it has been manipulated to move the electrodes 207 and 211 to extend the distal ends 209 and 213, respectively, to a first position comparable to that shown based on manipulation of the user interface 4801. Referring to FIG. 104B, the primary actuator grip 10235 extends from the primary actuator 10232 through the first channel 10231. Also, as in FIG. 104B, the secondary channel 10331 remains shrouded by the outer housing 10210.

Referring to FIG. 104C, the distal end 209 of the primary electrode 207 is extended beyond the distal end 105 of the sheath 103, with the distal end 209 piercing the target tissue 202 near the reference point 201. The distal end 213 of the secondary electrode 211 remains positioned within the distal end 209 of the primary electrode 207. The secondary electrode 211 moves with primary electrode 207 because, as shown in FIG. 105A, the secondary actuator grip 10355 initially rests at a rearward end 10357 (FIG. 103) of the secondary channel 10331. Thus, the movement of the primary actuator 10232 toward the first end 10241 of the outer housing 10210 also moves the secondary actuator 10352 toward the first end 10241 of the outer housing 10210. This concerted movement of the primary actuator 10232 and the secondary actuator 10352 results in the concerted movement of the primary electrode 207 and the secondary electrode 211.

Referring to FIG. 105A, the primary actuator 10232 is rotated along a curve 10523. The movement of the primary actuator 10232 relative to the outer housing 10210 results in exposure of the secondary channel 10331 and the secondary actuator grip 10355. As previously described, the secondary actuator grip 10355 rests at a rearward edge 10357 of the secondary channel 10331, so that the sliding movement of the primary actuator 10232 to extend the primary electrode 207 described with reference to FIGS. 104A and 104C also results in the sliding movement of the secondary electrode 211. Now, with the primary electrode 207 extended as described with reference to FIG. 104C, the secondary actuator grip 10355 is exposed so that the secondary electrode 211 may be separately extended, as further described below with reference to FIGS. 106A-108C.

Referring to FIG. 105B, the primary actuator grip 10235 has been moved across the first channel 10231 and the secondary channel 10331 (which has been defined by the primary actuator 10232 being unshrouded by the outer housing 10210). Referring to FIG. 105C, the distal end 213 of the secondary electrode 211 remains positioned within the distal end 209 of the primary electrode 207 at the positions to which the distal ends 209 and 213 were positioned at shown in FIG. 104C. The rotational movement of the primary actuator grip 10255 thus unshrouds the secondary actuator grip 10355 for a next step, but does not result in movement of the electrodes 207 and 211.

In some embodiments of the user interface 10201, as, for example, some embodiments of the user interface 4801 of FIGS. 48-57C, the secondary actuator grip 10555 may be spring-loaded by a compressible element 10561 so that, when the secondary channel 10531 and secondary grip actuator 10555 are unshrouded, the secondary grip actuator 10555 extends outwardly from the secondary actuator 10552. As also described with reference to FIG. 56B, the outer housing 10210 may incorporate a ramp 10559 along at least a portion of the primary channel 10231 to make the extension of the secondary actuator grip 10555 gradual as the secondary actuator 10555 is exposed and/or to aid in compressing the secondary actuator grip 10555 when the steps described with reference FIGS. 104A-108C are reversed to retract the electrodes 207 and 211. It will be appreciated that such a spring-loaded secondary actuator grip configuration could be employed, although not expressly shown, with reference to the user interface 9401 of FIGS. 94-101C.

Referring to FIG. 106A, the secondary actuator 10352 is advanced toward the first end 10241 of the outer housing 10210 in a direction 10623, such as by a user sliding the secondary actuator grip 10355 toward the first end 10241 of the outer housing 10210. Referring to FIG. 101B, the secondary actuator grip 10355 is advanced to a position within the secondary channel 10331 and the primary channel 10231 alongside the primary actuator grip 10235. Referring to FIG. 101C, the distal end 213 of the secondary electrode 211 is shown in its extended position beyond the distal end 209 of the primary electrode 207, where the distal end 213 of secondary electrode 211 augers into the target tissue 202, as previously described with reference to other embodiments.

In contrast to the user interface 9401 of FIGS. 94-101C, the user interface 10201 provides for partial retraction of the primary electrode 207, similar to the partial retraction of the primary electrode as described, for example, with reference to the user interface 8201 described with reference to FIGS. 82-93B.

Referring to FIG. 107A, the primary actuator 10232 and the secondary actuator 10352 are rotated across the primary channel 10231 along a curve 10723, such as by a user engaging the primary actuator grip 10235 or the secondary actuator grip 10355 and sliding them across the primary channel 10231. Referring to FIG. 107B, the secondary actuator grip 10355 is advanced to a position within the secondary channel 10331 and the primary channel 10231 alongside the primary actuator grip 10235, but this time both the primary actuator grip 10235 and the secondary actuator grip 10355 are moved across the primary channel 10231.

Referring to FIG. 107C, the rotation of the primary actuator 10232 and the secondary actuator 10352 does not move either the primary electrode 207 or the secondary electrode 211. The rotation of the primary actuator 10232 and the secondary actuator 10352 merely prepares the user interface 10201 for a next step in positioning the electrodes 207 and 211.

Referring to FIG. 108A, the primary actuator 10232 is moved in a direction 10823 away from the first end 10241 of the outer housing 10210 to cause a partial retraction of the primary electrode 207. A user may engage the primary actuator grip 10235 to manipulate the primary actuator 10232 to slide it in the direction 10823. Referring to FIG. 108B, the secondary actuator grip 10355 is positioned within the secondary channel 10331 and the primary channel 10231 alongside the primary actuator grip 10235, where there positions partially overlap across the primary channel 10231 as shown in FIG. 108A.

Referring to FIG. 108C, the movement of the primary actuator 10232 results in a partial retraction of the primary electrode 207 without commensurate movement of the secondary electrode 211. Thus, the distal end 213 of the secondary electrode 211 remains coiled in the target tissue 202 where the distal end 213 of the secondary electrode 211 was positioned at the end of the step described with reference to FIGS. 106C and 107C. However, the distal end 209 of the primary electrode 207 is moved away from the distal end 213 of the secondary electrode 211, thereby exposing an insulated section 215 of the primary electrode 211 and creating two electrically separated contacts with the distal ends 209 and 213 of the electrodes 207 and 211 being separated by the insulated section 215.

Referring to FIG. 109, another embodiment of a user interface 10901 is shown. The user interface 10901 has similarities to the user interface 9401 described with reference to FIGS. 94-101C. Although the user interface 10901 has some similarities with the user interface 9401 of FIGS. 94-101C, the user interface 10901 includes one or more locking features that may be used to restrict movement of the actuators and the electrodes. The structure of these components and operation of these features are further described below Still referring to FIG. 109, the user interface 10901 includes components that are moved parallel with an axis 10921 or rotated along a curve 10923 around the axis 10921, as further described below. As also further described below, the user interface 10901 generally is controlled by moving actuators, such as a primary actuator 10932, by engaging a primary actuator grip 10935 that extends from a first channel 10931 defined in an outer housing 10910. The primary actuator 10932 may be moved along the axis 10921 by engaging and manipulating the primary actuator grip 10935 and sliding the primary actuator grip 10935 along the axis 10921 toward a first end 10241 of the housing 10210.

In contrast to the user interface 9401, however, before the primary actuator 10932 may be advanced, the primary actuator grip 10935 is depressed to cause the primary actuator grip 10925 to be rotated at a pivot 10938 (that is secured to the primary actuator 10932) to unlock movement of the primary actuator 10932, as further described with reference to FIG. 110. After the primary actuator 10932 is moved to a desired position in moving the primary electrode (not shown in FIG. 109), the primary actuator grip 10935 may be released to relock the primary actuator 10932 in place. As further described below, once the primary actuator 10932 is moved to a position where the primary electrode is extended, the primary actuator 10932 may be rotated around the axis 10921 to provide access to the secondary actuator (not shown in FIG. 109). By shrouding the secondary actuator, the outer housing 10910 prevents the secondary actuator from being moved to extend the secondary electrode before it is desired to do so.

Referring to FIG. 110, in various embodiments, a primary actuator grip 10935 is rotatably mounted to the primary actuator 10932 at a pivot 10938. The pivot 10938 may be spring-loaded. At a resting position at shown in FIG. 110, a latch 11037 on the primary actuator grip 10932 engages a notch 11072 in a locking structure 11070 in the user interface 10901. The engagement of the latch 11037 with the notch 11072 prevents sliding of the primary actuator 10932 until the primary actuator grip 10935 is depressed to disengage the latch 11037 from the notch 11072. The rotatable locking mechanism of the primary actuator grip 10935 is one example of a locking mechanism that may be used with embodiments of the user interface 10901. Translating, sliding, or other locking mechanisms also may be used to lock the primary actuator 10932 at desired locations.

Referring to FIG. 111, the user interface 10901 includes a number of components, including the outer housing 10910, the primary actuator 10932, a secondary actuator 11152, the locking structure 11072, and components of the sheath actuator 10904, including the slidable sleeve 10912, the sheath lock 10906, and the coupling 10920. Operation of the sheath actuator 10904 may be similar to operation of the sheath actuators previously described, such as in the operation of the sheath actuator 9404 of the user interface 9401 described with reference to FIGS. 96A-97B.

Movement of the primary actuator 10932 may provide access to the secondary actuator 11152 and a secondary actuator grip 11155 when the primary actuator 10932 has been positioned as desired. The primary actuator 10932, which may be manipulated by a user engaging the primary actuator grip 10935, slides and rotates within the outer housing 10910, similar to the description of operation of the user interface 9401 as described with reference to FIGS. 99A and 100A. The primary actuator 10932 is engaged with a primary electrode (not shown in FIG. 111) so that movement of the primary actuator 10932 moves the primary electrode. The secondary actuator 11152 is engaged with a secondary electrode (not shown in FIG. 111) and causes the secondary electrode to move. The secondary actuator 11152 includes a secondary actuator grip 11155 that enables a user to slide the secondary actuator 11152. The secondary actuator grip 11155 may also be configured with a locking mechanism The secondary actuator grip 11155 moves within a second channel 11131 in the primary actuator 10932. As a result, and as previously described with reference to similar embodiments, only when the primary actuator 10932 has been moved to position the primary electrode at a desired location can the primary actuator 10932 be further moved to expose the second channel 11131 and the secondary actuator grip 11155. Thus, the secondary actuator 11152 can only be moved once the primary actuator 10932 has been moved to a prerequisite position, with the outer housing 10910 shrouding the secondary electrode actuator 11132 until a preceding step to be performed with the primary actuator 10932 is first accomplished. As previously described, the primary actuator 10932 may be first moved and then rotated in order to unshroud the secondary actuator grip 11155 to enable movement of the secondary actuator 11132.

Unlike previously described embodiments, however, the user interface 10901 includes the locking structure 11070 which may include the notch 11072 as previously described and one or more other notches 11174 to permit the primary actuator 10932 to be locked with the primary electrode (not shown in FIG. 110) at an initial position and an extended position. If the user interface 10901 is adapted to facilitate partial retraction of the primary electrode after the secondary electrode has been extended (as described, for example, with reference to the user interface 10201 of FIGS. 102-108C), another notch may be included in the locking structure to secure the primary electrode in a partially retracted position. The locking structure 11070 may represent a separate body fixably secured with the outer housing 10910 or may be integrated within the outer housing 10910 to secure the primary actuator 10932 at desired positions. In the embodiment of the locking structure 11070, it should be noted that the notches 11072 and 11074 are elongated perpendicular to the axis 10921 (FIG. 109) so that the latch 11037 (FIG. 110) and, thus, the primary actuator grip 10935 and the primary actuator 10932 may rotate relative to the axis even when the latch 11037 engages one of the notches 11072 or 11174 to, for example, expose the secondary actuator grip 11155.

Referring to FIG. 112A, the primary actuator grip 10935 is in a locked position and situated at an initial position within the first channel 10931. The primary actuator grip 10935 is locked in position as described with reference to FIG. 110. Referring to FIG. 112B, the distal end 209 of the primary electrode 207 is positioned within a distal end 105 of the sheath 103, with the distal end 105 of the sheath 103 having been positioned proximate the reference point 201. The distal end 213 of the secondary electrode 211 is positioned within the distal end 209 of the primary electrode 207.

Referring to FIG. 113A, the primary actuator grip 10935 is depressed so as to rotate the primary actuator grip 10935 to withdraw the latch 11037 from a notch (not shown in FIG. 113A). With the primary actuator grip 10955 in an unlocked position, the primary actuator grip 10935 and, thus, the primary actuator 10932, may be moved to extend the primary electrode. However, just rotating the primary actuator grip 10935 to unlock the primary actuator grip 10935 does not move the electrodes. Referring to FIG. 113B, the distal end 209 of the primary electrode 207 remains positioned within a distal end 105 of the sheath 103, with the distal end 105 of the sheath 103 having been positioned proximate the reference point 201. The distal end 213 of the secondary electrode 211 remains positioned within the distal end 209 of the primary electrode 207.

Referring to FIG. 114A, the primary actuator grip 10935 and, thus, the primary actuator 10935 is moved in a direction 11423 and then released to lock the primary actuator grip 10935 at an extended position. Referring to FIG. 114B, the distal end 209 of the primary electrode 207 is extended beyond the distal end 105 of the sheath 103, with the distal end 209 piercing the target tissue 202 near the reference point 201. The distal end 213 of the secondary electrode 211 remains positioned within the distal end 209 of the primary electrode 207. The secondary electrode 211 moves with primary electrode 207 because, as shown in FIG. 111, the secondary actuator grip 11155 initially rests at a rearward end 11157 (FIG. 111) of the secondary channel 11131 formed in the primary actuator 10932. Thus, the movement of the primary actuator 10932 toward the first end 10941 of the outer housing 10910 also moves the secondary actuator 11152 toward the first end 10941 of the outer housing 10910, as previously described with reference to, for example, user interface 9401 of FIGS. 94-101C. This concerted movement of the primary actuator 10932 and the secondary actuator 11152 results in the concerted movement of the primary electrode 207 and the secondary electrode 211. Further movement of the secondary electrode 211 and/or the primary electrode 207 may be accommodated by structures and their operation such as those performed as described with reference to the user interface 9401 of FIGS. 94-101C or the user interface 10201 of FIGS. 102-108C. Put another way, the user interface 9401 or the user interface 10201 may be adapted to use one or more locking actuator grips as described with reference to FIGS. 109-114B to add the capacity to lock the actuators as desired.

Referring to FIG. 115, another embodiment of the user interface 11501 for positioning electrodes is shown. The user interface 11501 includes components that are moved parallel with an axis 11521 or rotated along a curve 11523 around the axis 11521, as further described below. As also further described below, the user interface 11501 generally is controlled by moving actuators, such as the primary actuator 11532, by engaging a primary actuator grip 11535 that extends from a first channel 11531 defined in an outer housing 11510. The primary actuator 11532 may be moved along the axis 11521 by engaging and manipulating the primary actuator grip 11535 and sliding the primary actuator grip 11535 along the axis 11521 toward a first end 11541 of the housing 11510. As further described below, once the primary actuator 11532 is moved to a position where the primary electrode is extended, the access to the secondary actuator (not shown in FIG. 115) is provided. By shrouding the secondary electrode actuator, the outer housing 11510 prevents the secondary electrode actuator from being moved to extend the secondary electrode before it is desired to do so. The first channel 11531 is formed to permit partial retraction of the primary electrode with the primary actuator grip 11532, as well as extension and retraction of the primary electrode and the secondary electrode. The structure and operation of these components are further described below.

The user interface 11501 includes a coupling 11520 to engage a port on an electrosurgical apparatus, such as a bronchoscope, as described with reference to FIGS. 1, 7, and 8. The user interface 11501 also includes a sheath actuator 11504 to position a sheath (not shown in FIG. 115) as previously described with reference to FIGS. 7-11. The sheath actuator 11504 includes a slidable sleeve 11512 and a sheath lock 11506 to engage the slidable sleeve 11512 and to secure the slidable sleeve 11512 in place at the first end 11541 of the housing 11510, as described further below. It will be appreciated that, as described with reference to FIG. 35 regarding another embodiment of the user interface 3501, a sheath actuator may be part of the bronchoscope or a separate device inserted between the user interface 11501 and the bronchoscope (not shown in FIG. 115). Thus, in some embodiments the sheath actuator 11504 may not be a part of the user interface 11501. Also, although not shown in FIG. 115, as in embodiments shown in FIGS. 1 and 11, leads from a switchable current source are received at the user interface 11501 and a sheath (that contains primary and secondary electrodes) extends from the user interface 11501 via the coupling 11520.

Referring to FIG. 116, the user interface 11501 includes a number of components, including the outer housing 11510, the primary actuator 11532, a secondary actuator 11652, and components of the sheath actuator 11504, including the slidable sleeve 11512, the sheath lock 11506, and the coupling 11520. Movement of the primary actuator 11532 provides access to the secondary actuator 11652 and a secondary actuator grip 11655 when the primary actuator 11532 has been positioned as desired.

The primary actuator 11532, which may be manipulated by a user engaging the primary actuator grip 11535, slides and rotates within the outer housing 11510 as further described below with reference to FIG. 121A. The primary actuator 11532 is engaged with a primary electrode (not shown in FIG. 116) so that movement of the primary actuator 11532 moves the primary electrode. The secondary actuator 11652 is engaged with a secondary electrode (not shown in FIG. 116) and causes the secondary electrode to move. The secondary actuator 11652 includes a secondary actuator grip 11655 that enables a user to slide the secondary actuator 11652, as described further below.

The secondary actuator grip 11655 moves within a second channel 11631 in the primary actuator 11532. As a result, and as will be further described below, only when the primary actuator 11532 has been moved to position the primary electrode at a desired location can the primary actuator 11532 be further moved to expose the second channel 11631 and the secondary actuator grip 11655. Thus, the secondary actuator 11652 can only be moved once the primary actuator 11532 has been moved to a prerequisite position, with the outer housing 11510 shrouding the secondary electrode actuator 11632 until a preceding step to be performed with the primary actuator 11532 is first accomplished.

Referring to FIGS. 117A, 117B, 118A, and 118B, operation of the sheath actuator 11504 is depicted. The operation of the sheath actuator 11504 of the user interface 11501 is very similar to that of the sheath actuator 8204 of the user interface 8201 of FIGS. 88A, 89A, 90A, and 90B and other sheath actuators, as previously described. Referring to FIGS. 96A and 96B and as used in conjunction with a user interface 11501, the sheath actuator 11504 controls a position of the sheath 103. Specifically, a position of the sheath 103 is controlled by sliding the slidable sleeve 11512 within the coupling 11520 and securing the sheath 103 at the desired location by securing the slidable sleeve 11512 with the sheath lock 11506. The sheath actuator 11504 may operate similarly to the sheath lock 706 of FIG. 9, as previously described. The slidable sleeve 11512 is fixably mounted to the outer housing 11510 and is slidably received within the coupling 11520. When the slidable sleeve 11512 is situated to position the sheath 103 containing the electrodes 207 and 211 at a desired location, the sheath lock 11506 is locked to secure the slidable sleeve 11512 in place. The sheath lock 11506 may be a spring-loaded lock, a thumbscrew, or another similar mechanism as previously described with reference to FIGS. 7-10 to secure the slidable sleeve 11512 in place to secure the position of the sheath 103.

As previously described and as shown in FIG. 117B, in illustrative embodiments the secondary electrode 211 is received within the primary electrode, with a distal end 213 of the secondary electrode 211 initially resting just within the distal end 209 of the primary electrode 207. In turn, the distal end 209 of the primary electrode 207 rests just within the distal end 105 of the sheath 103. Before the sheath actuator 8204 is used to position the distal end 105 of the sheath 103 near the reference point 201, the distal end of the sheath 103 may initially rest at a position away from or immediately adjacent to the reference point 201.

Referring to FIGS. 118A and 118B and as used in conjunction with a user interface 11501, the sheath actuator 11504 is used to move the distal end 105 of the sheath 103 to a position closer to the reference point 201 as shown in FIG. 97B. A relative movement of the outer housing 11510 toward the coupling 11520 by a distance 11819 moves the distal end 105 of the sheath 103 a corresponding distance to move the distal end 105 of the sheath 103 closer to the reference point 201. In turn, the distal end 209 of the primary electrode 207 and the distal end 213 of the secondary electrode 211 are also moved closer to the reference point 201. The relative movement of the outer housing 11510 toward the coupling 11520 is accomplished by the slidable sleeve 11512 being at least partially received within the coupling 11520 and then secured with the sheath lock 11506, as previously described. As shown in FIG. 118B, the distal end 209 of the primary electrode 207 remains positioned within a distal end 105 of the sheath 103, with the distal end 105 of the sheath 103 having been positioned proximate the reference point 201. The distal end 213 of the secondary electrode 211 remains positioned within the distal end 209 of the primary electrode 207.

FIGS. 119A-123C show how the user interface 11501 moves the electrodes 207 and 211 based on manipulation of the user interface 11501. Referring to FIG. 119A with regard to the user interface 11501, the primary actuator grip 11535 extends from the primary actuator 11532 upward through the first channel 11531 of the outer housing 11510 and is situated at an initial position at a rear end 11937 within the first channel 11531. Referring to FIG. 119B, the primary actuator grip 11535 extends from the primary actuator 11532 through the first channel 11531 in the outer housing 11510. At the point of the cross-section, although the secondary channel 11631 is exposed within the primary channel 11531, as shown in FIG. 119A, the secondary actuator grip 11655 remains shrouded by the outer housing 11510. Also, in some embodiments, the secondary actuator grip 11655 may be spring-loaded by a compressible element 11959. As a result, the secondary actuator grip 11655 may be both shrouded and compressed by the outer housing 11510 when the primary actuator grip 11535 is in the initial position.

With the primary actuator 11532 in an initial position, as shown in FIG. 119C, the distal end 209 of the primary electrode 207 remains positioned within a distal end 105 of the sheath 103, with the distal end 105 of the sheath 103 having been positioned proximate the reference point 201. The distal end 213 of the secondary electrode 211 remains positioned within the distal end 209 of the primary electrode 207.

Referring to FIG. 120A, the primary actuator 11532 is moved to extend the primary electrode 207, such as by the user engaging the primary electrode grip 11535 and sliding toward the first end 11541 of the outer housing 11510. With the movement of the primary actuator 11532, the secondary actuator grip 11655 and, thus, the secondary actuator 11652, are moved toward the first end 11541 of the outer housing 11510. In the initial position, the secondary actuator 11655 rests at a trailing end 11657 of the secondary channel 11631 defined in the primary actuator 11531. As a result, moving the primary actuator grip 11535 toward the first end 11541 of the outer housing 11510 moves the secondary channel 11631 and, thus, moves the secondary actuator grip 11655 and, in turn, the secondary actuator 11652.

Referring to FIG. 120B, the primary actuator grip 11535 extends from the primary actuator 11532 through the first channel 11531 in the outer housing 11510. Also, as in FIG. 120B, the secondary actuator grip 11655, unshrouded and uncompressed by the outer housing 11510, now extends upwardly through the secondary channel 11631 and the primary channel 11531. Referring to FIG. 120C, the distal end 209 of the primary electrode 207 is extended beyond the distal end 105 of the sheath 103, with the distal end 209 piercing the target tissue 202 near the reference point 201. Because the secondary electrode actuator 11652 moves in concert with the primary electrode actuator 11532 in this first extension of the primary electrode 207, the distal end 213 of the secondary electrode 211 remains positioned at a same position relative to the distal end 209 of the primary electrode 207.

Figure 121A:
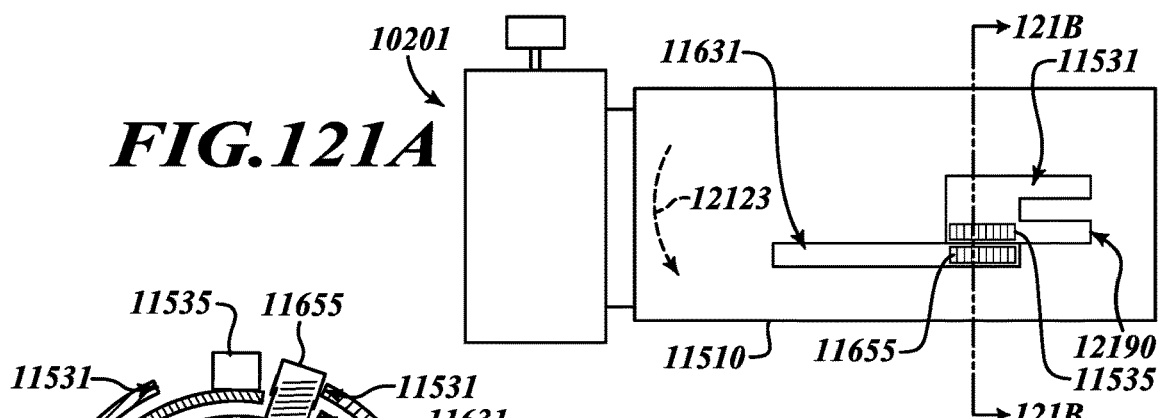
Figure 121B:
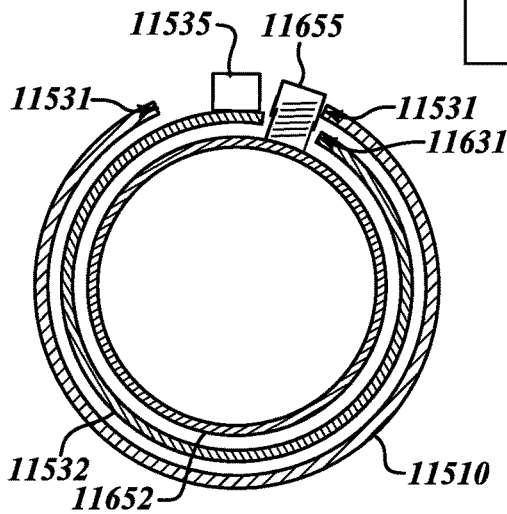
Figure 121C:
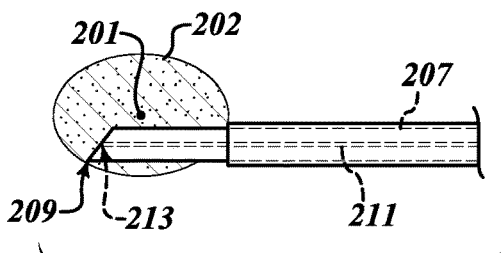

Referring to FIG. 121A, the primary actuator grip 11535 and the secondary actuator grip 11655, along with the primary actuator 11532 and the secondary actuator 11652, are rotated along a curve 12123. The movement of the primary actuator 11532 and the secondary actuator 11652 relative to the outer housing 11510 places the secondary actuator grip 11555 in a position to extend the secondary electrode in a next step, as further described with reference to FIGS. 122A-122C. Referring to FIG. 121B the primary actuator grip 11535 and the secondary actuator grip 11655 have been moved across the first channel 11531 in the outer housing 11510. Referring to FIG. 121C, the distal ends 209 and 213 of the electrodes 207 and 211, respectively, do not change position. The rotational movement of the primary actuator grip 11532 and the secondary actuator 11652 prepare the user interface 11501 for a next step, but do not move the electrodes 207 and 211.

Figure 122A:
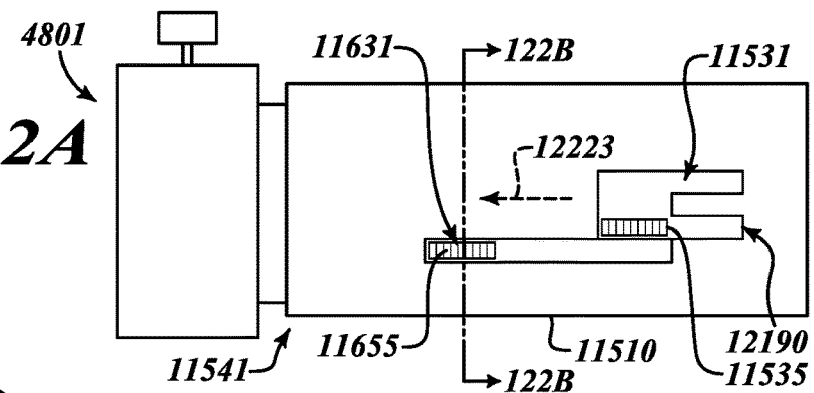
Figure 122B:
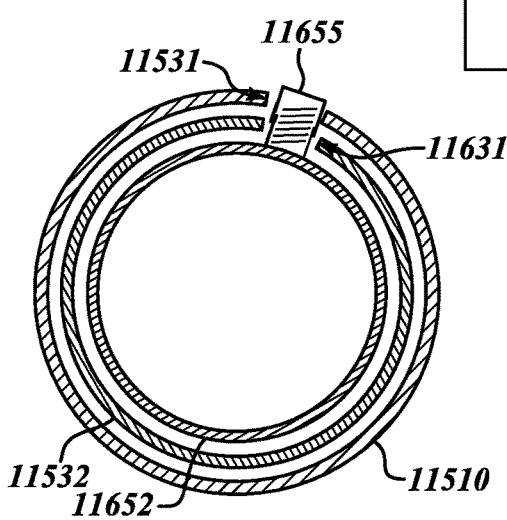
Figure 122C:
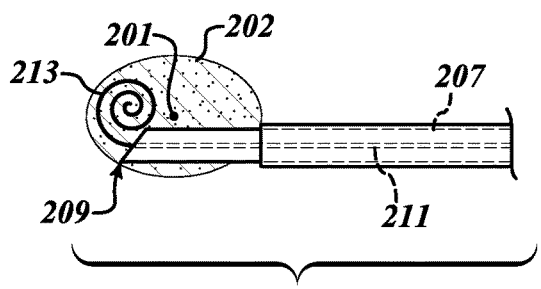

Referring to FIG. 122A, the secondary actuator 11652 is advanced toward the first end 11541 of the outer housing 11510 in a direction 12223, such as by a user sliding the secondary actuator grip 11655 toward the first end 11541 of the outer housing 11510. Referring to FIG. 122B, in a cross-sectional view taken along the axis 121B of FIG. 121A, the secondary actuator grip 11655 is shown to an advanced position within the secondary channel 11631 and the primary channel 11531. Referring to FIG. 122C, the distal end 213 of the secondary electrode 211 is shown in its extended position beyond the distal end 209 of the primary electrode 207, where the distal end 213 of secondary electrode 211 augers into the target tissue 202, as previously described with reference to other embodiments.

Referring to FIGS. 121A and 122A, after the rotation of the primary actuator grip 11535 and the secondary actuator grip 11655, the primary actuator grip 11535 is positioned at a rearward section 12190 of the primary channel 11531. Referring to FIG. 123A, with the secondary actuator grip 11655 remaining in the extended position, the primary actuator grip is drawn away from the first end 11541 of the outer housing 11510 in a direction 12323. Referring to FIG. 123C, the primary actuator 11535 is received in the rearward section 12190 of the primary channel 11531. Referring to FIG. 123C, the movement of the primary actuator grip 11535 and the resulting movement of the primary actuator 11532 partially retracts the distal end 209 of the primary electrode 207, thereby exposing the insulated section 215 to electrically separate the distal ends 209 and 213 of the electrodes 207 and 211, respectively.

Referring to FIG. 124, an illustrative method 12400 of positioning electrodes for treatment is provided. The method 12400 starts at a block 12405. At a block 12410, a sheath containing a primary electrode and a secondary electrode is extended, where the secondary electrode is contained within the primary electrode and initially coupled to move with the primary electrode as previously described, for example, with reference to FIGS. 8, 51, 61, 88A-89B, and 117A-118B. At a block 12420, the primary electrode is moved to a first location near a reference point as previously described, for example, with reference to FIGS. 14, 38, 53, 64, 90A-90B, 97A-97B, 104-104C, 114A-114B, and 119A-119C. At a block 12430, the primary actuator is moved to move a shrouding device to permit access to a secondary actuator configured to move the secondary electrode, as previously described, for example, with reference to FIGS. 90A-90B, 100A-100C, 105A-105C, and 120A-120C. At a block 12440, the secondary electrode is moved to a second location near the reference point as previously described, for example, with reference to FIGS. 20, 45, 55, 66, 91A-91B, 101A-101C, 106A-106C, and 122A-122C. The method 12400 ends at a block 12445, with the electrodes now positioned for the administration of treatment.

Referring to FIG. 125, an illustrative method 12500 of positioning electrodes for treatment is provided. The method 12500 starts at a block 12505. At a block 12510, a sheath containing a primary electrode and a secondary electrode is extended, where the secondary electrode is contained within the primary electrode and initially coupled to move with the primary electrode as previously described, for example, with reference to FIGS. 8, 51, 61, 88A-89B, and 117A-118B. At a block 12520, the primary electrode is moved to a first location near a reference point as previously described, for example, with reference to FIGS. 14, 38, 53, 64, 90A-90B, 97A-97B, 104-104C, 114A-114B, and 119A-119C. At a block 12530, the primary actuator is rotated to expose a secondary actuator that previously was at least partially covered by the primary actuator and coupled with the secondary electrode to permit access to the secondary actuator to move the secondary electrode, as previously described, for example, with reference to FIGS. 100A-100C and 105A-105C. At a block 12540, the secondary electrode is moved to a second location near the reference point as previously described, for example, with reference to FIGS. 20, 45, 55, 66, 91A-91B, 101A-101C, 106A-106C, and 122A-122C. The method 12500 ends at a block 12545, with the electrodes now positioned for the administration of treatment.

Referring to FIG. 126, an illustrative method 12600 of positioning electrodes for treatment is provided. The method 12600 starts at a block 12605. At a block 12610, a sheath containing a primary electrode and a secondary electrode is extended, where the secondary electrode is contained within the primary electrode and initially coupled to move with the primary electrode as previously described, for example, with reference to FIGS. 8, 51, 61, 88A-89B, and 117A-118B. At a block 12620, a primary actuator grip is slid within a channel defined in an outer handle to move a primary actuator to move the primary electrode to a first location near a reference point, as previously described, for example, with reference to FIGS. 14, 38, 53, 64, 90A-90B, 97A-97B, 104-104C, 114A-114B, and 119A-119C. At a block 12630, the primary actuator is rotated to expose a secondary actuator that previously was at least partially covered by the primary actuator and coupled with the secondary electrode to permit access to the secondary actuator to move the secondary electrode, as previously described, for example, with reference to FIGS. 100A-100C and 105A-105C. At a block 12640, the secondary electrode is moved to a second location near the reference point as previously described, for example, with reference to FIGS. 20, 45, 55, 66, 91A-91B, 101A-101C, 106A-106C, and 122A-122C. The method 12500 ends at a block 12645, with the electrodes now positioned for the administration of treatment.

It will be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An apparatus for slidably moving multiple features relative to a sheath insertable into a body and positionable relative to a reference point, the apparatus comprising:
    a primary actuator configured to move a primary electrode to a first position;
    a secondary actuator configured to move a secondary electrode to a second position; and
    a shrouding device configured to selectively prevent access to the secondary actuator until the primary actuator has been manipulated to extend the primary electrode to the first position,
    wherein the secondary actuator is nested within the primary actuator.

2. The apparatus of claim 1, wherein the shrouding device defines a first access opening configured to permit access to the secondary actuator after the primary actuator has been manipulated to move the primary electrode to the first position.

3. The apparatus of claim 2, wherein the shrouding device is configured to expose the first access opening configured to permit access to the secondary actuator after the primary actuator has been rotated after being manipulated to move the primary electrode.

4. The apparatus of claim 2, further comprising an outer handle configured to house the primary actuator and the secondary actuator, the shrouding device being integrated into the outer handle.

5. The apparatus of claim 1, further comprising a primary actuator lock that must be released before the primary actuator is moveable to the first position.

6. The apparatus of claim 5, wherein the primary actuator lock includes a spring-loaded lever configured to be depressed at a first end to release a latch to permit movement of the primary actuator.

7. The apparatus of claim 1, wherein the primary actuator is further configured to be moved to partially retract the primary electrode to a partially retracted position after the secondary electrode has been moved to the secondary position.

8. The apparatus of claim 7, wherein the shrouding device is further configured to prevent the primary actuator from being moved to partially retract the primary electrode to the partially retracted position until after the secondary electrode has been moved to the secondary position.

9. The apparatus of claim 8, wherein the shrouding device is integrated into the primary actuator.

10. The apparatus of claim 9, wherein the shrouding device is further configured to be rotatable relative to the primary actuator to permit the primary actuator to be moved to permit partially retracting the primary electrode to the partially retracted position.

11. The apparatus of claim 9, wherein the shrouding device defines an access opening configured to permit the primary actuator to be moved to permit partially retracting the primary electrode to the partially retracted position.

12. The apparatus of claim 1, wherein:
    the sheath that houses distal portions of the primary electrode and the secondary electrode; and further comprising:
    a sheath actuator configured to move the sheath relative to the reference point; and
    a sheath lock configured to fix a position of a distal end of the sheath relative to the reference point.

13. A system for treating tissue at a reference point, the system comprising:
    a controllable electrical power source configured to selectively provide electrical power between a first pole and a second pole;
    an electrosurgical apparatus configured to be inserted into a body to convey a sheath that houses a primary electrode electrically coupled to the first pole of the electrical power source and a secondary electrode electrically coupled to the second pole of the electrical power source to a vicinity of the reference point; and
    an electrode control apparatus including:
        a primary actuator configured to move the primary electrode to a first position;
        a secondary actuator configured to move the secondary electrode to a second position; and a shrouding device configured to selectively prevent access to the secondary actuator until the primary actuator has been manipulated to extend the primary electrode to the first position,
wherein the secondary actuator is nested within the primary actuator.

14. The system of claim 13, further comprising:
a sheath actuator configured to move the sheath relative to the reference point;
a sheath lock configured to selectively fix a position of the sheath relative to the reference point.

15. The system of claim 13, wherein the shrouding device is configured to be rotatable relative to the primary actuator to permit access to the secondary actuator after the primary actuator has been manipulated to move the primary electrode to the first position.

16. The system of claim 13, wherein the shrouding device is integrated into the primary actuator.

17. The system of claim 13, wherein:
the shrouding device being integrated into an outer handle of the electrode control apparatus; and
the electrode control apparatus being configured to house the primary actuator and the secondary actuator.

18. The system of claim 13, wherein the electrode control apparatus further includes a primary actuator lock that must be released before the primary actuator is moveable to the first position.

19. The apparatus of claim 18, wherein the primary actuator lock includes a spring-loaded lever configured to be depressed at a first end to release a latch to permit movement of the primary actuator.

20. The system of claim 13, wherein the primary actuator is further configured to be moved to partially retract the primary electrode to a partially retracted position after the secondary electrode has been moved to the secondary position.

21. An apparatus for slidably moving multiple features relative to a sheath insertable into a body and positionable relative to a reference point, the device comprising:
a shaft configured to enable slidable passage of a primary electrode and a secondary electrode therethrough;
a primary actuator coupled with the primary electrode and configured to slidably move over the shaft to move the primary electrode to a first position near a reference point;
a secondary actuator coupled with the secondary electrode and configured to slidably move over the shaft to move the secondary electrode to a second position, the secondary actuator nested within the primary actuator; and
a shroud device incorporated in the primary actuator and configured to at least partially prevent access to the secondary actuator, the primary actuator being configured to slidably and rotatably move relative to the shaft, and wherein, after the primary actuator has been moved to slidably move the primary electrode to the first position, the primary actuator is further configured to be rotated to move the shroud device to permit access to the secondary actuator.

22. The apparatus of claim 21, wherein the primary actuator and the secondary actuator are configured to be coupled such that, when the primary actuator is moved to move the primary electrode to the first position, the secondary actuator is moved in concert to cause the secondary electrode to move with the first electrode.

23. The apparatus of claim 21, wherein the shrouding device defines an access opening and is configured to be rotated so that the access opening permits access to the secondary actuator after the primary actuator has been manipulated to move the primary electrode to the first position and rotated.

24. The apparatus of claim 23, wherein the primary actuator is further configured to permit the primary actuator to be moved to partially retract the primary electrode to a partially retracted position after the secondary electrode has been moved to the second position.

25. The apparatus of claim 24, wherein the primary actuator is further configured to be rotated to permit partial retraction of the primary electrode after the secondary electrode has been moved to the second position.

26. The apparatus of claim 25, wherein the primary actuator further includes a grip to facilitate slidable movement of the primary actuator.

27. The apparatus of claim 26, further comprising an outer handle configured to house the primary actuator and the secondary actuator, and wherein when the primary actuator is rotated to permit access to the secondary actuator, the outer handle at least partially covers the grip to at least partially interfere with movement of the primary actuator.

28. The apparatus of claim 21, further comprising:
a sheath actuator configured to move a sheath relative to the reference point, wherein the sheath houses distal portions of the primary electrode and the secondary electrode; and
a sheath lock configured to fix a position of a distal end of the sheath relative to the reference point.

29. A system for treating tissue at a reference point, the system comprising:
a controllable electrical power source configured to selectively provide electrical power between a first pole and a second pole;
an electrosurgical apparatus configured to be inserted into a body to convey a sheath that houses a primary electrode electrically coupled to the first pole of the electrical power source and a secondary electrode electrically coupled to the second pole of the electrical power source to a vicinity of the reference point; and
an electrode control apparatus, further including:
a shaft configured to enable slidable passage of the primary electrode and the secondary electrode therethrough;
a primary actuator coupled with the primary electrode and configured to slidably move over the shaft to move the primary electrode to a first position near the reference point;
a secondary actuator coupled with the secondary electrode and configured to slidably move over the shaft to move the secondary electrode to a second position, wherein the secondary actuator is nested within the primary actuator; and
a shroud device incorporated in the primary actuator and configured to at least partially prevent access to the secondary actuator, the primary actuator being configured to slidably and rotatably move relative to the shaft, and wherein, after the primary actuator has been moved to slidably move the primary electrode to the first position, the primary actuator is further configured to be rotated to move the shroud device to permit access to the secondary actuator.

30. The system of claim 29, wherein the primary actuator and the secondary actuator are configured to be coupled such that, when the primary actuator is moved to move the primary electrode to the first position, the secondary actuator is moved in concert to cause the secondary electrode to move with the first electrode.

31. The apparatus of claim 29, wherein the shrouding device defines an access opening and is configured to be rotated so that the access opening permits access to the secondary actuator after the primary actuator has been manipulated to move the primary electrode to the first position and rotated.

32. The system of claim 31, wherein the primary actuator is further configured to permit the primary actuator to be moved to partially retract the primary electrode to a partially retracted position after the secondary electrode has been moved to the second position.

33. The system of claim 32, wherein the primary actuator is further configured to be rotated to permit partial retraction of the primary electrode after the secondary electrode has been moved to the second position.

34. The system of claim 33, wherein the primary actuator further includes a grip to facilitate slidable movement of the primary actuator.

35. The system of claim 34, wherein the electrode control apparatus includes an outer handle configured to house the primary actuator and the secondary actuator, and wherein when the primary actuator is rotated to permit access to the secondary actuator, the outer handle at least partially covers the grip to at least partially interfere with movement of the primary actuator.

36. The system of claim 29, further comprising:
a sheath actuator configured to move the sheath relative to the reference point, wherein the sheath houses distal portions of the primary electrode and the secondary electrode; and
a sheath lock configured to fix a position of a distal end of the sheath relative to the reference point.

37. An apparatus for slidably moving multiple features relative to a sheath insertable into a body and positionable relative to a reference point, the device comprising:
a primary actuator configured to move a primary electrode to a first position when a primary actuator grip is slidably moved toward a first end;
a secondary actuator configured to move a secondary electrode to a second position when a secondary actuator grip is slidably moved toward the first end, wherein the secondary actuator is nested within the primary actuator; and
an outer handle configured to selectively prevent access to the secondary actuator grip of the secondary actuator until the primary actuator has been manipulated to extend the primary electrode to the first position and rotated relative to the primary actuator to expose the secondary actuator.

38. The apparatus of claim 37, wherein:
the secondary actuator grip aligns with a first channel defined in the primary actuator when the primary actuator is rotated to expose the secondary actuator.

39. The apparatus of claim 38, wherein the outer handle defines a second channel into which the primary actuator grip and the secondary actuator grip slide, the second channel being configured to selectively control a relative movement of the primary actuator grip and the secondary actuator grip.

40. The apparatus of claim 39, wherein the secondary actuator grip is configured to extend outwardly from the secondary actuator and into the first channel after the outer handle is rotated relative to the primary actuator to expose the secondary actuator grip.

41. The apparatus of claim 40, wherein the outer handle is further configured to be rotatable relative to the primary actuator after the secondary actuator is moved to move the secondary electrode to the second position to permit the primary actuator to be moved to permit partially retract the primary electrode to the partially retracted position.

42. The apparatus of claim 41, wherein the first channel prevents sliding movement of the secondary actuator grip to prevent movement of the secondary actuator when the primary actuator is moved to partially retract the primary electrode.

43. The apparatus of claim 37, further comprising a primary actuator lock configured so that the primary actuator lock must be released before the primary actuator is moveable to the first position.

44. The apparatus of claim 37, wherein:
the sheath that houses distal portions of the primary electrode and the secondary electrode; and further comprising:
a sheath actuator configured to move the sheath relative to a reference point; and
a sheath lock configured to fix a position of a distal end of the sheath relative to the reference point.

45. A system for treating tissue at a reference point, the system comprising:
a controllable electrical power source configured to selectively provide electrical power between a first pole and a second pole;
an electrosurgical apparatus configured to be inserted into a body to convey a sheath that houses a primary electrode electrically coupled to the first pole of the electrical power source and a secondary electrode electrically coupled to the second pole of the electrical power source to a vicinity of the reference point; and
an electrode control apparatus, further comprising:
a primary actuator configured to move the primary electrode to a first position when a primary actuator grip is slidably moved toward a first end;
a secondary actuator configured to move the secondary electrode to a second position when a secondary actuator grip is slidably moved toward the first end; and
an outer handle configured to selectively prevent access to the secondary actuator grip of the secondary actuator until the primary actuator has been manipulated to extend the primary electrode to the first position and rotated relative to the primary actuator to expose the secondary actuator grip,
wherein the secondary actuator is nested within the primary actuator.

46. The system of claim 45, wherein:
the secondary actuator grip aligns with a first channel defined in the primary actuator when the primary actuator is rotated to expose the secondary actuator.

47. The system of claim 46, wherein the outer handle defines a second channel into which the primary actuator grip and the secondary actuator grip slide, the second channel being configured to selectively control a relative movement of the primary actuator grip and the secondary actuator grip.

48. The system of claim 47, wherein the second actuator grip is configured to extend outwardly from the secondary actuator and into the first channel after the outer handle is rotated relative to the primary actuator to expose the secondary actuator grip.

49. The system of claim 48, wherein the outer handle is further configured to be rotatable relative to the primary actuator after the secondary actuator is moved to move the secondary electrode to the second position to permit the primary actuator to be moved to permit partially retract the primary electrode to the partially retracted position.

50. The system of claim 49, wherein the first channel prevents sliding movement of the secondary grip to prevent movement of the secondary actuator grip when the primary actuator is moved to partially retract the primary electrode.

51. The system of claim 45, further comprising a primary actuator lock configured so that the primary actuator lock must be released before the primary actuator is moveable to the first position.

52. The system of claim 45, wherein:
- the sheath that houses distal portions of the primary electrode and the secondary electrode; and further comprising:
- a sheath actuator configured to move the sheath relative to a reference point; and
- a sheath lock configured to fix a position of a distal end of the sheath relative to the reference point.

* * * * *